United States Patent
Monje-Deisseroth et al.

(10) Patent No.: US 10,377,818 B2
(45) Date of Patent: Aug. 13, 2019

(54) METHOD OF TREATING GLIOMA

(71) Applicant: The Board of Trustees of the Leland Stanford Junior University, Stanford, CA (US)

(72) Inventors: Michelle Monje-Deisseroth, Stanford, CA (US); Humsa S. Venkatesh, Milpitas, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 15/011,260

(22) Filed: Jan. 29, 2016

(65) Prior Publication Data

US 2016/0222100 A1 Aug. 4, 2016

Related U.S. Application Data

(60) Provisional application No. 62/110,257, filed on Jan. 30, 2015.

(51) Int. Cl.

| | |
|---|---|
| *C07K 16/22* | (2006.01) |
| *C07K 16/28* | (2006.01) |
| *G01N 33/50* | (2006.01) |
| *A61K 45/06* | (2006.01) |
| *A61K 39/00* | (2006.01) |
| *A61K 38/17* | (2006.01) |
| *A61K 38/12* | (2006.01) |
| *A61K 31/366* | (2006.01) |
| *A61K 31/5377* | (2006.01) |
| *A61K 31/436* | (2006.01) |
| *A61K 31/44* | (2006.01) |
| *A61K 31/541* | (2006.01) |
| *A61K 31/496* | (2006.01) |
| *A61K 38/13* | (2006.01) |
| *A61K 31/55* | (2006.01) |
| *A61K 31/12* | (2006.01) |
| *A61K 31/437* | (2006.01) |
| *A61K 31/4985* | (2006.01) |
| *A61K 31/515* | (2006.01) |
| *A61K 38/16* | (2006.01) |

(52) U.S. Cl.
CPC .............. *C07K 16/22* (2013.01); *A61K 31/12* (2013.01); *A61K 31/366* (2013.01); *A61K 31/436* (2013.01); *A61K 31/437* (2013.01); *A61K 31/44* (2013.01); *A61K 31/496* (2013.01); *A61K 31/4985* (2013.01); *A61K 31/515* (2013.01); *A61K 31/5377* (2013.01); *A61K 31/541* (2013.01); *A61K 31/55* (2013.01); *A61K 38/12* (2013.01); *A61K 38/13* (2013.01); *A61K 38/16* (2013.01); *A61K 38/177* (2013.01); *A61K 45/06* (2013.01); *C07K 16/28* (2013.01); *C07K 16/2863* (2013.01); *G01N 33/5058* (2013.01); *A61K 2039/505* (2013.01)

(58) Field of Classification Search
CPC .............. A61P 35/00; A61K 2039/505; A61K 39/39558
See application file for complete search history.

(56) References Cited

U.S. PATENT DOCUMENTS

| | | | |
|---|---|---|---|
| 5,017,563 | A | 5/1991 | Liu et al. |
| 5,066,807 | A | 11/1991 | Anzeveno et al. |
| 5,214,050 | A | 5/1993 | Bitoni et al. |
| 5,222,982 | A | 6/1993 | Ommaya et al. |
| 5,362,718 | A | 11/1994 | Skotnicki et al. |
| 5,385,582 | A | 1/1995 | Ommaya et al. |
| 5,720,720 | A | 2/1998 | Laske et al. |
| 5,837,709 | A | 11/1998 | Willenborg et al. |
| 6,172,064 | B1 | 1/2001 | Andrews et al. |
| 6,191,150 | B1 | 2/2001 | Andrews et al. |
| 6,288,025 | B1 | 9/2001 | Bunn et al. |
| 6,329,400 | B1 | 12/2001 | Andrews et al. |
| 7,091,213 | B2 | 8/2006 | Chester et al. |
| 2003/0022831 | A1 | 1/2003 | Rothbard et al. |

(Continued)

FOREIGN PATENT DOCUMENTS

| | | |
|---|---|---|
| WO | WO94/05322 | 3/1994 |
| WO | WO2012/010396 | 1/2012 |

(Continued)

OTHER PUBLICATIONS

Prasad et al., Neuro-Oncology, 13(4):384-392, 2011.*
ClinicalTrials.gov Identifier: NCT01349660, published onlineMar. 15, 2014. Retrieved at at <Combination of BKM120 and Bevacizumab in Refractory Solid Tumors and Relapsed/Refractory Glioblastoma Multiforme—No Study Results Posted—ClinicalTrials.gov>. Retrieved on May 10, 2017.*
Wolpert et al., Neuro-Oncology, 16(3):382-391, published online Dec. 9, 2013.*
Bhattacharya et al., PLoS ONE, 12(3): e 0171355, Mar. 2017.*

(Continued)

*Primary Examiner* — Kimberly Ballard
*Assistant Examiner* — Stacey N MacFarlane
(74) *Attorney, Agent, or Firm* — Edward J. Baba; Payal B. Sud; Bozicevic, Field & Francis LLP

(57) ABSTRACT

Methods of treating glioma are provided. Aspects of the invention include administering a therapeutically-effective amount of an agent that inhibits the activity of one or more neuronal activity-regulated proteins selected from: neuroligin-3, brain-derived neurotrophic factor (BDNF), or brevican, to a patient with a glioma. In certain embodiments, the subject methods involve treating a neurological dysfunction, reducing invasion of a glioma cell into brain tissue, and/or reducing the growth rate of a glioma in the patient. Also provided herein are methods for identifying an agent that modulates the mitotic index of a glial cell, and methods for stimulating the proliferation of a glial cell. Kits that find use in practicing the subject methods are also provided.

16 Claims, 52 Drawing Sheets

Specification includes a Sequence Listing.

(56) References Cited

U.S. PATENT DOCUMENTS

| | | |
|---|---|---|
| 2003/0032593 A1 | 2/2003 | Wender et al. |
| 2003/0083256 A1 | 5/2003 | Rothbard et al. |
| 2003/0180925 A1 | 9/2003 | Day |
| 2003/0220334 A1 | 11/2003 | Wender et al. |
| 2005/0130973 A1 | 6/2005 | Xiang et al. |
| 2007/0053996 A1 | 3/2007 | Boyden et al. |
| 2007/0054319 A1 | 3/2007 | Boyden et al. |
| 2007/0254842 A1 | 11/2007 | Bankiewicz |
| 2007/0261127 A1 | 11/2007 | Boyden et al. |
| 2008/0081064 A1 | 4/2008 | Jelle et al. |
| 2008/0085265 A1 | 4/2008 | Schneider et al. |
| 2009/0093403 A1 | 4/2009 | Zhang et al. |
| 2009/0099038 A1 | 4/2009 | Deisseroth et al. |
| 2009/0196903 A1 | 8/2009 | Kliman |
| 2010/0143450 A1 | 6/2010 | Liu et al. |
| 2010/0145418 A1 | 6/2010 | Zhang et al. |
| 2010/0190229 A1 | 7/2010 | Zhang et al. |
| 2010/0234273 A1 | 7/2010 | Boyden et al. |
| 2011/0009468 A1 | 1/2011 | Bozzoni et al. |
| 2011/0020779 A1 | 1/2011 | Hannaford et al. |
| 2011/0105998 A1 | 5/2011 | Zhang et al. |
| 2011/0166632 A1 | 7/2011 | Delp et al. |
| 2011/0311489 A1 | 12/2011 | Deisseroth et al. |
| 2011/0319475 A1 | 12/2011 | Collard et al. |
| 2012/0165397 A1 | 6/2012 | Ge et al. |
| 2012/0177723 A1 | 7/2012 | Torchilin et al. |
| 2013/0019325 A1 | 1/2013 | Deisseroth et al. |

FOREIGN PATENT DOCUMENTS

| | | |
|---|---|---|
| WO | WO2013/138783 | 9/2013 |
| WO | WO2014/114779 | 7/2014 |

OTHER PUBLICATIONS

Paugh et al, J Clinical Oncology, 28(18):3061-68, (Year: 2010).*
Floyd et al., Neuro-Oncology, 14(10):1215-1226, (Year: 2012).*
Aguilar et al., (2012) "The Spectrum of Vaccine Therapies for Patients with Glioblastoma Multiforme" Curr Treat Options Oncol 13(4):437-450.
Alonso et al., (2002) "BDNF—triggered events in the rat hippocampus are required for both short-and long-term memory formation" Hippocampus 12(4):551-560.
Altschul et al., (1990) "Basic local alignment search tool" J Mol Biol 215(3):403-410.
Altschul et al., (1997) "Gapped BLAST and PSI-BLAST: a new generation of protein database search programs" Nucleic Acids Res 25(17):3389-3402.
Arnaoutova et al., (2003) "Recycling of Raft-associated Prohormone Sorting Receptor Carboxypeptidase E Requires Interacction with ARF6" Mol Biol Cell 14:4448-4457.
Attenello et al., (2008) "Use of Gliadel (BCNU) wafer in the surgical treatment of malignant glioma: a 10-year institutional experience" Ann Surg Oncol 15(10):2887-2893.
Baker-Herman et al., (2004) "BDNF is necessary and sufficient for spinal respiratory plasticity following intermittent hypoxia" Nat Neurosci 7(1):48-55.
Balis and Poplack, (1989) "Central nervous system pharmacology of antileukemic drugs" Journal of Pediatric Hematology/Oncology 11(1):74-86.
Cazorla et al., (2010) "Cyclotraxin-B, the First Highly Potent and Selective TrkB Inhibitor, Has Anxiolytic Properties in Mice" PLoS One, 5(3)(e9777): 1-17.
Cazorla et al., (2011) "Identification of a low—molecular weight TrkB antagonist with anxiolytic and antidepressant activity in mice" J Clin Invest 121(5):1846-1857.
Corpet, (1988) "Multiple sequence alignment with hierarchical clustering" Nucl Acids Res 16(22):10881-10890.
Futaki et al., (2003) "Structural variety of membrane permeable peptides" Curr Protein Pept Sci 4(2): 87-96.

Higgins et al., (1988) "CLUSTAL: a package for performing multiple sequence alignment on a microcomputer" Gene 73:237-244.
Higgins and Sharp, (1989) "Fast and sensitive multiple sequence alignments on a microcomputer" CABIOS Comm 5(2):151-153.
Huang et al., (1992) "Parallelization of a local similarity search algorithm" CABIOS 8(2):155-165.
Huang et al., (2010) "TrkB antibody elicits cytotoxicity and suppresses migration/invasion of transitional cell carcinoma cells" Int J Oncol 37:943-949.
Ichtchenko et al., (1996) "Structures, Alternative Splicing, and Neurexin Binding of Multiple Neuroligins" J Biol Chem 271(5):2676-2682.
Jacobs et al., (1999) "HSV-1-based vectors for gene therapy of neurological diseases and brain tumors: part II. Vector systems and applications" Neoplasia, 1(5): 402-416.
Jacobs et al., (2005) "Human gene therapy and imaging in neurological diseases" Eur J Nucl Med Mol Imaging 32(Suppl 2):S358-S383.
Karlin and Altschul, (1990) "Methods for assessing the statistical significance of molecular sequence features by using general scoring schemes" Proc Natl Acad Sci USA 87(6): 2264-2268.
Karlin and Altschul, (1993) "Applications and statistics for multiple high-scoring segments in molecular sequences" Proc Natl Acad Sci USA 90(12): 5873-5877.
Louis et al., (2007) "The 2007 WHO Classification of Tumours of the Central Nervous System" Acta Neuropathol 114:97-109.
Ma et al. (2011) "Region-Specific Involvement of BDNF Secretion and Synthesis in Conditioned Taste Aversion Memory Formation" J Neurosci 31(6):2079-2090.
Myers and Miller, (1988) "Optimal alignments in linear space" Comput Appl Biosci CABIOS 4(1):11-17.
Needleman and Wunsch, (1970) "A General Method Applicable to the Search for Similarities in the Amino Acid Sequence of Two Proteins" J Mol Biol 48(3):443-453.
Park et al., (2008) "A Bi-directional Carboxypeptidase E—driven transport mechanism controls BDNF vesicle homeostasis in hippocampal neurons" Mol Cell Neurosci 39(1):63-73.
Park et al., (2008) "Carboxypeptidase E cytoplasmic tail-driven vesicle transport is key for activity-dependent secretion of peptide hormones" Mol Endocrinol 22(4):989-1005.
Pearson et al., (1988) "Improved tools for biological sequence comparison" Proc Natl Acad Sci USA 85(8):2444-2448.
Pearson, (1994) "Using the FASTA program to search protein and DNA sequence databases" Methods Mol Biol 24:307-331.
Pettersson et al., (2014) "Injury-Associated PACAP Expression in Rat Sensory and Motor Neurons Is Induced by Endogenous BDNF" PLoS One 9(6)(e100730):1-12.
Reardon and Wen, (2006) "Therapeutic advances in the treatment of glioblastoma: rationale and potential role of targeted agents" Oncologist 11(2):152-164.
Redwine and Evans, (2002) "Markers of central nervous system glia and neurons in vivo during normal and pathological conditions" Curr Top Microbiol Immunol 265:119-140.
Schrøder et al., (2014), "The identification of AF38469: an orally bioavailable inhibitor of the VPS10P family sorting receptor Sortilin" Bioorg Med Chem Lett 24(1):177-180.
Schulte et al., (2007) "Mirror neuron and theory of mind mechanisms involved in face-to-face interactions: a functional magnetic resonance imaging approach to empathy" J Cogn Neurosci 19(8):1354-1372.
Smith and Waterman, (1981) "Comparison of biosequences" Adv Appl Math 2(4):482-489.
Uemura et al., (2002) "Recombinant angiopoietin-1 restores higher-order architecture of growing blood vessels in mice in the absence of mural cells" J Clin Invest 110(11):1619-1628.
Wang et al., (2010) "Cis and trans actions of the cholinesterase-like domain within the thyroglobulin dimer" Journal of Biological Chemistry 285(23):17564-17573.
Wender et al., (2000) "The design, synthesis, and evaluation of molecules that enable or enhance cellular uptake: peptoid molecular transporters" Proc Natl Acad Sci USA 97(24):13003-13008.

(56) References Cited

OTHER PUBLICATIONS

Zage et al., (2011) "The selective Trk inhibitor AZ623 inhibits brain-derived neurotrophic factor—mediated neuroblastoma cell proliferation and signaling and is synergistic with topotecan" Cancer 117(6):1321-1329.

* cited by examiner

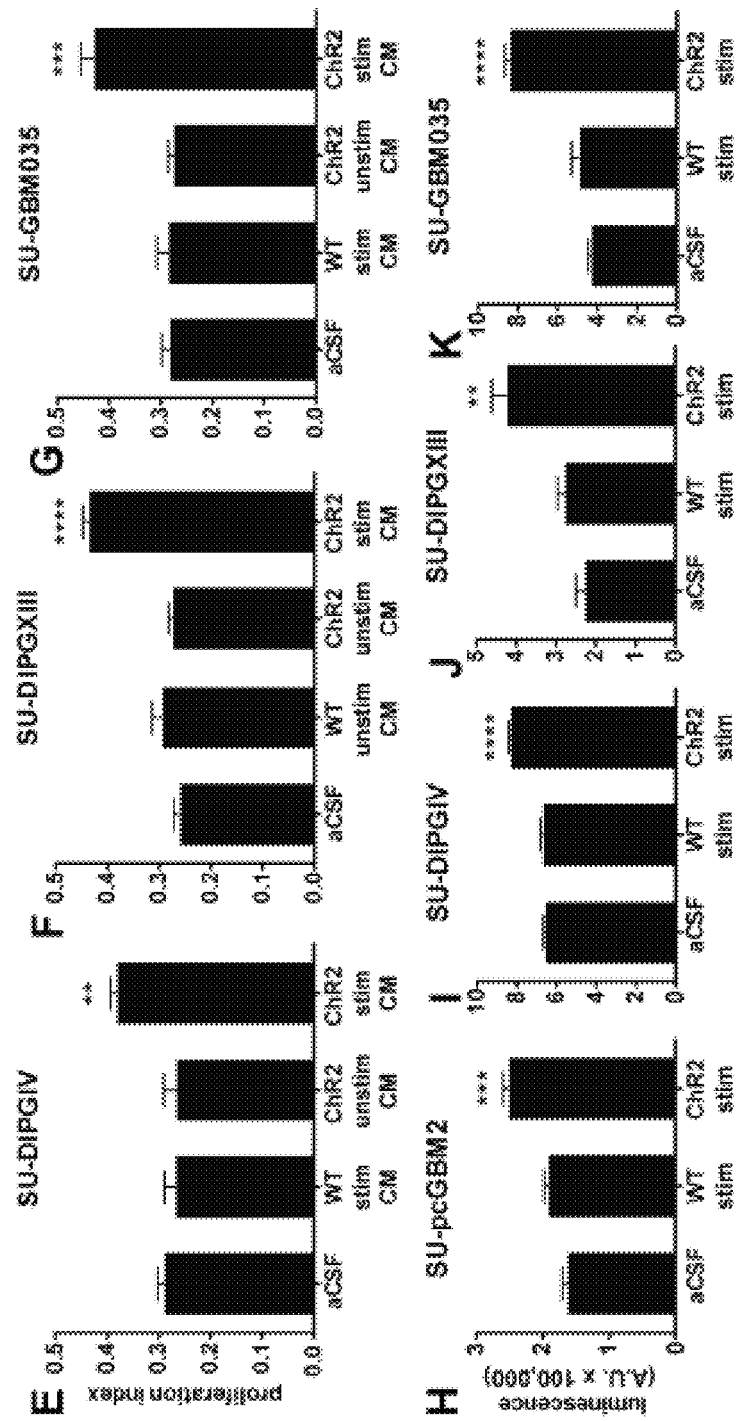
FIG. 2, cont.

FIG. 3, cont.

FIG. 4, cont.
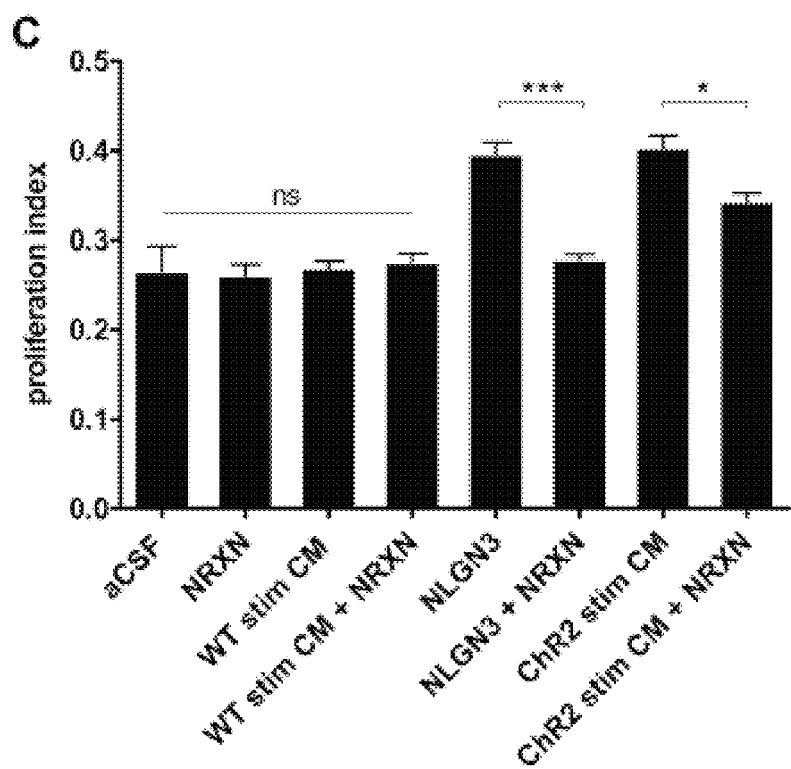

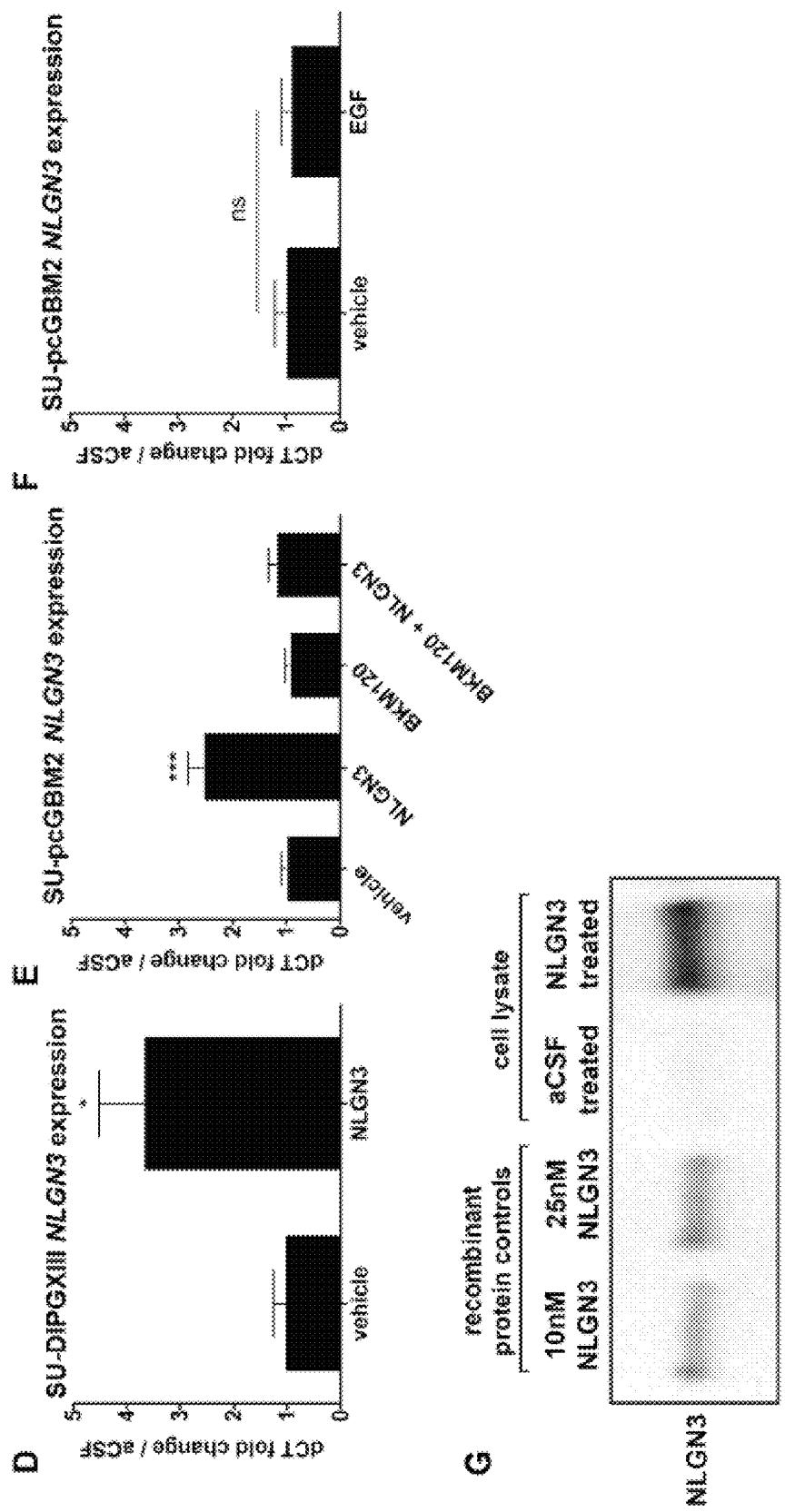
FIG. 5, cont.

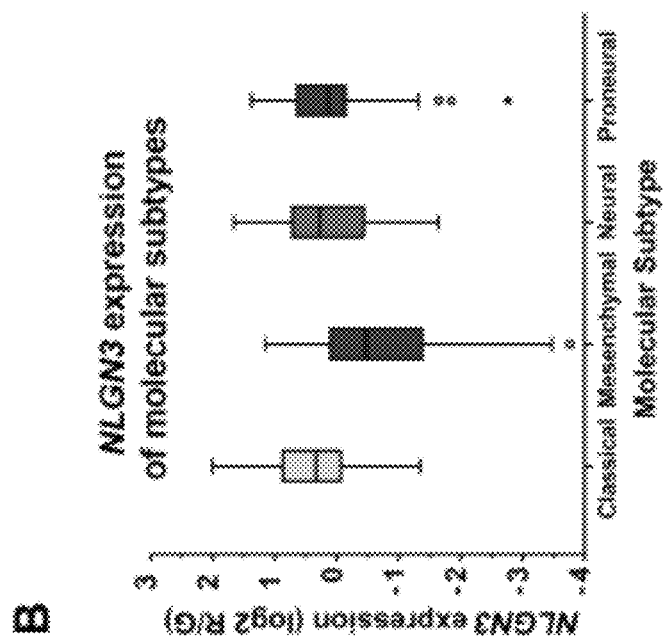
FIG. 7, cont.

FIG. 8, cont.
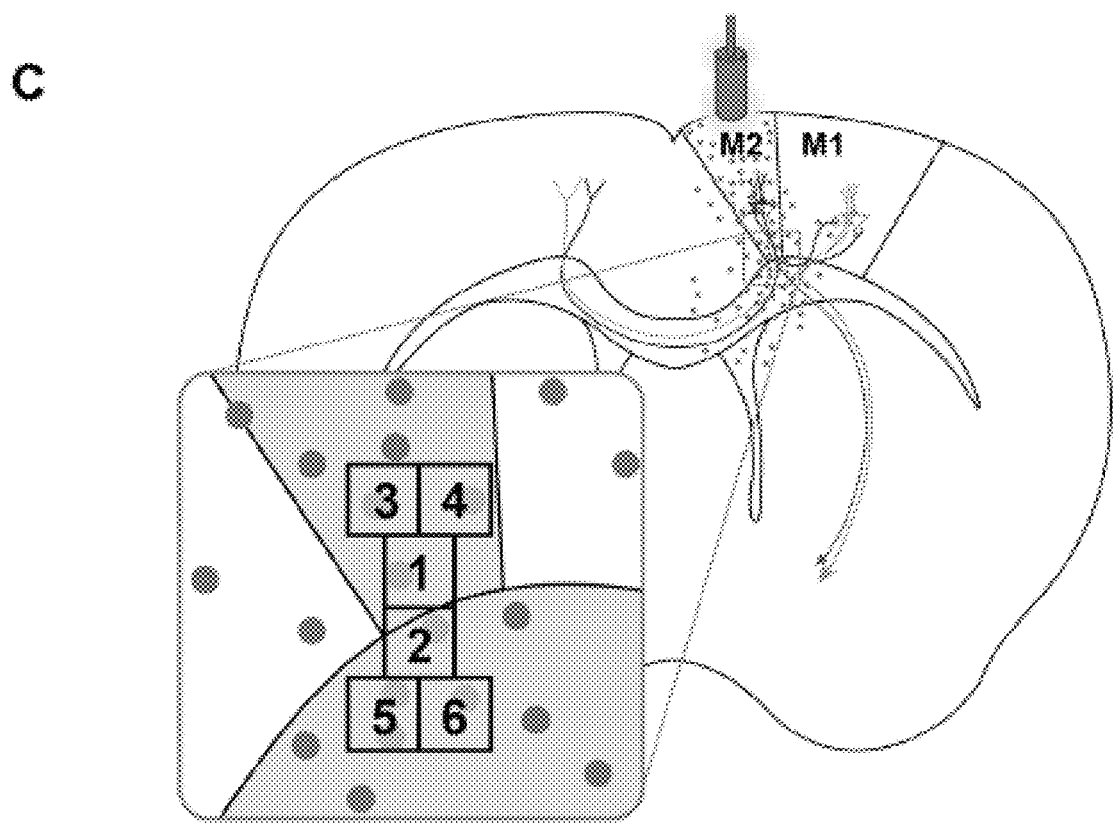

FIG. 12

MWLQPSLSLS PTPTVGRSLC LTLGFLSLVL RASTQAPAPT VNTHFGKLRG
ARVPLPSEIL GPVDQYLGVP YAAPPIGEKR FLPPEPPPSW SGIRNATHFP
PVCPQNIHTA VPEVMLPVWF TANLDIVATY IQEPNEDCLY LNVYVPTEDG
SGAKKQGEDL ADNDGDEDED IRDSGAKPVM VYIHGGSYME GTGNMIDGSV
LASYGNVIVI TLNYRVGVLG FLSTGDQAAK GNYGLLDQIQ ALRWVSENIA
FPGGDPRRIT VFGSGIGASC VSLLTLSHHS EGLFQRAIIQ SGSALSSWAV
NYQPVKYTSL LADKVGCNVL DTVDMVDCLR QKSAKELVEQ DIQPARYHVA
FGPVIDGDVI PDDPEILMEQ GEFLNYDIML GVNQGEGLKF VEGVVDPEDG
VSGTDFDYSV SNFVDNLYGY PEGKDTLRET IKFMYTDWAD RDNPETRRKT
LVALFTDHQW VEPSVVTADL HARYGSPTYF YAFYHHCQSL MKPAWSDAAH
GDEVPYVFGV PMVGPTDLFP CNFSKNDVML SAVVMTYWTN FAKTGDPNKP
VPQDTKFIHT KANRFEEVAW SKYNPRDQLY LHIGLKPRVR DHYRATKVAF
WKHLVPHLYN LHDMFHYTST TTKVPPPDTT HSSHITRRPN GKTWSTKRPA
ISPAYSNENA PGSWNGDQDA GPLLVENPRD <u>YSTELSVTIA VGASLLFLNV</u>
<u>LAFAALYYRK DKRRQEPLRQ PSPQRGTGAP ELGTAPEEEL AALQLGPTHH</u>
<u>ECEAGPPHDT LRLTALPDYT LTLRRSPDDI PLMTPNTITM IPNSLVGLQT</u>
<u>LHPYNTFAAG FNSTGLPHSH STTRV</u>

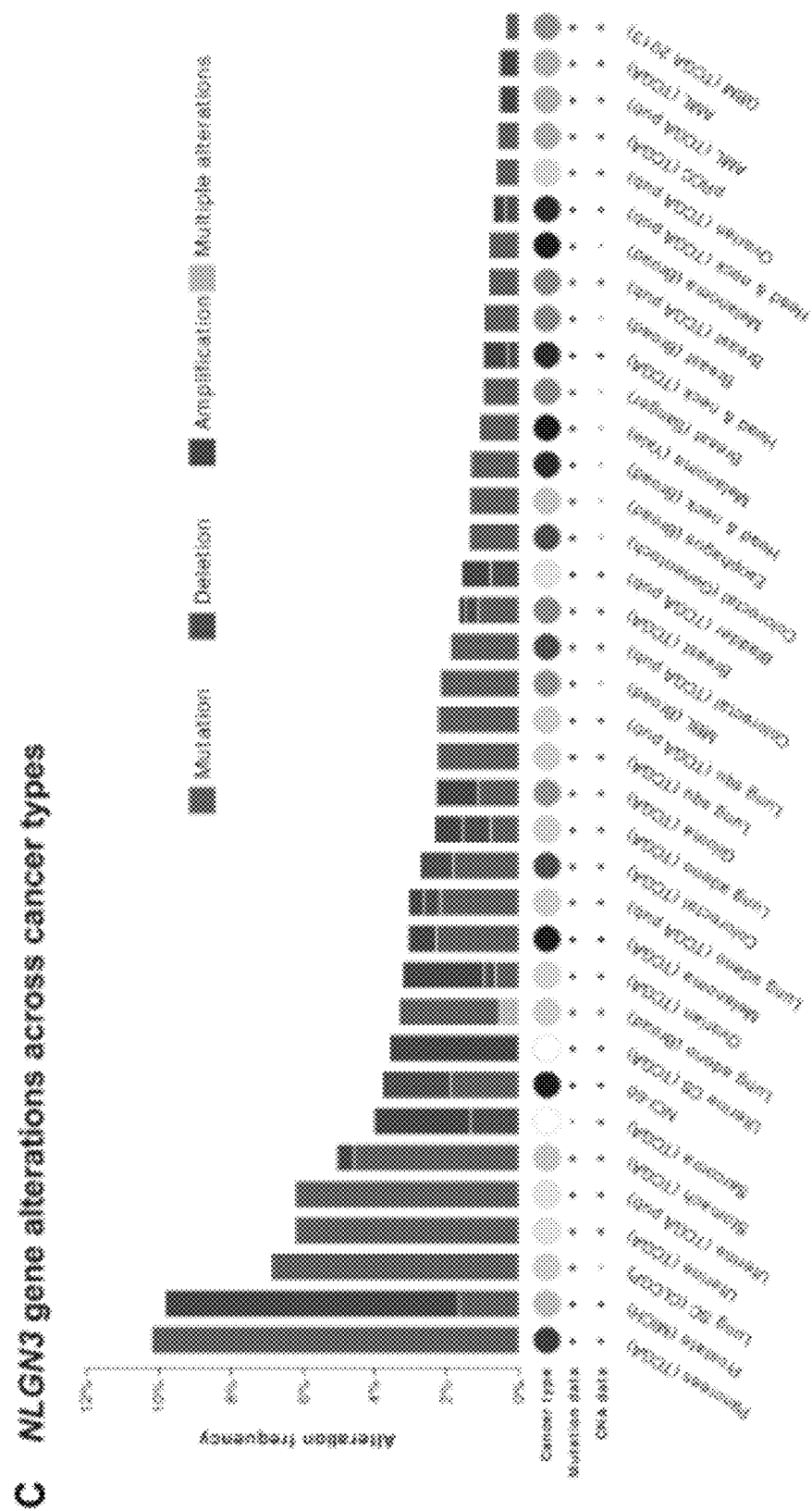
FIG. 14, cont.

FIG. 16

| Culture ID | Tumour type, location and grade | Age at diagnosis (years) | Sex | Histone-3 mutational status | Other genomic characteristics | Timepoint tissue obtained | Prior therapy | Survival (months) |
|---|---|---|---|---|---|---|---|---|
| SU-pcGBM2 | Pediatric cortical glioblastoma; frontal lobe; WHO grade IV | 10 | M | WT | p53 mutated; EGFR amplified; PTEN WT | Biopsy at diagnosis | none | N/A |
| SU-DIPGIV | DIPG; pons; WHO grade III | 2 | F | H3.3K27M | p53 WT; MDM4 amplified; ACVR1 G328V | Early postmortem autopsy | XRT; carboplatin; irinotecan | 8 |
| SU-DIPGVI | DIPG; pons; WHO grade III | 7 | F | H3.3K27M | p53 mutated | Early postmortem autopsy | XRT; vorinostat | 8 |
| SU-DIPGXIII | DIPG; pons; WHO grade III | 6 | F | H3.3K27M | N/A | Early postmortem autopsy | XRT | 4 |
| JHH-DIPGI | DIPG; pons; WHO grade IV | 6 | M | H3.3K27M | p53 mutated | Early postmortem autopsy | XRT + TMZ; irinotecan; bevacizumab | 2.5 |

FIG. 16, cont. 1

| Culture ID | Tumor type, location and grade | Age at diagnosis (years) | Sex | Histone-3 mutational status | Other genomic characteristics | Transplant tissue obtained | Prior therapy? | Survival (months) |
|---|---|---|---|---|---|---|---|---|
| SU-GBM034 | Glioblastoma; Temporal lobe; WHO grade IV | 70 | M | N/A | IDH-/WT; PTEN mutated | Biopsy at diagnosis | none | N/A |
| SU-GBM035 | Glioblastoma; temporal lobe; WHO grade IV | 60 | M | N/A | IDH-/WT | Biopsy at recurrence | XRT, TMZ | N/A |
| SU-GBM047 | Epithelioid glioblastoma; temporal lobe; WHO grade IV | 38 | M | N/A | BRAF; P53 WT; EGFR WT; PTEN WT | Second resection | Prior resection, no other therapy | <3 |
| SU-GBM050 | Glioblastoma; temporal lobe; WHO grade IV | 58 | F | N/A | P53 mutated | Biopsy at time of progression from oligodendroglioma grade II (1p19q WT, IDH WT) | Prior resection and TMZ | N/A |
| SU-AO0 | Anaplastic oligodendroglioma; frontal lobe; WHO grade III | 36 (44 at recurrence) | M | N/A | 1p/19q deletion; IDH1 mutated | Biopsy at time of recurrence | TMZ | N/A |

FIG. 16, cont. 2

Short tandem repeat DNA fingerprinting of HGG cell lines

| STR Fingerprint | AMEL | CSF1PO | D13S317 | D16S539 | D21S11 | D5S818 | D7S820 | TH01 | TPOX | vWA |
|---|---|---|---|---|---|---|---|---|---|---|
| SU-pcGBM2 | X/Y | 10/11 | 11/ | 9/11 | 29/30.2 | 11/ | 11/12 | 9.3/ | 8/12 | 17/18 |
| SU-DIPGIV | X/X | 9/10 | 7/12 | 9/12 | 29/31 | 12/13 | 10/11 | 6/9.3 | 8/ | 15/19 |
| SU-DIPGVI | X/X | 8/10 | 11/11 | 8/13 | 29/31 | 10/12 | 8/9 | 7/8 | 8/11 | 17/18 |
| SU-DIPGXIII | X/X | 9/10 | 11/12 | 11/12 | 30/OL | 12/12 | 9/9 | 8/7 | OL/8 | 13/18 |
| JHH-DIPGI | X/Y | 11/13 | 12/ | 11/ | 30/ | 13/13 | 11/12 | 6/ | 8/12 | 18/19 |
| SU-GBM034 | X/Y | 10/12 | 8/8 | 10/12 | 29/30 | 11/13 | 8/11 | 7/7 | 8/11 | 18/18 |
| SU-GBM035 | X/Y | 10/11 | 10/ | 13/13 | 30/ | 11/13 | 10/ | 7/9.3 | 9/12 | 18/20 |
| SU-GBM047 | X/Y | 12/12 | 8/8 | 11/12 | 29/31 | 12/12 | 9/11 | 6/9.3 | 8/11 | 19/19 |
| SU-GBM052 | X/X | 11/11 | 11/12 | 13/11 | 27/28 | 11/11 | 11/13 | 6/9.3 | 8/11 | 16/18 |
| SU-AO2 | X/Y | 11/13 | 8/12 | 8/11 | 30/33.2 | 11/12 | 8/10 | 9/9 | 8/11 | 16/18 |

FIG. 17

| Peptide | Peptide Prophet Score |
|---|---|
| K.ELVEQDIQPAR.Y | 0.9978 |
| K.FMYTDWADR.D | 0.9991 |
| K.GNYGLLDQIQALR.W | 0.9998 |
| K.KQGEDLADNDGDEDEDIR.D | 1.0000 |
| K.QGEDLADNDGDEDEDIR.D | 0.9994 |
| K.TGDPNKPVPQDTK.F | 0.9994 |
| K.YTSLLADK.V | 0.9994 |
| R.FLPPEPPPSWSGIR.N | 0.9252 |
| R.VGVLGFLSTGDQAAK.G | 0.9967 |
| R.VGVLGFLSTGDQAAK.G | 0.9997 |
| R.VGVLGFLSTGDQAAK.G | 0.9999 |
| R.VGVLGFLSTGDQAAK.G | 1.0000 |
| R.VPLPSEILGPVDQYLGVPYAAPPIGEK.R | 0.9636 |
| R.VPLPSEILGPVDQYLGVPYAAPPIGEK.R | 0.9654 |
| R.VPLPSEILGPVDQYLGVPYAAPPIGEK.R | 0.9711 |
| R.VPLPSEILGPVDQYLGVPYAAPPIGEK.F | 0.9875 |
| R.VPLPSEILGPVDQYLGVPYAAPPIGEK.F | 0.9999 |
| R.VPLPSEILGPVDQYLGVPYAAPPIGEK.F | 1.0000 |
| R.VPLPSEILGPVDQYLGVPYAAPPIGEK.F | 1.0000 |
| R.WVSENIAFFGGDPR.R | 0.9999 |

FIG. 18

| \multicolumn{4}{c|}{Upregulated} |
| --- | --- | --- | --- |
| Gene symbol | Gene | Log-fold change | p-value |
| SLC1A2 | solute carrier family 1 (glutamate transporter) | 1.74891 | 0.0001 |
| MEGF10 | multiple EGF-like-domains 10 | 1.81571 | 0.00005 |
| FOSB | FBJ murine osteosarcoma viral oncogene homolog B | 2.45218 | 0.00005 |
| CHI3L1 | chitinase 3-like 1 (cartilage glycoprotein-39) | 1.23813 | 0.00005 |
| PKDCC | protein kinase domain containing, cytoplasmic | 1.1845 | 0.00005 |
| GPR37L1 | G protein-coupled receptor 37-like 1 | 1.2238 | 0.00005 |
| GLRA2 | glycine receptor, alpha 2 | 1.37799 | 0.0001 |
| FOS | FBJ murine osteosarcoma viral oncogene homolog | 1.5734 | 0.00005 |
| AQP4 | aquaporin 4 | 3.46852 | 0.00005 |
| SPP1 | secreted phosphoprotein 1 - osteopontin | 2.80657 | 0.00005 |
| TTYH1 | tweety homolog 1 (Drosophila) | 1.99447 | 0.0001 |
| FIGNL1 | fidgetin-like 1 | 1.98589 | 0.00005 |
| NLGN3 | neuroligin 3 | 1.70827 | 0.00005 |

FIG. 18, cont 1.

| \multicolumn{4}{|c|}{Downregulated} | | | |
|---|---|---|---|
| Gene symbol | Gene | Log-fold change | p-value |
| KISS1R | KISS1 receptor | -1.84404 | 0.0001 |
| NPTX1 | neuronal pentraxin I | -1.30674 | 0.00005 |
| NRN1 | neuritin 1 | -1.27069 | 0.00005 |
| PPP1R3C | protein phosphatase 1, regulatory subunit | -1.32044 | 0.00005 |
| RASA4 | RAS p21 protein activator 4 | -1.71909 | 0.00005 |
| ACAN | aggrecan | -2.00655 | 0.0001 |
| ARRDC3 | arrestin domain containing 3 | -1.16970 | 0.00005 |
| BHLHE40 | basic helix-loop-helix family, member e40 | -1.13484 | 0.0001 |
| CA9 | carbonic anhydrase IX | -1.44267 | 5.00E-05 |
| CBWD3 | COBW domain containing 3 | -2.77365 | 0.00005 |
| CCZ1 | vacuolar protein trafficking and biogenesis | -1.48314 | 0.00005 |
| CCZ1B | CCZ1 vacuolar protein trafficking and biogenesis | -1.42827 | 0.00005 |
| CD9 | CD9 molecule | -1.13779 | 5.00E-05 |
| COL15A1 | collagen, type XV, alpha 1 | -1.16860 | 0.00005 |
| CRABP2 | cellular retinoic acid binding protein 2 | -1.18289 | 0.00005 |
| EDN2 | endothelin 2 | -2.76228 | 5.00E-05 |

FIG. 18, cont 2.

| Downregulated | | | |
|---|---|---|---|
| Gene symbol | Gene | Log-fold change | p-value |
| ERO1L | ERO1-like (S. cerevisiae) | -1.18193 | 0.00005 |
| FAM180A | family with sequence similarity 180, member A | -1.31291 | 0.00005 |
| GOLGA8B | golgin A8 family, member B | -1.37121 | 0.00005 |
| LAYN | layilin | -1.30685 | 5.00E-05 |
| PIWIL2 | piwi-like 2 (Drosophila) | -1.93229 | 5.00E-05 |
| POLR2J2 | polymerase (RNA) II (DNA directed) polypeptide J2 | -2.39848 | 0.00005 |
| RPS4Y2 | ribosomal protein S4, Y-linked 2 | -4.53176 | 0.00005 |
| RRN3P2 | RNA polymerase I transcription factor pseudogene 2 | -1.34428 | 0.00005 |
| SORCS3 | sortilin-related VPS10 domain containing receptor 3 | -1.26770 | 0.00005 |
| SPNS2 | spinster homolog 2 (Drosophila) | -1.55928 | 0.00005 |
| SYTL2 | synaptotagmin-like 2 | -1.32393 | 0.0001 |
| TMPRSS2 | transmembrane protease, serine 2 | -1.56557 | 0.00005 |

FIG. 19

| Tumor type | Tumor subtype | Tumors with somatic NLGN3 mutations | Number of SSM-tested tumors | Mutation frequency (%) |
|---|---|---|---|---|
| Thyroid cancer | Papillary thyroid carcinoma | 5 | 15 | 33.3 |
| Gastric cancer | Adenocarcinoma | 19 | 289 | 6.6 |
| Ovarian cancer | Serous cystadenocarcinoma | 6 | 93 | 6.5 |
| Colon cancer | Adenocarcinoma | 10 | 216 | 4.6 |
| Renal cancer | Renal cell carcinoma | 4 | 95 | 4.2 |
| Rectal cancer | Adenocarcinoma | 3 | 80 | 3.8 |
| Pancreatic cancer | Ductal adenocarcinoma | 4 | 112 | 3.6 |
| Liver cancer | Hepatocellular carcinoma (alcohol and adiposity) | 1 | 29 | 3.4 |
| Lung cancer | Squamous cell carcinoma | 6 | 178 | 3.4 |

FIG. 19, cont.

| Tumor type | Tumor subtype | Tumors with somatic NLGN3 mutations | Number of SSM-tested tumors | Mutation frequency (%) |
|---|---|---|---|---|
| Breast cancer | Triple negative/lobular/other | 1 | 117 | 0.9 |
| Liver cancer | Hepatocellular carcinoma (Virus associated)* | 2 | 244 | 0.8 |
| Pediatric brain tumors | Medulloblastoma, pilocytic astrocytoma | 1 | 248 | 0.4 |
| Brain cancer | Glioblastoma multiforme | 1 | 268 | 0.4 |
| Rectal cancer | Clear cell carcinoma | 1 | 404 | 0.2 |

FIG. 20

Human Neurexin 1α mgtallqrggcfllclslllgcwaelgsglefpgaegqwtrfpkwnaccesemsfqlktrsarglvlyf
ddegfcdfleliltrggrlqlsfsifcaepatlladtpvndgawhsvrirrqfrnttlfidqveakwvev
kskrrdmtvfsglfvgglppelraaalkltlasvrerepfkgwirdvrvnssqvlpvdsgevklddeppn
sgggspceageegeggvclnggvcsvvddqavcdcsrtgfrgkdcsqeikfglqcvlpvllhdndqgkyc
cintakpltekdnnveglahlmmgdqgkskgkeeyiatfkgseyfcydlsqnpiqsssdeitlsfktlqr
nglmlhtgksadyvnlalkngavslvinlgsgafealvepvngkfndnawhdvkvtrnlrqhsgighamv
nklhcsvtisvdgiltttgytqedytmlgsddffyvggspstadlpgspvsnnfmgclkevvyknndvrl
elsrlakqgdpkmkihgvvafkcenvatldpitfetpesfislpkwnakktgsisfdfrttepnglilfs
hgkprhqkdakhpqmikvdffaiemldghlyllldmgsgtikikallkkvndgewyhvdfqrdgrsgtis
vntlrtpytapgeseildlddelylgglpenkaglvfptevwtallnygyvgcirdlfidgqskdirqma
evqstagvkpscsketakpclsnpcknngmcrdgwnryvcdcsgtgylgrscereatvlsydgsmfmkiq
lpvvmhteaedvslrfrsqraygilmattsrdsadtlrleldagrvkltvnldcirincnsskgpetlfa
gynlndnewhtvrvvrrgkslkltvddqqamtgqmagdhtrlefhnietgiiterrylssvpsnfighlq
sltfngmayidlckngdidycelnarfgfrniiadpvtfktkssyvalatlqaytsmhlffqfkttsldg
lilynsgdgndfivvelvkgylhyvfdlgnganlikgssnkplndnqwhnvmisrdtsnlhtvkidtkit
tqitagarnldlksdlyiggvaketykslpklvhakegfqgclasvdlngrlpdlisdalfcngqiergc
egpsttcqedscsnqgvclqqwdgfscdcsmtsfsgplcndpgttyifskgggqitykwppndrpstrad
rlaigfstvqkeavlvrvdsssglgdylelhihqgkigvkfnvgtddiaieesnaiindgkyhvvrftrs
ggnatlqvdswpvierypagnndnerlaiarqripyrlgrvvdewlldkgrqltifnsqatiiiggkeqg
qpfqgqlsglyynglkvlnmaaendaniaivgnvrlvgevpssmttestatamqsemstsimettttlat
starrgkpptkepisqttddilvasaecpsddedidpcepssgglanptraggrepypgsaeviresssst
tgmvvgivaaaalcililyamykyrnrdegsyhvdesrnyisnsaqsngavvkekqpssakssnknkkn
kdkeyyv

Human Neurexin 1β myqrmlrcgaelgspgggggggggggaggrlallwivpltlsgllgvawqasslgahhihhfhqsskhhs
vpiaiyrspaslrgghagttyifskgggqitykwppndrpstradrlaigfstvqkeavlvrvdsssglg
dylelhihqgkigvkfnvgtddiaieesnaiindgkyhvvrftrsggnatlqvdswpvierypagrqlti
fnsqatiiiggkeqgqpfqgqlsglyynglkvlnmaaendaniaivgnvrlvgevpssmttestatamqs
emstsimettttlatstarrgkpptkepisqttddilvasaecpsddedidpcepssgglanptraggre
pypgsaviresssttgmvvgivaaaalcililyamykyrnrdegsyhvdesrnyisnsaqsngavvke
kqpssakssnknkknkdkeyyv

FIG. 21

Human Neurexin 2α
masgsrwrptppplllllllalaaradglefgggpgqwaryarwagaassgelsfslrtnatralllyld
dggdcdflelllvdgrlrlrftlscaepatlqldtpvaddrwhmvlltrdarrtalavdgearaaevrsk
rremqvasdlfvggippdvrlsaltlstvkyeppfrgllanlklgerppallgsqglrgatadplcapar
npcangglctvlapgevgcdcshtgfggkfcseeehpmegpahltlnsevgsllfseggagrggagdvhq
ptkgkeefvatfkgneffcydlshnpiqsstdeitlafrtlqrnglmlhtgksadyvnlslksgavwlvi
nlgsgafealvepvngkfndnawhdvrvtrnlrqhagighamvnklhylvtisvdgiltttgytqedytm
lgsddffyiggspntadlpgspvsnnfmgclkdvvyknndfklelsrlakegdpkmklqgdlsfrcedva
aldpvtfespeafvalprwsakrtgsisldfrttepnglllfsqgrragggagshssaqradyfamelld
ghlyllldmgsggiklrassrkvndgewchvdfqrdgrkgsisvnsrstpflatgdseildleselylgg
lpeggrvdlplppevwtaalragyvgcvrdlfidgrsrdlrglaeaqgavgvapfcsretlkqcasapcr
nggvcregwnrficdcigtgflgrvcereatvlsydgsmymkimlpnamhteaedvslrfmsqrayglmm
attsresadtlrleldgqqmkltvnldclrvgcapskgpetlfaghklndnewhtvrvvrrgkslqlsvd
nvtvegqmagahmrlefhnietgimterrfisvvpsnfighlsglvfngqpymdqckdgdityceInarf
glraivadpvtfksrssylalatlqayasmhlffqfkttapdglllfnsgngndfivielvkgyihyvfd
lgngpslmkgnsdkpvndnqwhnvvvsrdpgnvhtlkidsrtvtqhsngarnldlkgelyigglsknmfs
nlpklvasrdgfqgclasvdlngrlpdliadalhrigqvergcdgpsttcteescanqgvclqqwdgftc
dctmtsygpvcndpgttyifgkggalitywppndrpstrmdrlavgfsthqrsavlvrvdsasglgdy
lqlhidqgtvgvifnvgtdditidepnaivsdgkyhvvrftrsggnatlqvdswpvnerypagnfdnerl
aiarqripyrlgrvvdewlldkgrqltifnsqaaikiggrdqgrpfqgqvsglyynglkvlalaaesdpn
vrteghlrlvgegpsvllsaettattlladmattimettttmattttrrgrsptlrdsttqntddllvas
aecpsddedleecepstggelilpiitedsldpppvatrspfvppppptfypfltgvgatqdtlpppaarr
ppsggpcqaerddsdceepieasgfasgevfdsslpptddedfyttfplvtdrttllsprkpaprpnlrt
dgatgapgvlfapsapapnlpagkmnhrdplqpllenpplgpgaptsfeprrpplrpgvtsapgfphlp
tanptgpgergppgaveviressstttgmvvgivaaaalcililllyamykyrnrdegsyqvdqsrnyisns
aqsngavvkekapaapktpskakknkdkeyyv

Human Neurexin 2β
mppgqsgpggcprrppalagplppppppppppllpllplllllllgaaegarvsssistthhvhhfhskh
gtvpiainrmpfltrgghagttyifgkggalitytwppndrpstrmdrlavgfsthqrsavlvrvdsasg
lgdylqlhidqgtvgvifnvgtdditidepnaivsdgkyhvvrftrsggnatlqvdswpvnerypagnfd
nerlaiarqripyrlgrvvdewlldkgrqltifnsqaaikiggrdqgrpfqgqvsglyynglkvlalaae
sdpnvrteghlrlvgegpsvllsaettattlladmattimettttmattttrrgrsptlrdsttqntddl
lvasaecpsddedleecepstggelilpiitedsldpppvatrspfvppppptfypfltgvgatqdtlppp
aarrppsggpcqaerddsdceepieasgfasgevfdsslpptddedfyttfplvtdrttllsprkpaprp
nlrtdgatgapgvlfapsapapnlpagkmnhrdplqpllenpplgpgaptsfeprrpplrpgvtsapgf
phlptanptgpgergppgaveviressstttgmvvgivaaaalcililllyamykyrnrdegsyqvdqsrny
isnsaqsngavvkekapaapktpskakknkdkeyyv

FIG. 22

Human Neurexin 3α mlgsddffyvggspstadlpgspvsnnfmgclkevvyknndirlelsrlariadtkmkiygevvfkcenv
atldpinfetpeayislpkwntkrmgsisfdfrttepnglilfthgkpqerkdarsqkntkvdffavell
dqnlyllldmgsgtikvkatqkkandgewyhvdiqrdgrsgtisvnsrrtpftasgeseildlegdmylg
glpenraglilptelwtamlnygyvgcirdlfidgrsknirqlaemqnaagvksscsrmsakqcdsypck
nnavckdgwnrficdctgtgywgrtcereasilsydgsmymkiimpmvmhteaedvsfrfmsqrayglllv
attsrdsadtlrleldggrvklmvnldcirincnsskgpetlyagqklndnewhtvrvvrrgkslkltvd
ddvaegtmvgdhtrlefhnietgimtekryisvvpssfighlqslmfngllyidlckngdidycelkarf
glrniiadpvtfktkssylslatlqaytsmhlffqfkttspdgfilfnsgdgndfiavelvkgyihyvfd
lgngpnvikgnsdrplndnqwhnvvitrdnsnthslkvdtkvvtqvingaknldlkgdlymaglaqgmys
nlpklvasrdgfqgclasvdlngrlpdlindalhrsgqiergcegpsttcqedscanqgvcmqqwegftc
dcsmtsysgnqcndpgatyifgksgglilytwpandrpstrsdrlavgfsttvkdgilvridsapglqdf
lqlhieqgkigvvfnigtvdisikeertpvndgkyhvvrftrnggnatlqvdnwpvnehyptgrqltifn
tqaqiaiggkdkgrlfqgqlsglyydglkvlnmaaennpnikingsvrlvgevpsilgttqttsmppems
ttvmetttttmattttrknrstasiqptsddlvssaecssddedfvecepstanptepgirrvpgasevir
esssttgmvvgivaaaalcililllyamykyrnrdegsyqvdetrnyisnsaqsngtlmkekqqssksghk
kqknkdreyyv

Human Neurexin 3β

Mhlriharrspprrpawtlgiwflfwgcivssvwsssnvasssstssspgshsqhehhfhgskhhsvpis
iyrspvslrqghagatyifgksgglilytwpandrpstrsdrlavgfsttvkdgilvridsapglgdflq
lhieqgkigvvfnigtvdisikeertpvndgkyhvvrftrnggnatlqvdnwpvnehyptgrqltifntq
aqiaiggkdkgrlfqgqlsglyydglkvlnmaaennpnikingsvrlvgevpsilgttqttsmppemstt
vmetttttmattttrknrstasiqptsddlvssaecssddedfvecepstggelvipllvedplatppiat
rapsitlpptfrplltiiettkdslsmtseaglpclsdqgsdgcdddglvisgygsgetfdsnlpptdde
dfyttfslvtdkslstsifeggykahapkweskdfrpnkvsetsrttttslspelirftassssgmvpkl
pagkmnnrdlkpqpdivllplptayeldstklksplitspmfrnvptanptepgirrvpgaseviresss
ttgmvvgivaaaalcililllyamykyrnrdegsyqvdetrnyisnsaqsngtlmkekqqssksghkkqkn
kdreyyv

FIG. 23

Human Thyroglobulin malvleiftllasicwvsanifeyqvdaqplrpcelqretaflkqadyvpqcaedgsfqtvqcqndgrsc
wcvgangsevlgsrqpgrpvaclsfcqlkqqillsgyinstdtsylpqcqdsgdyapvqcdvqqvqcwc
vdaegmevygtrqlgrpkrcprsceirnrrllhgvgdksppqcsaegefmpvqckfvnttdmmifdlvhs
ynrfpdafvtfssfqrrfpevsgychcadsqgrelaetglellldeiydtifagldlpstftettlyril
qrrflavqsvisgrfrcptkceverftatsfghpyvpscrrngdyqavqcqtegpcwcvdaqgkemhgtr
qqgeppscaegqscaserqqalsrlyfgtsgyfsqhdlfsspekrwasprvarfatscpptikelfvdsg
llrpmvegqsqqfsvsenllkeairaifpsrglarlalqfttnpkrlqqnlfggkflvnvgqfnlsgalg
trgtfnfsqffqqlqlasflnggrqedlakplsvqldsnsstgtpeaakkdgtmnkptvgsfgfeinlqe
nqnalkflasllelpefllflqhaisvpedvardlgdvmetvlssqtceqtperlfvpscttegsyedvq
cfsgecwcvnswgkelpgsrvrggqprcptdcekqrarmqslmgsqpagstlfvpactseghflpvqcfn
secycvdaegqaipgtrsaigkpkkcptpcqlseqaflrtvqallsnssmlptlsdtyipqcstdgqwr
qvqcngppeqvfelyqrweaqnkgqdltpakllvkimsyreaasgnfslfiqslyeagqqdvfpvlsqyp
slqdvplaalegkrpqprenillepylfwqilngqlsqypgsysdfstplahfdlrncwcvdeagqeleg
mrsepsklptcpgsceeaklrvlqfireteeivsasnssrfplgesflvakgirlrnedlglpplfppre
afaeqflrgsdyairlaaqstlsfyqrrrfspddsagasallrsgpympqcdafgswepvqchagtghcw
cvdekggfipgsltarslqipqcpttceksrtsgllsswkqarsqenpspkdlfvpacletgeyarlqas
gagtwcvdpasqeelrpgssssaqcpslcnvlksgvlsrrvspgyvpacraedggfspvqcdqaqgscwc
vmdsgeevpgtrvtgqqpacesprcplpfnasevvggtilcetisgptgsamqqcqllcrqgswsvfppg
plicslesgrwesqlpqpracqrpqlwqtiqtqghfqlqlppgkmcsadyadllqtfqvfildeltargf
cqiqvktfgtlvsipvcnnssvqvgcltrerlgvnvtwksrledipvaslpdlhdieralvgkdllgrft
dliqsgsfqlhldsktfpaetirflqgdhfgtsprtwfgcsegfyqvltseasqdglgcvkcpegsysqd
eecipcpvgfyqeqagslacvpcpvgrttisagafsqthcvtdcqrneaglqcdqngqyrasqkdrgsgk
afcvdgegrrlpwweteapledsqclmmqkfekvpeskvifdanapvavrskvpdsefpvmqcltdcted
eacsfftvsttepeiscdfyawtsdnvacmtsdqkrdalgnskatsfgslrcqvkvrshgqdspavylkk
gqgstttlqkrfeptgfqnmlsglynpivfsasganltdahlfcllacdrdlccdgfvltqvqggaiicg
llsspsvllcnvkdwmdpseawanatcpgvtydqeshqvilrlgdqefiksltplegtqdtftnfqqvyl
wkdsdmgsrpesmgcrkdtvprpaspteagltteltspvdlnqvivngnqslssqkhwlfkhlfsaqqan
lwclsrcvqehsfcqlaeitesaslyftctlypeaqvcddimesnaqgcrlilpqmpkalfrkkviledk
vknfytrlpfqklmgisirnkvpmseksisngffecerrcdadpcctgfgflnvsqlkggevtcltlnsl
giqmcseenggawrildcgspdievhtypfgwyqkpiaqnnapsfcplvvlpsltekvsldswqslaiss
vvvdpsirhfdvahvstaatsnfsavrdlclsecsqheaclittlqtqpgavrcmfyadtqscthslqgq
ncrllreeathiyrkpgisllsyeasvpsvpisthgrllgrsqaiqvgtswkqvdqflgvpyaapplae
rrfqapeplnwtgswdaskprascwqpgtrtstspgvsedclylnvfipqnvapnasvlvffhntmdree
segwpaidgsflaavgnlivvtasyrvgvfgflssgsgevsgnwglldqvaaltwvqthirgfggdprrv
slaadrggadvasihlltaratnsqlfrravlmggsalspaavisheraqqqaialakevscpmsssqev
vsclrqkpanvlndaqtkllavsgpfhywgpvidghflrepparalkrslwvevdlligssqddglinra
kavkqfeesrgrtssktafyqalqnslggedsdarveaaatwyyslehstddyasfsralenatrdyfii
cpiidmasawakrargnvfmyhapenyghgslelladvqfalglpfypayegqfsleekslslkimqyfs
hfirsgnpnypyefsrkvptfatpwpdfvpraggenykefsellpnrqglkkadcsfwskyisslktsad
gakggqsaeseeeeltagsglredllslqepgsktysk

FIG. 24

Human TrkB msswirwhgpamarlwgfcwlvvgfwraafacptsckcsasriwcsdpspgivafprlepnsvdpenite
ifianqkrleiineddveayvglrnltivdsglkfvahkaflknsnlqhinftrnkltslsrkhfrhldl
selilvgnpftcscdimwiktlqeaksspdtqdlyclnessskniplanlqipncglpsanlaapnltvee
gksitlscsvagdpvpnmywdvgnlvskhmnetshtqgslritnissddsgkqiscvaenlvgedqdsvn
ltvhfaptitflesptsdhhwcipftvkgnpkpalqwfyngailneskyictkihvtnhteyhgclqldn
pthmnngdytliakneygkdekqisahfmgwpgiddganpnypdviyedygtaandigdttnrsneipst
dvtdktgrehlsvyavvviasvvgfcllvmlfllklarhskfgmkdfswfgfgkvksrqgvgpasvisnd
ddsasplhhisngsntpssseggpdaviigmtkipvienpqyfgitnsqlkpdtfvqhikrhnivlkrel
gegafgkvflaecynlcpeqdkilvavktlkdasdnarkdfhreaelltnlqhehivkfygvcvegdpli
mvfeymkhgdlnkflrahgpdavlmaegnppteltqsqmlhiaqqiaagmvylasqhfvhrdlatrnclv
genllvkigdfgmsrdvystdyyrvgghtmlpirwmppesimyrkfttesdvwslgvvlweiftygkqpw
yqlsnneviecitqgrvlqrprtcpqevyelmlgcwqrephmrknikgihtllqnlakaspvyldilg FIG. 31, cont.
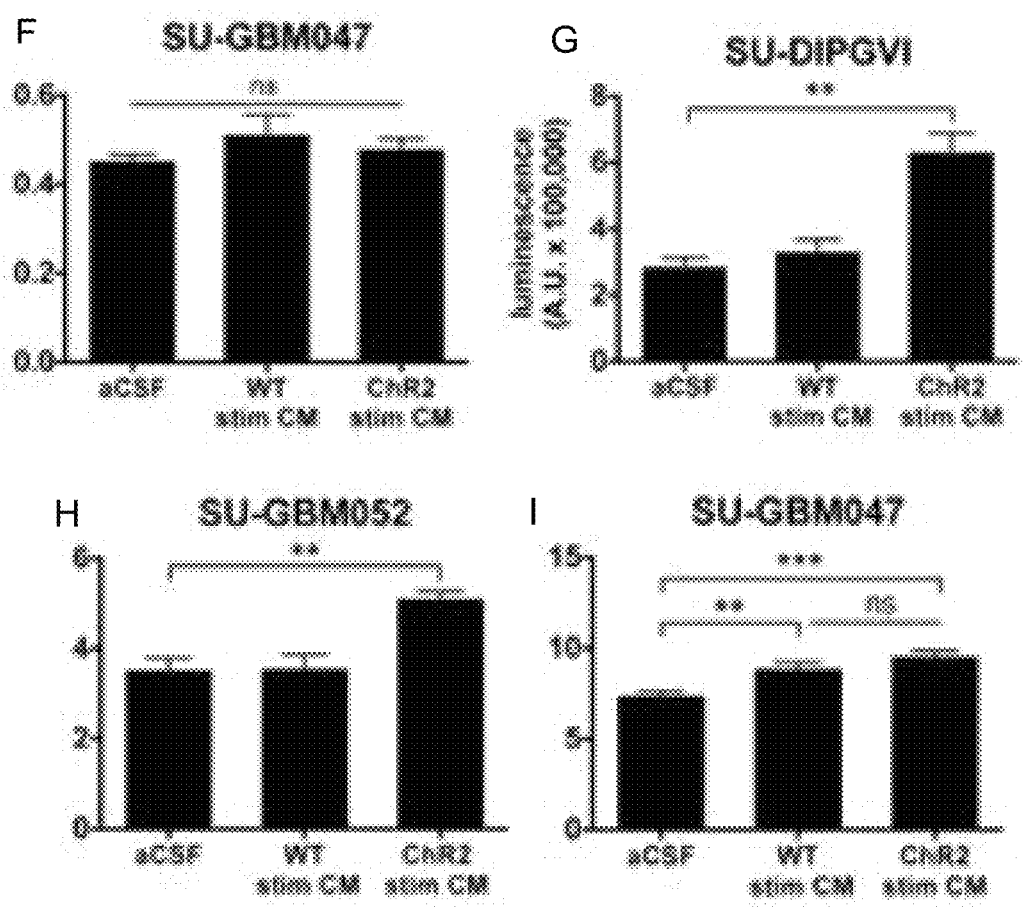

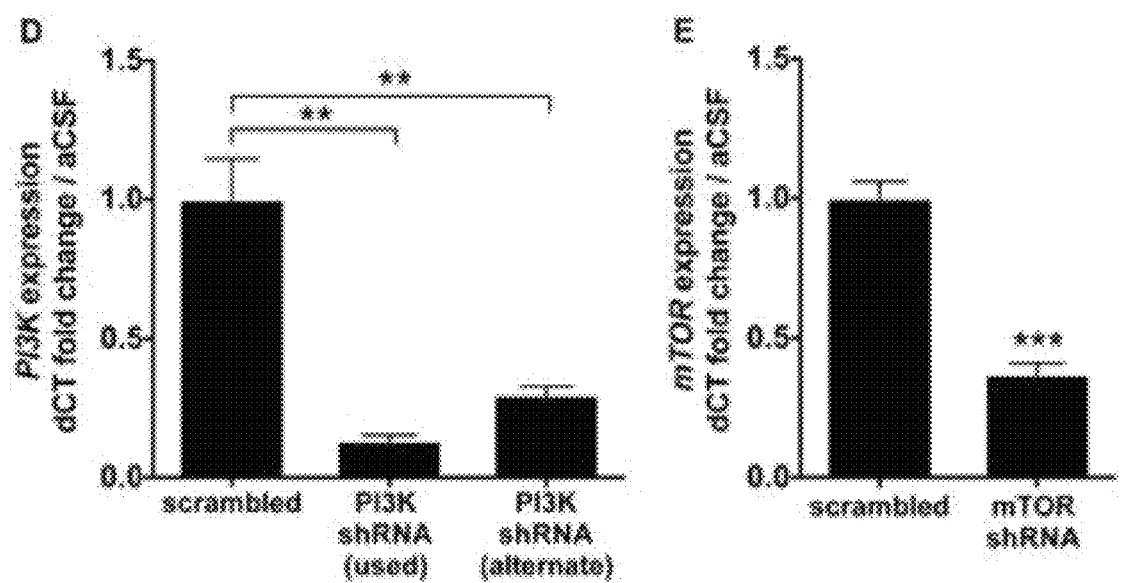
FIG. 34, cont.

METHOD OF TREATING GLIOMA

CROSS-REFERENCE TO RELATED APPLICATIONS

This application claims priority to U.S. Provisional Application No. 62/110,257 filed on Jan. 30, 2015, which application is herein incorporated by reference in its entirety.

GOVERNMENT RIGHTS

This invention was made with Government support under contract NS070926 awarded by the National Institutes of Health. The Government has certain rights in the invention.

INCORPORATION BY REFERENCE OF SEQUENCE LISTING

A Sequence Listing is provided herewith as a text file, "STAN-1180_S14-408_SeqList_ST25" created on Jan. 29, 2016 and having a size of 94 KB. The contents of the text file are incorporated by reference herein in their entirety.

INTRODUCTION

High-grade gliomas (HGGs) are the leading cause of brain tumor death in both children and adults. Current standard of care for treating HGG include surgical resection, chemo- and radiotherapy; however, median survival time for patients with, e.g., glioblastoma multiforme, is less than 18 months. Thus, many HGG are incurable diseases that lead to neurological demise and death, and there is a need to develop new therapies to treat HGG.

HGGs occur in a striking spatiotemporal pattern that highlights the critical importance of the tumor microenvironment. Molecularly-defined subtypes of HGG parse by neuroanatomical site of origin and age of the patient, with pontine and thalamic HGGs typically occurring in mid-childhood, cortical gliomas of childhood occurring in older children and young adults, and HGG of later adulthood occurring chiefly in the frontotemporal lobes. While the cellular origins of HGG remain an open question, converging evidence implicates oligodendroglial precursor cells (OPCs) and earlier neural precursor cells (NPCs) as the putative cellular origins for many forms of HGG. However, microenvironmental determinants of glioma cell behavior are incompletely understood.

SUMMARY

Methods of treating glioma are provided. Aspects of the invention include administering a therapeutically-effective amount of an agent that inhibits the activity of one or more neuronal activity-regulated proteins selected from: neuroligin-3, brain-derived neurotrophic factor (BDNF), or brevican, to a patient with a glioma. In certain embodiments, the subject methods involve treating a neurological dysfunction, reducing invasion of a glioma cell into brain tissue, and/or reducing the growth rate of a glioma in the patient. Also provided herein are methods for identifying an agent that modulates the mitotic index of a glial cell, and methods for stimulating the proliferation of a glial cell. Kits that find use in practicing the subject methods are also provided.

Aspects of the present disclosure include methods of reducing a neurological dysfunction in a patient with a glioma tumor, the methods including administering to the patient a therapeutically-effective amount of an agent that inhibits the activity of neuroligin-3, brain-derived neurotrophic factor (BDNF), or brevican in the glioma tumor to reduce the neurological dysfunction in the patient.

In some embodiments, the neurological dysfunction includes pain, numbness, seizures, neuromuscular dysfunction, cognitive impairment, or personality changes. In some embodiments, the agent includes a monoclonal antibody. In some embodiments, the agent includes a polypeptide that binds to a secreted domain of neuroligin-3, BDNF, or brevican. In certain embodiments, the polypeptide contains a portion of a protein selected from the group consisting of: Neurexin-1α, Neurexin-1β, Neurexin-2α, Neurexin-2β, Neurexin-3α, Neurexin-3β, Thyroglobulin and TrkB. In some embodiments, the polypeptide contains an amino acid sequence that is at least 80% identical to any one of SEQ ID NOs: 1-9, or a portion thereof.

In some embodiments, the agent is selected from ADAM10 inhibitor, MMP9 inhibitor, castanospermine, wortmannin, LY294002, BKM120, AF38469, prinomastat, Ro 28-2653, 3-hydroxypyran-4-one, cyclosporin A, tacrolimus, bortezomib, curcumin, BMS-345541, bosutinib, temsirolimus, everolimus, ridaforolimus, rapamycin, AZ623, ANA12 or a pharmaceutically acceptable salt thereof.

In some embodiments, the agent is administered to the subject orally, intravenously, locally or intrathecally. In some embodiments, the agent is formulated for sustained release.

Further aspects of the present disclosure include methods of preventing a glioma tumor cell from invading a brain tissue in a patient, the methods including administering to the patient a therapeutically-effective amount of an agent that inhibits the activity of neuroligin-3, brain-derived neurotrophic factor (BDNF), or brevican to prevent the glioma tumor cell from invading the brain tissue.

In some embodiments, the agent includes a monoclonal antibody. In some embodiments, the agent includes a polypeptide that binds to a secreted domain of neuroligin-3, BDNF, or brevican. In certain embodiments, the polypeptide contains a portion of a protein selected from the group consisting of: Neurexin-1α, Neurexin-1β, Neurexin-2α, Neurexin-2β, Neurexin-3α, Neurexin-3β, Thyroglobulin and TrkB, or fragments thereof. In some embodiments, the polypeptide contains an amino acid sequence that is at least 80% identical to any one of SEQ ID NOs: 1-9, or a portion thereof.

In some embodiments, the agent is selected from castanospermine, wortmannin, LY294002, BKM120, AF38469, prinomastat, Ro 28-2653, 3-hydroxypyran-4-one, cyclosporin A, tacrolimus, bortezomib, curcumin, BMS-345541, bosutinib, AZ623, ANA12 or a pharmaceutically acceptable salt thereof.

In some embodiments, the agent is administered to the subject orally, intravenously, locally or intrathecally. In some embodiments, the agent is formulated for sustained release.

Other aspects of the present disclosure include methods of reducing a growth rate of a glioma tumor cell in a patient, the methods including administering to the patient a therapeutically-effective amount of an agent that inhibits the activity of neuroligin-3, brain-derived neurotrophic factor (BDNF), or brevican to reduce the growth rate of the glioma tumor cell.

In some embodiments, the agent includes a monoclonal antibody. In some embodiments, the agent includes a polypeptide that binds to a secreted domain of neuroligin-3, BDNF, or brevican. In some embodiments, the polypeptide contains a portion of a protein selected from the group consisting of: Neurexin-1α, Neurexin-1β, Neurexin-2α, Neurexin-2β, Neurexin-3α, Neurexin-3β, Thyroglobulin and TrkB, or fragments thereof. In certain embodiments, the polypeptide contains an amino acid sequence that is at least 80% identical to any one of SEQ ID NOs: 1-9, or a portion thereof.

In some embodiments, the agent is selected from castanospermine, wortmannin, LY294002, BKM120, AF38469, prinomastat, Ro 28-2653, 3-hydroxypyran-4-one, cyclosporin A, tacrolimus, bortezomib, curcumin, BMS-345541, bosutinib, temsirolimus, everolimus, ridaforolimus, rapamycin, AZ623, ANA12 or a pharmaceutically acceptable salt thereof.

In some embodiments, the agent is administered to the subject orally, intravenously, locally or intrathecally. In some embodiments, the agent is formulated for sustained release.

Aspects of the present disclosure include methods for identifying an agent that modulates a mitotic index of a glial cell, the methods including genetically modifying a nerve cell to express a light-activated ion channel, contacting the genetically modified nerve cell with a light beam to activate the light-activated ion channel, thereby resulting in the production of a neuronal activity-regulated protein, contacting a glial cell with the neuronal activity-regulated protein, and measuring a mitotic index of the glial cell, wherein a change in the mitotic index of the glial cell in the presence of the neuronal activity-regulated protein compared to the mitotic index in the absence of the neuronal activity-regulated protein indicates that the neuronal activity-regulated protein modulates the mitotic index of the glial cell.

In some embodiments, the glial cell is a healthy cell. In some embodiments, the glial cell is an abnormal cell. In certain embodiments, the abnormal cell is derived from a patient that has been diagnosed with a condition selected from glioma, amyotrophic lateral sclerosis, Alzheimer's disease, Parkinsons's disease, Huntington's disease, and multiple sclerosis.

In some embodiments, the glial cell is an astrocyte, oligodendrocyte, radial glia, ependymocyte, or microglia. In some embodiments, the glial cell is a glial precursor cell. In certain embodiments, the glial precursor cell is an oligodendrocyte precursor cell.

In some embodiments, the nerve cell is a central or peripheral nervous system nerve cell. In some embodiments, the nerve cell is a cortical, hippocampal, cerebellar, thalamic, amygdala, basal ganglion, spinal cord, retinal, or dorsal root ganglion neuron.

Aspects of the present disclosure include methods of stimulating the proliferation of a glial cell, the methods including contacting a glial cell with an effective amount of one or more neuronal activity-regulated proteins selected from: neuroligin-1, neuroligin-3, BDNF and brevican, or a fragment thereof, to stimulate the proliferation of the glial cell.

In some embodiments, the glial cell is a healthy cell. In some embodiments, the glial cell is an abnormal cell. In some embodiments, the glial cell is an astrocyte, oligodendrocyte, radial glia, ependymocyte, or microglia.

In some embodiments, the glial cell is a glial precursor cell. In certain embodiments, the glial precursor cell is an oligodendrocyte precursor cell.

In some embodiments, the methods include administering to a patient an effective amount of the one or more neuronal activity-regulated proteins to stimulate the proliferation of a glial cell in the patient. In some embodiments, the patient has been diagnosed with a condition resulting from and/or exacerbated by insufficient proliferation of one or more glial cells. In certain embodiments, the condition is selected from multiple sclerosis, leukodystrophy, chemotherapy-induced cognitive disfunction, Alzheimer's disease and central nervous system (CNS) injury.

Further aspects of the present disclosure include methods for treating a glioma tumor in a subject, the methods including administering to the subject a therapeutically-effective amount of an agent that inhibits the activity of one or more neuronal activity-regulated proteins selected from: neuroligin-3, BDNF, and brevican.

In some embodiments, the agent inhibits a binding activity of the one or more neuronal activity-regulated proteins to an extracellular binding partner. In some embodiments, the agent includes a monoclonal antibody.

In some embodiments, the agent includes a polypeptide that binds to a secreted domain of the one or more neuronal activity-regulated proteins. In some embodiments, the polypeptide includes a portion of a protein selected from Neurexin-1α, Neurexin-1β, Neurexin-2α, Neurexin-2β, Neurexin-3α, Neurexin-3β, Thyroglobulin and TrkB. In certain embodiments, the polypeptide includes an amino acid sequence that is at least 80% identical to any one of SEQ ID NOs: 1-9, or a portion thereof.

In some embodiments, the agent reduces expression of the one or more neuronal activity-regulated proteins. In certain embodiments, the agent inhibits transcription of the one or more neuronal activity-regulated proteins. In some embodiments, the agent inhibits post-translational modification of the one or more neuronal activity-regulated proteins.

In some embodiments, the agent includes a small molecule. In some embodiments, the agent is selected from the group consisting of: ADAM10 inhibitor, MMP9 inhibitor, castanospermine, wortmannin, LY294002, BKM120, AF38469, prinomastat, Ro 28-2653, 3-hydroxypyran-4-one, cyclosporin A, tacrolimus, bortezomib, curcumin, BMS-345541, bosutinib, temsirolimus, everolimus, ridaforolimus, rapamycin, AZ623, ANA12 or a pharmaceutically acceptable salt thereof.

In some embodiments, the agent includes a nucleic acid. In certain embodiments, the nucleic acid is a ribonucleic acid (RNA).

In some embodiments, the agent is administered to the subject orally, intravenously, locally or intrathecally. In some embodiments, the agent is formulated for sustained release.

BRIEF DESCRIPTION OF THE DRAWINGS

FIG. 12 shows peptide sequences identified in mass spectrometry of recombinant NLGN3 (SEQ ID NO: 1).

FIG. 16 is a collection of tables that show some characteristics of patient-derived high-grade glioma cell lines. Legend: WHO=World Health Organization; DIPG=diffuse intrinsic pontine glioma; XRT=radiotherapy; TMZ=temozolomide; STR=short tandem repeat.

FIG. 17 is a table that shows NLGN3 peptides observed by mass spectrometry. From top to bottom, respectively, positions 335-347 (SEQ ID NO: 16), 432-442 (SEQ ID NO: 17), 230-244 (SEQ ID NO: 18), 154-173 (SEQ ID NO: 19), 155-173 (SEQ ID NO: 20), 543-557 (SEQ ID NO: 21), 306-315 (SEQ ID NO: 22), 80-95 (SEQ ID NO: 23), 215-231 (SEQ ID NO: 24), 215-231 (SEQ ID NO: 24), 215-231 (SEQ ID NO: 24), 215-231 (SEQ ID NO: 24), 52-80 (SEQ ID NO: 25), 52-80 (SEQ ID NO: 25), 52-80 (SEQ ID NO: 25), 52-81 (SEQ ID NO: 26), 52-81 (SEQ ID NO: 26), 52-81 (SEQ ID NO: 26), 52-81 (SEQ ID NO: 26), and 243-258 (SEQ ID NO: 27) of SEQ ID NO: 1.

FIG. 18 is a table that shows RNA-seq data of genes differentially expressed in SU-pcGBM2 cells following exposure to active conditioned media (CM).

FIG. 19 is a table that shows frequency of somatic NLGN3 gene mutations across various cancer types. Data was gleaned from the International Cancer Genome Consortium (ICGC) database. * RIKEN, Japan study. ** National Cancer Center (NCC), Japan.

FIG. 20 shows the amino acid sequences of human neurexin 1α (top; SEQ ID NO: 2) and human neurexin 1β (bottom; SEQ ID NO: 3).

FIG. 21 shows the amino acid sequences of human neurexin 2α (top; SEQ ID NO: 4) and human neurexin 2β (bottom; SEQ ID NO: 5).

FIG. 22 shows the amino acid sequences of human neurexin 3α (top; SEQ ID NO: 6) and human neurexin 3β (bottom; SEQ ID NO: 7).

FIG. 23 shows the amino acid sequence of human thyroglobulin (SEQ ID NO: 8).

FIG. 24 shows the amino acid sequence of human TrkB (SEQ ID NO: 9).

FIG. 38, Panel B shows glioma cell proliferation in the presence of ADAM17 inhibitor TAPI.

DETAILED DESCRIPTION

Figure 1:
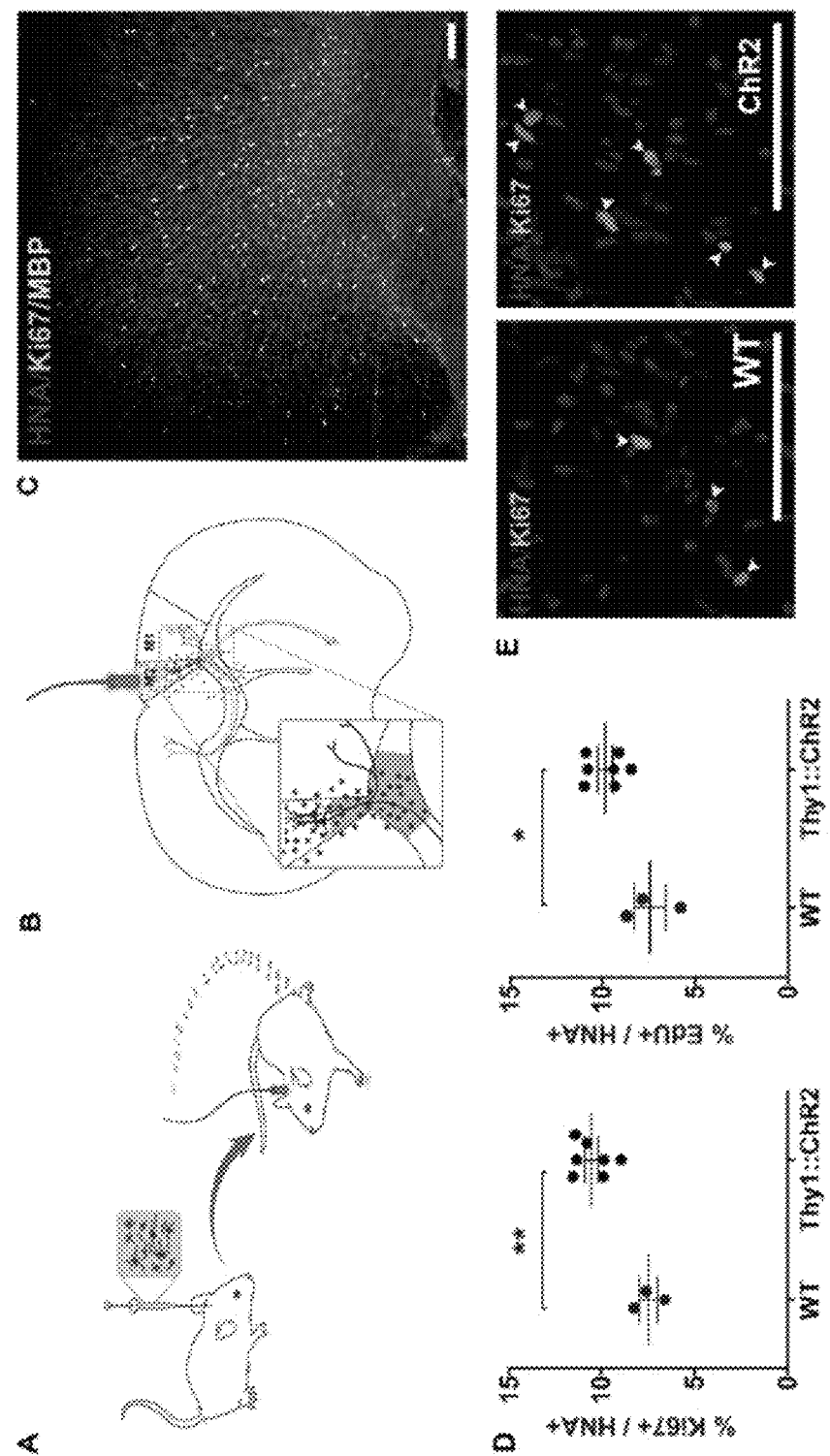
FIG. 1, Panels A-E show a collection of images and graphs that show the effect of neuronal activity on high-grade glioma proliferation in vivo.

Methods of treating glioma are provided. Aspects of the invention include administering a therapeutically-effective amount of an agent that inhibits the activity of one or more neuronal activity-regulated proteins selected from: neuroligin-3, brain-derived neurotrophic factor (BDNF), or brevican, to a patient with a glioma. In certain embodiments, the subject methods involve treating a neurological dysfunction, reducing invasion of a glioma cell into brain tissue, and/or reducing the growth rate of a glioma in the patient. Also provided herein are methods for identifying an agent that modulates the mitotic index of a glial cell, and methods for stimulating the proliferation of a glial cell. Kits that find use in practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, 4$^{th}$ edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), ANTIBODIES, A LABORATORY MANUAL SECOND EDITION (Greenfield, ed. (2012)), and CULTURE OF ANIMAL CELLS, 6$^{th}$ Edition (R. I. Freshney, ed. (2010)).

In further describing various aspects of embodiments of the invention in greater detail, aspects of the systems and devices of various embodiments are reviewed first in greater detail, followed by a discussion of methods and kits according to certain embodiments of the invention.

Definitions

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The terms "polypeptide", "peptide" and "protein" are used interchangeably herein to refer to polymers of amino acids of any length. The polymer may be linear or branched, it may include modified amino acids, and it may be interrupted by non-amino acids. The terms also encompass an amino acid polymer that has been modified; for example, by disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Any suitable means for making this adjustment may be used. This may involve scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Any suitable methods of alignment of sequences for comparison may be employed. Thus, the determination of percent identity between any two sequences can be accomplished using a mathematical algorithm. Preferred, non-limiting examples of such mathematical algorithms are the algorithm of Myers and Miller, CABIOS, 4:11 (1988), which is hereby incorporated by reference in its entirety; the local homology algorithm of Smith et al, Adv. Appl. Math., 2:482 (1981), which is hereby incorporated by reference in its entirety; the homology alignment algorithm of Needleman and Wunsch, JMB, 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karlin and Altschul, Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST programs of Altschul et al., JMB, 215:403 (1990); Nucl. Acids Res., 25:3389 (1990), which are hereby incorporated by reference in their entirety, are based on the algorithm of Karlin and Altschul supra.

Software for performing BLAST analyses is publicly available through the National Center for Biotechnology Information (NCBI; worldwideweb.ncbi.nlm.nih.gov).

By "treatment" is meant that at least an amelioration of the symptoms associated with the condition afflicting a subject is achieved, where amelioration refers to at least a reduction in the magnitude of a parameter, e.g., a symptom, associated with the condition being treated. As such, treatment includes situations where the condition, or at least symptoms associated therewith, are reduced or avoided. Thus treatment includes: (i) preventing, that is, reducing the risk of development of a disease or condition, including causing the disease or condition not to develop, e.g., preventing onset of the disease or condition; and (ii) inhibition, that is, arresting the development or further development of a disease or condition.

By "subject" is meant a human or non-human animal (e.g., a non-human primate, mouse, rat, etc.) selected for treatment or therapy. A "patient," as used herein, refers to a subject in need of treatment of therapy or a subject who has been diagnosed with a disease.

"Binding," as used herein, refers to a specific interaction between any two members, e.g., two proteins, two nucleic acids, a protein and a nucleic acid, etc., where the affinity between a two specific binding members is characterized by a $K_D$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower $K_D$.

By "antibody" is meant a protein of one or more polypeptides that specifically binds an antigen, and that are substantially encoded by all or part of the recognized immunoglobulin genes. The recognized immunoglobulin genes, for example in humans, include the kappa (κ), lambda (λ), and heavy chain genetic loci, which together contain the myriad variable region genes, and the constant region genes mu (μ), delta (δ), gamma (γ), sigma (σ), and alpha (α) which encode the IgM, IgD, IgG, IgE, and IgA antibody "isotypes" or "classes" respectively. Antibody herein is meant to include full length antibodies and antibody fragments, and may refer to a natural antibody from any organism, an engineered antibody, or an antibody generated recombinantly for experimental, therapeutic, or other purposes. The term "antibody" includes full length antibodies, and antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. Methods for generating antibodies that bind specifically to a target protein or antigen of interest are known. See, e.g., Greenfield, supra.

The term "down-stream," as used in reference to a biological signaling pathway, refers to a relative position within the signaling pathway wherein events occur later in time relative to a reference, e.g., a reference signaling pathway member or a reference signaling event, in the signaling pathway. Thus, a signaling event or molecule down-stream of a receptor, e.g., a ligand-activated receptor, may refer to events, such as phosphorylation, translocation, regulation of gene expression, etc., or molecules, such as kinases, transcription factors, that occur after and as a consequence of the ligand binding to its receptor.

The term "glioma" refers to a tumor that arises from glial cells or their precursors of the brain or spinal cord. Gliomas are histologically defined based on whether they exhibit primarily astrocytic or oligodendroglial morphology, and are graded by cellularity, nuclear atypia, necrosis, mitotic figures, and microvascular proliferation—all features associated with biologically aggressive behavior. Astrocytomas are of two main types—high-grade and low-grade. High-grade tumors grow rapidly, are well-vascularized, and can easily spread through the brain. Low-grade astrocytomas are usually localized and grow slowly over a long period of time. High-grade tumors are much more aggressive, require very intensive therapy, and are associated with shorter survival lengths of time than low grade tumors. The majority of astrocytic tumors in children are low-grade, whereas the majority in adults are high-grade. These tumors can occur anywhere in the brain and spinal cord. Some of the more common low-grade astrocytomas are: Juvenile Pilocytic Astrocytoma (JPA), Fibrillary Astrocytoma Pleomorphic Xantroastrocytoma (PXA) and Desembryoplastic Neuroepithelial Tumor (DNET). The two most common high-grade astrocytomas are Anaplastic Astrocytoma (AA) and Glioblastoma Multiforme (GBM).

"Tumor", as used herein, refers to any neoplastic cell growth and proliferation of a cell that in certain cases may originate from or be in proximity to glia, whether malignant or benign, and any pre-cancerous and cancerous cells and tissues.

An "agent," as used herein, refers to a molecule, e.g., a protein or polypeptide, nucleic acid, lipid, carbohydrate, antibody, small molecule, inorganic molecule, etc., that affects a molecular and/or therapeutic function of interest.

A "portion" or a "fragment," as used in reference to a portion or a fragment of a protein or a polypeptide, refers to a contiguous sequence of amino acids that is at least 50 amino acids, e.g., at least 75 amino acids, at least 100 amino acids, at least 150 amino acids, at least 200 amino acids, at least 250 amino acids, at least 300 amino acids or more in length that is found in the protein or polypeptide. In some cases, a portion or fragment of a protein may include an amino acid sequence sufficient to perform a function of interest that is normally carried out by the full length protein or polypeptide. Thus, in some cases, a portion or fragment of a protein may include an amino acid sequence contained in the protein or polypeptide that is sufficient to bind a binding partner of the protein or polypeptide under suitable, physiological conditions.

By "small molecule" is meant a non-peptidic, non-oligomeric organic compound that may be synthetic or natural. A small molecule may contain one or more carbon-carbon bonds, and may have a molecular weight of 1500 or less.

Agents that Inhibit the Activity of Neuroligin-3, BDNF or Brevican

Aspects of the present disclosure include agents, e.g., therapeutic agents, that are administered to a subject for the treatment of glioma. As summarized above, the subject agents inhibit the activity of one or more neuronal activity-regulated proteins, thereby treating one or more symptoms of glioma in the patient, e.g., reducing neurological symptoms of glioma, reducing growth of the glioma, reducing invasion of the glioma, etc.

In certain embodiments, the methods involve administering to a patient a therapeutically-effective amount of an agent that inhibits the activity of a neuroligin-3 polypeptide. Inhibitors in accordance with embodiments of the invention may inhibit neuroligin-3 from any species. In some embodiments, an agent may inhibit the activity of human neuroligin-3 (Gene ID: 54413), mouse neuroligin-3 (Gene ID: 245537), rat neuroligin-3 (Gene ID: 171297), or a non-human primate neuroligin-3 (Gene ID: 473660), etc.

In certain embodiments, an agent may inhibit the activity of a protein having an amino acid sequence that is 80% or more, such as 90% or more, 95% or more, or 100% identical to SEQ ID NO: 1, or a neuronal activity-regulated form thereof (e.g., a secreted form thereof). In certain embodiments, a neuronal activity-regulated form of SEQ ID NO: 1 includes amino acids 1-678 of SEQ ID NO: 1.

In certain embodiments, the subject methods involve administering to a patient a therapeutically-effective amount of an agent that inhibits the activity of brain-derived neurotrophic factor (BDNF). Inhibitors in accordance with embodiments of the invention may inhibit BDNF from any species. In some embodiments, an agent may inhibit the activity of human BDNF (Gene ID: 627), mouse BDNF (Gene ID: 12064), rat BDNF (Gene ID: 24225), or a non-human primate BDNF (Gene ID: 503511), etc.

In certain embodiments, the subject methods involve administering to a patient a therapeutically-effective amount of an agent that inhibits the activity of brevican. Inhibitors in accordance with embodiments of the invention may inhibit brevican from any species. In some embodiments, an agent may inhibit the activity of human brevican (Gene ID: 63827), mouse brevican (Gene ID: 12032), rat brevican (Gene ID: 25393), or a non-human primate brevican (Gene ID: 457401), etc.

Without being held to theory, the mode of inhibition by the agent that inhibits the activity of one or more neuronal activity-regulated proteins may include inhibition of transcription, translation, one or more post-translational modifications, secretion and/or activity of the neuronal activity-regulated protein. The activity of the one or more neuronal activity-regulated proteins that is inhibited by the agent may include a biologically relevant activity of the neuronal activity-regulated protein that can be inhibited for therapeutic effect on a glioma, e.g., to reduce neurological symptoms of glioma, to reduce growth of the glioma, to reduce invasion of the glioma, etc. In such cases, the biologically relevant activity of the neuronal activity-regulated protein may include binding activity of the neuronal activity-regulated protein with an endogenous binding partner (i.e., a binding partner whose binding to the neuronal activity-regulated protein results in a biologically relevant effect in the context of the organism, tissue, tumor, cell, etc.), downstream signaling mediated by the neuronal activity-regulated protein (e.g., phosphorylation, translocation, regulation of gene expression, etc., induced specifically by the neuronal activity-regulated protein), and the like.

Thus, in certain embodiments, an agent inhibits the activity of a neuronal activity-regulated neuroligin-3, BDNF, or brevican by inhibiting transcription of neuroligin-3, BDNF, or brevican. In some embodiments, the agent inhibits the activity of a neuronal activity-regulated neuroligin-3, BDNF, or brevican by inhibiting translation of a neuronal activity-regulated neuroligin-3, BDNF, or brevican. In some embodiments, the agent inhibits the activity of a neuronal activity-regulated neuroligin-3, BDNF, or brevican by inhibiting one or more post-translational modification of neuroligin-3, BDNF, or brevican. In some embodiments, the agent inhibits the activity of a neuronal activity-regulated neuroligin-3, BDNF, or brevican by inhibiting secretion of neuroligin-3, BDNF, or brevican. In some embodiments, the agent inhibits the activity of a neuronal activity-regulated neuroligin-3, BDNF, or brevican by inhibiting binding of neuroligin-3, BDNF, or brevican to a binding partner. In some embodiments, the agent inhibits the activity of a neuronal activity-regulated neuroligin-3, BDNF, or brevican by inhibiting a signaling molecule or event down-stream of a neuronal activity-regulated neuroligin-3, BDNF, or brevican.

In certain embodiments, the subject methods may involve administering to a patient a therapeutically-effective amount of an agent that inhibits the secretion of neuroligin-3 (NLGN3). In certain aspects, the agent may be an inhibitor of a protease required for NLGN3 secretion. In certain aspects, the protease may be a metalloprotease (also called metalloproteinase). Examples of metalloproteases include the matrix metalloproteases (MMPs) such as the collagenases (MMP1, MMP8, MMP13), the gelatinases (MMP2, MMP9), the stromelysins (MMP3, MMP10, MMP 11), matrilysin (MMPI), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteases such as aggrecanase, the endothelin converting enzyme family and the angiotensin converting enzyme family.

In certain aspects, the protease required for NLGN3 secretion may be ADAM10. The subject methods may involve administering an inhibitor of ADAM10 to the patient. The inhibitor of ADAM10 may be an agent that reduces activity of ADAM10 by decreasing its expression level or function. In certain cases, the reduction in expression level of ADAM10 may be achieved by administering an anti sense RNA or a siRNA that specifically reduces the levels of ADAM10 mRNA. In certain cases, the inhibition of activity of ADAM10 may be achieved by administering an antibody, a peptide, or a small molecule that inhibits ADAM10 function. In certain cases, the subject methods may involve administering the ADAM10 inhibitor GI254023X. ADAM10 inhibitors include compounds, polypeptides, peptides, nucleic acids or ligands, including pharmaceutically acceptable salts thereof, that inhibit the production or function of the ADAM10 enzyme. In certain aspects an inhibitor reduces or inhibits the metalloprotease activity of ADAM10. ADAM10 inhibitors include GM6001, TIMP3, or TAPI-1 (N—(R)-[2-hydroxyaminocarbonyl) methyl]-4-methylpentanoyl-L-napthylalanyl-L-alanine, 2-aminoethyl amide), INCB7839 (trastuzumab, Incyte Co.), INCB3619; XL784; XL081; XL781; (Exelixis), and GI254023X (Roche Molecular Biochemicals, described in Schulte et al., 2007 and U.S. Pat. Nos. 6,172,064, 6,191,150, and 6,329,400, each of which is incorporated herein by reference) or GW280264X. In particular embodiments, the ADAM10 inhibitor GI254023X may be used in the subject methods.

In another aspect, the protease required for NLGN3 secretion may be MMP9. In certain aspects, a MMP9 inhibitor such as agents or compounds that reduce the expression (transcription or translation), stability and/or activity of MMP9 polypeptide may be used in the subject methods for reducing a neurological dysfunction in a patient with a glioma tumor. Such inhibitors include nucleic acids (antisense RNA, siRNA), peptides, small molecules, antibodies and the like. Commercially available inhibitors of MMP9 (which may inhibit other MMPs in addition to MMP9) may also be used. In certain aspects, the MMP9 inhibitor may be GM 6001 (CAS 142880-36-2; synonyms: Galardin; Ilomastat); Actinonin (CAS 13434-13-4; synonym: N'-hydroxy-N-[1-[2-(hydroxymethyl)pyrrolidin-1-yl]-3-methyl-1-oxobutan-2-yl]-2-pentylbutanediamide), SB-3CT (CAS 292605-14-2; synonym: 2-((4-phenoxyphenylsulfonyl)methyl)thiirane); Marimastat (CAS 154039-60-8; synonym: BB2516), MMP Inhibitor II (CAS 203915-59-7; synonym: N-Hydroxy-1,3-bis(4-methoxyphenyl- sulfonyl)-5,5-dimethylhexahydropyrimidine-2-carboxamide), MMP-2/MMP-9 Inhibitor II (CAS 193807-60-2; (2R)—N-hydroxy-3-phenyl-2-[(4-phenylphenyl)sulfonylamino]propanamide), Ageladine A, TFA (CAS 643020-13-7), MMP-2/MMP-9 Inhibitor V (CAS 869577-53-7), Chlorhexidine, Dihydrochloride (CAS 3697-42-5), MMP-2/MMP-9 Inhibitor I (CAS 193807-58-8), MMP-9/MMP-13 inhibitor I (CAS 204140-01-2; synonym: N-Hydroxy-1-(4-methoxyphenyl)sulfonyl-4-(4-biphenylcarbonyl)piperazine-2-carboxamide), CP 471474 (CAS 210755-45-6), MMP Inhibitor V (CAS 223472-31-9), cis-ACCP (CAS 777075-44-2), MMP-9/MMP-13 Inhibitor II (Cat. No. sc-311439, ChemCruz Biochemicals), 4-Aminobenzoyl-Gly-Pro-D-Leu-D-Ala hydroxamic acid (CAS 124168-73-6), Keracyanin chloride (CAS 18719-76-1), or Batimastat (CAS 130370-60-4). In certain cases, the MMP9 inhibitor used in the subject methods may not include MMP-9 Inhibitor I (CAS 1177749-58-4; synonyms: CTK8G1150; AG-L-66085). In particular embodiments, the subject methods may involve administering the MMP9 inhibitor Batimastat.

The inhibitors described herein also encompass derivates and analogues which retain the core structure and function of the inhibitors. Such derivatives and analogs include compounds in which the inhibitor molecule has been derivatized or has been fused to molecules that increase the stability or activity of the inhibitor molecule. It is also understood that more than one inhibitor may be used in the subject methods. A combination of inhibitors may be administered sequentially or simultaneously. The inhibitors may target the same protease or may target different proteases. In certain cases, two or more inhibitors of ADAM10 may be used in the subject methods. In other cases, two or more inhibitors of MMP9 may be used in the subject methods. In other aspects, at least one inhibitor of ADAM10 and at least one inhibitor of MMP9 may be administered to the subject.

In certain embodiments, the subject methods involve administering to a patient a therapeutically-effective amount of an agent that inhibits the activity of BDNF by inhibiting TrkB activity. In certain embodiments, an agent that inhibits the activity of BDNF includes an agent that inhibits a signaling molecule down-stream of the BDNF molecule, such as, but not limited to, TrkB (neurotrophic tyrosine kinase, receptor, type 2, or NTRK2). Inhibitors in accordance with embodiments of the invention may inhibit TrkB from any species. In some embodiments, an agent may inhibit the activity of human TrkB (Gene ID: 4915), mouse TrkB (Gene ID: 18212), rat TrkB (Gene ID: 25054), or a non-human primate TrkB (Gene ID: 735394), etc. Thus, in certain embodiments, an agent that inhibits the activity of a BDNF molecule includes an agent that inhibits TrkB, such as human TrkB.

In certain embodiments, the subject therapeutic agent inhibits the activity of a post-translationally modified form of neuroligin-3, BDNF, or brevican that is produced as a result of neuronal activity. In certain embodiments, the post-translationally modified form of neuroligin-3, BDNF, or brevican that is produced specifically as a result of neuronal activity is a secreted form of neuroligin-3, BDNF, or brevican, respectively. The secreted form or domain of the neuronal activity-regulated protein may include the extracellular domain of neuroligin-3 or brevican. In certain cases, the secreted form of neuroligin-3, BDNF, or brevican may be generated by post-translational modification, e.g., proteolytic cleavage, of a precursor form of neuroligin-3, BDNF, or brevican, respectively. In certain embodiments, where the full-length form of the neuronal activity-regulated protein is a membrane-bound polypeptide, the membrane-bound protein is proteolytically cleaved at one or more extracellular sites along the polypeptide to generate the neuronal activity-regulated protein.

In certain embodiments, an agent is a polypeptide that inhibits the activity of neuroligin-3, BDNF, or brevican. In some embodiments, such an inhibitory polypeptide inhibits the binding of an endogenous binding partner to neuroligin-3, BDNF, or brevican. In certain embodiments, an agent is an inhibitory peptide mimetic of neuroligin-3, BDNF, or brevican, or a portion thereof.

In certain embodiments, the amino- or carboxyl-terminus of a polypeptide that inhibits the activity of neuroligin-3, BDNF, or brevican can be fused to an immunoglobulin Fc region (e.g., human Fc) to form a fusion conjugate (or fusion molecule). Fc fusion conjugates are known to increase the systemic half-life of biopharmaceuticals, and thus the biopharmaceutical product may require less frequent administration to the patient.

Such polypeptides may be fused to a polypeptide domain that increases solubility of the product. The domain may be linked to the polypeptide through a defined protease cleavage site, e.g., a TEV sequence, which is cleaved by TEV protease. The linker may also include one or more flexible sequences, e.g., from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

Where the agent that inhibits the activity of a neuronal activity-regulated protein is an intracellular protein, the polypeptide may contain the polypeptide sequences of interest fused to a cell membrane permeant domain. Any suitable permeant domains may be used to fuse to a polypeptide agent that inhibits one or more neuronal activity-regulated proteins. For example, a permeant peptide may be derived from the third alpha helix of *Drosophila melanogaster* transcription factor Antennapaedia, referred to as penetratin. As another example, the permeant peptide contains the HIV-1 tat basic region amino acid sequence, which may include, for example, amino acids 49-57 of naturally-occurring tat protein. Other permeant domains include polyarginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24): 13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

Where the agent that inhibits the activity of a neuronal activity-regulated protein functions extracellularly (e.g., is an extracellular soluble protein), the polypeptide may be formulated for improved stability. For example, the peptides may be PEGylated, where the polyethyleneoxy group provides for enhanced lifetime in the blood stream. The subject polypeptide may be fused to another polypeptide to provide for added functionality, e.g., to increase the in vivo stability. Generally, such fusion partners are a stable plasma protein, which may, for example, extend the in vivo plasma half-life of the subject polypeptide when present as a fusion, in particular wherein such a stable plasma protein is an immunoglobulin constant domain, as described above. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the subject polypeptide also will be produced and employed as a multimer having substantially the same structure as the stable plasma protein precursor. These multimers will be homogeneous with respect to the polypeptide agent they contain, or they may contain more than one polypeptide agent.

In certain embodiments, an agent that inhibits the activity of neuroligin-3 includes a polypeptide that binds to the extracellular domain of neuroligin-3 (e.g., amino acids 1-678 of SEQ ID NO: 1). In some instances, a polypeptide that binds to the extracellular domain of neuroligin-3 is a polypeptide that contains an esterase-like domain. Neuroligins and other esterase-like domain-containing polypeptides are described in, e.g., Ichtchenko et al., 1996 J Biol Chem. 271:2676; Wang et al., 2010 J Biol Chem. 285:17564, which are incorporated herein by reference. Examples of suitable esterase-like domain-containing proteins include, but are not limited to: Neurexin-1α (SEQ ID NO: 2), Neurexin-1β (SEQ ID NO: 3), Neurexin-2α (SEQ ID NO: 4), Neurexin-2β (SEQ ID NO: 5), Neurexin-3α (SEQ ID NO: 6), Neurexin-3β (SEQ ID NO: 7) and Thyroglobulin (SEQ ID NO: 8).

In certain embodiments, an agent that inhibits the activity of neuroligin-3 includes at least a portion of Neurexin-1α (SEQ ID NO: 2). In certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of SEQ ID NO: 2. In certain embodiments, the agent that inhibits the activity of neuroligin-3 includes at least a portion of the mature form of Neurexin-1α (SEQ ID NO: 2). Thus, in certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 31-1547 of SEQ ID NO: 2. In certain embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-1α (SEQ ID NO: 2). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of amino acids 31-1468 of SEQ ID NO: 2. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 31-1468 of SEQ ID NO: 2.

In certain embodiments, the amino- or carboxyl-terminus of a polypeptide that inhibits the activity of neuroligin-3 includes at least a portion of Neurexin-1α (SEQ ID NO: 2), wherein the polypeptide can further be fused with an immunoglobulin Fc region (e.g., human Fc) to form a fusion conjugate (or fusion molecule). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-1α (SEQ ID NO: 2), wherein the polypeptide is fused at the amino- or carboxy-terminus to a human Fc region. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 31-1468 of SEQ ID NO: 2, wherein the polypeptide is fused at the amino- or carboxy-terminus to a human Fc region. In certain embodiments, the polypeptide may contain a linker sequence between the immunoglobulin Fc region and the at least a portion of Neurexin-1α (SEQ ID NO: 2).

In certain embodiments, an agent that inhibits the activity of neuroligin-3 includes at least a portion of Neurexin-1β (SEQ ID NO: 3). In certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of SEQ ID NO: 3. In certain embodiments, the agent that inhibits the activity of neuroligin-3 includes at least a portion of the mature form of Neurexin-1β (SEQ ID NO: 3). Thus, in certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 51-442 of SEQ ID NO: 3. In certain embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-1β (SEQ ID NO: 3). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of amino acids 51-363 of SEQ ID NO: 3. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 51-363 of SEQ ID NO: 3.

In certain embodiments, the amino- or carboxyl-terminus of a polypeptide that inhibits the activity of neuroligin-3 includes at least a portion of Neurexin-1 β (SEQ ID NO: 3), wherein the polypeptide can further be fused with an immunoglobulin Fc region (e.g., human Fc) to form a fusion conjugate (or fusion molecule). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-1 β (SEQ ID NO: 3), wherein the polypeptide is fused at the amino- or carboxy-terminus to a human Fc region. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 51-363 of SEQ ID NO: 3, wherein the polypeptide is fused at the amino- or carboxy-terminus to a human Fc region. In certain embodiments, the polypeptide may contain a linker sequence between the immunoglobulin Fc region and the at least a portion of Neurexin-1β (SEQ ID NO: 3).

In certain embodiments, an agent that inhibits the activity of neuroligin-3 includes at least a portion of Neurexin-2α (SEQ ID NO: 4). In certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of SEQ ID NO: 4. In certain embodiments, the agent that inhibits the activity of neuroligin-3 includes at least a portion of the mature form of Neurexin-2α (SEQ ID NO: 4). Thus, in certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 29-1712 of SEQ ID NO: 4. In certain embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-2α (SEQ ID NO: 4). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of amino acids 29-1636 of SEQ ID NO: 4. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 29-1636 of SEQ ID NO: 4.

In certain embodiments, the amino- or carboxyl-terminus of a polypeptide that inhibits the activity of neuroligin-3 includes at least a portion of Neurexin-2α (SEQ ID NO: 4), wherein the polypeptide can further be fused with an immunoglobulin Fc region (e.g., human Fc) to form a fusion conjugate (or fusion molecule). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-2α (SEQ ID NO: 4), wherein the polypeptide is fused at the amino- or carboxy-terminus to a human Fc region. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 29-1636 of SEQ ID NO: 4, wherein the polypeptide is fused at the amino- or carboxy-terminus to a human Fc region. In certain embodiments, the polypeptide may contain a linker sequence between the immunoglobulin Fc region and the at least a portion of Neurexin-2α (SEQ ID NO: 4).

In certain embodiments, an agent that inhibits the activity of neuroligin-3 includes at least a portion of Neurexin-2β (SEQ ID NO: 5). In certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of SEQ ID NO: 5. In certain embodiments, the agent that inhibits the activity of neuroligin-3 includes at least a portion of the mature form of Neurexin-2β (SEQ ID NO: 5). Thus, in certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 51-666 of SEQ ID NO: 5. In certain embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-2β (SEQ ID NO: 5). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of amino acids 51-590 of SEQ ID NO: 5. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 51-590 of SEQ ID NO: 5.

In certain embodiments, the amino- or carboxyl-terminus of a polypeptide that inhibits the activity of neuroligin-3 includes at least a portion of Neurexin-2β (SEQ ID NO: 5), wherein the polypeptide can further be fused with an immunoglobulin Fc region (e.g., human Fc) to form a fusion conjugate (or fusion molecule). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-2β (SEQ ID NO: 5), wherein the polypeptide is fused at the amino- or carboxy-terminus to a human Fc region. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 51-590 of SEQ ID NO: 5, wherein the polypeptide is fused at the amino- or carboxy-terminus to a human Fc region. In certain embodiments, the polypeptide may contain a linker sequence between the immunoglobulin Fc region and the at least a portion of Neurexin-2β (SEQ ID NO: 5).

In certain embodiments, an agent that inhibits the activity of neuroligin-3 includes at least a portion of Neurexin-3α (SEQ ID NO: 6). In certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of SEQ ID NO: 6. In certain embodiments, the agent that inhibits the activity of neuroligin-3 includes at least a portion of the mature form of Neurexin-3α (SEQ ID NO: 6). In certain embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-3α (SEQ ID NO: 6). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of amino acids 1-985 of SEQ ID NO: 6. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 1-985 of SEQ ID NO: 6.

In certain embodiments, the amino- or carboxyl-terminus of a polypeptide that inhibits the activity of neuroligin-3 includes at least a portion of Neurexin-3α (SEQ ID NO: 6), wherein the polypeptide can further be fused with an immunoglobulin Fc region (e.g., human Fc) to form a fusion conjugate (or fusion molecule). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-3α (SEQ ID NO: 6), wherein the polypeptide is fused at the amino- or carboxy-terminus to a human Fc region. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 1-985 of SEQ ID NO: 6, wherein the polypeptide is fused at the amino- or carboxy-terminus to a human Fc region. In certain embodiments, the polypeptide may contain a linker sequence between the immunoglobulin Fc region and the at least a portion of Neurexin-3α (SEQ ID NO: 6).

In certain embodiments, an agent that inhibits the activity of neuroligin-3 includes at least a portion of Neurexin-3β (SEQ ID NO: 7). In certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of SEQ ID NO: 7. In certain embodiments, the agent that inhibits the activity neuroligin-3 includes at least a portion of the mature form of Neurexin-3β (SEQ ID NO: 7). Thus, in certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 36-637 of SEQ ID NO: 7. In certain embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-3β (SEQ ID NO: 7). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of amino acids 36-561 of SEQ ID NO: 7. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 36-561 of SEQ ID NO: 7.

In certain embodiments, the amino- or carboxyl-terminus of a polypeptide that inhibits the activity of neuroligin-3 includes at least a portion of Neurexin-3β (SEQ ID NO: 7), wherein the polypeptide can further be fused with an immunoglobulin Fc region (e.g., human Fc) to form a fusion conjugate (or fusion molecule). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Neurexin-3β (SEQ ID NO: 7), wherein the polypeptide is fused at the amino- or carboxy-terminus to a human Fc region. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 36-561 of SEQ ID NO: 7, wherein the polypeptide is fused at the amino- or carboxy-terminus to a human Fc region. In certain embodiments, the polypeptide may contain a linker sequence between the immunoglobulin Fc region and the at least a portion of Neurexin-3β (SEQ ID NO: 7).

In certain embodiments, an agent that inhibits the activity of neuroligin-3 includes at least a portion of the protein Thyroglobulin (SEQ ID NO: 8). In certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of SEQ ID NO: 8. In certain embodiments, the agent that inhibits the activity of neuroligin-3 includes the cholinesterase (amino acids 2196-2768) or I-II-III (amino acids 20-2195) domains of Thyroglobulin (SEQ ID NO: 8). Thus, in certain embodiments, the agent that inhibits the activity of neuroligin-3 includes a polypeptide containing an amino acid sequence at least 80%, e.g., at least 85%, at least 90%, at least 95%, at least 97%, or 100% identical to at least a portion of amino acids 2196-2768 or 20-2195 of SEQ ID NO: 8. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 2196-2768 or 20-2195 of SEQ ID NO: 8.

In certain embodiments, the amino- or carboxyl-terminus of a polypeptide that inhibits the activity of neuroligin-3 includes at least a portion of Thyroglobulin (SEQ ID NO: 8), wherein the polypeptide can further be fused with an immunoglobulin Fc region (e.g., human Fc) to form a fusion conjugate (or fusion molecule). Thus, in some embodiments, the agent that inhibits the activity of neuroligin-3 includes a polypeptide containing an amino acid sequence at least 80%, e.g., at least 85%, at least 90%, at least 95%, at least 97%, or 100% identical to the extracellular domain of the mature form of Thyroglobulin (SEQ ID NO: 8), wherein the polypeptide is fused at the amino- or carboxy-terminus to a human Fc region. In certain embodiments, the agent that inhibits the activity of neuroligin-3 includes a polypeptide containing an amino acid sequence at least 80%, e.g., at least 85%, at least 90%, at least 95%, at least 97%, or 100% identical to amino acids 2196-2768 or 20-2195 of SEQ ID NO: 8, wherein the polypeptide is fused at the amino- or carboxy-terminus to a human Fc region. In certain embodiments, the polypeptide may contain a linker sequence between the immunoglobulin Fc region and the at least a portion of Thyroglobulin (SEQ ID NO: 8).

In certain embodiments, the agent that inhibits the activity of BDNF includes at least a portion of TrkB (SEQ ID NO: 9). In certain embodiments, the agent that inhibits the activity of BDNF includes a polypeptide containing an amino acid sequence at least 80%, e.g., at least 85%, at least 90%, at least 95%, at least 97%, or 100% identical to at least a portion of SEQ ID NO: 9. In certain embodiments, the agent that inhibits the activity of BDNF includes at least a portion of the mature form of TrkB (SEQ ID NO: 9). Thus, in certain embodiments, the agent that inhibits the activity of BDNF includes a polypeptide containing an amino acid sequence at least 80%, e.g., at least 85%, at least 90%, at least 95%, at least 97%, or 100% identical to amino acids 32-838 of SEQ ID NO: 9. In certain embodiments, the agent that inhibits the activity of BDNF includes a polypeptide containing an amino acid sequence at least 80%, e.g., at least 85%, at least 90%, at least 95%, at least 97%, or 100% identical to the extracellular domain of the mature form of TrkB (SEQ ID NO: 9). Thus, in some embodiments, the agent that inhibits the activity of BDNF includes a polypeptide containing an amino acid sequence at least 80%, e.g., at least 85%, at least 90%, at least 95%, at least 97%, or 100% identical to at least a portion of amino acids 32-430 of SEQ ID NO: 9. In certain embodiments, the agent that inhibits the activity of BDNF includes a polypeptide containing an amino acid sequence at least 80%, e.g., at least 85%, at least 90%, at least 95%, at least 97%, or 100% identical to amino acids 32-430 of SEQ ID NO: 9.

In certain embodiments, the amino- or carboxyl-terminus of a polypeptide that inhibits the activity of BDNF includes at least a portion of TrkB (SEQ ID NO: 9), wherein the polypeptide can further be fused with an immunoglobulin Fc region (e.g., human Fc) to form a fusion conjugate (or fusion molecule). Thus, in some embodiments, the agent that inhibits the activity of BDNF includes a polypeptide containing an amino acid sequence at least 80%, e.g., at least 85%, at least 90%, at least 95%, at least 97%, or 100% identical to the extracellular domain of the mature form of TrkB (SEQ ID NO: 9), wherein the polypeptide is fused at the amino- or carboxy-terminus to a human Fc region. In certain embodiments, the agent that inhibits the activity of BDNF includes a polypeptide containing an amino acid sequence at least 80%, e.g., at least 85%, at least 90%, at least 95%, at least 97%, or 100% identical to amino acids 32-430 of SEQ ID NO: 9, wherein the polypeptide is fused at the amino- or carboxy-terminus to a human Fc region. In certain embodiments, the polypeptide may contain a linker sequence between the immunoglobulin Fc region and the at least a portion of TrkB (SEQ ID NO: 9).

In certain embodiments, a polypeptide that inhibits the activity of BDNF includes a plasmin inhibitor, such as, but not limited to, plasminogen activator inhibitor (PAI)-1, PAI-2, aprotinin (bovine pancreatic trypsin inhibitor), $\alpha_1$-antitrypsin and $\alpha_2$-antiplasmin. Any suitable method for preparation and use of plasmin inhibitors may be used, such as those described in, e.g., U.S. Pat. No. 6,288,025; US App. Pub. No. 20030180925; and PCT Pub. No. WO1994/005322, which are incorporated herein by reference.

In certain embodiments, a polypeptide that inhibits the activity of BDNF includes a cytoplasmic tail of carboxypeptidase E. Any suitable polypeptide that includes the cytoplasmic tail of carboxypeptidase E may be used, such as those described in, e.g., Park et al., 2008 Mol Endocrinol. 22:989; Park et al., 2008 Mol Cell Neurosci. 39:63; and Arnaoutova et al., 2003 Mol Biol Cell. 14:4448, which are incorporated herein by reference.

In certain embodiments, an agent that inhibits the activity of BDNF through inhibition of TrkB is an inhibitory peptide mimetic of BDNF, such as, but not limited to, cyclotraxin-B, as described in Cazorla et al. PLoS One. 2010 5:e9777, which is incorporated by reference.

In certain embodiments, an agent is an antibody that inhibits the activity of a neuronal activity-regulated protein, e.g., an antagonistic antibody. In certain embodiments, the agent that inhibits the activity of neuroligin-3, BDNF, or brevican includes an antibody that specifically binds to neuroligin-3, BDNF, or brevican. In certain embodiments, the agent that inhibits the activity of BDNF includes an antibody that specifically binds to TrkB, e.g., the extracellular domains of TrkB. Antibodies in accordance with embodiments of the invention may be monoclonal or polyclonal antibodies. Any suitable antibody that blocks activity of neuroligin-3, BDNF, or brevican may be used in the subject methods. In certain embodiments, the antibody specifically binds to the extracellular domain of neuroligin-3 or brevican. In certain embodiments, the antibody specifically binds to mature BDNF. Any suitable BDNF function-blocking antibodies may be used, such as those described in, e.g., Ma et al., 2011, J Neurosci. 31:2079; and Alonso et al., 2002, Hippocampus 12:551, which are incorporated by reference. In certain embodiments, the antibody specifically binds to TrkB. In certain embodiments, the antibody specifically binds to the extracellular domain of TrkB. Any suitable TrkB function-blocking antibodies may be used, such as those described in, e.g., Huang et al., Int J Oncol. 2010 37:943, which is incorporated by reference.

In certain embodiments, an agent is a nucleic acid that inhibits the activity of a neuronal activity-regulated protein. In some embodiments, the agent is a nucleic acid that inhibits the expression, e.g., translation, of neuroligin-3, BDNF, or brevican. In some embodiments, the nucleic acid is a ribonucleic acid (RNA) that inhibits the expression, e.g., translation, of neuroligin-3, BDNF, or brevican. In certain embodiments, the nucleic acid is a small-interfering RNA (siRNA) or short hairpin RNA (shRNA) that is designed to target neuroligin-3, BDNF, or brevican. In some embodiments, the nucleic acid is an expression vector, e.g., a viral expression vector that is configured to express in a host cell, e.g., a neuronal host cell, an siRNA or shRNA that is designed to target neuroligin-3, BDNF, or brevican. Any suitable method may be used to design and administer a nucleic acid to target neuroligin-3, BDNF, or brevican. Suitable methods are described, e.g., in US App. Pub. Nos. 20100143450; 20110009468; 2011020779; 20110319475; 20120165397; 20120177723; PCT Pub. No. WO2013/138783; Baker-Herman et al., 2004 Nat Neurosci. 7:48; Pettersson et al., 2014 PLoS One 9:e100730; Jacobs et al., 1999 Neoplasia 1:402, which are incorporated herein by reference. Commercial sources of siRNA and/or shRNA include Santa Cruz Biotech and Thermo Fisher.

In certain embodiments, the agent is a small molecule that inhibits the activity of a neuronal activity-regulated protein. In certain embodiments, the small molecule that inhibits the activity of neuroligin-3 is castanospermine ((1S,6S,7R,8R,8aR)-1,2,3,5,6,7,8,8a-octahydroindolizine-1,6,7,8-tetrol), or a derivative thereof. Castanospermine and derivatives thereof that are suitable for inhibiting the activity of neuroligin-3 are described in, e.g., U.S. Pat. Nos. 5,017,563; 5,066,807; 5,214,050; and 5,837,709, which patents are incorporated by reference.

In certain embodiments, a small molecule that inhibits the activity of neuroligin-3 is a modulator of phosphatidylinositol-4,5-bisphosphate 3-kinase (PI3K), including wortmannin, PX-866 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5-h]isochromen-10-yl] acetate), LY294002 (2-morpholin-4-yl-8-phenylchromen-4-one), and BKM120 (5-(2,6-dimorpholin-4-ylpyrimidin-4-yl)-4-(trifluoromethyl)pyridin-2-amine hydrochloride).

In certain embodiments, a small molecule that inhibits the activity of neuroligin-3 is a modulator of mammalian target of rapamycin (mTOR) signaling, such as rapamycin, temsirolimus, everolimus, and ridaforolimus. A description and preparation of ridaforolimus is found in U.S. Pat. No. 7,091,213, which is hereby incorporated by reference. A description and preparation of temsirolimus is found in U.S. Pat. No. 5,362,718, which is hereby incorporated by reference. A description and preparation of everolimus is found in, e.g., PCT Pub. No. WO2012/10396, which is hereby incorporated by reference.

In certain embodiments, a small molecule that inhibits the activity of BDNF interferes with sorting and maturation of BDNF, such as AF38469 (2-((6-methylpyridin-2-yl)carbamoyl)-5-(trifluoromethyl)benzoic acid), described in Schrøder et al., 2014, Bioorg Med Chem Lett. 24:177; and PCT Pub. No. WO2014/114779, which are incorporated herein by reference. In certain embodiments, a small molecule that inhibits the activity of BDNF interferes with maturation of BDNF, such as prinomastat ((3S)—N-hydroxy-2,2-dimethyl-4-(4-pyridin-4-yloxyphenyl)sulfonylthiomorpholine-3-carboxamide), Ro 28-2653 (5-[4-(4-nitrophenyl)piperazin-1-yl]-5-(4-phenylphenyl)-1,3-diazinane-2,4,6-trione), 3-hydroxypyran-4-one, etc.

In certain embodiments, an agent that inhibits the activity of BDNF is a small molecule, such as, but not limited to, AZ623, K252a and ANA12, as described in Zage et al., Cancer 2011 117:1321 and Cazorla et al., J Clin Invest. 2011 121:1846, which are incorporated by reference. Without being bound to theory, such small molecule inhibitors may inhibit the activity of BDNF by inhibiting binding and/or signaling activity of TrkB.

In certain embodiments, a small molecule that inhibits the activity of BDNF inhibits expression, e.g., transcription, of BDNF. In some embodiments, a small molecule that inhibits transcription of neuronal activity-regulated BDNF includes cyclosporine A, tacrolimus, bortezomib ([(1R)-3-methyl-1-[[(2S)-3-phenyl-2-(pyrazine-2-carbonylamino)propanoyl]amino]butyl]boronic acid), curcumin ((1E,6E)-1,7-bis(4-hydroxy-3-methoxyphenyl)hepta-1,6-diene-3,5-dione), BMS-345541 (N'-(1,8-dimethylimidazo[1,2-a]quinoxalin-4-yl)ethane-1,2-diamine;hydrochloride), and bosutinib (4-(2,4-dichloro-5-methoxyanilino)-6-methoxy-7-[3-(4-methylpiperazin-1-yl)propoxy]quinoline-3-carbonitrile), etc.

In certain embodiments, a small molecule that inhibits the activity of brevican includes biaryl sulfonamides, such as those described in, e.g., US App. Pub. No. 20050130973, which is incorporated by reference.

Formulations and Dosage Forms

Therapeutic agents of the present disclosure, e.g., agents that inhibit the activity of a neuronal activity-regulated protein, can be formulated in a pharmaceutical composition suitable for administration to a patient by any desired route of administration. A composition containing an agent of the present disclosure may include any suitable pharmaceutically acceptable excipient.

Pharmaceutically acceptable excipients have been described in a variety of publications, including, for example, "Remington: The Science and Practice of Pharmacy", 19th Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

A pharmaceutical composition containing an agent that inhibits the activity of a neuronal activity-regulated protein of the present disclosure may include other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

In some cases, a subject pharmaceutical composition will be suitable for injection into a subject, e.g., will be sterile. For example, in some embodiments, a subject pharmaceutical composition will be suitable for injection into a subject, e.g., where the composition is sterile and is free of detectable pyrogens and/or other toxins.

In some embodiments, an agent that inhibits the activity of a neuronal activity-regulated protein is formulated in a sustained release dosage form that is designed to release the agent at a predetermined rate for a specific period of time. Such sustained release formulations may include, for example, formulations for use in drug delivery implants or devices, e.g., ingestible devices.

For oral preparations, an agent that inhibits the activity of a neuronal activity-regulated protein can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In certain embodiments, an agent that inhibits the activity of a neuronal activity-regulated protein can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Unit dosage forms for oral administration such as syrups, elixirs, and suspensions may be provided wherein each dosage unit, for example, teaspoonful, tablespoonful, or tablet, contains a predetermined amount of the agents of the present disclosure. Similarly, unit dosage forms for injection or intravenous administration may include one or more agents that inhibit the activity of a neuronal activity-regulated protein in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of the agent of the present invention calculated in an amount sufficient to produce the desired effect in association with a pharmaceutically acceptable diluent, carrier or vehicle. The specifications for the unit dosage forms of the present disclosure depend on the particular agent or agents employed and the effect to be achieved, and the pharmacodynamics associated with each agent in the subject.

Any suitable pharmaceutically acceptable excipients, such as vehicles, adjuvants, carriers or diluents may be employed in the subject methods. Moreover, any suitable pharmaceutically acceptable auxiliary substances, such as pH adjusting and buffering agents, tonicity adjusting agents, stabilizers, wetting agents and the like, may be used.

Any of the therapeutic agents of the present disclosure may be formulated for use in any route of administration or dosage form disclosed herein.

Routes of Administration

In practicing the methods of the present disclosure, routes of administration may be selected according to any of a variety of factors, such as properties of the therapeutic agent(s) to be delivered, the type of condition to be treated (e.g., type of glioma), and the like. For instance the therapeutic agents of the present disclosure, e.g., agents that inhibit the activity of a neuronal activity-regulated protein, may be delivered systemically or locally. In some instances, therapeutic agents of the present disclosure are administered orally, such as through the digestive tract (enteral administration), buccal, sublabial, or sublingual administration. Such dosage forms may be pills, tablets, capsules, time-release formulations, osmotic controlled release formulations, solutions, softgels, hydrogels, suspensions, emulsions, syrups, orally disintegrating tablets, films, lozenges, chewing gums, mouthwashes, ointments, and the like.

Therapeutic agents of the present disclosure, e.g., agents that inhibit the activity of a neuronal activity-regulated protein, can be administered by direct injection into a target tissue or into the blood stream, including intradermal, subcutaneous, intravenous, intramuscular, intraosseous, or intraperitoneal injection. Therapeutic agents of the present disclosure can be administered by intracavernous or intravitreal delivery to organs or tissues, or administered by intracerebral, intrathecal, or epidural delivery to tissues of the central nervous system.

For some conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic agents of the invention when the agents are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic agents for use in the invention to facilitate transport across the endothelial wall of the blood vessel.

Local administration of the therapeutic agents may include intrathecal administration, which may be carried out through the use of an Ommaya reservoir, in accordance with known techniques (F. Balis et al., Am J. Pediatr. Hematol. Oncol. 11, 74, 76 (1989), see also, e.g. U.S. Pat. Nos. 5,222,982 and 5,385,582, incorporated herein by reference).

Where the therapeutic agents are locally administered in the brain, one method for administration of the therapeutic agents of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass (see e.g. US Application No. 20070254842, incorporated here by reference). Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic agent to the brain and/or tumor mass. Such devices are described in U.S. Pat. No. 5,720,720, incorporated fully herein by reference.

Local administration may also include locally implanting a biocompatible device for delivering a therapeutic agent of the present disclosure directly at the site of the tumor or after removal of the tumor by surgical means. The local implantation of a biocompatible wafer loaded with a therapeutic agent for treatment of glioma is described in, e.g., Attenello et al. Ann. Surg. Oncol., 2008 15:2887-93, which is incorporated herein by reference. See also, e.g. US Application Nos. 20080081064 and 20090196903, incorporated herein by reference.

In the methods of the present disclosure, the therapeutic agents may be administered to the patient using any convenient routes of administration that are capable of resulting in the desired treatment of glioma. Thus, the therapeutic agents can be incorporated into a variety of formulations for therapeutic administration. More particularly, the therapeutic agents of the present disclosure can be formulated into pharmaceutical compositions by combination with appropriate, pharmaceutically acceptable carriers or diluents, and may be formulated into preparations in solid, semi-solid or liquid forms, such as tablets, capsules, powders, granules, ointments, solutions and injections.

In pharmaceutical dosage forms, the therapeutic agents of the present disclosure may be administered in the form of their pharmaceutically acceptable salts, or they may also be used alone or in appropriate association, as well as in combination, with other pharmaceutically active compounds. The previously-described routes of administration and dosage forms are merely exemplary and are in no way limiting.

Methods of Use
Methods of Treating a Subject

Aspects of the invention include methods of treating a subject or patient who has been diagnosed with a brain tumor, e.g., glioma, including: diffuse intrinsic pontine glioma (DIPG), thalamic glioma, gliobastoma multiforme, ependymoma, astrocytoma, oligodendroglioma, optic nerve glioma, spinal cord glioma or any combination thereof. Methods in accordance with embodiments of the invention include administering to a subject diagnosed with one or more of the conditions described above an agent that inhibits the activity of a neuronal activity-regulated protein, e.g., neuroligin-3, BDNF or brevican, to treat the condition.

In some embodiments, the therapeutic agents of the present disclosure may be administered to treat a pediatric or adult patient diagnosed with glioma. The glioma may be diagnosed as a low-grade or high-grade glioma, and in some instances may be a grade I, II, III or IV glioma, as defined by the World Health Organization (WHO), and described in, e.g., Louis et al., 2007 Acta Neuropathol. 114:97, which is incorporated herein by reference. In certain embodiments, the therapeutic agents of the present disclosure may be administered to treat a patient diagnosed with pediatric high-grade glioma.

In some embodiments, treating a glioma tumor in a subject may include: reducing the growth rate of the glioma; reducing the size of the glioma; preventing growth and/or survival of the glioma; preventing invasion of the glioma into other areas of the patient's tissue or other organs; reducing a neurological dysfunction in the patient; or a combination thereof, by administering to the patient an agent that inhibits the activity of one or more neuronal activity-regulated proteins, as described above. Any suitable method may be used to monitor the therapeutic effect of the agent that inhibits the activity of one or more neuronal activity-regulated proteins on a glioma tumor in a patient. In certain embodiments, the methods involve monitoring the progression or status of a glioma tumor using imaging methods, including, but not limited to, magnetic resonance imaging (MRI), positron emission tomography (PET) scans and/or X-ray computed tomography (CT) scans, as described in, e.g., Jacobs et al., 2005 Eur J Nucl Med Mol Imaging. 32 Suppl 2:S358, which is incorporated by reference. The therapeutic effect of an agent that inhibits the activity of one or more neuronal activity-regulated proteins in a patient diagnosed with glioma may be defined using any suitable clinical endpoint. Thus, in certain embodiments, the methods involve determining one or more clinical endpoints after administering an agent that inhibits the activity of one or more neuronal activity-regulated proteins to a patient diagnosed with glioma. Suitable clinical endpoints may include, but are not limited to, overall survival, time to progression, response duration and progression-free survival.

In certain embodiments, administering an agent that inhibits the activity of one or more neuronal activity-regulated proteins to a patient diagnosed with a glioma tumor may increase the overall survival rate of treated subjects by 10% or more, e.g., 15% or more, 20% or more, 25% or more, 30% or more, 40% or more, or 50% or more, and may increase the overall survival rate of subjects diagnosed with the glioma tumor by 100% or less, e.g., 90% or less, 80% or less, 70% or less, 60% or less, or 50% or less, compared to the rate in non-treated subjects. In certain embodiments, administering an agent that inhibits the activity of one or more neuronal activity-regulated proteins to a subject diagnosed with the glioma tumor may increase the overall survival rate of patients diagnosed with the glioma tumor by a range of 10 to 100%, e.g., 15 to 95%, 20 to 90%, 25 to 85%, 30 to 80%, including 40 to 70% compared to the rate in non-treated subjects.

In certain embodiments, administering an agent that inhibits the activity of one or more neuronal activity-regulated proteins to a subject diagnosed with the glioma tumor may increase the progression-free survival of the treated subject by 10% or more, e.g., 15% or more, 20% or more, 25% or more, 30% or more, 40% or more, or 50% or more, and may increase the progression-free survival of patients diagnosed with the glioma tumor by 100% or less, e.g., 90% or less, 80% or less, 70% or less, 60% or less, or 50% or less, compared to a non-treated subject. In certain embodiments, administering an agent that inhibits the activity of one or more neuronal activity-regulated proteins to a subject diagnosed with the glioma tumor may increase the progression-free survival of the subject diagnosed with the glioma tumor by a range of 10 to 100%, e.g., 15 to 95%, 20 to 90%, 25 to 85%, 30 to 80%, including 40 to 70% compared to a non-treated subject.

In certain embodiments, administering an agent that inhibits the activity of one or more neuronal activity-regulated proteins to a subject diagnosed with the glioma tumor may increase the time to progression of the treated subject by 10% or more, e.g., 15% or more, 20% or more, 25% or more, 30% or more, 40% or more, or 50% or more, and may increase the time to progression of patients diagnosed with the glioma tumor by 100% or less, e.g., 90% or less, 80% or less, 70% or less, 60% or less, or 50% or less, compared to a non-treated subject. In certain embodiments, administering an agent that inhibits the activity of one or more neuronal activity-regulated proteins to a subject diagnosed with the glioma tumor may increase the time to progression of the subject diagnosed with the glioma tumor by a range of 10 to 100%, e.g., 15 to 95%, 20 to 90%, 25 to 85%, 30 to 80%, including 40 to 70% compared to a non-treated subject.

In certain embodiments, an agent that inhibits the activity of one or more neuronal activity-regulated proteins reduces a neurological dysfunction when administered to a patient with a glioma tumor. The neurological dysfunction may include pain, numbness, seizures, neuromuscular dysfunction, cognitive impairment, or personality changes. In some cases, pain may include a headache or back pain. In some instances, neurological dysfunction may include memory loss or a language deficit. In some instances, neurological dysfunction may include visual problems. In certain instances, the agent that inhibits the activity of one or more neuronal activity-regulated proteins in a patient with a glioma tumor alters or ameliorates a neurological symptom associated with the glioma. In some instances, the neurological symptom includes: dementia, personality change, gait disturbance, expressive aphasia, seizure associated with the frontal lobe; receptive aphasia, sensory loss, hemianopia, spatial disorientation associated with the parietal lobe; complex partial or generalized seizure; behavior change, including symptoms of autism, memory loss, and quadrantanopia, associated with the temporal lobe; contralateral hemianopia, associated with the occipital lobe; contralateral sensory loss, behavior change, language disorder, associated with the thalamus; ataxia, dysmetria, nystagmus, associated with the cerebellum; and/or cranial nerve dysfunction, ataxia, papillary abnormalities, nystagmus, hemiparesis, autonomic dysfunction, associated with the brain stem.

In some instances the neurological dysfunction may be caused, prolonged and/or exacerbated by the glioma tumor in the subject. In certain instances, the neurological dysfunction may be a chronic neurological dysfunction. In certain instances, the neurological dysfunction may be a progressive neurological dysfunction. Any suitable method may be used to determine and/or measure a neurological dysfunction in a subject or patient diagnosed with a glioma tumor.

In certain embodiments, administering an agent that inhibits the activity of one or more neuronal activity-regulated proteins to a subject diagnosed with the glioma tumor may reduce the neurological dysfunction of the treated subject by 10% or more, e.g., 15% or more, 20% or more, 25% or more, 30% or more, 40% or more, or 50% or more, and may reduce the neurological dysfunction of patients diagnosed with the glioma tumor by 100% or less, e.g., 90% or less, 80% or less, 70% or less, 60% or less, or 50% or less, compared to a non-treated subject. In certain embodiments, administering an agent that inhibits the activity of one or more neuronal activity-regulated proteins to a subject diagnosed with the glioma tumor may reduce the neurological dysfunction of a subject diagnosed with the glioma tumor by a range of 10 to 100%, e.g., 15 to 95%, 20 to 90%, 25 to 85%, 30 to 80%, including 40 to 70% compared to a non-treated subject.

In certain embodiments, an agent that inhibits the activity of one or more neuronal activity-regulated proteins reduces a growth rate of the glioma tumor when administered to a patient with a glioma tumor. Reducing a growth rate may include reducing the growth rate of the glioma tumor to a negative growth rate, thereby shrinking the tumor. Reducing a growth rate may include reducing the growth rate of the glioma tumor to a smaller magnitude, thereby slowing the growth of the tumor. In other embodiments, reducing a growth rate may include reducing the growth rate of the glioma tumor to essentially zero, thereby stopping further growth of the tumor.

In certain embodiments, administering the one or more neuronal activity-regulated proteins to a subject diagnosed with the glioma tumor may reduce the growth rate of the glioma tumor by 10% or more, e.g., 20% or more, 30% or more, 40% or more, 50% or more, 60% or more, 80% or more, 90% or more, or 100% or more, and may reduce the growth rate of the glioma tumor by 200% or less, e.g., 190% or less, 180% or less, 170% or less, 160% or less, 150% or less, 120% or less, 100% or less, 90% or less, 80% or less, 70% or less, 60% or less, or 50% or less, compared to the growth rate of a glioma tumor in a non-treated subject. In certain embodiments, administering the one or more neuronal activity-regulated proteins to a subject diagnosed with the glioma tumor may reduce the growth rate of the glioma tumor by a range of 10 to 200%, e.g., 20 to 180%, 30 to 160%, 35 to 140%, 40 to 120%, including 45 to 100% compared to the growth rate of a glioma tumor in a non-treated subject.

In certain embodiments, an agent that inhibits the activity of one or more neuronal activity-regulated proteins reduces the rate of proliferation of a glioma tumor cell in a subject. In certain embodiments, the agent that inhibits the activity of one or more neuronal activity-regulated proteins reduces the mitotic or proliferation index of a glioma tumor cell.

In certain embodiments, administering an agent that inhibits the activity of one or more neuronal activity-regulated proteins to a subject diagnosed with the glioma tumor may reduce the mitotic index of the glioma tumor by 10% or more, e.g., 20% or more, 30% or more, 40% or more, 50% or more, 60% or more, 80% or more, 90% or more, or 100% or more, and may reduce the mitotic index of the glioma tumor by 200% or less, e.g., 190% or less, 180% or less, 170% or less, 160% or less, 150% or less, 120% or less, 100% or less, 90% or less, 80% or less, 70% or less, 60% or less, or 50% or less, compared to the mitotic index of a glioma tumor in a non-treated subject. In certain embodiments, administering an agent that inhibits the activity of one or more neuronal activity-regulated proteins to a subject diagnosed with the glioma tumor may reduce the mitotic index of the glioma tumor by a range of 10 to 200%, e.g., 20 to 180%, 30 to 160%, 35 to 140%, 40 to 120%, including 45 to 100% compared to the mitotic index of a glioma tumor in a non-treated subject.

In certain embodiments, an agent that inhibits the activity of one or more neuronal activity-regulated proteins prevents a glioma tumor cell from invading a brain tissue, i.e., invading a healthy or normal brain tissue, when administered to a patient with a glioma tumor. In some instances, an agent that inhibits the activity of one or more neuronal activity-regulated proteins slows the rate at which a glioma tumor cell invades a brain tissue or other tissue when administered to a patient with a glioma tumor. In some cases, the agent may reduce the migration rate of a glioma tumor cell into a brain tissue or other tissue when administered to a patient with a glioma tumor.

In certain embodiments, administering an agent that inhibits the activity of one or more neuronal activity-regulated proteins to a patient diagnosed with the glioma tumor may reduce or retard invasion of the glioma tumor into a brain tissue or other tissue by 10% or more, e.g., 20% or more, 30% or more, 40% or more, 50% or more, 60% or more, or 80% or more, and may reduce or retard invasion of the glioma tumor into a brain tissue or other tissue by 100% or less, e.g., 90% or less, 80% or less, 70% or less, 60% or less, or 50% or less, compared to a glioma tumor in a non-treated subject. In certain embodiments, administering an agent that inhibits the activity of one or more neuronal activity-regulated proteins to a subject diagnosed with the glioma tumor may reduce or retard invasion of the glioma tumor into a brain tissue or other tissue by an amount ranging from 10 to 100%, e.g., 15 to 80%, 20 to 70%, 25 to 60%, including 30 to 60%, compared to a glioma tumor in a non-treated subject.

In certain embodiments, an agent that inhibits the activity of one or more neuronal activity-regulated proteins may be administered at a dosage that is sufficient to treat glioma in a subject, as described above. Thus, the dosage of the therapeutic agent will vary, depending upon the nature of the disease, the frequency of administration, the manner of administration, the clearance of the agent from the subject, and the like.

In certain embodiments, a small molecule that inhibits the activity of one or more neuronal activity-regulated proteins is administered at a dose ranging from 0.1 µg/kg to 200 mg/kg body weight, e.g., 0.5 µg/kg to 175 mg/kg body weight, 1 µg/kg to 150 mg/kg body weight, 5 µg/kg to 125 mg/kg body weight, 10 µg/kg to 100 mg/kg body weight, 20 µg/kg to 50 mg/kg body weight, 50 µg/kg to 20 mg/kg body weight, 75 µg/kg to 10 mg/kg body weight, 100 µg/kg to 5 mg/kg body weight, including 100 µg/kg to 1 mg/kg body weight, to treat glioma in a subject. In certain embodiments, a small molecule that inhibits the activity of one or more neuronal activity-regulated proteins may be administered at a dose of 0.1 µg/kg or more, e.g., 0.5 µg/kg or more, 1 µg/kg or more, 5 µg/kg or more, 10 µg/kg or more, 20 µg/kg or more, 50 µg/kg or more, 100 µg/kg or more, 200 µg/kg or more, 500 µg/kg or more 1 mg/kg or more, 5 mg/kg or more, 10 mg/kg or more, 20 mg/kg or more, 50 mg/kg or more, 75 mg/kg or more, 100 mg/kg or more, by body weight, and in some cases the dose may be 200 mg/kg or less, e.g., 150 mg/kg or less, 100 mg/kg or less, 75 mg/kg or less, 50 mg/kg or less, 25 mg/kg or less, 10 mg/kg or less, 5 mg/kg or less, 1 mg/kg or less, 750 µg/kg or less, 500 µg/kg or less, 250 µg/kg or less, 100 µg/kg or less, 75 µg/kg or less, 50 µg/kg or less, 20 µg/kg or less, 10 µg/kg or less, 5 µg/kg or less or 1 µg/kg or less, by body weight, to treat a glioma in a subject. In certain embodiments, a small molecule that inhibits the activity of one or more neuronal activity-regulated proteins is administered at a dose or in a dosage regimen that provides for a target tissue and/or blood concentration in the range of 0.1 to 1000 nM, e.g., 1 to 500 nM, 10 to 400 nM, 20 to 300 nM, 25 to 250 nM, 30 to 200 nM, including 50 to 150 nM.

In certain embodiments, a polypeptide or antibody that inhibits the activity of one or more neuronal activity-regulated proteins may be administered at a dose ranging from 1 µg/kg to 150 mg/kg body weight, e.g., 5 µg/kg to 125 mg/kg body weight, 10 µg/kg to 100 mg/kg body weight, 20 µg/kg to 75 mg/kg body weight, 50 µg/kg to 50 mg/kg body weight, 75 µg/kg to 20 mg/kg body weight, 100 µg/kg to 10 mg/kg body weight, including 100 µg/kg to 1 mg/kg body weight, to treat a glioma in a subject. In certain embodiments, a polypeptide or antibody that inhibits the activity of one or more neuronal activity-regulated proteins may be administered at a dose of 1 µg/kg or more, e.g., 5 µg/kg or more, 10 µg/kg or more, 50 µg/kg or more, 100 µg/kg or more, 200 µg/kg or more, 500 µg/kg or more 1 mg/kg or more, 5 mg/kg or more, 10 mg/kg or more, 20 mg/kg or more, 50 mg/kg or more, 75 mg/kg or more, 100 mg/kg or more, by body weight, and in some cases the dose may be 200 mg/kg or less, e.g., 150 mg/kg or less, 100 mg/kg or less, 75 mg/kg or less, 50 mg/kg or less, 25 mg/kg or less, 10 mg/kg or less, 5 mg/kg or less, 1 mg/kg or less, 750 µg/kg or less, 500 µg/kg or less, 250 µg/kg or less, 100 µg/kg or less, 75 µg/kg or less, 50 µg/kg or less, 20 µg/kg or less, or 10 µg/kg or less, by body weight, to treat a glioma in a subject. In certain embodiments, a polypeptide that inhibits the activity of one or more neuronal activity-regulated proteins is administered at a dose or in a dosage regimen that provides for a target tissue and/or blood concentration in the range of 1 to 1,000 nM, e.g., 5 to 900 nM, 10 to 800 nM, 20 to 750 nM, 50 to 700 nM, 100 to 600 nM, including 200 to 600 nM. In certain embodiments, an antibody that inhibits the activity of one or more neuronal activity-regulated proteins is administered at a dose or in a dosage regimen that provides for a target tissue and/or blood concentration in the range of 0.01 to 1,000 µg/ml, e.g., 0.05 to 500 µg/ml, 0.1 to 250 µg/ml, 0.5 to 100 µg/ml, 1 to 50 µg/ml, 1 to 40 µg/ml, including 1 to 25 µg/ml.

A therapeutic agent that inhibits the activity of one or more neuronal activity-regulated proteins may be administered according to any suitable dosage regimen, including, but not limited to, daily administration, weekly administration, biweekly administration, monthly administration, semiannual administration, etc.

Combination Therapy

Aspects of the present disclosure includes administering to a patient with a glioma tumor an agent that inhibits the activity of one or more neuronal activity-regulated proteins, as described above, in combination with one or more other active agents (e.g., one or more anti-cancer, or anti-neoplastic agents), and/or in combination with other therapies, such as (but not limited to) radiation therapy, blood transfusions, and/or surgery. Administration of an agent that inhibits the activity of one or more neuronal activity-regulated proteins and another active agent to a patient can occur simultaneously, sequentially or separately by the same or different routes of administration. The suitability of a particular route of administration employed for a particular active agent will depend on the active agent itself (e.g., whether it can be administered orally without decomposing prior to entering the blood stream) and the particular condition being treated.

Agents that may, for example, be administered in combination with an agent that inhibits the activity of one or more neuronal activity-regulated proteins include chemotherapeutic or anti-cancer agents (for example, including bleomycin, doxorubicin, adriamycin, 5FU, neocarcinostatin, platinum drugs such as cis-platin, taxol, methotrexate, alkylating agents and other agents that produce DNA adducts) or other agents such as antibiotics, antivirals, anti-inflammatory agents including steroids and NSAIDS, hormones, growth factors, cytokines, antibodies and kinase inhibitors. Thus, in certain embodiments, the subject methods of treating glioma include administering an agent that inhibits the activity of one or more neuronal activity-regulated proteins in combination with one or more anti-cancer agents, e.g., an anti-glioma agent, such as, but not limited to, temozolomide, carmustine (BCNU), 06-benzylguanine and cisplatin. Other specific examples of anti-cancer agents include: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginin deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; dioxamycin; diphenyl spiromustine; docetaxel; docosanol; dolasetron; doxifluridine; doxorubicin; droloxifene; dronabinol; duocarmycin; ebselen; ecomustine; edelfosine; edrecolomab; eflornithine; elemene; emitefur; epirubicin; eprinteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib, imiquimod; immunostimulant peptides; insulin-like growth factor-1 receptor inhibitor; interferon agonists; interferons; interleukins; iobenguane; iododoxorubicin; ipomeanol, iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human, chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhithxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; spienopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In certain embodiments, the subject methods of treating a glioma include administering to a patient an agent that inhibits the activity of a neuronal activity-regulated protein in conjunction or in combination with specific active agents, which may include, but are not limited to, bleomycin, bortezomib, oblimersen, remicade, docetaxel, celecoxib, melphalan, dexamethasone, steroids, gemcitabine, temozolomide, etoposide, cyclophosphamide, temodar, carboplatin, procarbazine, gliadel, tamoxifen, topotecan, methotrexate, Arisas, taxol, taxotere, tamoxifen, Gleevec, Herceptin, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin, ganciclovir, adriamycin, estramustine sodium phosphate, sulindac, and etoposide.

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the other active agent will depend on the specific agent used, the type of glioma being treated or managed, the severity and stage of disease, and the amount of the first agent that inhibits the activity of one or more neuronal activity-regulated proteins and any optional additional active agents concurrently administered to the patient.

In certain embodiments, the subject methods of treating a glioma include administering to a patient an agent that inhibits the activity of one or more neuronal activity-regulated proteins, as described above, in combination with an immunotherapy, such as a glioma tumor vaccine. Vaccine therapy for glioma is described, e.g., in Aguilar et al., 2012 Curr Treat Options Oncol. 13:347, which is incorporated herein by reference. Other suitable therapies for administering in conjunction with an agent that inhibits the activity of one or more neuronal activity-regulated proteins are described in, e.g., Reardon et al., 2006. Oncologist 11:152, which is incorporated herein by reference.

Screening Methods

Aspects of the present disclosure further include methods for identifying an agent that modulates a mitotic index of a glial cell. In certain embodiments, the methods include genetically modifying a nerve cell to express a light-activated ion channel, contacting the genetically modified nerve cell with a light beam to activate the light-activated ion channel, thereby resulting in the production of a neuronal activity-regulated protein, contacting a glial cell with the neuronal activity-regulated protein, and measuring a mitotic index of the glial cell, wherein a change in the mitotic index of the glial cell in the presence of the neuronal activity-regulated protein compared to the mitotic index in the absence of the neuronal activity-regulated protein indicates that the neuronal activity-regulated protein modulates the mitotic index of the glial cell.

Any suitable method maybe used to genetically modify a nerve cell to express a light-activated ion channel. In certain embodiments, a nerve cell is modified using a viral vector that contains a nucleic acid with a nucleotide sequence encoding a light-activated ion channel. In certain embodiments, the genetically modified nerve cell is provided by a transgenic animal, e.g., a transgenic mouse, that has been genetically modified to express a light-activated ion channel in nerve cells. Thus, in some instances, the methods include obtaining a nerve cell genetically modified to express a light-activated ion channel.

Any suitable genetically-encoded light-activated ion channels may be used to carry out the subject methods of identifying an agent that modulates a mitotic index of a glial cell. Such light-activated ion channels include, but are not limited to, channel rhodopsins obtained from *Chlamydomonas reinhardtii, Volvox carteri, Scherffelia dubia, Haloarcula (Halobacterium) salinarum*, and derivatives and chimeric combinations thereof. Suitable genetically-encoded light-activated ion channels and their use in activating a genetically modified neuron are described in, e.g., U.S. Patent Application Publication Nos: 2007/0054319, 2010/0234273, 2007/0261127, 2007/0053996, 2010/0145418, 2009/0093403, 2008/0085265, 2010/0190229, 2009/

0099038, 2011/0105998, 2011/0166632, 2011/0311489, 2013/0019325, which are incorporated herein by reference in their entirety.

Any suitable method may be used to contact the genetically modified nerve cell expressing a light-activated ion channel with a light beam to activate the light-activated ion channel. In certain embodiments, the methods for identifying an agent that modulates a mitotic index of a glial cell includes contacting a genetically modified nerve cell in vivo, a genetically modified nerve cell in a brain tissue slice, or a genetically modified dissociated neuron in vitro, with a light beam to activate the light-activated ion channel, thereby resulting in the production of a neuronal activity-regulated protein. The light beam may be provided by, e.g., a fiber optic wire connected to a light source at one end and implanted in a region of the brain in vivo at the other end, or may be part of a microscope configured to provide light to a brain tissue slice or dissociated neurons in vitro. The wavelength of light provided is a wavelength suitable to excite or activate the light-activated ion channel expressed in the genetically modified nerve cell, such as 475 nm for channelrhodopsin 2. The intensity of light provided is any intensity suitable to excite or activate the light-activated ion channel expressed in the genetically modified nerve cell. In certain embodiments, the intensity of light provided by the light source to activate the light-activated ion channel expressed in the genetically modified nerve cell is in the range of 0.1 to 100 mW, e.g., 1 to 50 mW, 2 to 30 mW, including 5 to 15 mW, measured at, e.g., the tip of the fiber optic cable. In certain embodiments, the power density of light provided by the light source to activate the light-activated ion channel expressed in the genetically modified nerve cell is in the range of 0.1 to 200 mW/cm$^2$, e.g., 1 to 100 mW/cm$^2$, 5 to 80 mW/cm$^2$, including 10 to 50 mW/cm$^2$, measured at, e.g., the tip of the fiber optic cable. In certain embodiments, the power density of light provided by the light source to activate the light-activated ion channel expressed in the genetically modified nerve cell is in the range of 0.1 to 100 mW/cm$^2$, e.g., 0.5 to 50 mW/cm$^2$, 1 to 30 mW/cm$^2$, including 2 to 10 mW/cm$^2$, measured at the tissue location of the genetically modified nerve cell. The pattern and duration of application of the light beam is sufficient to induce production of one or more neuronal activity-regulated proteins. In certain embodiments, the light beam is provided at one or more frequencies, such as 20 Hz, with a specific paradigm, e.g., 30 seconds on and 90 seconds off, repeated over a period of time, e.g., 30 minutes. Thus, in certain embodiments, the genetically modified nerve cell is contacted with a light beam with appropriate wavelength to activate a light-activated ion channel expressed on the nerve cell at a frequency ranging from 0.1 Hz to 1000 Hz, e.g., 0.5 Hz to 500 Hz, 0.5 Hz to 100 Hz, 0.5 Hz to 60 Hz, 1 Hz to 50 Hz, 2 Hz to 40 Hz, 5 Hz to 30 Hz, including 10 Hz to 25 Hz. In certain embodiments, the genetically modified nerve cell is contacted with a light beam according to a specific paradigm of exposure, such that the light beam is alternately turned on for a time period ranging from 5 seconds to 90 seconds, e.g., 10 seconds to 60 seconds, 15 seconds to 50 seconds, including 20 second to 40 seconds, and turned off for a time period ranging from 5 seconds to 5 minutes, e.g., 20 seconds to 4 minutes, 45 seconds to 3 minutes, including 1 minute to 2 minutes, to expose the genetically modified nerve cell to the light beam. In certain embodiments, the genetically modified nerve cell is contacted with a light beam with appropriate wavelength and intensity to activate a light-activated ion channel expressed on the nerve cell following a paradigm, as described above, repeated for a time period ranging from 10 seconds to 3 hours, e.g., 30 seconds to 2 hours, 1 minute to 90 minutes, 5 minutes to 60 minutes, 10 minutes to 50 minutes, including 20 minutes to 40 minutes. In certain embodiments, the genetically modified nerve cell is contacted with a light beam according to a stimulation protocol as described above for one or more days, e.g., two or more consecutive days, three or more consecutive days, 4 or more consecutive days, 5 or more consecutive days, 6 or more consecutive days, 7 or more consecutive days, 8 or more consecutive days, 9 or more consecutive days, 10 or more consecutive days, or more.

In certain embodiments, contacting the genetically modified nerve cell expressing a light-activated ion channel with a light beam results in the production of one or more neuronal activity-regulated proteins. Thus, in certain embodiments, the genetically modified nerve cell expressing a light-activated ion channel is contacted with a light beam having a wavelength, intensity, pattern and duration that are sufficient to produce one or more neuronal activity-regulated proteins.

In certain instances, the neuronal activity-regulated protein is produced by the genetically modified neuron upon activating the light-activated ion channel with a light beam. In certain instances, the neuronal activity-regulated protein is produced by cells other than the genetically modified neuron upon activating the light-activated ion channel with a light beam. Thus, in some instances, the neuronal activity-regulated protein is produced by a neuron that has direct or indirect synaptic connections to the genetically modified neuron expressing the light-activated ion channels, upon activating the light-activated ion channel with a light beam. In some instances, the neuronal activity-regulated protein is produced by glial cells that are stimulated by and/or in communication with the genetically modified neuron expressing the light-activated ion channels, upon activating the light-activated ion channel with a light beam.

Contacting a glial cell with the neuronal activity-regulated protein may be achieved by any suitable means. In certain embodiments, a culture medium surrounding the genetically modified nerve cell is obtained, i.e., is separated from the genetically modified nerve cell, and the obtained medium is contacted with the glial cell by mixing the obtained medium with the medium surrounding the glial cell. In certain embodiments, the medium surrounding the genetically modified nerve cell is frozen after being collected.

The mitotic index of the glial cell may be measured using any convenient method. In some instances, the mitotic index is measured by detecting the incorporation of bromodeoxyuriding (BrdU) or 5-ethyl-2'-deoxyuridine (EdU) into the DNA of glial cells. In certain embodiments, a change in the mitotic index of the glial cell in the presence of the neuronal activity-regulated protein compared to the mitotic index in the absence of the neuronal activity-regulated protein indicates that the neuronal activity-regulated protein modulates the mitotic index of the glial cell. In certain embodiments, the mitotic index of the glial cell exposed to one or more neuronal activity-regulated proteins is increased by 10% or more, e.g., 15% or more, 20% or more, 30% or more, 40% or more, 50% or more, 60% or more, 70% or more, 80% or more, 90% or more, or 100% or more, and in some cases is increased by 150% or less, e.g., 130% or less, 120% or less, 110% or less, 100% or less, 90% or less, 80% or less, 70% or less, 60% or less, or 50% or less, compared to a glial cell that is not exposed to the one or more neuronal activity-regulated proteins. In certain embodiments, the proliferation of the glial cell exposed to one or more neuronal activity-regulated proteins is increased by a range of 5 to 150%, e.g., 10 to 130%, 15 to 120%, 20 to 110%, 25 to 100%, 30 to 90%, including 30 to 80%, compared to a glial cell that is not exposed to the one or more neuronal activity-regulated proteins. In certain embodiments, the mitotic index of the glial cell exposed to one or more neuronal activity-regulated proteins is reduced by 10% or more, e.g., 15% or more, 20% or more, 30% or more, 40% or more, 50% or more, 60% or more, 70% or more, 80% or more, 90% or more, or 100% or more, and in some cases is reduced by 150% or less, e.g., 130% or less, 120% or less, 110% or less, 100% or less, 90% or less, 80% or less, 70% or less, 60% or less, or 50% or less, compared to a glial cell that is not exposed to the one or more neuronal activity-regulated proteins. In certain embodiments, the proliferation of the glial cell exposed to one or more neuronal activity-regulated proteins is reduced by a range of 5 to 150%, e.g., 10 to 130%, 15 to 120%, 20 to 110%, 25 to 100%, 30 to 90%, including 30 to 80%, compared to a glial cell that is not exposed to the one or more neuronal activity-regulated proteins.

In certain embodiments, the glial cell is a healthy cell, e.g., a glial cell obtained from a healthy individual or a glial cell obtained from a patient who may be suffering from a disease or disorder, but that is obtained from a healthy tissue of the patient, e.g., a tissue that is not affected by the disease or disorder. In certain embodiments, the glial cell is an abnormal cell, e.g., a glial cell obtained from a diseased tissue in a patient. In some instances, the abnormal glial cell is obtained from a patient who has been diagnosed with a condition selected from amyotrophic lateral sclerosis, Alzheimer's disease, Parkinsons's disease, Huntington's disease, or multiple sclerosis.

In certain embodiments, the glial cell is an astrocyte, oligodendrocyte, radial glia, ependymocyte, or microglia. In certain embodiments, the glial cell is a glial precursor cell, e.g., an immature glial cell, a pluripotent cell that gives rise to a glial cell, or a stem cell that can differentiate into a glial cell. In certain embodiments, the glial precursor cell is an oligodendrocyte precursor cell. Different types of glial cells and different developmental stages of glial cells may be distinguished using any suitable method. In certain embodiments, glial cell type and developmental stage may be distinguished based on expression of glial cell type- and developmental stage-specific markers. In certain embodiments, glial cell type and developmental stage may be distinguished based on cell morphology. In certain embodiments, glial cell type and developmental stage may be distinguished based on the neuroanatomical origin of the glial cell. Suitable glia markers are described in, e.g., Redwine et al., 2002 Curr Top Microbiol Immunol 265:119, which is incorporated herein by reference.

A nerve cell in accordance with embodiments of the invention may be a central or peripheral nervous system nerve cell. In certain embodiments, the nerve cell is a cortical, hippocampal, cerebellar, thalamic, amygdala, basal ganglion, spinal cord, retinal, or dorsal root ganglion neuron.

Methods of Promoting Proliferation of Glial Cells

Further aspects of the present disclosure include methods of stimulating the proliferation of one or more glial cells. In certain embodiments, the methods include contacting a glial cell with an effective amount of one or more neuronal activity-regulated proteins selected from: neuroligin-1, neuroligin-3, BDNF and brevican, or a fragment thereof. Further aspects of the subject methods include administering to a patient an effective amount of the one or more neuronal activity-regulated proteins to stimulate the proliferation of a glial cell in the patient.

Proliferation of a glial cell may be measured by a proliferation assay, such as bromodeoxyuridine (BrdU) or 5-ethynyl-2'-deoxyuridine (EdU) incorporation assay, as described above. In certain embodiments, the proliferation of a glial cell exposed to one or more neuronal activity-regulated proteins is increased by 10% or more, e.g., 15% or more, 20% or more, 30% or more, 40% or more, 50% or more, 60% or more, 70% or more, 80% or more, 90% or more, or 100% or more, and in some cases is increased by 150% or less, e.g., 130% or less, 120% or less, 110% or less, 100% or less, 90% or less, 80% or less, 70% or less, 60% or less, or 50% or less, compared to a glial cell that is not exposed to the one or more neuronal activity-regulated proteins. In certain embodiments, the proliferation of the glial cell exposed to one or more neuronal activity-regulated proteins is increased by a range of 5 to 150%, e.g., 10 to 130%, 15 to 120%, 20 to 110%, 25 to 100%, 30 to 90%, including 30 to 80%, compared to a glial cell that is not exposed to the one or more neuronal activity-regulated proteins.

In certain embodiments, the one or more neuronal activity-regulated proteins include neuroligin-1, which may be from any suitable organism, including human neuroligin-1 (Gene ID: 22871), mouse neuroligin-1 (Gene ID: 192167), rat neuroligin-1 (Gene ID: 116647), or a non-human primate neuroligin-1 (Gene ID: 470999), etc. In certain embodiments, the method of stimulating the proliferation of a glial cell includes contacting a glial cell with an effective amount of the extracellular domain of neuroligin-1. Thus, in certain embodiments, the methods of stimulating the proliferation of a glial cell include contacting a glial cell with an effective amount of a polypeptide that includes an amino acid sequence 80% or more, such as 90% or more, 95% or more, or 100% identical to a neuroligin-1 polypeptide sequence, or a fragment thereof. In certain embodiments, the methods of stimulating the proliferation of a glial cell include contacting a glial cell with an effective amount of a polypeptide that includes an amino acid sequence 80% or more, such as 90% or more, 95% or more, or 100% identical to a neuroligin-1 extracellular domain polypeptide sequence, or a fragment thereof.

In certain embodiments, the one or more neuronal activity-regulated proteins include neuroligin-3, which may be from any suitable organism, such as, but not limited to, human neuroligin-3 (Gene ID: 54413), mouse neuroligin-3 (Gene ID: 245537), rat neuroligin-3 (Gene ID: 171297), or a non-human primate neuroligin-3 (Gene ID: 473660), etc. In certain embodiments, the methods of stimulating the proliferation of a glial cell include contacting a glial cell with an effective amount of the extracellular domain of neuroligin-3. Thus in certain embodiments, the methods of stimulating the proliferation of a glial cell include contacting a glial cell with an effective amount of a protein having an amino acid sequence 80% or more, such as 90% or more, 95% or more, or 100% identical to SEQ ID NO: 1, or the extracellular domain thereof. In certain embodiments, the methods of stimulating the proliferation of a glial cell include contacting a glial cell with an effective amount of a polypeptide that includes an amino acid sequence 80% or more, such as 90% or more, 95% or more, or 100% identical to amino acids 1-678 of SEQ ID NO: 1, or a fragment thereof.

In certain embodiments, the one or more neuronal activity-regulated proteins include BDNF, which may be from any convenient subject, such as, but not limited to, human BDNF (Gene ID: 627), mouse BDNF (Gene ID: 12064), rat BDNF (Gene ID: 24225), or a non-human primate BDNF (Gene ID: 503511), etc. In certain embodiments, the methods of stimulating the proliferation of a glial cell include contacting a glial cell with an effective amount of the mature, secreted form of BDNF. Thus, in certain embodiments, the methods of stimulating the proliferation of a glial cell include contacting a glial cell with an effective amount of a polypeptide that includes an amino acid sequence 80% or more, such as 90% or more, 95% or more, or 100% identical to a mature, secreted BDNF polypeptide sequence. In certain embodiments, the methods of stimulating the proliferation of a glial cell include contacting a glial cell with an effective amount of proBDNF. Thus, in certain embodiments, the methods of stimulating the proliferation of a glial cell include contacting a glial cell with an effective amount of a polypeptide that includes an amino acid sequence 80% or more, such as 90% or more, 95% or more, or 100% identical to a proBDNF polypeptide sequence.

In certain embodiments, the one or more neuronal activity-regulated proteins include brevican, which may be from any convenient subject, such as, but not limited to, human brevican (Gene ID: 63827), mouse brevican (Gene ID: 12032), rat brevican (Gene ID: 25393), or a non-human primate brevican (Gene ID: 457401), etc. In certain embodiments, the methods of stimulating the proliferation of a glial cell include contacting a glial cell with an effective amount of a polypeptide that includes an extracellular domain of brevican. Thus, in certain embodiments, the methods of stimulating the proliferation of a glial cell include contacting a glial cell with an effective amount of a polypeptide that includes an amino acid sequence 80% or more, such as 90% or more, 95% or more, or 100% identical to a brevican polypeptide sequence, or a fragment thereof. In certain embodiments, the methods of stimulating the proliferation of a glial cell include contacting a glial cell with an effective amount of a polypeptide that includes an amino acid sequence 80% or more, such as 90% or more, 95% or more, or 100% identical to a brevican extracellular domain polypeptide sequence, or a fragment thereof.

In certain embodiments, the glial cell is a healthy cell, e.g., a glial cell obtained from a healthy individual or a glial cell obtained from a patient with a disease or disorder, but that is obtained from healthy tissue, e.g., a tissue that is not affected by the disease or disorder. In certain embodiments, the glial cell is an abnormal cell, e.g., a glial cell obtained from a diseased tissue in a patient. In some instances, an abnormal glial cell is obtained from a patient who has been diagnosed with a condition selected from glioma, amyotrophic lateral sclerosis, Alzheimer's disease, Parkinsons's disease, Huntington's disease, or multiple sclerosis.

In certain embodiments, a glial cell is an astrocyte, oligodendrocyte, radial glia, ependymocyte, or microglia. In certain embodiments, a glial cell is a glial precursor cell, e.g., an immature glial cell, a pluripotent cell that gives rise to a glial cell, or a stem cell that can differentiate into a glial cell. In certain embodiments, the glial precursor cell is an oligodendrocyte precursor cell. Different types of glial cells and different developmental stages of glial cells may be distinguished using any suitable method, as discussed above.

In certain embodiments, the contacting step of the subject methods includes contacting a glial cell in vitro with an effective amount of one or more neuronal activity-regulated proteins, e.g., neuroligin-1, neuroligin-3, BDNF and brevican. Thus, in some embodiments, the methods include obtaining an in vitro culture of a glial cell, and contacting the glial cell with an effective amount of one or more neuronal activity-regulated proteins. In certain embodiments, the glial cell is a healthy glial cell. In some embodiments, the glial cell is an abnormal glial cell, e.g., a glial cell obtained from a pathological tissue.

The amount of the one or more neuronal activity-regulated proteins that is effective to stimulate the proliferation of a glial cell in vitro, may vary, depending on a number of factors, including, but not limited to, the type of glial cell, the developmental stage of the glial cell, etc. In some instances the amount of the one or more neuronal activity-regulated proteins that is effective to stimulate the proliferation of a glial cell in vitro may range from 5 to 150 nM, e.g., 10 to 130 nM, 15 to 110 nM, 20 to 100 nM, 25 to 80 nM, 30 to 70 nM, including 40 to 60 nM in the culture medium.

In certain embodiments, the contacting step includes contacting a glial cell in vivo with an effective amount of one or more neuronal activity-regulated proteins, e.g., neuroligin-1, neuroligin-3, BDNF and brevican. Thus, in some embodiments, the method includes administering one or more neuronal activity-regulated proteins to a patient. Any convenient method may be used to administer the one or more neuronal activity-regulated proteins to the patient, as described above. In certain embodiments, the neuronal activity-regulated protein is administered intravenously, subcutaneously, orally, intracerebrally, intrathecally, etc.

The amount of the one or more neuronal activity-regulated proteins that is effective to stimulate the proliferation of a glial cell in vivo, may vary, depending on a number of factors, including, but not limited to, the route of administration, the target tissue, whether the glial cell is healthy or pathological, etc. In some instances, the dose of the one or more neuronal activity-regulated proteins that is administered to stimulate the proliferation of a glial cell in vivo may range from 1 µg/kg to 100 mg/kg body weight, e.g., 5 µg/kg to 75 mg/kg body weight, 10 µg/kg to 50 mg/kg body weight, 20 µg/kg to 25 mg/kg body weight, 50 µg/kg to 1 mg/kg body weight, including 100 µg/kg to 1 mg/kg body weight. In some instances, the dose of the one or more neuronal activity-regulated proteins that is administered to stimulate the proliferation of a glial cell in vivo is 1 µg/kg or more, e.g., 5 µg/kg or more, 10 µg/kg or more, 25 µg/kg or more, 50 µg/kg or more, 100 µg/kg or more, 200 µg/kg or more, 500 µg/kg or more, 1 mg/kg or more, 5 mg/kg or more, 10 mg/kg or more, 20 mg/kg or more, 50 mg/kg or more, 75 mg/kg or more, 100 mg/kg or more, by body weight, and in some cases the dose may be 200 mg/kg or less, e.g., 150 mg/kg or less, 100 mg/kg or less, 75 mg/kg or less, 50 mg/kg or less, 25 mg/kg or less, 10 mg/kg or less, 5 mg/kg or less, 1 mg/kg or less, 750 µg/kg or less, 500 µg/kg or less, 250 µg/kg or less, 100 µg/kg or less, 75 µg/kg or less, 50 µg/kg or less, 20 µg/kg or less, or 10 µg/kg or less, by body weight. In certain embodiments, the amount of the neuronal activity-regulated protein that is administered in any given dose or dosage regimen provides for a target tissue and/or blood concentration in the range of 5 to 150 nM, e.g., 10 to 130 nM, 15 to 110 nM, 20 to 100 nM, 25 to 80 nM, 30 to 70 nM, including 40 to 60 nM. The neuronal activity-regulated protein may be administered according to any suitable dosage regimen, including, but not limited to, daily, weekly, biweekly, monthly, semiannually, etc.

In certain embodiments, the patient has been diagnosed with a condition or disease resulting from and/or exacerbated by insufficient proliferation of one or more glial cells. For example, the patient may be diagnosed with a disease condition such as, but not limited to, multiple sclerosis, leukodystrophy, chemotherapy-induced cognitive dysfunction, Alzheimer's disease or central nervous system (CNS)

injury. Central nervous system (CNS) injuries may include traumatic brain injury, stroke, ischemic brain injury, spinal cord injury, etc. Thus in certain embodiments, the method of stimulating the proliferation of a glial cell includes administering to a patient diagnosed with one or more of multiple sclerosis, leukodystrophy, chemotherapy-induced cognitive dysfunction, Alzheimer's disease or central nervous system (CNS) injury, a therapeutically effective amount of the one or more neuronal activity-regulated proteins to stimulate the proliferation of a glial cell in the patient.

Further aspects of the present disclosure include monitoring the status of the disease condition using any suitable method, before and/or after administering to a patient a therapeutically effective amount of one or more neuronal activity-regulated proteins to stimulate the proliferation of a glial cell in the patient. In certain embodiments, the subject therapeutic methods can reduce symptoms of the disease in the patient by 10% or more, e.g., 15% or more, 20% or more, 30% or more, 40% or more, 50% or more, 60% or more, 70% or more, or 80% or more, and in some instances may reduce symptoms of the disease diagnosed in the patient by 100% or less, 90% or less, 80% or less, 70% or less, 60% or less, or 50% or less compared to the symptoms experienced or exhibited by the patient before administering the one or more neuronal activity-regulated proteins. In certain embodiments, the subject therapeutic methods can reduce symptoms of the disease in the patient by a range of 10 to 100%, 15 to 90%, 20 to 80%, 25 to 70%, 30 to 65%, including 30 to 60%, compared to the symptoms experienced or exhibited by the patient before administering the one or more neuronal activity-regulated proteins.

Kits

Also provided herein are kits that find use in practicing the subject methods, as described herein. In certain embodiments, a subject kit may include an agent, e.g., an antibody, polypeptide, small molecule, nucleic acid, etc., as described above, that inhibits the activity of one or more neuronal activity-regulated proteins for administering to a subject with a glioma tumor. In certain embodiments, a subject kit may be provided with other active agents, e.g., anti-cancer drugs, to be co-administered with the agent that inhibits activity of the one or more neuronal activity-regulated proteins.

In certain embodiments, a kit includes a neuronal activity-regulated protein, or a fragment thereof, that simulates the proliferation of a glial cell. In certain embodiments, the neuronal activity-regulated protein that simulates the proliferation of a glial cell includes neuroligin-1, neuroligin-3, BDNF and brevican, as described above. Thus, in certain embodiments, a kit includes the extracellular domain of neuroligin-1, neuroligin-3 or brevican, as described above. In certain embodiments, the neuronal activity-regulated protein may be provided in solution, e.g., in a buffer. In certain embodiments, the neuronal activity-regulated protein may be provided in dry form, e.g., as a freeze-dried or lyophilized form. In some embodiments, the kit contains a buffer suitable for dissolving or reconstituting the neuronal activity-regulated protein.

In certain embodiments, a subject kit includes instructions for carrying out the subject methods, as discussed above, which are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub-packaging) etc. In other embodiments, the instructions are present as an electronic storage data file present on a suitable computer-readable storage medium, e.g., a digital storage medium, e.g., a CD-ROM, USB drive, Flash drive, etc. The instructions may take any form, including complete instructions for how to use the element(s) of the kit, or as a website address with which instructions posted on the Internet may be accessed.

EXAMPLES

In embodiments of the present disclosure, an agent that inhibits the activity of a neuronal activity-regulated protein is administered to a subject with a glioma tumor. Examples of suitable agents are shown in Table 1.

TABLE 1

Agents that inhibit the activity of a neuronal activity-regulated protein.

| Neuronal activity-regulated protein | Agent that inhibits activity |
|---|---|
| Neuroligin-3 | An antibody that binds to the extracellular domain of neuroligin-3. |
| | A polypeptide that binds to the extracellular domain of neuroligin-3, e.g., the extracellular domain of α and β neurexins 1-3. |
| | A small molecule, e.g., wortmannin, PX-866, BKM120, temsirolimus, ridaforolimus, rapamycin and everolimus. |
| BDNF | An antibody that binds to mature BDNF or TrkB. |
| | A polypeptide that binds to mature BDNF, e.g., TrkB-Fc. |
| | A peptide mimetic of BDNF, e.g., cyclotraxin-B. |
| | A small molecule, e.g., AF38469, prinomastat, tacrolimus, bortezomib, bosutinib, cyclosporine A, AZ623, ANA12. |
| Brevican | An antibody that binds to the extracellular domain of brevican. |
| | A polypeptide that binds to the extracellular domain of brevican. |
| | A small molecule, e.g., biaryl sulfonamides. |

Example 1: Optogenetic Control of Cortical Neuronal Activity in a Patient-Derived Pediatric Cortical HGG Orthotopic Xenograft Model To test the role of neuronal activity in high-grade glioma (HGG) growth, in vivo optogenetic stimulation of the pre-motor cortex in awake, freely-behaving mice bearing patient-derived orthotopic xenografts of pediatric cortical glioblastoma was employed (FIG. 1, panels A-C). The well-characterized Thy1::ChR2 mouse model expressing the excitatory opsin channelrhodopsin-2 (ChR2) in deep layer cortical projection neurons was crossed onto an immunodeficient background (NOD-SCIDIL2R γ-chain-deficient, NSG), resulting in a mouse model (Thy1::ChR2;NSG) amenable to both in vivo optogenetic stimulation and orthotopic xenografting. ChR2-expressing neurons respond to pulses of blue (473-nm) light with millisecond precision. This allows for neuronal spiking frequency to be determined by the frequency of light pulses delivered. Expression of ChR2 does not alter the electrical properties of neurons in the absence of blue light, does not affect neuronal survival under basal conditions, and does not result in neuronal injury with blue light stimulation using standard experimental parameters. When the optical fiber is placed just below the pial surface (FIG. 1, panel B), approximately 10% of the blue light penetrates about halfway through the cortex, thus stimulating the apical dendrites of deep cortical layer projection neurons expressing ChR2. Stimulating the premotor circuit unilaterally at 20 Hz, a frequency consistent with the 10-40 Hz physiological firing rate of motor cortex projection neurons, elicits complex motor behavior (unidirectional ambulation). Optogenetic stimulation of the premotor circuit elicits a substantial increase in neural precursor and oligodendroglial precursor cell proliferation. At baseline, precursor cell proliferation is equivalent in the two genotypes. In this experimental paradigm, the microglial inflammatory response to the superficial optical fiber placement and subsequent blue light stimulation is minimal in deep cortex where the ChR2-expressing neurons reside, resolves within days and is equal in Thy1::ChR2 mice and identically-manipulated wild type (WT) controls.

FIG. 1: Neuronal Activity Promotes High-Grade Glioma Proliferation In Vivo.

A) in vivo optogenetic, high-grade glioma orthotopic xenograft model. Patient-derived pediatric cortical high-grade glioma cells (pHGG) are xenografted into the right premotor cortex of Thy1::ChR2;NSG mice or WT;NSG mice and allowed to engraft for ~10 weeks. A minimum of seven days after placement of the optical-neural interface, the premotor cortex was then stimulated with blue light pulses at 20 Hz over a 30-minute session and sacrificed after 24 hours. B) Schematic illustration of the optogenetically stimulatable premotor circuit. Thy1::ChR2+ premotor cortex (M2) neurons are shown extending branched processes in the magnified view; human glioma cells are shown as dots. Primary motor cortex (M1) projection neurons are also shown. Dark background indicates approximate region of interest for quantification. C) Confocal micrograph illustrating infiltrating pHGG cells expressing human nuclear antigen (HNA), proliferation marker Ki67 in the deep layers of the premotor cortex and subjacent corpus callosum (MBP). D) Proliferation index of human tumor cells in stimulated Thy1::ChR2 (n=7) and identically-stimulated WT (n=3) mice measured by the proportion of human tumor cells (HNA+) expressing 5-ethynyl-2'-deoxyuridine (EdU) (left graph) or Ki67 (right graph) 24 hours following in vivo optogenetic stimulation. Data are shown as mean±-SEM. *P<0.05 and **P<0.01 by unpaired two-tailed Student's t-test. E) Confocal micrograph illustrating proliferating (Ki67+) human tumor cells (HNA) in WT;NSG (left) or Thy1::ChR2;NSG mice (right) bearing a pediatric cortical high-grade glioma xenograft (SU-pcGBM2 cells). Xenografted human tumor cells (human nuclear antigen, HNA+) co-expressing Ki67 are shown (arrowhead). Error bars, SEM. Scale bars=100 μm.

To develop an orthotopic xenograft model appropriate to the juvenile premotor cortex, a tumor neurosphere culture was established from pre-treatment biopsy tissue of a frontal cortex glioblastoma (World Health Organization (WHO) grade IV) from a 15-year-old male and grown in defined medium; (this culture was designated SU-pcGBM2; clinical characteristics, genomic characterization and short tandem repeat DNA fingerprinting details of this tumor culture are described in Table shown in FIG. 16). These patient-derived pediatric cortical highgrade glioma (pHGG) cells were xenografted unilaterally into premotor (M2) cortex of juvenile Thy1::ChR2;NSG mice, resulting in diffusely infiltrating glioma cells throughout premotor cortex and the subjacent corpus callosum (FIG. 1, panel C). Wild type (no opsin present) littermate control NSG mice (WT;NSG) were identically manipulated and used for comparison. After tumors were allowed to engraft for a 2-month period, an optical-neural interface was placed ipsilateral to the xenograft. The unilateral premotor cortex was optogenetically stimulated (473-nm light at 20 Hz for cycles of 30 seconds on, 90 seconds off over a 30-minute period) in awake mice, resulting in complex motor behavior (unidirectional ambulation). The presence of the pHGG xenograft did not impede the behavioral response to optogenetically stimulated premotor circuit activity. Blue light stimulation had no behavioral effect in identically manipulated xenografted WT;NSG mice. Mice were given a single dose of EdU to label proliferating cells at the time of optogenetic manipulation and sacrificed 24 hours later to examine the acute effects of neuronal activity on glioma cell proliferation.

Neuronal Activity Promotes High-Grade Glioma Growth In Vivo

Figure 8:
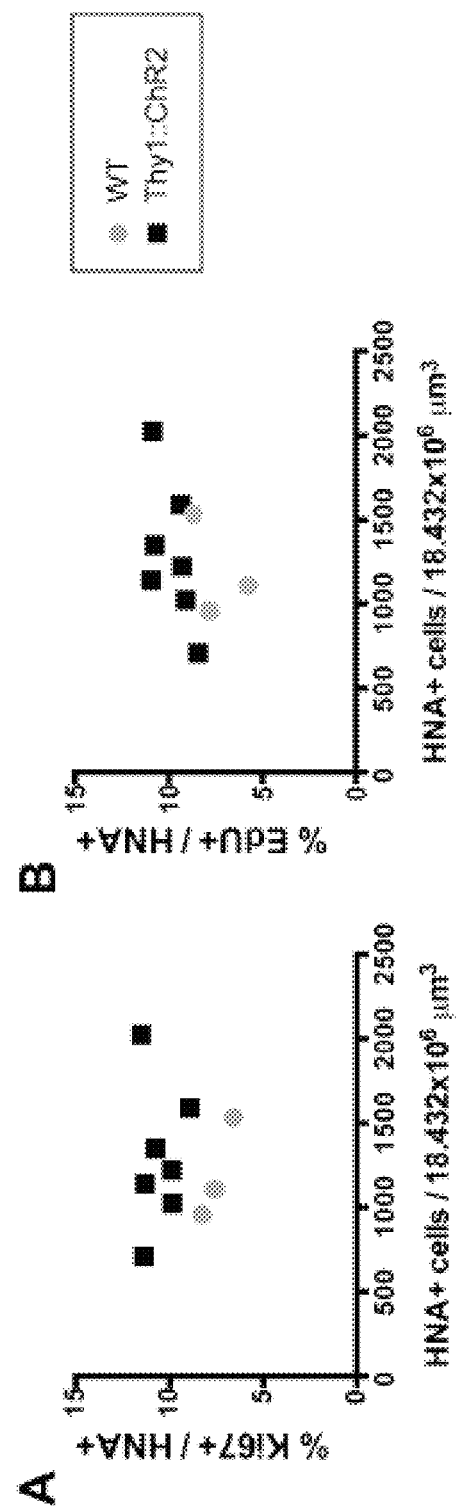
FIG. 8, Panels A-C show a collection of graphs and images that show xenograft

Tumor cell burden and distribution did not differ between groups at the time of stimulation (P=0.74; FIG. 8, panels A-B). Xenografted human tumor cells (human nuclear antigen, HNA+) co-expressing EdU indicates those glioma cells proliferating at the time of EdU administration and optogenetic stimulation, while co-expression of Ki67 indicates those cells proliferating at the time of sacrifice 24 hours following optogenetic stimulation. Within the premotor circuit (FIG. 1, panel B), an increase in the proliferation index of the human tumor cells in optogenetically stimulated Thy1::ChR2;NSG mice was found compared to that of identically-manipulated WT mice, measured both as the percent of human tumor cells co-expressing EdU (9.83%±0.38 vs 7.43%±0.86; n=7 Thy1::ChR2;NSG mice, 3 WT;NSG mice, respectively; P<0.05; FIG. 1, panel D) or co-expressing Ki67 (10.53%±0.37 vs. 7.48%±0.48; n=7 Thy1::ChR2;NSG mice, 3 WT;NSG mice, respectively; P<0.001, FIG. 1, panels D-E). This range of observed proliferation indices is consistent with expected proliferation rates in human glioma, in which typical low-grade astrocytomas exhibit a proliferation index of <5%, anaplastic astrocytomas (WHO grade III) exhibit a proliferation index of 5-15%, and glioblastomas (WHO grade IV) exhibit a proliferation index of 10-20%; increasing proliferation indices correlate inversely with prognosis, with a proliferation index above 10% generally indicating poor prognosis.

FIG. 8. Equivalent Xenografted Cell Density in the Premotor Circuits of Both Genotypes.

Given that the density of a tumor can affect its mitotic rate, the density of tumor cells within the optogenetically stimulated premotor circuit in Thy1::ChR2 (squares) and identically-manipulated WT (circles) mice was assessed to demonstrate equivalent tumor engraftment between the two genotypes. The proliferation index of xenografted human nuclear antigen+ (HNA+) tumor cells at an acute (24 hour) time point, measured by co-labeling with Ki67 (A) or EdU (B) and as also depicted in FIG. 1, is expressed as a function of tumor cell density within the total quantified area of the premotor circuit as indicated below in panel C. Note that 24 hours is earlier than the ~2 day doubling time for this patient-derived cell culture, and thus no change in cell density resulting from the activity-regulated increase in proliferation rate would be expected at this early time point. Tumor cell density did not differ between genotypes in the acute period following optogenetic stimulation, indicating well-matched tumor density in both groups. n=7 Thy1::ChR2, n=3 WT; P=0.74 by unpaired two-tailed Student's t-test. C) Schematic illustrating the location of 6 selected quantification fields for live cell counting at 400× magnification. Fields were systematically selected as depicted within the active circuit in premotor cortex and subjacent white matter, using the cingulum bundle as an anatomic landmark. Field selection and quantification was repeated for each of 3 consecutive 40-μm slices of a 1 in 6 series

Figure 2:
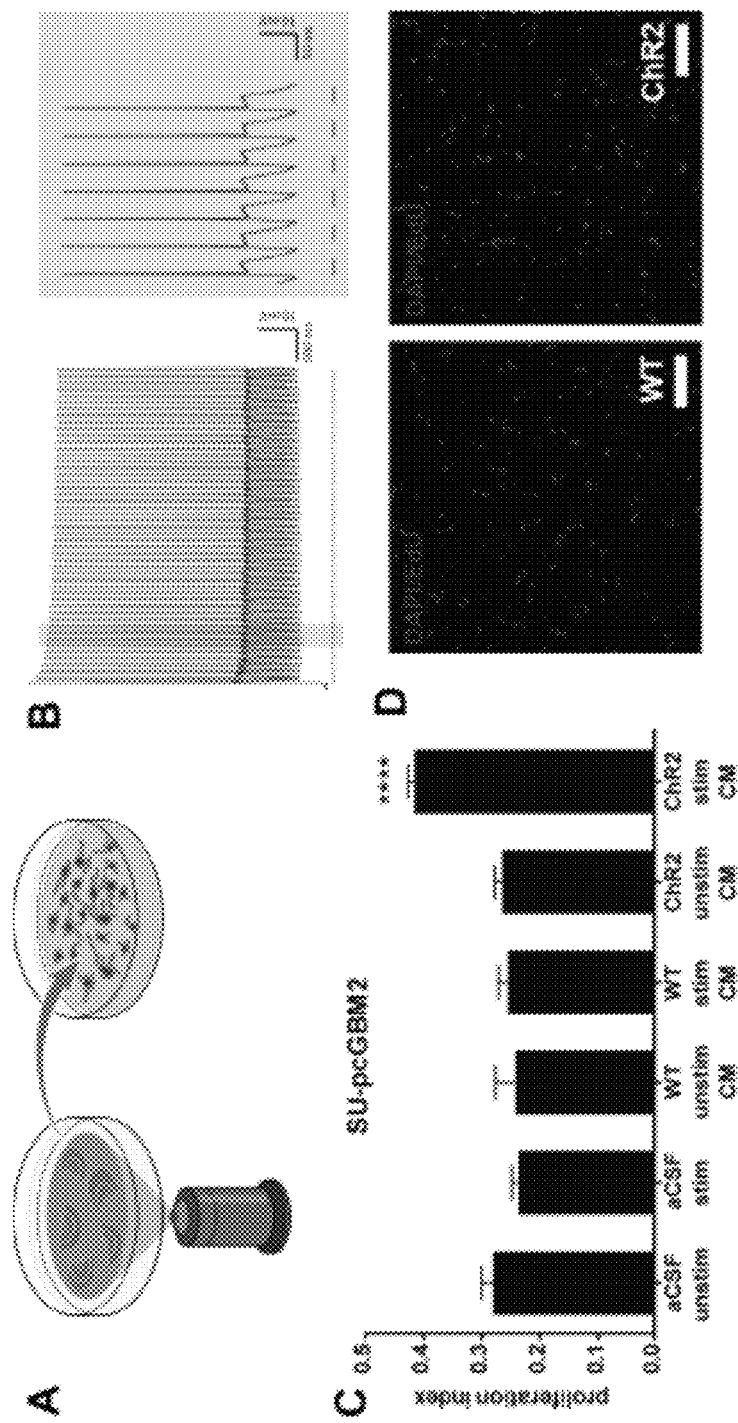
FIG. 2, Panels A-K show a collection of images and graphs that show the effect of activity-regulated secreted factors on glioma cell proliferation, according to an embodiment of the present disclosure.
Figure 9:
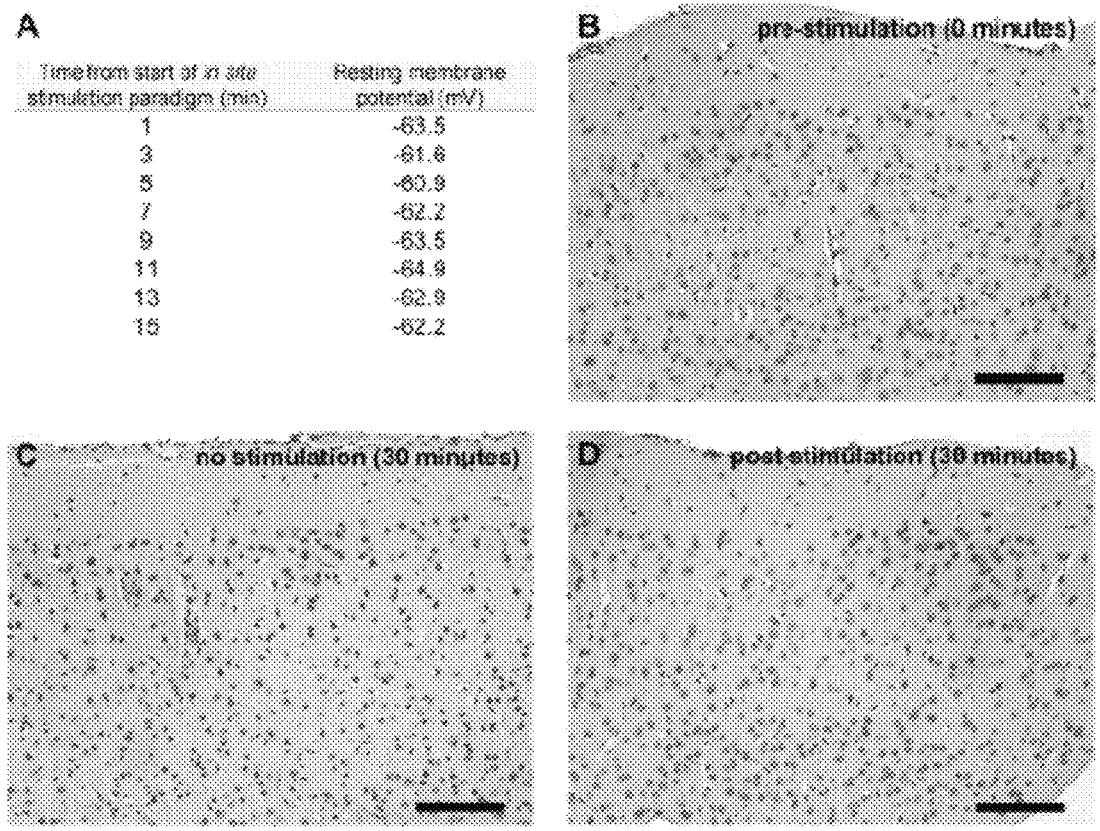
FIG. 9, Panels A-D show a collection of data and tissue images that relate to acute cortical slice health.
Figure 10:
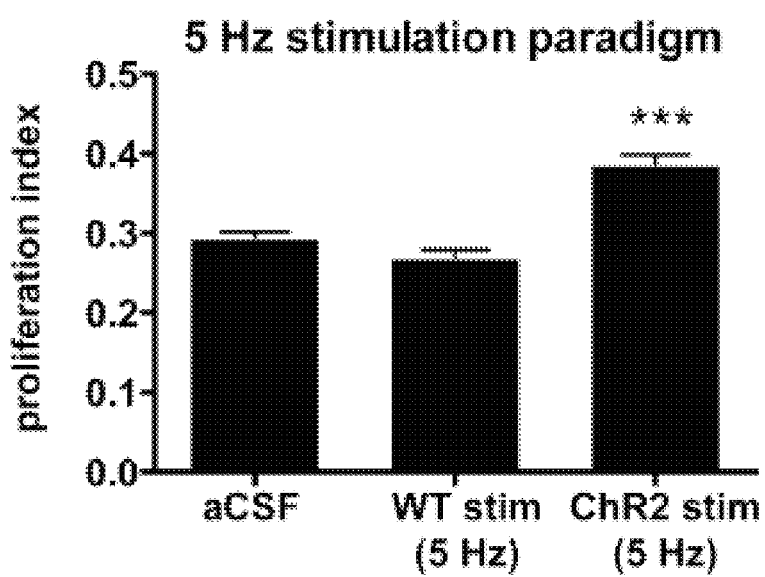
FIG. 10 is a graph that shows the effects of a 5 Hz stimulation paradigm on glioma mitogen secretion, according to an embodiment of the present disclosure.
Figure 31:
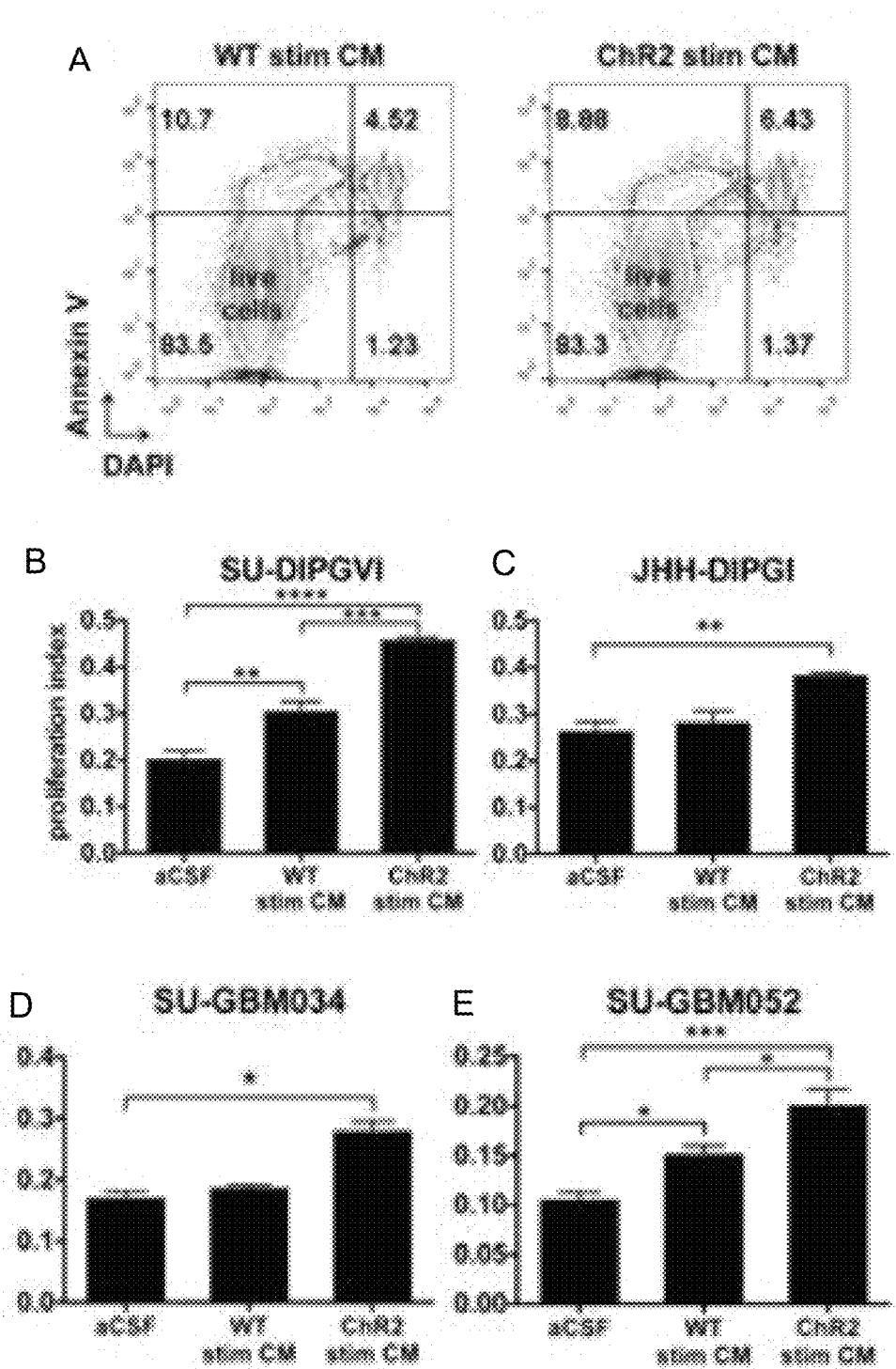
FIG. 31, Panels A-I show a collection of graphs that show the effect of activity-regulated secreted glioma mitogens from in situ optogenetic stimulation paradigm on glioma cell proliferation, according to an embodiment of the present disclosure.

Example 2: Neuronal Activity Promotes Glioma Proliferation Through Secreted Factors To determine if neurons stimulate glioma proliferation through secretion of an activity-regulated mitogen or mitogens, acute cortical slices from Thy1::ChR2 or identically-manipulated WT mice were optogenetically stimulated in situ and the conditioned medium (CM) was collected. Patient-derived HGG cultures were then exposed to the collected CM (FIG. 2, panel A). The slice stimulation paradigm mirrored the in vivo paradigm, using 473-nm light at 20 Hz for cycles of 30 seconds on, 90 seconds off over a 30-minute period. For this in situ optogenetic model, the expected neuronal firing response to blue light was validated electrophysiologically, confirming 20-Hz spike trains for 30-second periods throughout the 30-minute stimulation paradigm (FIG. 2, panel B). Maintenance of slice health throughout the stimulation paradigm was confirmed histologically and electrophysiologically (FIG. 9). Cortical slices from WT mice were identically manipulated for comparison. In parallel, CM was collected from Thy1::ChR2 and WT cortical slices that were not exposed to pulses of blue light. Patient-derived HGG cultures were then exposed to CM from stimulated (light-exposed) or unstimulated cortical slices (FIG. 2, panel A). The pHGG cell proliferation index (fraction of total cells in S-phase as detected by EdU incorporation) was determined following 24 hours of exposure to CM from the acute cortical slice conditions described above. The CM from optogenetically stimulated Thy1::ChR2 cortical slices increased the in vitro proliferation index of pHGG (SU-pcGBM2) cells in comparison to the CM from all control conditions, including identically-manipulated WT, unstimulated Thy1::ChR2, unstimulated WT cortical slices, or to blue light-exposed or non-exposed artificial cerebrospinal fluid (aCSF) medium lacking slices (n=3 wells of pHGG cells per group; F=15.49, $P<0.0001$; FIG. 2, panels C-D). Active CM did not alter glioma cell death, as assessed by Annexin V FACS analysis (FIG. 31, panel A). The secretion of activity-regulated mitogen(s) did not appear to be frequency-dependent, as the CM from Thy1::ChR2 cortical slices optogenetically stimulated at 5 Hz elicited the same proliferative effect on pHGG cells (FIG. 10).

FIG. 2: Activity-Regulated Secreted Factors Promote Glioma Cell Proliferation.

A) Schematic illustrating optogenetic stimulation of acute cortical slices and collection of conditioned media (CM). B) Electrophysiological demonstration by patch clamp recording (left; rectangle area is magnified at right) of 20-Hz neuronal firing in response to 20-Hz blue light stimulation over the course of the 30-second stimulation period in the Thy1::ChR2 cortical slice. C) Proliferation index of pHGG cells (SUpcGBM2) exposed to optogenetically stimulated or unstimulated Thy1::ChR2 cortical slice CM, blue light exposed or non-exposed WT cortical slice CM, or plain media (aCSF) (one-way analysis of variance (ANOVA), F=15.49, $P<0.0001$). D) Representative confocal micrographs illustrating increased uptake of EdU in cells exposed to CM from Thy1::ChR2 slices compared to those exposed to CM from WT slices. (E-G) CM from active slices similarly increased the proliferation index of pediatric diffuse intrinsic pontine glioma (DIPG) cells (patient-derived cell cultures SU-DIPGIV (E; one-way ANOVA, F=10.11, $P<0.01$), SU-DIPGXIII (F; F=47.92, $P<0.0001$)) and adult glioblastoma cells (patient-derived culture SU-GBM035 (G; F=17.42, $P<0.001$)). HK) Active CM increased the viable cell number measured by CellTiter-Glo, measured after 3 days of incubation with CM from blue light-stimulated Thy1::ChR2 slices or blue light-exposed WT slices in pHGG cells (SU-pcGBM2; H; one-way ANOVA, F=55.9, $P<0.0001$), DIPG cells (SU-DIPGIV (I; F=316, $P<0.0001$), SU-DIPGXIII (J; F=15.05, $P<0.01$)) and adult glioblastoma cells (SU-GBM035; K; F=85.19, $P<0.0001$). *$P<0.05$, $P<0.01$,*$P<0.001$. n.s. indicates $P>0.05$. Error bars, SEM. Scale bar=100 μm.

FIG. 9. Acute Cortical Slice Health.

The in situ optogenetic stimulation paradigm does not adversely affect slice health, as evidenced electrophysiologically and histologically. A) Constant resting membrane potential of layer V cortical projection neurons documented at regular 90 second intervals in between 30 second periods of in situ optogenetic stimulation with 473-nm light at 20 Hz. B-D) Hematoxylin and eosin (H&E) micrographs of cortical slices prior to optogenetic stimulation (B), with no optogenetic stimulation at 30 minutes (C) and after the 30-minute optogenetic stimulation paradigm (D). Histological review by a board-certified neuropathologist revealed no evidence of neuronal injury.

FIG. 10. 5 Hz Stimulation Paradigm Results in Secretion of Glioma Mitogens.

Proliferation index of pHGG cells (SU-pcGBM2) exposed to CM from Thy1::ChR2 cortical slices optogenetically stimulated at 5 Hz, CM from WT cortical slices exposed to blue light at 5 Hz or plain media (aCSF) (one-way ANOVA, F=50.38, $P<0.001$). ***$P<0.001$. Error bars, SEM.

FIG. 31. A)

Annexin V FACS analysis. After 24-hour exposure to PBS or active CM, SU-pcGBM2 cells were stained with DAPI and Annexin V-FITC to detect cell death by FACS analysis. Annexin V$^+$ cells are shown on the Y-axis and DAPI$^+$ cells on the X-axis. Live Annexin V$^-$/DAPI$^-$ cells are shown in the lower left quadrant, pre-apoptotic Annexin V$^+$/DAPI$^-$ cells are shown in the left upper quadrant and dead Annexin V$^+$/DAPI$^+$ cells are shown in the right upper quadrant of the contour plots. FACS analyses repeated in biological duplicate.

To test whether this proliferative response to neuronal activity-regulated secreted factor(s) was specific to this SU-pcGBM2 model or more broadly applicable, several additional patient-derived HGG cell cultures were tested (Table shown in FIG. 16). A similarly robust proliferative effect of CM from optogenetically stimulated cortical slices was found on patient-derived cultures of diffuse intrinsic pontine glioma, the most common form of HGG in children (DIPG; SU-DIPGIV and SU-DIPGXIII cultures; n=3 wells of cells per group for each culture; SU-DIPGIV $P<0.01$; SU-DIPGXIII $P<0.0001$) (FIG. 2, panels E-F, FIG. 31, panels B-C). To test whether adult glioblastoma is also sensitive to the effects of secreted factors regulated by neuronal activity, a patient-derived culture of adult GBM (SUGBM035) was used and a similar increase in cell proliferation in response to exposure to active CM from optogenetically stimulated cortical slices was found (n=3 wells of cells per group, $P<0.001$) (FIG. 2, panel G, FIG. 31, Panels D-E) in all but one, which was a young adult epithelioid BRAFV600E mutant GBM (SU-GBM047; FIG. 31, panel F).

FIG. 31. Panels B-F)

Effect of active CM on the proliferation of additional cell lines as measured by the EdU assay, including DIPG cultures (SU-DIPGVI, JHH-DIPGI), adult glioblastoma cultures (SU-GBM034, SUGBM052) and a culture from a young adult epithelioid glioblastoma (SU-GBM047).

Figure 26:
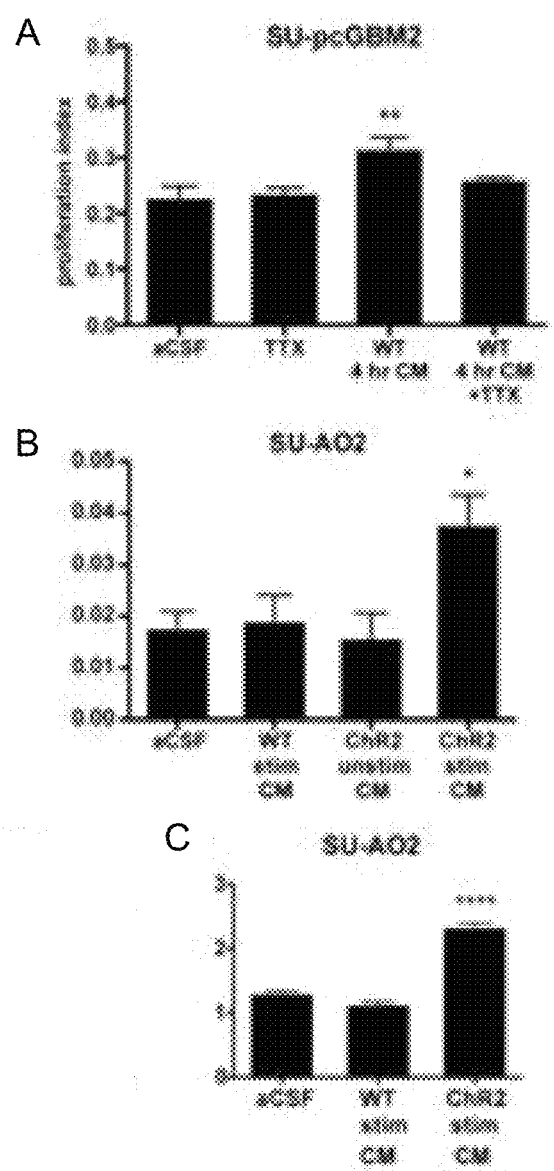
FIG. 26, Panels A-C show a collection of graphs that show the effect of activity-regulated secreted factors on glioma cell proliferation, according to an embodiment of the present disclosure.

As the mitogenic effect appears largely generalizable across distinct HGG classes, a patient-derived culture of adult anaplastic oligodendroglioma was also tested and increased cell proliferation in response to activity-regulated secreted factors was similarly observed (FIG. 26, panel B).

FIG. 26. Panel B)

Active CM increased the proliferation index of anaplastic oligodendroglioma cultures.

Consistent with spontaneous neuronal activity of WT slices, some cultures exhibit a small but significant increase in proliferation in response to light-exposed WT CM (e.g. SU-DIPGVI, proliferation index $0.21 \pm 0.01$ in aCSF vs. $0.31 \pm 0.02$ in WT CM vs. $0.46 \pm 0.002$ in active CM; FIG. 31, panels B, E).

Tumor growth is dependent on both rate of proliferation and tumor cell survival. To ascertain if the observed neuronal activity-dependent increase in tumor cell proliferation indicated an increase in overall tumor growth, the quantitative viable cell assay Cell Titer-Glo was used following a 72-hour period of exposure to cortical slice CM. Consistent with the observed effect of neuronal activity-regulated factor secretion on glioma cell proliferation, an increase in viable glioma cell number in cultures exposed to CM from stimulated Thy1::ChR2 cortical slices was found, compared to glioma cells exposed to CM from identically manipulated WT slices, or to aCSF (n=3 wells of cells per group for each culture; SU-pcGBM2 $P<0.001$; SU-DIPGIV $P<0.0001$; SU-DIPGXIIIP$<0.01$; SU-GBM035 $P<0.0001$; FIG. 2, panels H-K, FIG. 26, panel C and FIG. 31, panels G-I).

FIG. 26. Panel C)

Active CM increased the viable cell number measured by CellTiter-Glo after 72 hrs of incubation with active or light-exposed WT CM in anaplastic oligodendroglioma cells.

FIG. 31. Panels L-N)

Effect of active CM on the overall growth of additional cell lines as measured by the CellTiter-Glo assay. See also Table in FIG. 16 for the clinical and molecular characteristics of the cultured tumors. Data presented as mean±SEM. All experiments performed in three biological replicates and analyzed by one-way ANOVA with Tukey's post-hoc tests to examine pairwise differences. *$P<0.05$, $P<0.01$, *$P<0.001$, ****$P<0.0001$. n.s. indicates $P>0.05$.

Example 3: Activity-Regulated Glioma Mitogen(s) are Secreted Proteins

Figure 3:
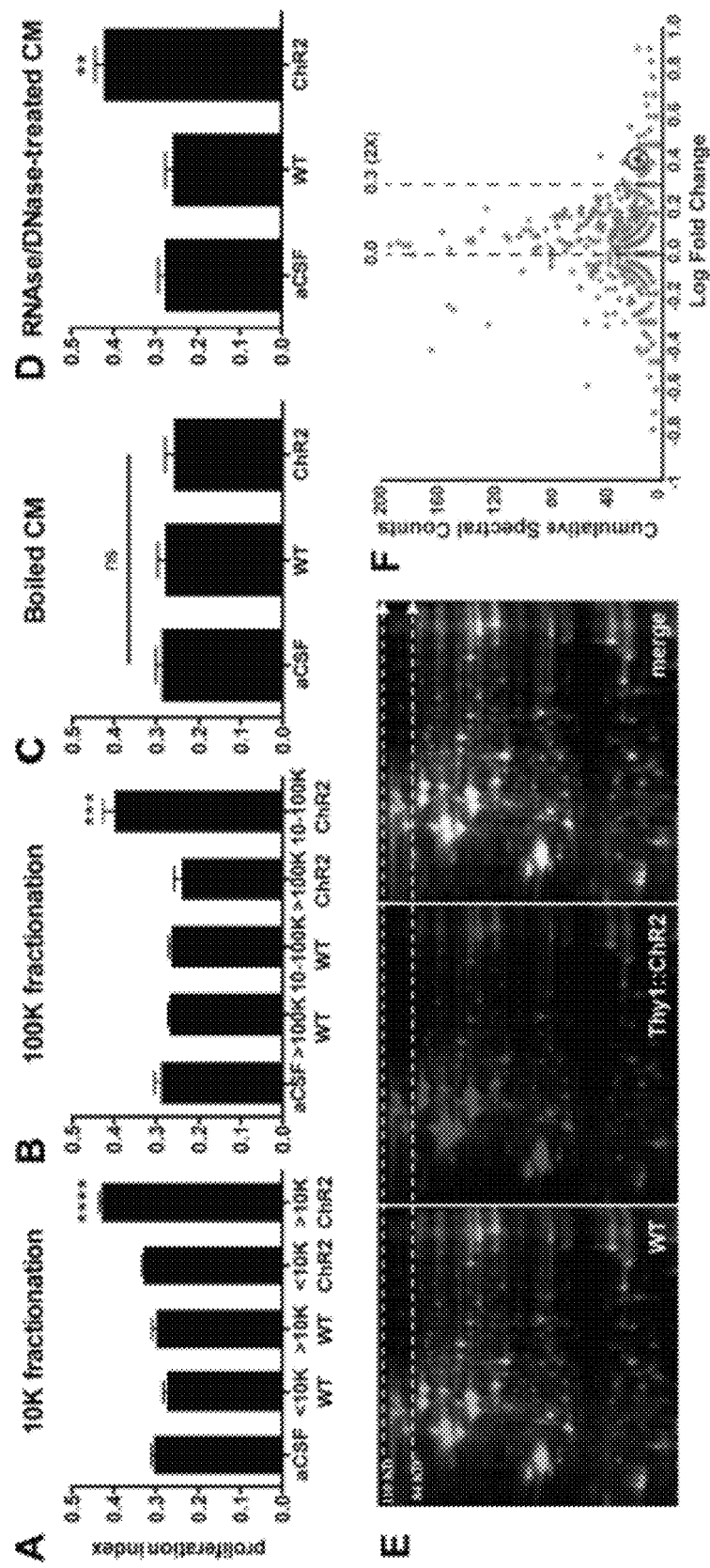
FIG. 3, Panels A-H show a collection of images and graphs that show identification of candidate neuronal activity-regulated proteins, and a peptide sequence of mouse neuroligin 3 (SEQ ID NO: 1), according to an embodiment of the present disclosure.

A series of biochemical analyses were employed to ascertain the nature of the activity-regulated mitogen(s). To determine if the mitogen(s) are small molecules or macromolecules, the CM from optogenetically stimulated Thy1::ChR2 or identically manipulated cortical slices was collected as above and fractionated by molecular size into <10 kDa and >10 kDa fractions. The in vitro proliferation assay was repeated and it was found that the >10 kDa macromolecular fraction, but not the <10 kDa fraction, increased the in vitro glioma proliferation index (FIG. 3, panel A). Subsequent fractionation indicated that the mitogen(s) were present in the <100 kDa fraction (FIG. 3, panel B). To determine the biochemical nature of the mitogen(s), stimulated cortical slice CM was heated to >100 degrees Celsius to denature proteins, resulting in loss of the proliferation-inducing capacity of the CM (FIG. 3, panel C). In contrast, treatment of the CM with RNase and DNase had no effect on the mitogenic effect of the CM on glioma cells (FIG. 3, panel D). Taken together, these data indicate that the neuronal activity-regulated secreted mitogen(s) is a protein between 10 and 100 kDa.

FIG. 3: Cortical Neuronal Activity-Regulated Glioma Mitogen(s) are Protein(s).

A, B) Fractionation of CM by molecular size reveals that the activity-regulated factors which promote glioma activity are greater than 10 kDa (A; one-way ANOVA, $F=65.04$, $P<0.0001$) and less than 100 kDa (B; $F=14.27$, $P<0.001$). C) Heating the CM to 100 degrees Celsius inactivates the mitogen(s) (one-way ANOVA, $F=0.483$, $P=0.639$). D) RNA and DNA digestion of the CM has no effect on the mitogen(s) (one-way ANOVA, $F=16.24$, $P<0.01$. $P<0.01$, *$P<0.001$, ****$P<0.0001$. n.s. indicates $P>0.05$. Error bars, SEM. E) Representative two-dimensional (2-D) gel electrophoresis separating proteins by size (vertical axis) and charge (horizontal axis). Conditioned media from blue light-exposed WT slices is left, that from blue light stimulated Thy1::ChR2 slices is the middle; merged images are shown in the right-most panel. F) Volcano plot of spectral counting data illustrating the ratio of peptides in a given protein found in media from stimulated slices versus that from unstimulated slices. Neuroligin-3 (NLGN3) is highlighted and circled. G) List of identified candidate proteins of interest emerging from proteomic analyses. H) Peptide sequence of NLGN3, found to be strongly upregulated in active slice CM across all proteomic analyses performed. Peptides shown in bold were identified by mass spectroscopy of the NLGN3 isolated from cortical slice CM. Despite the excellent coverage across the N-terminal ectodomain of the protein, no part of the C-terminal endodomain (transmembrane and intracellular domains, underlined) was identified in the isolated soluble NLGN3.

Figure 11:
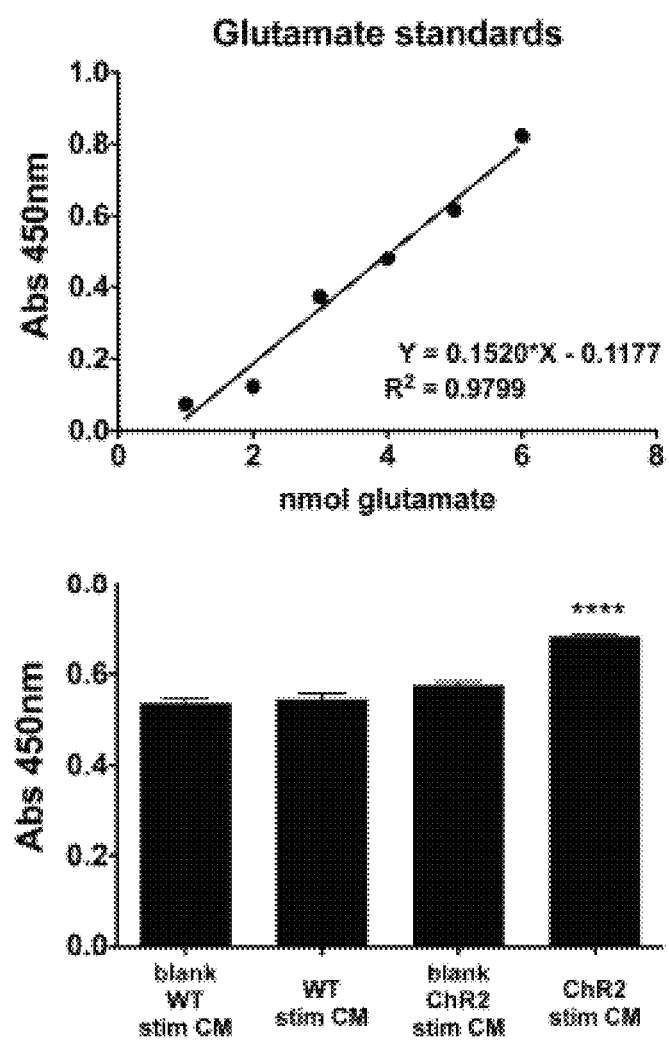
FIG. 11 is a collection of graphs that shows measurement of glutamate concentration in conditioned media.

With respect to small molecules, high levels of glutamate release into CM would not be expected in a healthy brain slice, as perisynaptic astrocytes take up released glutamate from the synaptic cleft. Indeed, there were low levels of glutamate present in CM from optogenetically stimulated slices (FIG. 11). Thus, this in situ experimental paradigm does not address the potential role of glutamate in neuronal activity-regulated glioma cell proliferation, which may play a role in vivo.

FIG. 11. Glutamate Assay.

The glutamate concentration was assayed in conditioned media from optogenetically stimulated Thy1::ChR2 cortical slices or from identically manipulated WT cortical slices. The standard curve illustrates calibration of the assay (linear regression, $R2=0.98$, $P<0.001$). Low glutamate levels were detected in the CM samples from optogenetically stimulated cortical slices (n=3 samples per condition, data presented as mean±SEM; one-way ANOVA, $F=51.39$, $P<0.0001$). ****$P<0.0001$. Error bars, SEM.

Example 4: Cortical Projection Neuronal Activity-Regulated Secretome

To identify the secreted protein(s) that increase the mitotic activity of glioma cellsin an activity-dependent manner, mass spectrometric analysis of the cortical slice CM was employed. It should be noted that neuronal activity may regulate secretion of proteins from neurons themselves, or from other cell types in response to active neurons. The CM from optogenetically stimulated Thy1::ChR2 cortical slices and from identically manipulated WT cortical slices were analyzed and compared using 2D gel electrophoresis that separated the secreted proteins by size and charge; differentially secreted protein spots were then identified by mass spectrometry. The 2D gel analyses were performed in duplicate using independent samples (FIG. 3, panel E). Quantitative mass spectrometric techniques of spectral counting and tandem mass tags (TMT) were then used with a third set of independent samples to further confirm the 2D gel results and to more precisely define the absolute and relative quantities of each protein in the CM samples. The intersection of these analyses most consistently and robustly identified neuroligin-3 (NLGN3) as the leading candidate mitogen (FIG. 3, panel F), present in the CM at a concentration of approximately 20 to 40 nM and upregulated by 2.6-fold in CM from Thy1::ChR2 cortical slices compared with CM from identically manipulated WT slices. Additional candidates identified are listed in FIG. 3, panel G.

The neuroligins are a family of synaptic proteins with a large N-terminal ecto domain, a single pass transmembrane domain, and a smaller C-terminal cytoplasmic domain that play critical roles in excitatory and inhibitory synaptic function. Neuroligin-1 (NLGN1), which plays important roles primarily at excitatory synapses similarly to NLGN3, is known to be secreted in an activity-regulated fashion by enzymatic cleavage of the N-terminal ectodomain. The 2D gel and quantitative mass spectrometric analyses across all three independent samples demonstrated excellent coverage of the NLGN3 ectodomain amino acid sequence (protein prophet score=1; Table shown in FIG. 17), identifying the protein with high confidence (FIG. 3, panel H). However, the C-terminal transmembrane and cytoplasmic domain of the protein was not detected in NLGN3 isolated from the neuronal activity-regulated CM (FIG. 3, panel H).

FIG. 17. Observed NLGN3 Peptides.

Peptide sequences detected by mass spectrometry with individual peptide prophet scores shown at right. NLGN3 was identified with high confidence (Protein Prophet score=1).

Example 5: Secreted Neuroligin-3 Promotes Glioma Cell Proliferation

Figure 27:
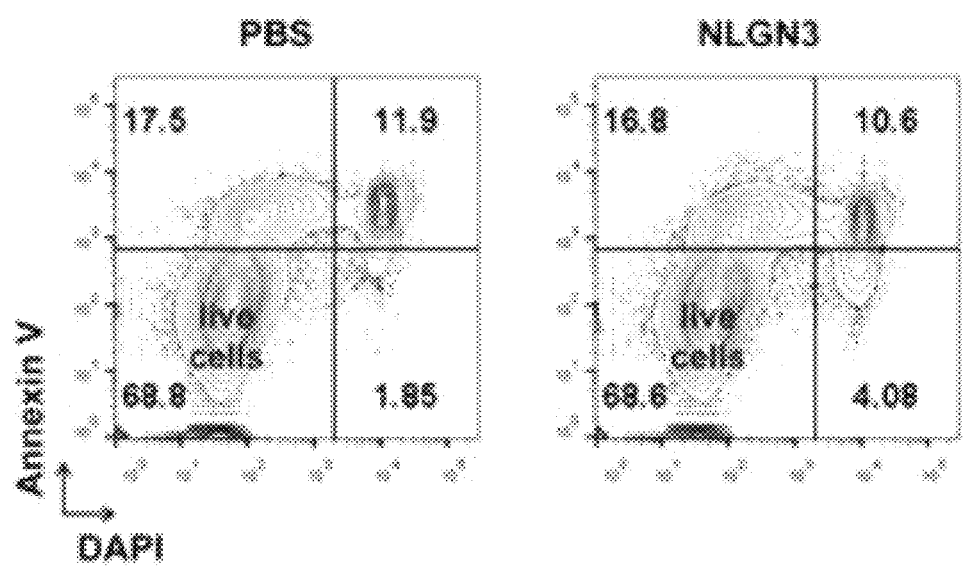
FIG. 27 is a collection of graphs that show the effect of secreted neuroligin-3 on glioma cell death.
Figure 32:
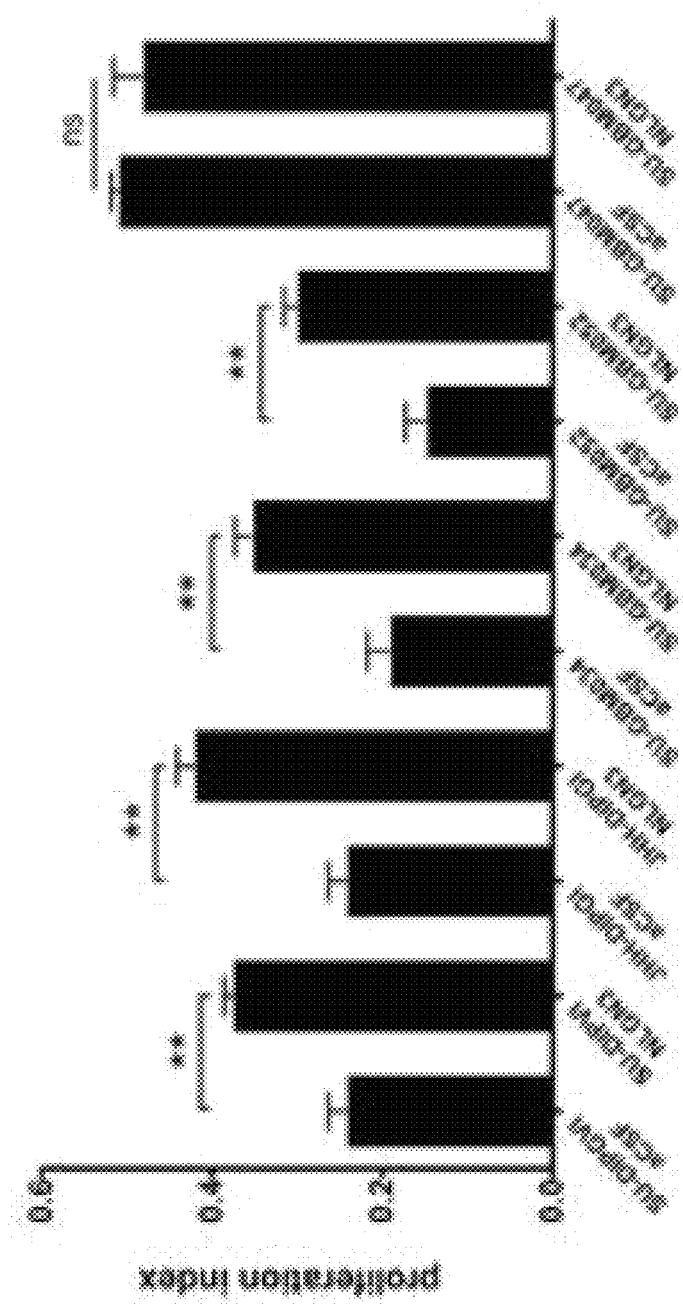
FIG. 32 is graph that shows the effect of secreted neuroligin-3 on activity-regulated proliferation of glioma, according to an embodiment of the present disclosure.

The sufficiency of NLGN3 to promote HGG cell proliferation was then tested in vitro. Recombinant full-length NLGN3 was obtained, and its identity and purity confirmed by mass spectrometry (FIG. 12). In contrast to the NLGN3 present in the CM, mass spectrometric analysis of recombinant full-length NLGN3 did identify peptide sequences within the C-terminal tail. Assaying the in vitro pHGG proliferation index following 24 hours of exposure to recombinant NLGN3 at various concentrations, it was found that NLGN3 promotes proliferation, matching the mitogenic effect of active CM at low nanomolar concentrations (FIG. 4, panel A), with no change in cell death as measured by Annexin V FACS analysis (FIG. 27). NLGN3 promoted a significant increase in the proliferation index of each patient-derived cell line tested, including pediatric cortical glioblastoma, DIPG, and adult glioblastoma, with the exception of the epithelioid GBM culture (FIG. 4, panel B and FIG. 32).

Figure 4:
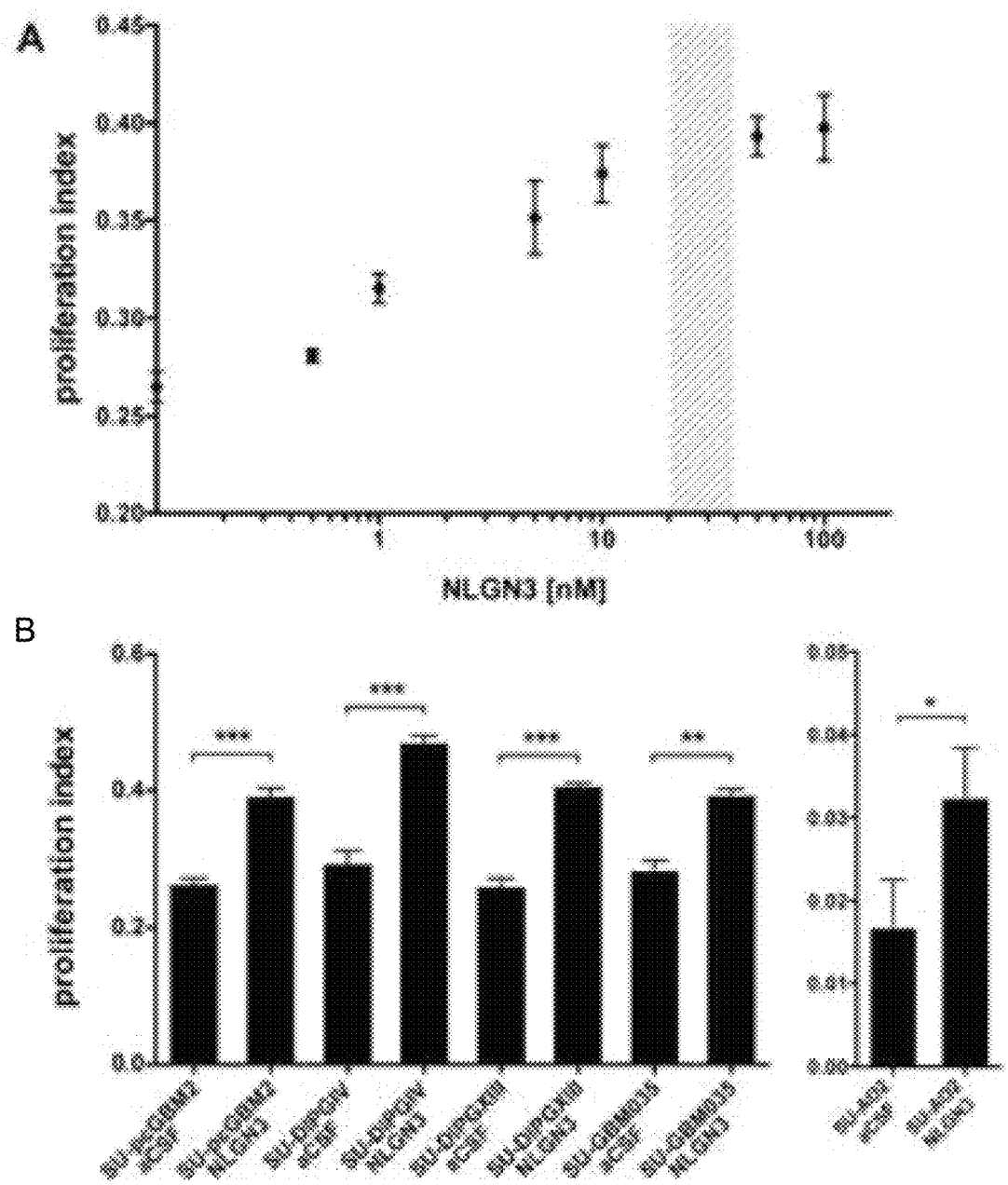
FIG. 4, Panels A-C show a collection of graphs that show the effect of secreted neuroligin-3 on activity-regulated proliferation of glioma, according to an embodiment of the present disclosure.

FIG. 4: Secreted Neuroligin-3 Mediates Neuronal Activity-Regulated Glioma Proliferation.

A) Recombinant NLGN3 promotes pediatric high-grade glioma cell proliferation in a dose-dependent manner, plateauing at a low nanomolar concentration. 7-point dose curve plots proliferation index as measured by EdU$^+$/DAPI$^+$ staining at 24 hours following exposure of SU-pcGBM2 cells to NLGN3 at concentrations ranging from 0-100 nM. Shaded region indicates concentration present in active CM. B) Proliferation indices of various HGG patient-derived cell lines exposed to 50 nM NLGN3 for 24 hours. Data are shown as mean±SEM. ***P<0.001 by unpaired two-tailed Student's t-tests. C) Neurexin-1β, which binds to NLGN3 with high affinity, abrogates the mitogenic effect of active slice CM. Neurexin-1β (NRXN; 500 nM) alone has no effect on proliferation, nor does it affect pHGG cell proliferation when added to conditioned media from WT slices (one-way ANOVA, F=0.136, P=0.936). Addition of neurexin-1β (500 nM) effectively blocks the proliferation-promoting effect of recombinant NLGN3 (50 nM) and abrogates the mitogenic effect of active slice CM (data shown as mean± SEM; *P<0.05, ***P<0.001 by unpaired two-tailed Student's t-tests.) Error bars, SEM.

FIG. 27: Panel B)

After 24-hr exposure to PBS or NLGN3 (50 nM), SU-pcGBM2 cells were stained with DAPI (X-axis) and Annexin V-FITC (Y-axis) to detect cell death by FACS analysis, performed in biological duplicate. Live Annexin V$^-$/DAPI$^-$ cells shown in lower left quadrant of contour plots; pre-apoptotic Annexin V$^+$/DAPI$^-$ cells, left upper quadrant; dead Annexin V$^+$/DAPI$^+$ cells, right upper quadrant. No increase in cell death was seen with NLGN3 exposure.

FIG. 32. Activity-Regulated Secretion of Glioma Mitogens. A)

NLGN3 promotes proliferation in a broad range of HGG cultures. Additional cell lines, including DIPG (SU-DIPGVI, JHH-DIPGI), adult glioblastoma (SU-GBM034, SUGBM052) and epithelioid BRAFV600E glioblastoma (SU-GBM047) were exposed to 50 nM recombinant NLGN3. After 24-hour exposure, all cell lines were evaluated with the EdU assay to determine proliferation index (unpaired two-tailed Student's t-tests).

FIG. 12. Mass Spectrometry of Full-Length Recombinant NLGN3.

Mass spectrometric analysis confirms the identity of the full-length recombinant NLGN3. Identified peptide sequences are shown in bold. Note identified peptide sequences in the C-terminal endodomain region (transmembrane domain+intracellular domain) of the recombinant protein (underlined), not observed in the secreted form of the protein found in optogenetically stimulated cortical slice conditioned media.

Figure 13:
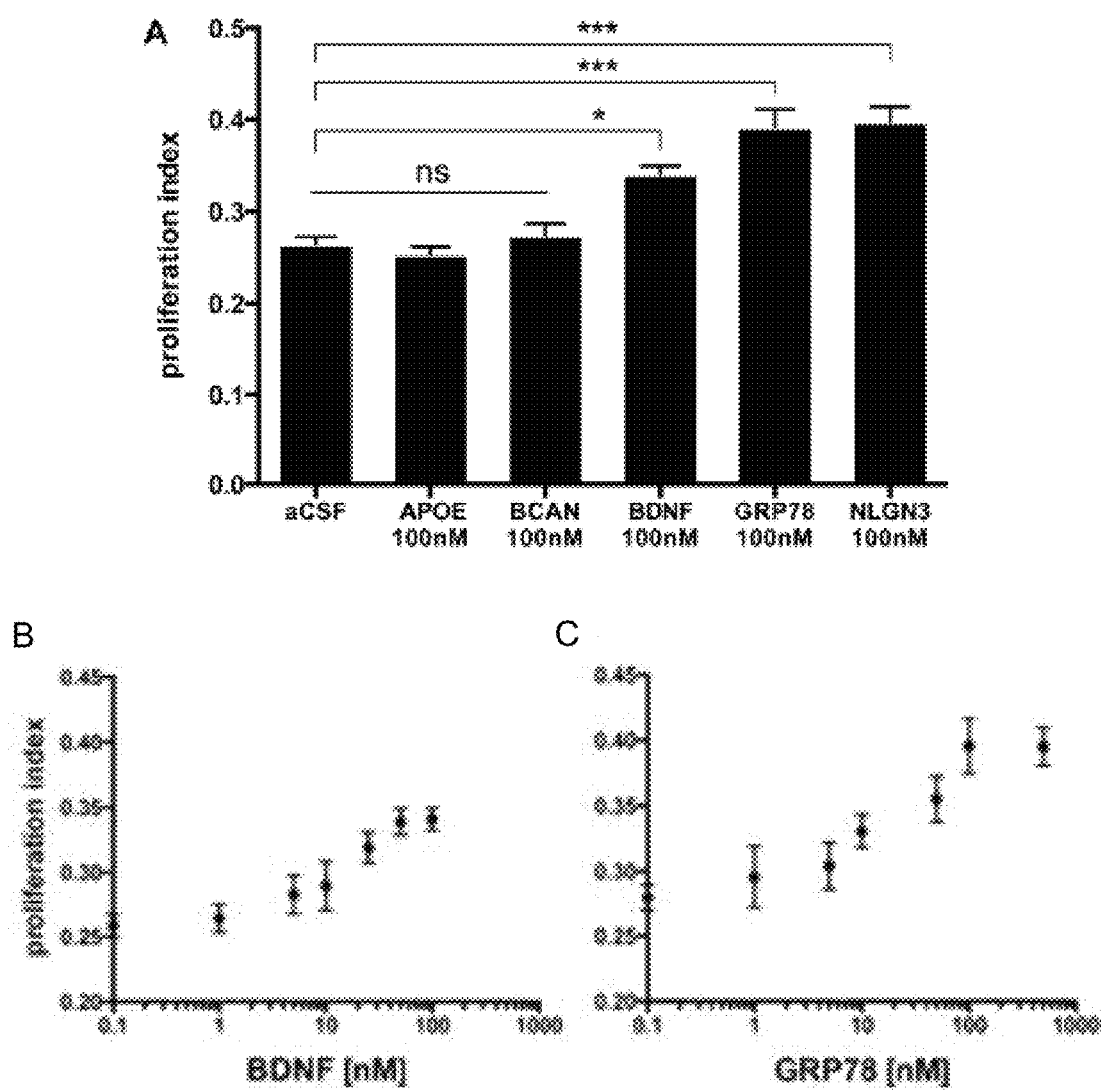
FIG. 13, Panels A-C show a collection of graphs that show testing of neuronal activity-regulated secreted candidate mitogens, according to an embodiment of the present disclosure.

Additional candidates identified in the proteomic analyses above were also screened in pHGG cells in vitro. Of these candidates, brain-derived neurotrophic factor (BDNF) and the known glioma mitogen 78-kDa glucose-regulated protein (GRP78) promoted the proliferation of pHGG cells, but less potently than NLGN3 (FIG. 13, panels A-C). Additional candidates tested did not elicit an effect on pHGG cell proliferation, even at high nanomolar concentrations (FIG. 13, panel A). Thus, NLGN3 emerged from these analyses as an unexpected cortical neuronal activity-regulated glioma mitogen, together with known mitogens BDNF and GRP78.

Figure 33:
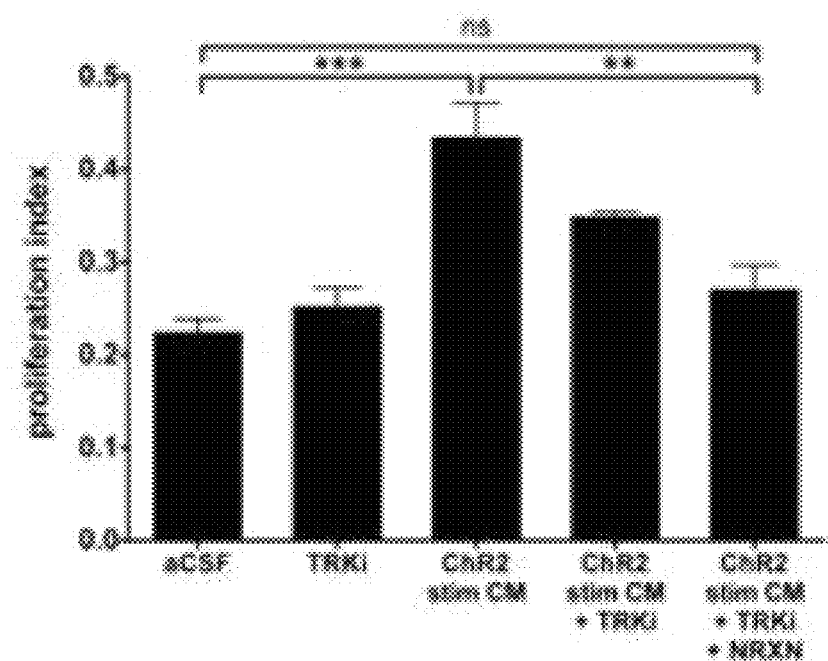
FIG. 33 is a graph that shows the effect of inhibiting TrkB and/or neuroligin-3 on proliferation of glioma, according to an embodiment of the present disclosure.

To test the necessity of NLGN3 for the proliferation-promoting effect of activity regulated CM, the highly specific and avid binding of neurexin-1β (NRXN1β) to NLGN3 was utilized to deplete NLGN3 from the cortical slice CM. Confirming that NRXN1β in this setting does deplete the available NLGN3, the addition of NRXN1β completely abrogated the mitogenic effect of exposure to recombinant NLGN3 (proliferation index 0.40±0.01 in pHGG cells exposed to 50 nM NLGN3 vs. 0.28±0.01 in cells exposed to 50 nM NLGN3+500 nM NRXN1β; n=3 wells of pHGG cells per group; P<0.001; FIG. 4, panel C). The addition of NRXN1β alone to aCSF or to CM from WT cortical slices had no effect on proliferation index (n=3 wells per group; F=0.136; FIG. 4, panel C). However, the addition of NRXN1β significantly decreased the mitogenic effect of active slice CM on pHGG cells (proliferation index 0.40±0.01 in cells exposed to Thy1::ChR2 CM vs. 0.34±0.01 with exposure to Thy1::ChR2 CM+NRXN1β; n=3 wells of pHGG cells per group; P<0.05; FIG. 4, panel C), indicating that secreted NLGN3 is necessary for the full mitogenic effect of cortical neuronal activity on glioma cells. The incomplete abrogation of the mitogenic effect of the CM with addition of NRXN1β is consistent with our finding of additional activity-regulated glioma mitogens GRP78 and BDNF present in the CM (FIG. 13). Indeed, pharmacological inhibition of the BDNF receptor TRKB in combination with NRXN1β completely abrogates the proliferative effect of active CM (FIG. 33).

FIG. 33.

BDNF receptor TRKB inhibition. The TRKB inhibitor ANA12 was used to determine the magnitude of BDNF contribution to the proliferative effect of the active CM. To that end, SU-pcGBM2 cells were exposed to active CM, 100 nM TRK inhibitor ANA12 (TRKi), and 500 nM NRXN, alone or in combination. Proliferation was evaluated using the EdU assay and analyzed using a oneway ANOVA with Tukey's post-hoc tests to examine pairwise differences. All experiments were performed in three biological replicates. Data presented as mean±SEM. *P<0.05; P<0.01; *P<0.001; n.s. indicates P>0.05.

FIG. 13. Neuronal Activity-Regulated Secreted Candidate Mitogen Testing.

A) Activity-regulated candidate mitogens identified by proteomic analyses of cortical slice conditioned media were tested. Pediatric HGG cells (SU-pcGBM2) were exposed to recombinant versions of the candidate proteins at 100 nM concentration for 24 hours, and proliferation index was determined as the fraction of DAPI+ cells co-expressing EdU. Of these, NLGN3, BDNF and GRP78 were found to promote glioma cell proliferation relative to aCSF control (n=3 wells of pHGG cells per group. One-way ANOVA, F=25.57, P<0.0001. Tukey's post-hoc tests to examine pairwise differences were as follows: NLGN3 vs. aCSF P<0.001; BDNF vs. aCSF P<0.001; GRP78 vs. aCSF P<0.05). Proliferation index did not differ among pHGG cells treated with aCSF, ApoE, or brevican (one-way ANOVA, F=1.098, P=0.392). *P<0.05, **P<0.001, n.s. denotes P>0.05. Error bars, SEM. B-C) 7-point dose curve plots proliferation index measured at 24 hours following exposure of SU-pcGBM2 cells to recombinant BDNF (B) or GRP78 (c) at concentrations ranging from 0-100 nM.

Figure 5:
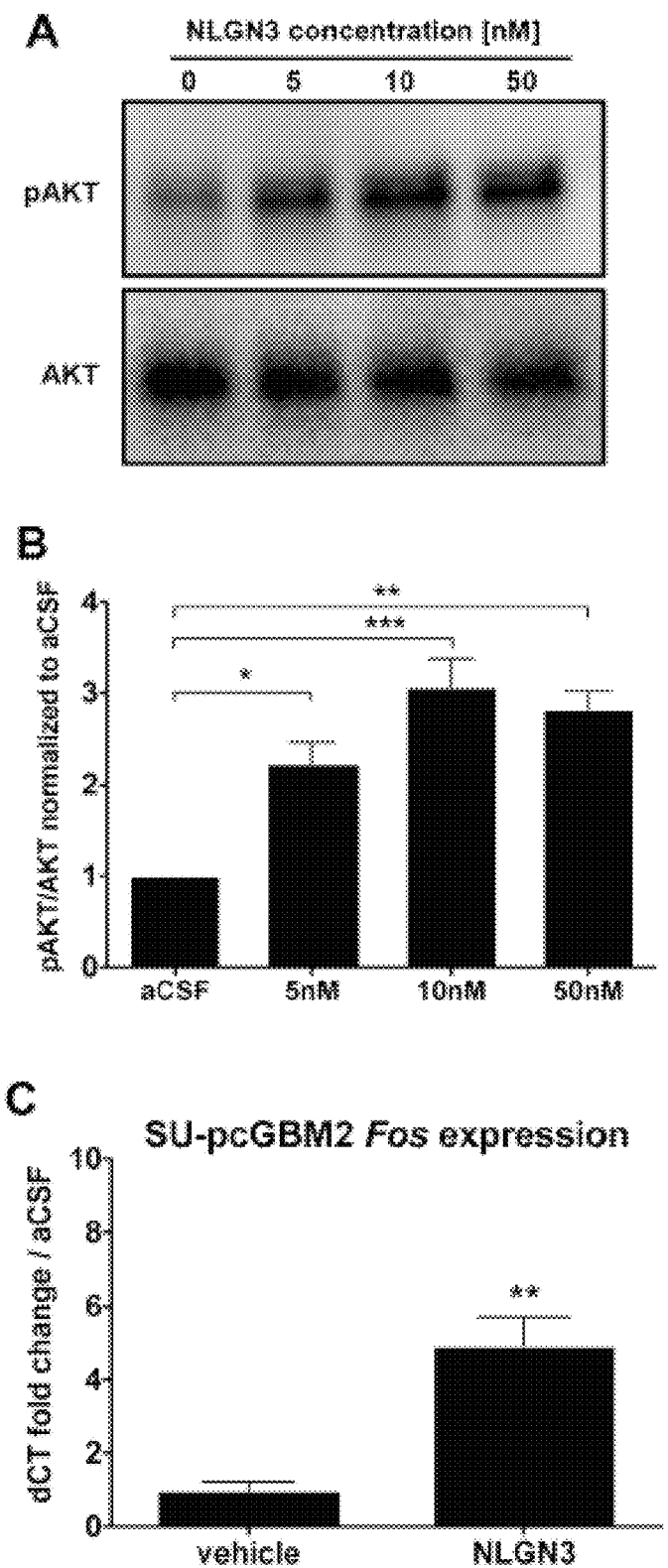
FIG. 5, Panels A-G show a collection of images and graphs that show the effect of secreted neuroligin-3 on recruitment of phosphatidylinositol-4,5-bisphosphate 3-kinase (PI3K) and expression of NLGN3.
Figure 34:
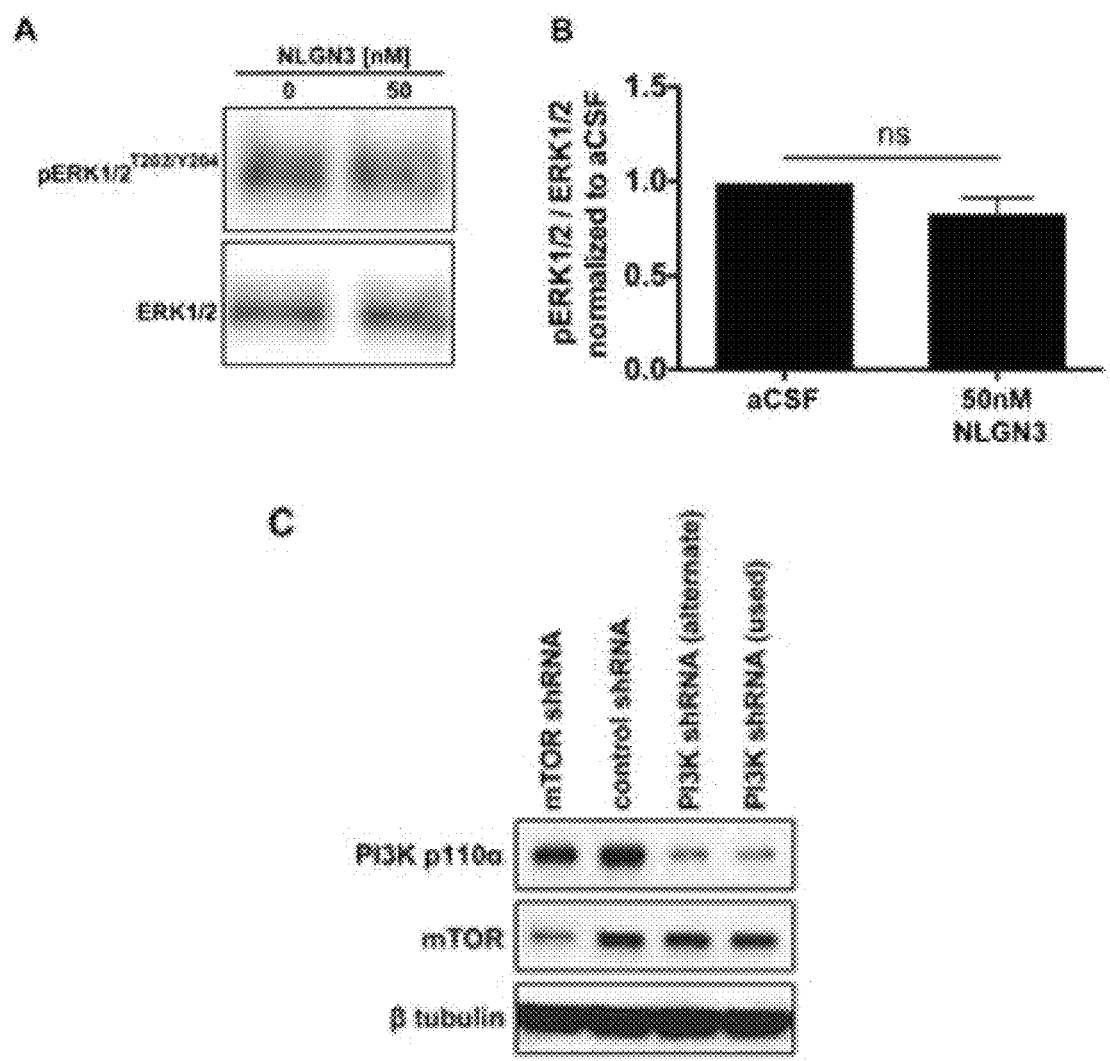
FIG. 34, Panels A-E show a collection of graphs and images that show the effect of secreted neuroligin-3 on MAPK pathway and validation of PI3K-mTOR pathway knockdown.

Example 6: Downstream Mechanisms of Neuronal Activity-Regulated Glioma Proliferation To begin to understand the intracellular signaling mechanisms by which neuronal activity promotes the proliferation of HGG cells, RNA-sequencing was performed to define the transcriptome of pHGG cells exposed to the CM from optogenetically stimulated Thy1::ChR2 cortical slices in comparison to cells exposed to CM from identically manipulated WT slices. Pathway analysis of this limited set of differentially regulated genes suggested the potential involvement of the PI3K pathway (Table shown in FIG. 18). Thus the degree to which the PI3K pathway is recruited by exposure to NLGN3 was examined, using Western blot analysis of phospho-AKT as an indicator of PI3K pathway activity. pHGG cells exposed to recombinant NLGN3 exhibit increased phospho-AKT levels relative to total AKT in a dose-dependent manner (FIG. 5, panels A-B; n=3 independent samples; P<0.001). Upregulation of the immediate early gene and proto-oncogene Fos, whose expression can be downstream of PI3K signaling amongst other signaling pathways, was also observed by RNA-seq following exposure to active CM (Table shown in FIG. 18). As expected, pHGG cell exposure to NLGN3 resulted in upregulation of Fos gene expression, determined by qPCR (n=3 independent samples, P<0.01; FIG. 5, panel C). Fos expression can be downstream of pathways that include PI3K-mTOR signaling or MAPK signaling. However, Western blot analysis did not reveal upregulation of phospho-ERK1/2$^{T202/Y204}$ as an indicator of MAPK pathway activation following NLGN3 exposure (FIG. 34, panels A, B). Neuronal activity-regulated secretion of NLGN3 thus recruits the PI3K pathway to promote glioma cell proliferation.

FIG. 18. RNA-Sequencing Reveals Genes Differentially Expressed in SU-pcGBM2 Cells Following Exposure to Activity-Regulated Secreted Factors.

pHGG cells (SU-pcGBM2) were exposed to conditioned media from optogenetically stimulated Thy1::ChR2 cortical slices or from identically manipulated WT control slices and differential gene expression was gleaned using RNA-seq.

FIG. 5: Secreted Neuroligin-3 Recruits the PI3K Pathway and Promotes Feedforward Expression of NLGN3.

A) Signaling through the PI3K pathway increases in response to NLGN3. Representative Western blot illustrating increased phosphorylation of AKT in response to various concentrations of NLGN3 ranging from 0-50 nM. p-AKT is shown in top panel; total AKT is shown in the bottom panel. B) Quantification of the increased fold change of pAKT/AKT ratio in response to NLGN3 at various doses (oneway ANOVA, F=17.99, P<001; data shown as mean± SEM; *P<0.05, P<0.01, *P<0.001 by Tukey's post-hoc tests to further examine pairwise comparisons). Fold change is normalized to blank media (aCSF). (C) Fos mRNA expression increases after 1 hour exposure to vehicle or to 50 nM NLGN3 (data shown as mean±SEM; **P<0.01 by unpaired two-tailed Student's t-test). D) NLGN3 mRNA expression increases after 12 hour exposure to 50 nM NLGN3 vs. vehicle in SU-DIPGXIII cells. Data shown as mean±SEM; *P<0.05 by unpaired two-tailed Student's t-test. E) NLGN3 mRNA expression in SU-pcGBM2 cells after 12 hour exposure to vehicle, to 50 nM NLGN3, to 500 nM BKM120, or to 50 nM NLGN3+500 nM BKM120 (one-way ANOVA, F=18.8, P<0.001). F) NLGN3 mRNA expression in SU-pcGBM2 cells does not change after 12 hour exposure to 50 nM EGF vs. vehicle (P=0.781; n.s. indicates P>0.05 by unpaired two-tailed Student's t-test). All qPCR data (C-F) are normalized to vehicle-treated samples and represent fold change of the delta CT in reference to β-actin. G) Western blot analysis illustrating NLGN3 protein expression. Lane 1 and 2 represent control lanes loaded with 10 nM and 25 nM recombinant NLGN3, respectively. Lane 3 represents lysate from SU-pcGBM2 cells exposed to aCSF, and Lane 4 represents lysate from SUpcGBM2 cells exposed to 50 nM recombinant NLGN3. Error bars, SEM.

FIG. 34. Evaluation of MAPK Pathway.

A) Western blot analysis of phosphorylated ERK1/2 (Thr202/Tyr204) and total ERK1/2 in SU-pcBGM2 cells after exposure to either aCSF or NLGN3 (50 nM). Representative Western blot shows phosphoERK1/2$^{T202/Y204}$ top panel; total ERK1/2 bottom panel. B) Phosphorylated ERK1/2 levels were normalized to total ERK1/2 levels. No significant change in ERK1/2 phosphorylation (Thr202/Tyr204) was seen with exposure to NLGN3 (n=3 biological replicates; unpaired two-tailed Student's t-test). All experiments performed in three biological replicates and analyzed by unpaired two-way Student's t-test. Data presented as mean±SEM. P<0.01, *P<0.001. n.s. indicates P>0.05.

Figure 29:
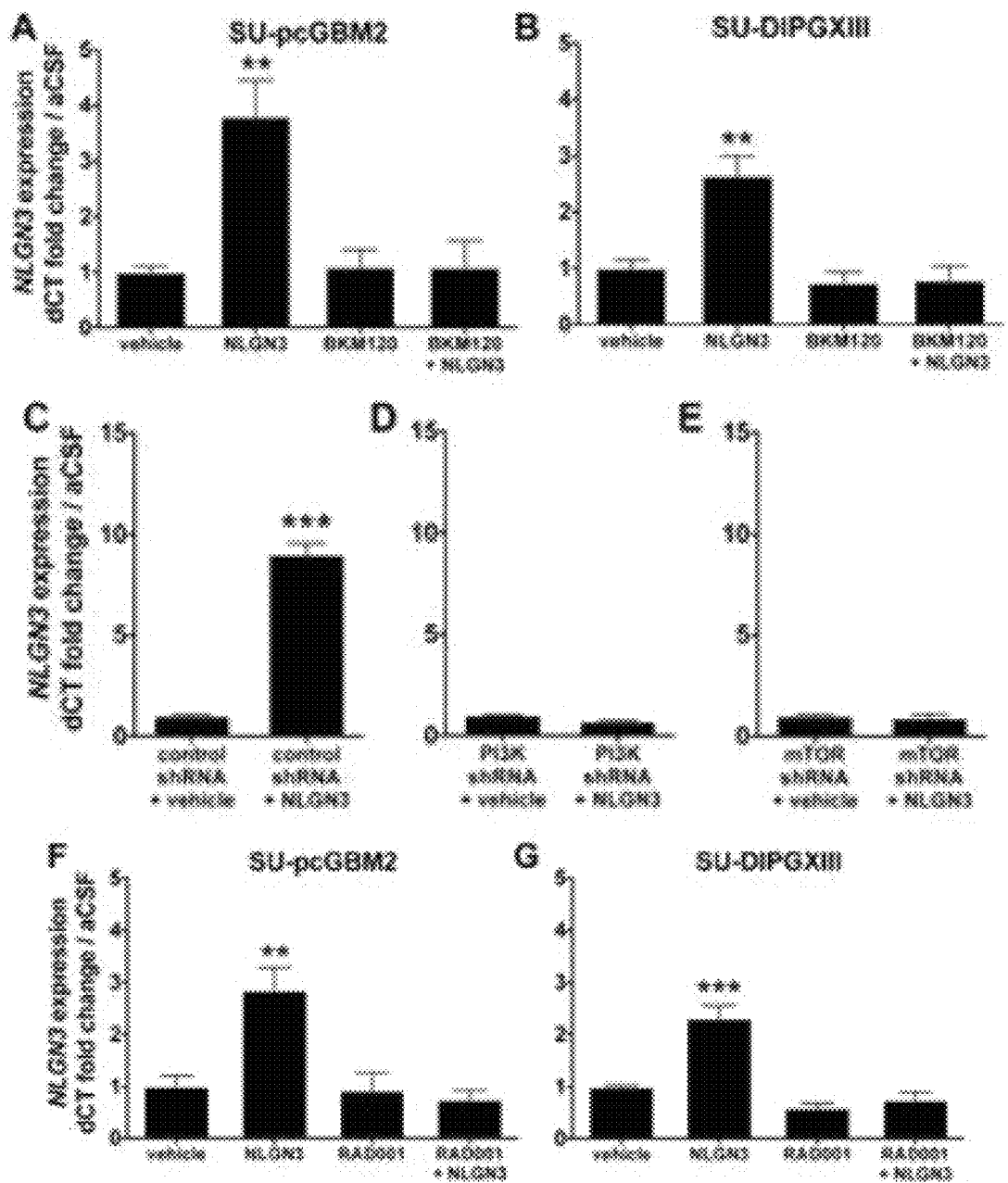
FIG. 29, Panels A-G show a collection of graphs that show the effect of secreted neuroligin-3 on recruitment of the PI3K-mammalian target of rapamycin (mTOR) pathway and expression of NLGN3.
Figure 35:
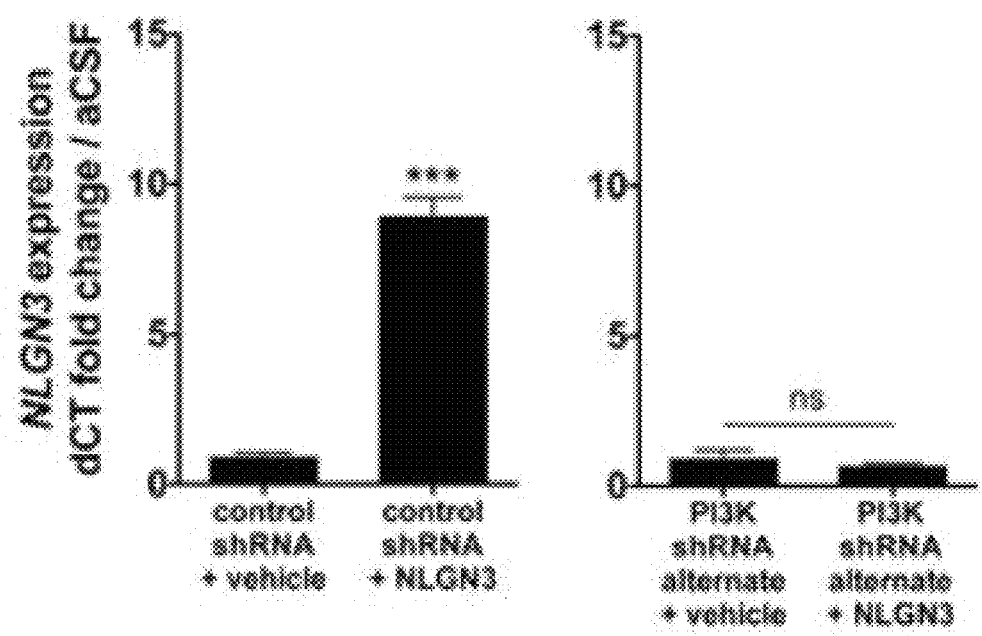
FIG. 35 is a collection of graphs that show the effect of PI3K knockdown on NLGN3 expression.

Surprisingly, upregulated expression of the neuroligin-3 gene (NLGN3) in pHGG cells exposed to active CM was also found (Table shown in FIG. 18), suggesting a positive feed-forward effect on glioma cell NLGN3 expression. To determine if soluble NLGN3 exposure induces its own expression, qPCR was performed in pHGG cells exposed to recombinant NLGN3 protein and found that this elicits an increase in glioma cell NLGN3 gene expression, tested in both DIPG cells (n=3 independent samples, P<0.05; FIGS. 5D and 29B) and pediatric cortical HGG cells (n=3 independent samples, F=18.80, P<0.001; FIGS. 5E and 29A). The role of PI3K pathway activity in the positive feed-forward effect on glioma cell NLGN3 gene expression was investigated using the specific PI3K inhibitor BKM120 or shRNA-mediated PI3K knockdown, both of which blocked the soluble NLGN3-induced increase in NLGN3 gene expression (FIG. 29, panels A-D, FIG. 35). While PI3K inhibition had no effect on NLGN3 expression in the absence of soluble NLGN3 exposure, treatment with 500 nM BKM120 blocked the soluble NLGN3-induced increase in NLGN3 gene expression (FIG. 5, panel E and FIG. 29, panels A-D). Similarly, the mTOR inhibitor RAD001 or shRNA-mediated mTOR knockdown prevented the feed-forward effect of NLGN3 on NLGN3 gene expression (FIG. 29, panels C, E-G). Soluble NLGN3 thus promotes glioma cell feed-forward expression of NLGN3 via the PI3K pathway. To determine if other ligands known to stimulate the PI3K pathway in glioma similarly affect NLGN3 expression, the effect of epidermal growth factor (EGF) exposure on glioma cell NLGN3 expression was tested and no effect was found (n=3 independent samples, P=0.781; FIG. 5, panel F), suggesting that NLGN3 gene expression is not a general indicator of PI3K pathway activity in glioma, but rather, it is specific to the context of NLGN3 exposure. Protein expression of NLGN3 following glioma cell NLGN3 exposure was confirmed using Western blot analysis; in contrast, glioma cell NLGN3 protein expression was not found at baseline culture conditions (FIG. 5, panel G). NLGN3 thus results in feed-forward expression at the transcriptional and translational levels. Together, these findings indicate that NLGN3 expression is an indicator of neuronal activity-dependent NLGN3 signaling to glioma cells (FIG. 6).

FIG. 29: Secreted Neuroligin-3 Promotes Feed-Forward Expression of NLGN3 Through Recruitment of the PI3K-mTOR Pathway.

Increases in NLGN3 feed-forward expression induced by exposure to soluble NLGN3 is blocked by genetic or pharmacological inhibition of PI3K or mTOR. A) NLGN3 mRNA expression in SUpcGBM2 cells after 12-hr exposure to vehicle, 50 nM NLGN3, 100 nM BKM120, or 50 nM NLGN3+100 nM BKM120. B) As in (A), SU-DIPGXIII NLGN3 mRNA expression after exposure to NLGN3 and BKM120 alone or in combination. C-E) NLGN3 mRNA expression in SU-pcGBM2 cells after shRNA-mediated knockdown of either PI3K or mTOR. Only cells exposed to scrambled shRNA control exhibit increased NLGN3 expression after NLGN3 exposure (unpaired two-tailed Student's t-test.) F-G) NLGN3 mRNA expression in SU-pcGBM2 cells after 12-hr exposure to vehicle, 50 nM NLGN3, 100 nM RAD001, or 50 nM NLGN3+100 nM RAD001. G) As in (F), SU-DIPGXIII NLGN3 mRNA expression after exposure to NLGN3 and RAD001 alone or in combination. n=3 biological replicates unless otherwise stated. Data shown as mean±SEM. *P<0.05, P<0.01, *P<0.001 by one-way ANOVA unless otherwise stated. n.s. indicates P>0.05. (See also FIG. 35.)

Figure 6:
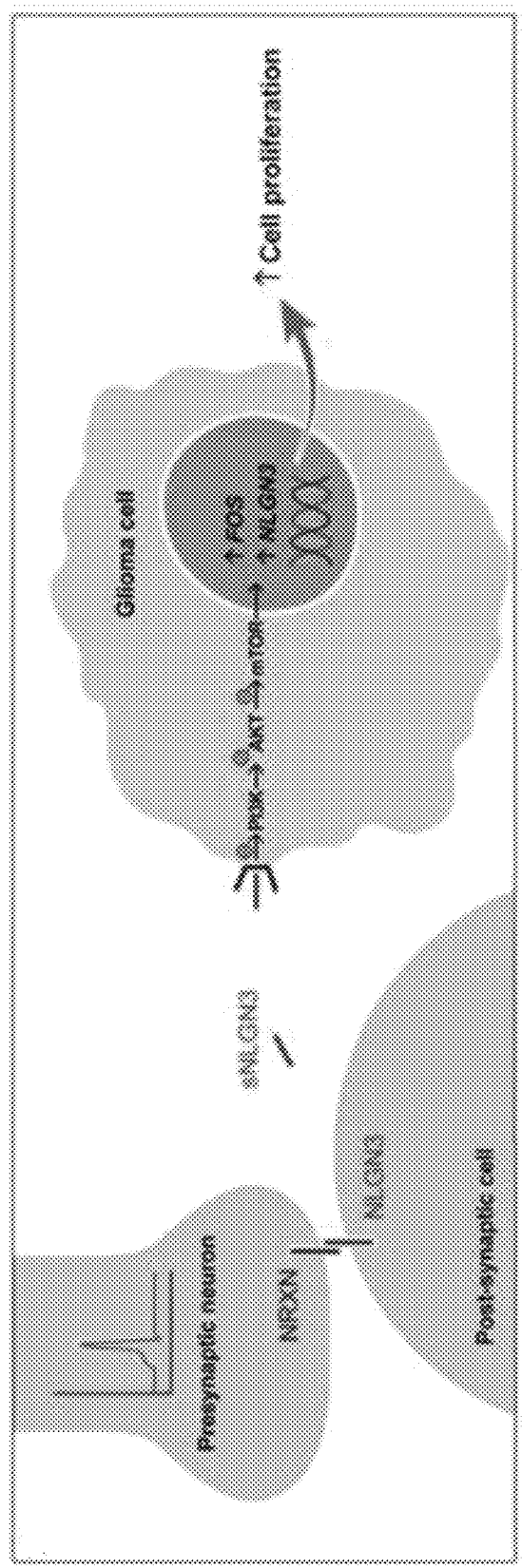
FIG. 6 is an illustration that shows a schematic model of activity-regulated glioma proliferation.

FIG. 6: Model of Activity-Regulated Glioma Proliferation.

Schematic illustrating the model of neuronal activity-regulated secretion of neuroligin-3 from a post-synaptic cell. Soluble neuroligin-3 (sNLGN3) acts on the glioma cell to induce upregulation of the PI3K-mTOR pathway and downstream increased expression of Fos and NLGN3, leading to increased glioma cell proliferation.

Figure 14:
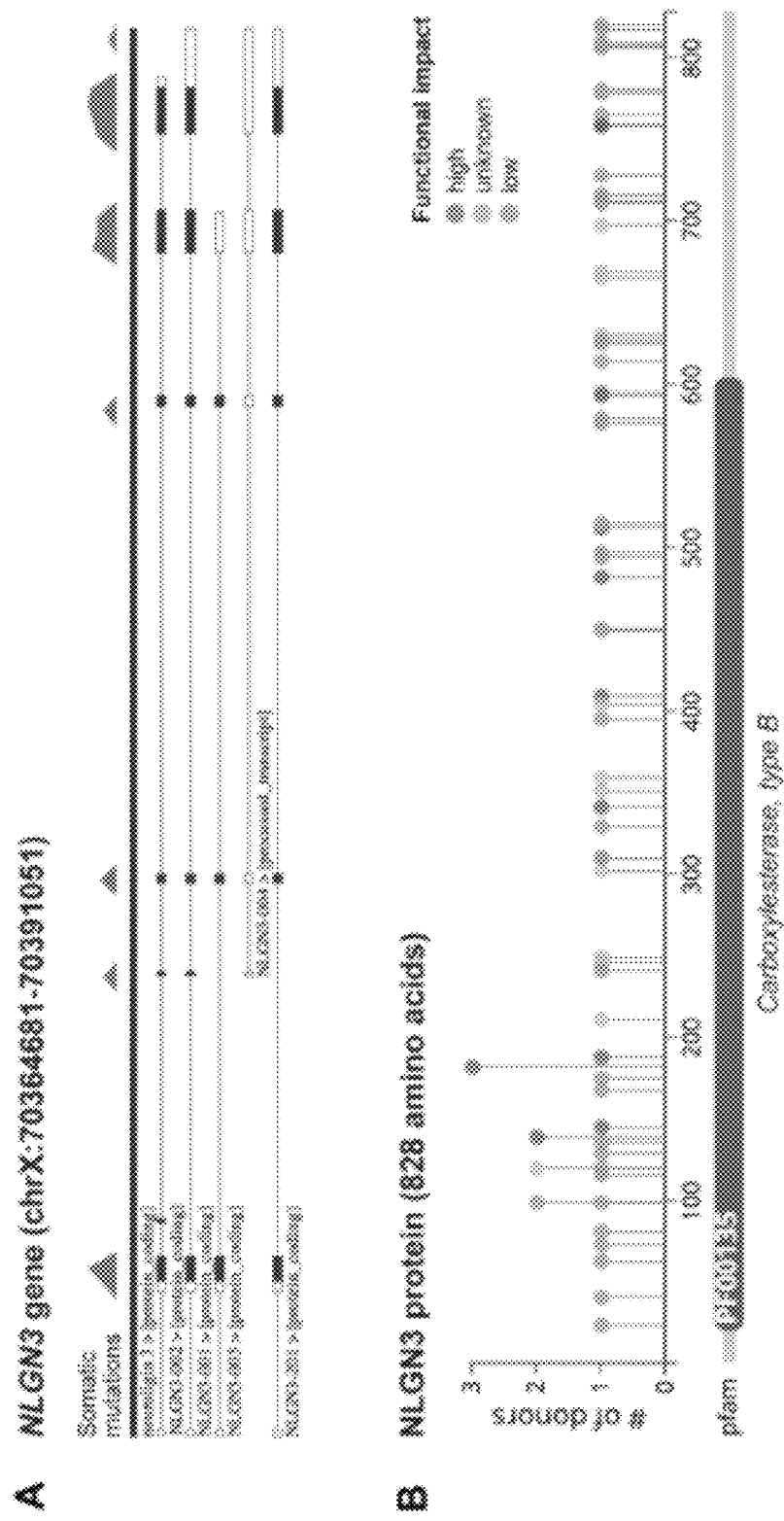
FIG. 14, Panels A-C show somatic mutations and copy number variations in the NLGN3 gene in human cancer.

Example 7: Neuroligin-3 Gene Expression is Associated with Decreased Survival in Human High-Grade Glioma As NLGN3 exposure increased tumor cell NLGN3 expression, whether the NLGN3 gene exhibited aberrations in glioma was determined. Analysis of data from The Cancer Genome Atlas (TCGA) showed that somatic mutations in NLGN3 are infrequent in pediatric (pilocytic astrocytoma/medulloblastoma, 0.4%) and adult brain tumors (low-grade gliomas, 1.1%; high-grade gliomas, 0.4%; FIG. 14). Interestingly, an extended analysis of NLGN3 mutations and copy number aberrations across multiple cancer types in the International Cancer Genome Consortium (ICGC) and the cBio Portal for Cancer Genomics databases revealed more frequent mutations and amplifications in other tumors, with particular predominance in thyroid, pancreatic, prostate and gastric cancer (FIG. 14, panel C, Table shown in FIG. 19).

FIG. 14. Somatic Mutations and Copy Number Variations in the NLGN3 Gene in Human Cancer.

A) Structure and reference sequence of human NLGN3 transcripts with frequency mapping of mutations, consisting mostly of single base substitutions, across seven coding exons. B) Mapping of these mutations to the 828-amino acid sequence of the NLGN3 protein with predictions of potential functional impact. C) Frequency of NLGN3 gene alterations, involving mutations and copy number variations, across various cancer types. Data gleaned from the cBio-Portal for Cancer Genomics database. Analysis of data from The Cancer Genome Atlas Project showed that somatic mutations in NLGN3 are infrequent in pediatric (pilocytic astrocytoma/medulloblastoma, 0.4%) and adult brain tumors (low-grade gliomas, 1.1%; glioblastoma, 0.4%). By contrast, an extended analysis of NLGN3 mutations across 22 projects encompassing multiple cancer types in the International Cancer Genome Consortium revealed 119 mutations, consisting mostly of single base substitutions, in 111 out of 4873 (2.3%) tumors of various histopathology with particular predominance in thyroid, gastric, and ovarian cancer (6.5-33.3%). Similarly, cross-cancer analysis of structural and gene dosage alterations in NLGN3 demonstrates the presence of mutations and/or copy number variations (frequency: 0.4-10.2%) in 37 of 69 cancer studies involving 17,584 tumors. Mutations mapped throughout all seven NLGN3 exons and across the entire 828-amino acid sequence of the NLGN3 protein with varying predicted functional impact. Taken together, the presence of NLGN3 mutations in various carcinomas support a potential tumor-promoting role of NLGN3 in human carcinogenesis, yet their paucity in brain tumors suggests primarily transcriptional or post-transcriptional mechanisms of NLGN3 deregulation in glial brain tumors.

Figure 7:
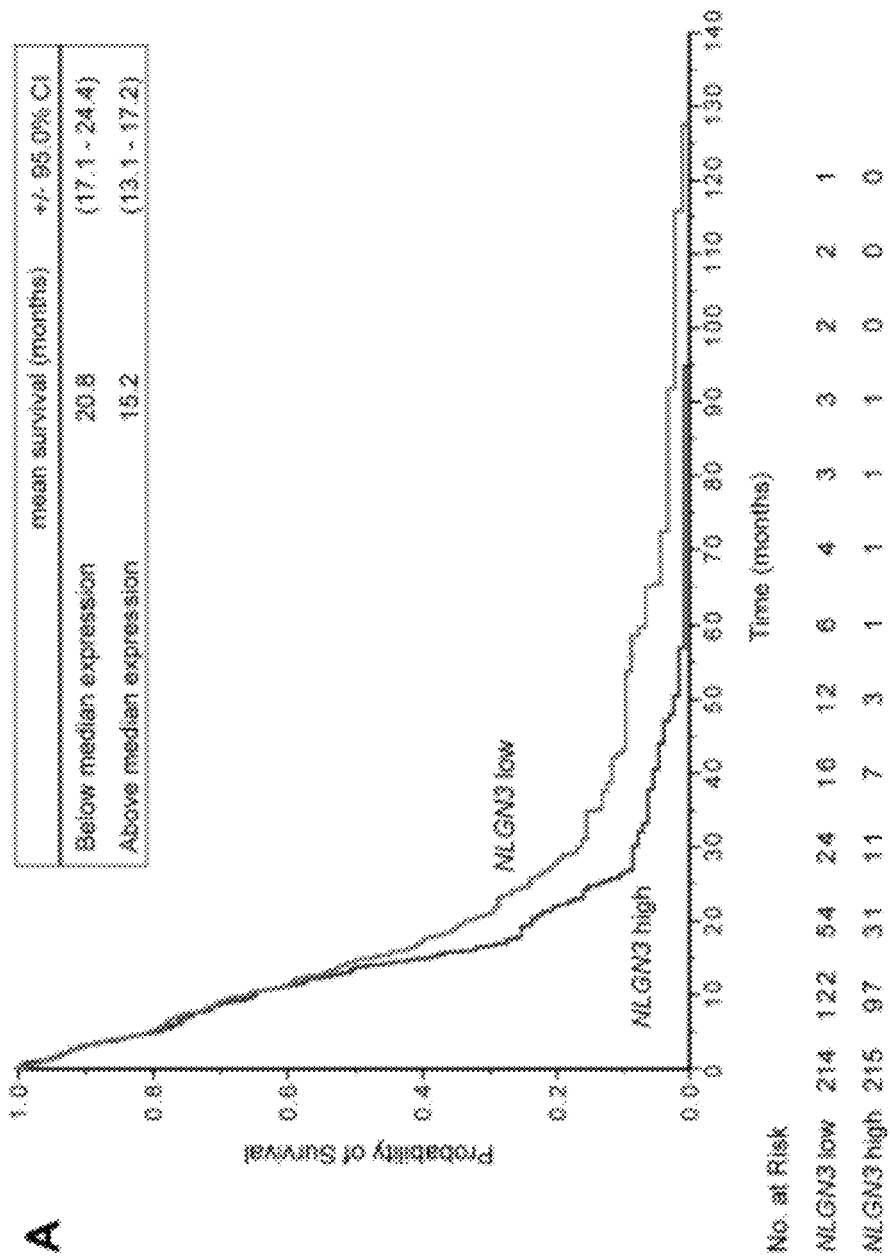
FIG. 7, Panels A-B show a collection of graphs that shows the correlation between neuroligin-3 expression and survival in human glioblastoma.

To validate the clinical significance of NLGN3 in human glioma pathophysiology, the relationship between NLGN3 gene expression and patient survival was examined in 429 cases of adult glioblastoma (GBM) in TCGA. It was found that the level of NLGN3 mRNA expression is inversely correlated with patient overall survival (FIG. 7). A two-class model in which patients were stratified according to median NLGN3 expression showed an association between higher NLGN3 expression and shorter survival (P<0.05 by the log-rank test; FIG. 7, panel A). In the cohort of patients whose tumors exhibited below-median NLGN3 expression, the estimated mean survival was 20.8 months (95% CI 17.1-24.4); in comparison, the mean survival in the patient cohort with above-median NLGN3 expression was 15.2 months (95% CI 13.1-17.2). On Cox regression analysis, the hazard ratio for death with high vs. low NLGN3 expression was 1.31 (95% CI 1.05-1.63). NLGN3 expression was also significantly inversely associated with patient survival in a continuous Cox proportional-hazards regression analysis, such that higher expression represented an unfavorable prognosis (hazard ratio for death with high vs. low NLGN3 expression, 1.15; 95% CI 1.01-1.30; P<0.05).

FIG. 7: Neuroligin-3 Expression Inversely Correlates with Survival in Human Glioblastoma.

A) A 2-class model stratified based on median NLGN3 expression in 429 GBM cases with molecular subtype data from the TCGA (http(colon-slash-slash)cancergenome(dot)nih(dot)gov). In the cohort of patients whose tumors exhibited below-median NLGN3 expression levels, the mean overall survival was 20.8 months (95% CI 17.1-24.4); in patients with above-median NLGN3 expression levels, mean survival was 15.2 months (95% CI 13.1-17.2). B) Glioblastoma subtype-specific NLGN3 expression. The box plots show the smallest and largest observations (upper and lower whiskers, respectively), the interquartile range (box), and the median (black line). Data points that are more than 1.5 times the interquartile range lower than the first quartile or 1.5 times the interquartile range higher than the third quartile were considered to be outliers (shown as circles outside the box and whisker plot). Corresponding Kruskal-Wallis one-way ANOVA of NLGN3 expression in the four subtypes with P-values indicating pairwise comparisons and significance of differential NLGN3 expressions.

Figure 15:
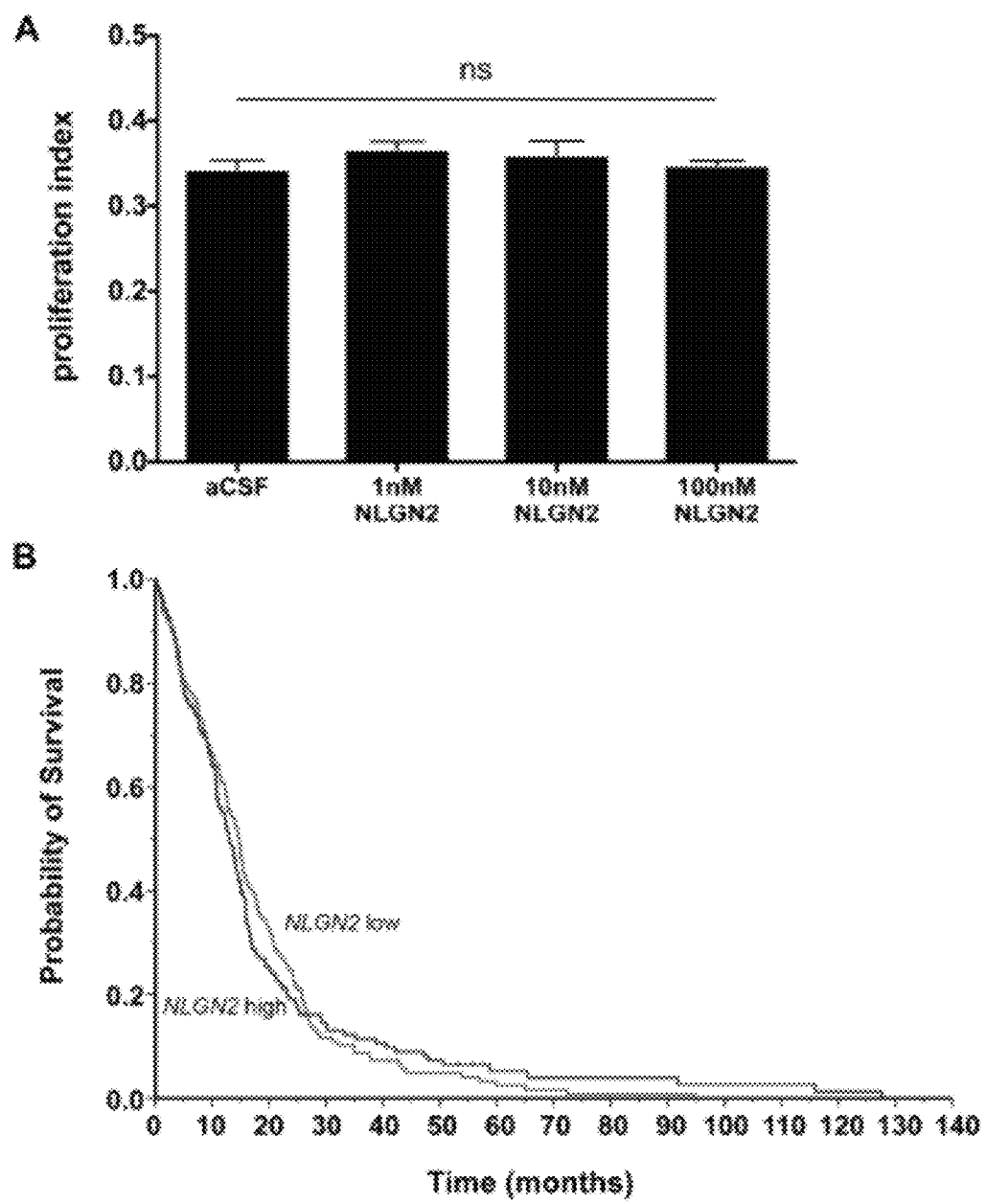
FIG. 15, Panel A-B show a collection of graphs that shows the effect of neuroligin 2 (NLGN2) on glioma cell proliferation and correlation of NLGN2 expression with patient survival.

To examine the specificity of these findings, the relationship of neuroligin-2 (NLGN2) to survival in human GBM was explored. Recombinant soluble NLGN2 does not promote the proliferation of HGG cells in vitro (FIG. 15, panel A). Likewise, there is no significant association between NLGN2 expression and patient survival in adult glioblastoma, assessed as above in a continuous Cox model (hazard ratio for death with high vs. low NLGN2 expression, 0.95; 95% CI 0.78-1.16; P=0.634) and in a two-class model stratified by median expression (P=0.795 by the log-rank test; FIG. 15, panel B).

FIG. 15. Neuroligin 2 (NLGN2) does not Promote Glioma Cell Proliferation and does not Correlate with Patient Overall Survival.

A) Pediatric HGG cells (SU-pcGBM2) were exposed to recombinant NLGN2 at 1, 10 or 100 nM concentration for 24 hours, and proliferation index was determined as the fraction of DAPI+ cells co-expressing EdU. No effect of NLGN2 on pHGG cell proliferation was observed (one-way ANOVA, F=1.045, P=0.424). n.s. denotes P>0.05. Error bars, SEM. B) A 2-class model stratified based on median NLGN2 expression in 429 GBM cases with molecular subtype data from the TCGA (http(colon-slash-slash)cancergenome(dot)nih(dot)gov). In the cohorts of patients whose tumors exhibited above or below median NLGN2 expression levels, the mean survival was not different (P=0.795 by the log-rank test).

Interestingly, upon examination of NLGN3 expression by molecular glioblastoma subtype as defined by TCGA, NLGN3 expression was significantly lower in the mesenchymal subtype compared to classical, neural and proneural subtypes (asymptotic significance of P<0.001 by independent-samples Kruskal-Wallis test; FIG. 7, panel B). Notably, NLGN3 expression remained significantly associated with patient survival in a multivariate Cox model that incorporates molecular subtype (hazard ratio for death with high vs. low NLGN3 expression, 1.15; 95% CI 1.01-1.30; P<0.05).

Figure 25:
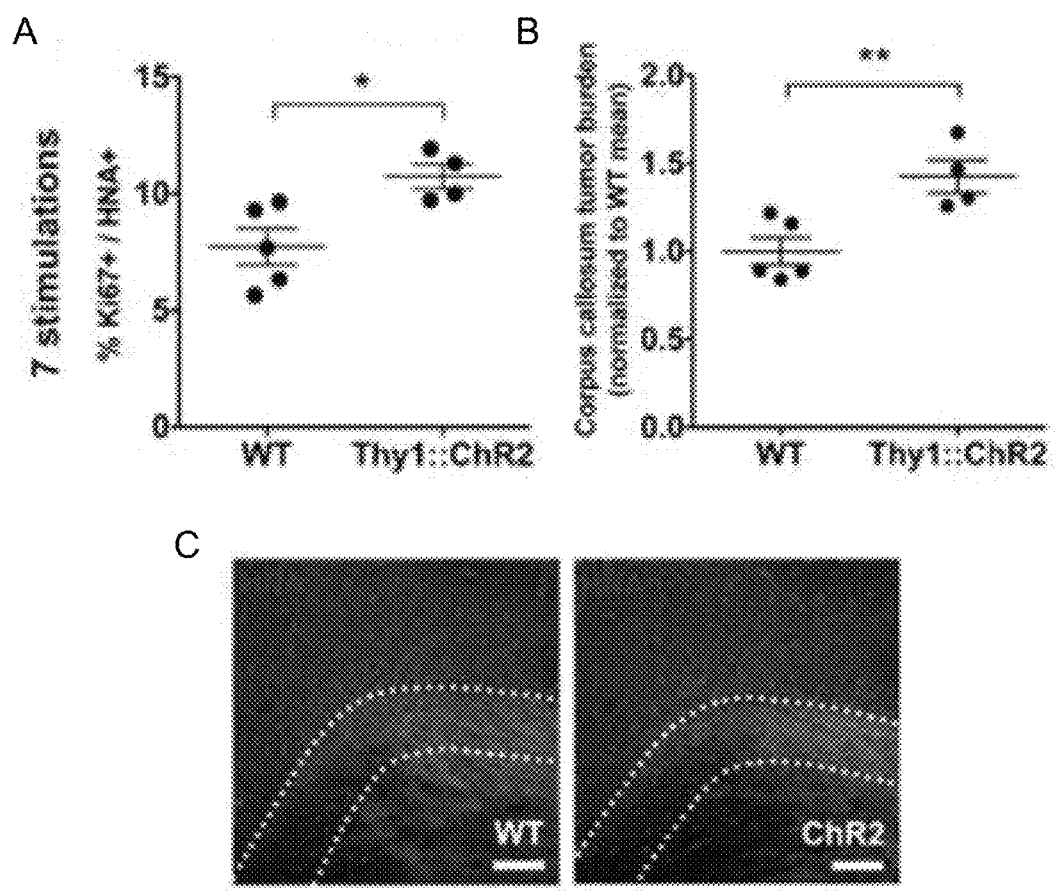
FIG. 25, Panels A-C show a collection of graphs and images that show the effect of neuronal activity on high-grade glioma proliferation in vivo.

Example 8: Influence of Neuronal Activity on Tumor Burden During the Exponential Growth Phase A simplified Galton-Watson mathematical model of tumor cell growth incorporating the neuronal activity-associated increase in proliferation index (b) and a fixed cell death rate (d) would predict an exponential growth effect of elevated neuronal activity within the active circuit ($xt=x0(1+(b-d))t$). Such a model utilizing the observed proliferation indices predicts an activity-regulated ~25% increase in tumor cell number after 7 cell divisions and ~50% tumor increase after 14 divisions. To test this prediction in vivo, a repetitive stimulation paradigm was used in which mice were optogenetically manipulated as above for 10 min daily on 7 consecutive days and sacrificed 48 hrs after the final session. Following repetitive elevations in premotor circuit activity, tumor cell proliferation index was increased in xenografted Thy1::ChR2;NSG mice to a similar degree as in the single optogenetic stimulation paradigm (10.74%±0.61 vs. 7.72%±0.88; n=4 Thy1::ChR2;NSG mice, n=5 WT;NSG mice; P<0.05, FIG. 25, panel A). Furthermore, as expected, periodically elevated neuronal activity for one week yielded a ~42% increase in tumor cell burden within the active circuit relative to identically manipulated WT controls (n=4 Thy1::ChR2;NSG, n=5 WT;NSG mice; P<0.01; FIG. 25, panels B-C). These data reflect the influence of neuronal activity on tumor burden during the exponential growth phase; over the course of the disease, as disruption of healthy tissue progresses and the microenvironment evolves, the effects of neuronal activity on glioma growth could change.

FIG. 25.

Repetitive optogenetic stimulation sessions paradigm. Xenografted WT;NSG (n=5) and Thy1::ChR2;NSG (n=4) mice evaluated 48 hrs after 7 daily sessions of optogenetic stimulation. A) Proliferation index ($Ki67^+/HNA^+$) as in (D) above after 7 stimulations. B) Tumor cell burden increases following one week of brief daily optogenetic stimulation sessions, measured as $HNA^+$ cell density within the region of corpus callosum containing active premotor projections; data normalized to WT mean. C) Confocal micrographs with differential interference contrast (DIC) background to illustrate regional tissue architecture; HNA+pHGG cells (red) are infiltrating premotor cortex and subjacent corpus callosum. Dotted line indicates region of analysis in corpus callosum. Data shown as mean±SEM. *P<0.05, **P<0.01 by unpaired two-tailed Student's t-test. Scale bars=100 μm. (See also FIGS. 8 and 30.)

Example 9: Spontaneous Neuronal Activity Regulates Secretion of a Glioma Mitogen WT cortical slices do exhibit spontaneous neuronal activity; thus, activity-regulated secreted factors are expected to be present in WT CM, albeit to a lesser extent than in media conditioned by Thy1::ChR2 slices with optogenetically elevated neuronal activity. To further explore the possible effects of spontaneous activity, WT slices were allowed to condition the media without blue light for 4 hrs rather than 30 min in the presence or absence of the specific voltage-gated sodium channel blocker tetrodotoxin (TTX; inhibits spontaneous action potentials). WT CM conditioned for a longer duration elicited an increase in pHGG proliferation; this effect was blocked in CM from slices incubated with TTX (proliferation index 0.32±0.03 with 4-hr WT CM exposure vs. ~0.25 with aCSF, aCSF+TTX or WT CM+TTX exposure; F=8.45; P<0.01; FIG. 26, panel A). Together, these data indicate that spontaneous neuronal activity regulates secretion of a glioma mitogen(s).

FIG. 26. Panel A)

Proliferation index of SU-pcGBM2 cells after exposure to CM generated from light-unexposed WT slice conditioning for 4 hrs in the presence or absence of 1 µM tetrodotoxin (TTX).

Example 10: The Effect of NLGN3 Exposure on mTOR Activity

Figure 28:
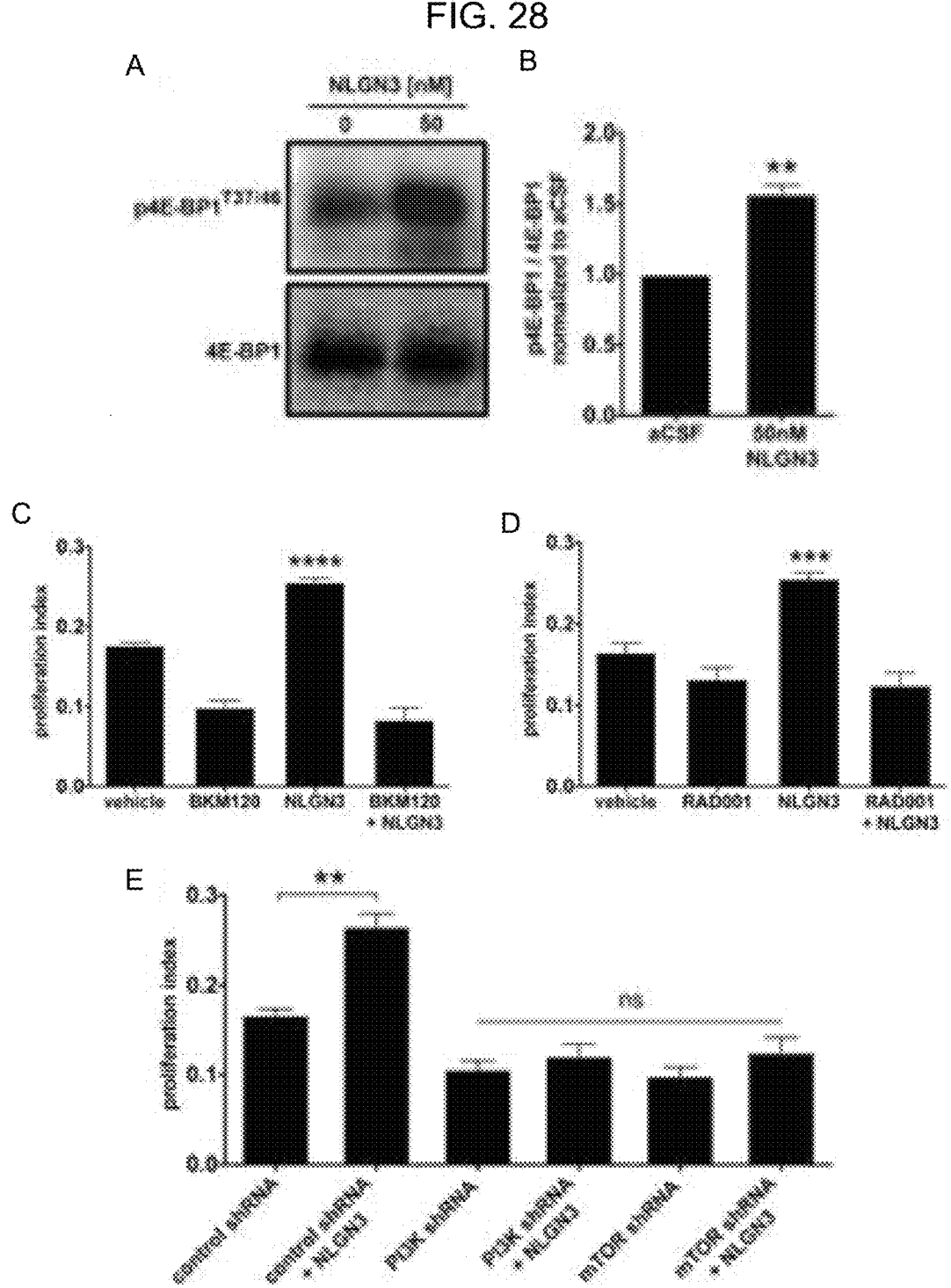
FIG. 28, Panels A-E show a collection of images and graphs that show the effect of secreted neuroligin-3 on recruitment of phosphatidylinositol-4,5-bisphosphate 3-kinase (PI3K) and expression of NLGN3.

PI3K canonically regulates mammalian target of rapamycin (mTOR), and thus the effect of NLGN3 exposure on mTOR activity was examined using Western blot analysis of phospho-4EBP1$^{T37/46}$. pHGG cells exposed to NLGN3 exhibited an increase in phospho-4E-BP1$^{T37/46}$ relative to total 4E-BP1 (FIG. 28, panels A-B). Blockade of PI3K or mTOR pharmacologically or via shRNA-mediated knockdown prevented the NLGN3-mediated mitogenic effect (FIG. 28, panels C-E, FIG. 34, panels C-E). Neuronal activity-regulated secretion of NLGN3 thus recruits the PI3K-mTOR pathway to promote glioma cell proliferation.

FIG. 28. Secreted Neuroligin-3 Recruits the PI3K Pathway.

A) Representative Western blot demonstrates increased phosphorylation of 4E-BP1, a downstream reporter of mTOR, after 50 nM NLGN3 exposure. Top panel, 4E-P1$^{T37/46}$; bottom panel, total 4E-BP1. B) Quantification of p4E-BP1T37/46/4E-BP1 ratio fold change after NLGN3 exposure normalized to aCSF control (unpaired two-tailed Student's t-test). C) 50 nM NLGN3-induced increase in SU-pcGBM2 proliferation index (EdU assay) is blocked by inhibition of PI3K by BKM120 (100 nM). D) Similar to (C), inhibition of mTOR by RAD001 (100 nM) blocks 50 nM NLGN3-induced proliferation in SUpcGBM2 cells. E) Genetic knockdown using specific shRNA against either PI3K or mTOR blocks effect of 50 nM NLGN3 on proliferation index (EdU assay in UpcGBM2). *P<0.05, P<0.01, *P<0.001, ****P<0.0001 by one-way ANOVA with Tukey's post-hoc tests to further examine pairwise comparisons unless otherwise indicated. All experiments performed in n=3 biological replicates. Data shown as mean±SEM. (See also FIG. 34, Table in FIG. 18.)

FIG. 34. Panel C)

Representative Western blots confirming the shRNA knockdown of PI3K and mTOR. From left, first lane represents cells exposed to mTOR shRNA knockdown construct, second lane represents cells exposed to scrambled shRNA control, third and fourth lanes represent cells exposed to PI3K knockdown constructs. Top row probed with anti-PI3K antibody, middle row probed with anti-mTOR antibody, bottom row probed with anti-β-tubulin antibody. D-E) PI3K and mTOR mRNA expression as quantified by qPCR in order to verify PI3K and mTOR knockdown in various constructs. "PI3K (used)" represents construct used in the FIGS. 28 and 29. "PI3K shRNA (alternate)" represents an additional construct used to verify observation and to control for off-target effects (see also FIG. 35). All experiments performed in three biological replicates and analyzed by unpaired two-way Student's t-test. Data presented as mean±SEM. P<0.01, *P<0.001. n.s. indicates P>0.05.

Figure 30:
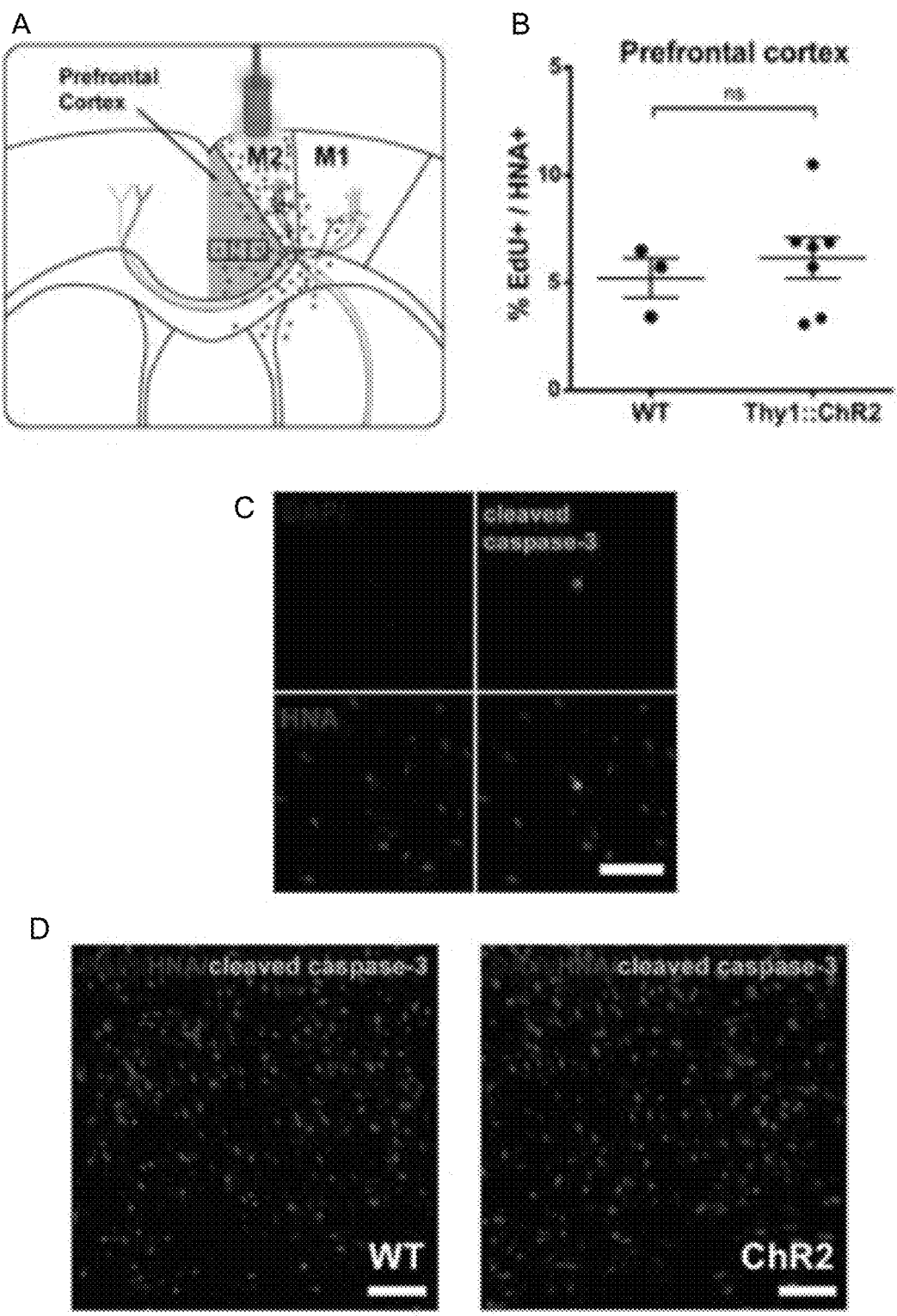
FIG. 30, Panels A-D show a collection of graphs and images that show the localized effects of activity on the circuit activated by ChR2 stimulation, and the effect of stimulation on caspase-3 activation.

Example 11: Activity-Regulated Increase in Glioma Cell Proliferation is Restricted and does not Lead to Caspase-3 Activation The observed activity-regulated increase in proliferation was restricted to the active circuit; in the prefrontal cortex, a region infiltrated by glioma cells but outside of the area stimulated by light, glioma cell proliferation indices were equivalent in Thy1::ChR2;NSG and WT;NSG mice (FIG. 30, panels A-B). While proliferation increased within the active circuit, glioma cell death remained constant, with only rare tumor cells expressing cleaved caspase-3 in either group (FIG. 30, panels C-D).

FIG. 30. Panels A-B.

The effects of activity on glioma cell proliferation are localized to the active circuit. Xenografted glioma cells infiltrating the neighboring prefrontal cortex (labeled in (A)), outside of the region of light stimulation and not a target of premotor circuit projections, do not exhibit an increase in proliferation index (E) in Thy1::ChR2;NSG mice compared to WT;NSG mice as assessed by incorporation of EdU delivered at the time of a single optogenetic stimulation session and assessed 24 hours later (n=7 Thy1::ChR2, n=3 WT; P=0.57 by unpaired two-tailed Student's t-test). C-D) Confocal micrographs demonstrating cleaved caspase-3 immunohistochemistry in pHGG xenografts (co-stained with HNA and DAPI). Only rare cleaved caspase-3+ cells were detected (C). (D) Representative images from optogenetically stimulated ("ChR2") or identically manipulated WT premotor area (cortex and subjacent corpus callosum) illustrates little to no apoptotic cell death in either group. Scale bars=50 µm. Data presented as mean±SEM. n.s. indicates P>0.05.

Example 12: Experimental Procedures

Isolation and Culture of the Primary Human Tumor Cells:
Tumor tissue was mechanically dissociated and cultured as described in extended experimental methods.

Orthotopic Xenografting:
600,000 SU-pcGBM2 cells were stereotactically implanted into the M2 premotor cortex region of Thy1::ChR2;NSG or WT;NSG littermate mice at P35. Cells were allowed to engraft for a minimum period of 2 months prior to placement of an optical-neural interface for optogenetic stimulation.

In Vivo Optogenetic Stimulation:
A minimum of 7 days prior to stimulation, the optical-neural interface was placed just below the pial surface of the cortex ipsilateral to xenografts. Animals were then stimulated with cycles of 473-nm light pulses at 20 Hz for 30 seconds, followed by 90 seconds of recovery over a 30-minute period and sacrificed 24 hours after stimulation.

Determination of Cell Proliferation In Vitro:
To assess the number of cells actively synthesizing new DNA in response to various conditions (see extended experimental procedures), SU-pcGBM2, SU-DIPGIV, SU-DIPGXIII, or SU-GBM035 cells were exposed to active CM or various recombinant proteins along with 10-μM EdU and fixed after 24 hours. EdU incorporation was determined using Click-iT EdU visualization (Invitrogen, Grand Island, N.Y.).

Western Blot Analysis:

Endogenous protein levels were determined using Western blot analysis. Briefly, after various treatments, 400,000 SU-pcGBM2 cells were lysed and loaded onto SDS-PAGE gels. Proteins were separated with gel electrophoresis and transferred to a PVDF membrane. Proteins were then probed for various antibodies as described in extended experimental procedures.

qPCR:

After various cell treatments (described in extended experimental procedures), RNA was extracted from 500,000 SU-pcGBM2 or SU-DIPGXIII cells using TRIzol reagent. cDNA was generated using RT-PCR, and gene expression changes were further probed using quantitative PCR.

Example 13: Extended Experimental Procedures

Mice and Housing Conditions:

All in vivo experiments were approved by the Stanford University Institutional Care and Use Committee and performed in accordance with institutional guidelines. Thy1::ChR2 mice (The Jackson Laboratory, Bar Harbor, Me.) were first intercrossed with NSG mice (NOD-SCID-IL2R gamma chain-deficient, The Jackson Laboratory, Bar Harbor, Me.) to produce the Thy1::ChR2;NSG genotype. All experiments were performed on animals either heterozygous for Thy1::ChR2 or wild type control NSG littermates. Animals were housed according to standard guidelines with free access to food and water in a 12-hour light/dark cycle.

Cell Culture:

Tissue from a pediatric cortical high-grade glioma (WHO grade IV) tumor was obtained at the time of initial biopsy from a 15-year-old male patient under sterile conditions. The tissue was dissociated mechanically, followed by gentle enzymatic dissociation with TrypLE (5 minutes at 37 degrees) and then passed through a 100-μm filter. The flow-through was collected and cultured in a T75 cm$_2$ flask. The filter was inverted and the tissue was flushed and cultured into a separate flask. A defined, serumfree medium designated "Tumor Stem Media (TSM)" was used throughout, consisting of Neurobasal(-A) (Invitrogen, Carlsbad, Calif.), B27(-A) (Invitrogen, Carlsbad, Calif.), humanbFGF (20 ng/mL) (Shenandoah Biotech, Warwick, Pa.), human-EGF (20 ng/mL) (Shenandoah, Biotech, Warwick, Pa.), human PDGF-AA (10 ng/mL) and PDGF-BB (10 ng/mL) (Shenandoah, Biotech, Warwick, Pa.) and heparin (2 ng/mL). When neurospheres were visible in the primary culture it was filtered through a 40-μm filter to remove debris and single cells such as RBCs; the matter that did not pass through the filter, containing the larger than 40-μm neurospheres, was recovered and subsequently dissociated using TrypLE. A second filtration was then performed using 40-μm filters, and the single cells in the flow-through were centrifuged at 300 g for 5 minutes and the pellet was resuspended in TSM and recultured, generating secondary neurospheres. This cell line was designated SU-pcGBM2 (Stanford University, pediatric cortical glioblastoma line 2), grown in nonadherent neurosphere culture in the above medium, and passaged every one to two weeks.

Diffuse intrinsic pontine glioma (DIPG) tumor neurosphere cultures were generated as previously described from early post-mortem tissue donations and grown as tumor neurospheres in defined, serum free TSM medium as above.

The adult high-grade glioma (WHO grade IV) used was obtained from a 61 year-old male at the time of biopsy and cultured as described previously for DIPG tissue but without PDGF-AA or BB supplementation.

Orthotopic Xenografting:

A single-cell suspension from cultured SU-pcGBM2 neurospheres at passage 19-22 was prepared in sterile PBS immediately prior to the xenograft procedure. Animals at p34-36 were anesthetized with 1-4% isoflurane and placed in a stereotactic apparatus. The cranium was exposed via midline incision under aseptic conditions. 600,000 SU-pcGBM2 cells in 3 μL sterile PBS were stereotactically implanted in the premotor cortex (M2) of the right hemisphere through a 31-gauge burr hole, using a digital pump at infusion rate of 0.4 μL/minute and 31-gauge Hamilton syringe. Stereotactic coordinates used were as follows: 0.5 mm lateral to midline, 1.0 mm anterior to bregma, −1.75 mm deep to cranial surface. At the completion of infusion, syringe needle was allowed to remain in place for a minimum of 2 minutes, then manually withdrawn at a rate of 0.875 mm/minute to minimize backflow of the injected cell suspension.

Fiber Optic Placement and In Vivo Optogenetic Stimulation:

Fiber optic placement was performed as previously described a minimum of 7 days prior to optogenetic stimulation. Animals were anesthetized with 1-4% isoflurane and placed in a stereotactic apparatus. The cranium was exposed using a midline incision under aseptic conditions. A fiber optic ferrule (Doric Lenses, Quebec, Canada) was placed at the premotor cortex (M2) of the right hemisphere using the following coordinates: 0.5 mm lateral to midline, 1.0 mm anterior to bregma, −0.75 mm deep to cranial surface in the right hemisphere. At 11 weeks post-xenograft (allowing a minimum of 7 days of recovery following ferrule placement procedure), all animals were connected to a 100-mW 473-nm DPSS laser system with a mono fiber patch cord, which freely permits wakeful behavior of the animal. Pulses of light with ~1 mW measured output at tip of the patch cord were administered at a frequency of 20 Hz for periods of 30 seconds, followed by 90-second recovery periods, for a total session duration of 30 minutes for single session stimulation paradigms, or 10 minutes per day for 7 days for the repetitive stimulation paradigm. This power represents ~30 mW/cm2 light density at the tip of the patch cord; with the optical ferrule placed just below the pial surface this would deliver ~3 mW/cm2 approximately midway through the cortex to reach the layer V apical dendrites. This was the minimum light required to reliably elicit complex motor behavioral output. This paradigm is modified slightly from that previously described, with a 90-second recovery period rather than 120 seconds and higher light density required to elicit the complex motor behavior in tumor-bearing NSG mice rather than non-tumor-bearing mice with a CD1/B6 mixed background. When tumor-bearing Thy1::Chr2;NSG animals are stimulated in parallel with non-tumor bearing Thy1::ChR2 animals on a mixed CD1/B6 background, the tumor-bearing NSG background mice consistently required higher light power to elicit the expected motor behavior (unidirectional ambulation). During periods of light administration, all Thy1::ChR2;NSG animals responded with unidirectional ambulation to the left for the duration of light exposure, confirming proper ferrule placement over right M2 and effective neuronal stimulation. All WT NSG animals demonstrated no change in behavioral output in response to light stimulation. Following the stimulation session, an intraperitoneal injection of 5-ethynyl-2'-deoxyuridine (EdU; 40 mg/kg; Invitrogen, Carlsbad, Calif.) was administered to the animal. Mice were sacrificed 24 hours after administration of EdU in the single session paradigm experiment. For the repetitive stimulation experiment, mice were sacrificed 48 hours following the final (7th) stimulation session.

Perfusion and Immunohistochemistry:

Animals were anesthetized with intraperitoneal Avertin (tribromoethanol), then transcardially perfused with 20 mL of PBS. Brains were fixed in 4% paraformaldehyde overnight at 4° C., then transferred to 30% sucrose for cryoprotection. Brains were embedded in Tissue-Tek O.C.T. (Sakura, Torrance, Calif.) and sectioned in the coronal plane at 40 µm using a sliding microtome (Microm HM450; Thermo Scientific, Waltham, Mass.). For immunohistochemistry, a 1 in 6 series of 40-µm coronal sections was stained using the Click-iT EdU cell proliferation kit and protocol (Life Technologies, Carlsbad, Calif.) to expose EdU labeling, then incubated in blocking solution (3% normal donkey serum, 0.3% Triton X-100 in TBS) at room temperature for 30 minutes. Mouse anti-human nuclei clone 235-1 (1:100; Millipore, Billerica, Mass.), rabbit anti-Ki67 (1:500; Abcam, Cambridge, Mass.), and rat anti-MBP (1:200; Abcam, Cambridge, Mass.) were diluted in 1% blocking solution (1% normal donkey serum in 0.3% Triton X-100 in TBS) and incubated overnight at 4° C. Sections were then rinsed 3 times in 1×TBS and incubated in secondary antibody solution (Alexa 488 goat antimouse IgG, 1:500 (Life Technologies, Carlsbad, Calif.); Alexa 488 donkey anti-rabbit IgG, 1:500 (Life Technologies, Carlsbad, Calif.); Alexa 647 donkey anti-rabbit IgG, 1:500, (Life Technologies, Carlsbad, Calif.); Alexa 594 donkey antimouse IgG, 1:500 (Life Technologies, Carlsbad, Calif.); Alexa 594 donkey anti-rat IgG, 1:1000 (Life Technologies, Carlsbad, Calif.)) in 1% blocking solution at 4° C. overnight. The next day, sections were rinsed 3 times in TBS and mounted with ProLong Gold Mounting medium with DAPI (Life Technologies, Carlsbad, Calif.).

Confocal Imaging and Quantification:

All cell quantification was performed by live counting at 400× magnification using a Zeiss LSM700 scanning confocal microscope and Zen 2011 imaging software (Carl Zeiss Inc., Pleasanton, Calif.). For the single-session stimulation paradigm, the area for quantification was selected as follows: of a 1 in 6 series of 40-µm coronal sections, 3 consecutive sections were selected at approximately 1.1-0.86 mm anterior to bregma (FIGS. 22, 23, 24; Franklin & Paxinos, *The Mouse Brain in Stereotaxic Coordinates*, 3$_{rd}$ Ed. 2008); using our stereotactic coordinates for tumor xenograft, these sections are expected to include the tissue most proximal to the site of tumor cell implantation in the coronal plane. For each of the three consecutive sections, the cingulum bundle was first identified as an anatomic landmark, and a 160×160-µm field area for quantification (FIG. 8, panel C, Field 1) was selected immediately superficial to this landmark within cortical layer 6b of M2. A second field (Field 2) was selected immediately deep to this landmark in the corpus callosum. Two additional quantification fields (3,4) were selected so as to lie within cortical layer 6b/6a, immediately superficial to the topmost edge of Field 1, and juxtaposed side-by-side about the Field 1 mediolateral midpoint. Similarly, two additional quantification fields (5,6) were selected so as to lie within the corpus callosum, immediately deep to the bottommost edge of Field 2, and juxtaposed side-by-side about the Field 2 mediolateral midpoint (see schematic FIG. 8, panel C). As each field was live-counted through the entire slice thickness of 40 µm, the total volume quantified per field was $1.024 \times 10^6$ µm$^3$; 6 fields within each of 3 coronal sections were selected for a total quantified volume of $18.432 \times 10^6$ µm$^3$ per animal. These selected premotor cortex and corpus callosum areas lie within the active premotor circuit, but are deep to the path of tumor cell injection by our stereotactic coordinates, and thus avoid the principal areas of inflammatory change involving tissue more proximal to the injection site. Within each field, all human nuclei antigen (HNA)-positive tumor cells were quantified to determine tumor burden within the areas quantified. Human nuclei-positive tumor cells were then assessed for double-labeling with either EdU or Ki67 (cell proliferation), or with cleaved caspase-3 (cell death). To calculate the proliferation index (percentage of proliferating tumor cells for each animal), the total number of human nuclei-positive cells co-labeled with EdU across all areas quantified was divided by the total number of human nuclei-positive cells counted across all areas quantified. This was repeated for human nuclei-positive cells assessed for double-labeling with Ki67 (proliferation index) or for cleaved caspase-3 (cell death). For cleaved caspase-3 staining, ischemic mouse brain tissue was used as a positive staining control.

Using the same selected coronal tissue sections of the 1 in 6 series, the area of quantification outside the active circuit was selected as follows: for each of the three consecutive sections per animal, the cingulum bundle was first identified as an anatomic landmark, and a 160×160-µm field area for quantification was selected in the prefrontal cortex adjacent to the longitudinal fissure and medial to the cingulum bundle. Two additional fields were selected side-by-side moving laterally in the prefrontal cortex but outside the active circuit, for a total quantified volume of $9.216 \times 10^6$ µm$^3$ per animal. Analysis of tumor cell burden: Animals were included that had well-matched xenografts with respect to location of injection tract in the rostro-caudal dimension and with respect to cortical depth. The target location was midway through the cortical depth and just outside of the rostro-caudal center of premotor area M2 but within ~240 µm of the premotor area M2 midpoint in the rostro-caudal dimension; in this way, the xenografted cells diffusely infiltrate the area of optogenetic stimulation in M2 and but xenograft needle injury and optical ferrule placement are not induced in the same coronal plane. For the repetitive stimulation experiment, two litters of mice born one day apart were xenografted two days apart at ~P35 using two separate flasks of pcGBM2 cells (at passage 19 and passage 20, respectively). The two litters had optical-neural interfaces placed as above at 9 weeks following xenotransplantation and were stimulated at 10 weeks following xenotransplantation in parallel. Because these two litters were xenografted on different days with cells from different flasks, the data were normalized to the mean tumor cell density of the identically manipulated WT control animals from each litter. Tumor cell burden was analyzed in the superior ~⅓ of the corpus allosum, 100 µm deep to the cortical-corpus callosum border, the region containing the most dense projections from both M2 and M1 motor cortices (Allen Brain Atlas). Quantification of HNA$^+$ cell density was performed by a blinded investigator as follows: three consecutive sections of a 1 in 2 series of 40-µm coronal sections were selected for closest proximity to the site of fiber optic placement. For each section, a maximum-intensity projection image of a z-stack of 6 slices 6 µm apart through the thickness of the section was obtained at 100× magnification using a Zeiss LSM700 scanning confocal microscope and Zen 2011 imaging software (Carl Zeiss Inc., Pleasanton, Calif.). HNA-positive tumor cells were then counted within five 100

μm×100 μm boxed counting areas aligned with the cortical-corpus callosum border and centered about the apex of the cingulum bundle in the maximum intensity projection images using Adobe Photoshop software (Adobe, San Jose, Calif.).

Electrophysiology in Slices:

Coronal brain sections containing the motor cortex were cut from Thy1::ChR2 mice. Following isoflurane anaesthesia, animals were decapitated and the brain rapidly removed and placed in ice-cold, oxygenated artificial CSF (aCSF) containing (in mM): 118 NaCl, 2.5 KCl, 2.5 NaHCO$_3$, 10 glucose, 1.3 MgCl$_2$, 2.5 CaCl$_2$, and 1.2 NaH$_2$PO$_4$. Slices were cut in (300 μm) sections using a vibratome (Leica VT 1200S, Buffalo Grove, Ill.), and incubated at 32° C. for 30 min before being allowed to equilibrate at room temperature for at least a further 30 min. During recording, slices were perfused with heated artificial CSF (32±2° C.). for whole cell current clamp recordings from Layer 5 (or ⅔) motor cortical pyramidal cells, recording pipettes (3-5 MΩ) fabricated from borosilicate glass were filled with a solution containing (in mM): 135 KMeSO$_4$, 8 NaCl, 10 HEPES, 2 Mg$_2$ATP, 0.3 Na$_3$GTP, 0.1 spermine, 7 phosphocreatine, and 0.3 EGTA. GABAA antagonist picrotoxin (100 μM) and AMPA receptor antagonist NBQX (10 μM) were added to the ACSF during all the experiments. 25 ms light pulses were delivered at 20 Hz for 15 min to evoke ChR2-mediated action potentials. All recordings were made using Multi-Clamp 700B (Molecular Devices), filtered at 10 kHz and digitized at 20 kHz using an ITC-16 board (Instru-Tech, Port Washington, N.Y.) and acquired using Axograph X software.

Verification of Slice Health:

All slices evaluated pre and post stimulation as in FIG. 9 were fixed in formalin, paraffin embedded, and stained with a standard hematoxylin and eosin protocol. Histological evaluation of cortical slice health was performed by a board-certified pathologist.

Generation of Conditioned Media:

Thy1::ChR2 or WT mice between the age of 4-7 weeks were briefly exposed to CO$_2$, and immediately decapitated. Extracted brains were placed in oxygenated sucrose solution and sliced in 350-μm sections using a vibratome (Leica VT 1200S, Buffalo Grove, Ill.). Slices were then placed in buffering solution (aCSF; 119 mM NaCl, 11 mM D-glucose, 25 mM NaHCO$_3$, 2.5 mM KCl, 1.2 mM NaH$_2$PO$_4$, 2.3 mM MgCl$_2$, and 2.5 mM CaCl$_2$) and allowed to recover for at least an hour. After recovery, slices were then moved into a 24 well plate and stimulated using a blue-light LED from a microscope objective. The stimulation paradigm mirrored in vivo experiments, using 20-Hz pulses of blue light for a 30 s on, 90 s off cycle over a period of 30 minutes. Surrounding medium was then collected for immediate use or frozen for future experiments.

EdU Incorporation Assay:

8-well chamber slides were coated with poly-L-lysine. Cells were then seeded at 40,000 cells per well and exposed to either aCSF, stimulated or unstimulated conditioned media from Thy1::ChR2 slices, blue light exposed WT slices, or recombinant protein (concentration vary by assay). 10 μM EdU was added to each well. Cells were fixed after 24 hours using 4% paraformaldehyde in PBS and stained using the Click-iT EdU kit and protocol (Invitrogen, Carlsbad, Calif.). Proliferation index was then determined by quantifying percentage of EdU labeled cells using confocal microscopy.

CellTiter-Glo Assay:

To assess overall cell number measurements, 5000 cells of SUpcGBM2, SU-DIPGIV, SU-DIPGXIII, or SU-GBM2 were seeded in a 96 well plate with either conditioned media from Thy1::ChR2 or WT slices or recombinant proteins of varying concentrations (see recombinant protein information). After 72 hours, CellTiter-Glo reagent (Promega, Madison, Wis.) was added at a 1:1 ratio. Luminescence was measured after 10-minute incubation at room temperature to stabilize signal.

Annexin V Apoptosis Assay:

SU-pcGBM2 cells were cultured in minimal growth media together with 50 nM NLGN-3 recombinant protein (dissolved in PBS) or PBS only as a vehicle control in duplicate for 24 hrs. Cells were harvested for FACS analyses of apoptosis using Annexin V-FITC Apoptosis Detection Kit II (556570, BD Biosciences) according to the manufacturer's instruction with slight modifications. DAPI was used in combination with Annexin V-FITC to stain the apoptotic cell population instead of PI. The stained cells were analyzed using a BD Fortessa FACS machine (BD Biosciences). The data were analyzed using Flowjo software (FLOWJO, LLC).

Biochemical Assays:

Fractionation experiments were done using Amicon ultra-centrifugal filters with either 10K or 100K cutoff membranes (Millipore, Billerica, Mass.). Conditioned medium from either blue light exposed WT or blue light stimulated Thy1::ChR2 slices was spun through filters at 12,000 rpm for 30 minutes. All proteins were resuspended in equal volumes of aCSF. Protein denaturation was achieved by boiling the conditioned media from blue light exposed WT or Thy1::ChR2 slices for 7 minutes at 100 degrees Celsius. Nucleic acid degradation was achieved by treatment of the conditioned media with RNase and DNase at a concentration of 2 μg/mL and incubated for 1 hour before being added to the cells. All experiments were done in triplicate.

Two Dimensional Gel Electrophoresis (2-D DIGE)

2-D DIGE and subsequent Protein ID were performed by Applied Biomics, Inc (Hayward, Calif.).

Preparation of Samples and CyDye Labeling:

Protein sample buffer was exchanged into 2-D cell lysis buffer (30 mM Tris-HCl, pH 8.8, containing 7 M urea, 2 M thiourea and 4% CHAPS). Protein concentration was measured using Bio-Rad protein assay method (Hercules, Calif.). For each sample, 30 ug of protein was mixed with 1.0 μL of diluted CyDye, and kept in dark on ice for 30 min. The labeling reaction was stopped by adding 1.0 μL of 10 mM Lysine to each sample, and incubating in dark on ice for additional 15 min. The labeled samples were then mixed together. The 2×2-D Sample buffer (8M urea, 4% CHAPS, 20 mg/ml DTT, 2% pharmalytes and trace amount of bromophenol blue), 100 μL destreak solution and Rehydration buffer (7M urea, 2M thiourea, 4% CHAPS, 20 mg/ml DTT, 1% pharmalytes and trace amount of bromophenol blue) were added to the labeling mix to make the total volume of 250 μL for the 13 cm IPG strip.

IEF and SDS-PAGE:

After loading the labeled samples IEF (pH 3-10) was run following the protocol provided by GE Healthcare. Upon finishing the IEF, the IPG strips were incubated in the freshly made equilibration buffer-1 (50 mM Tris-HCl, pH 8.8, containing 6M urea, 30% glycerol, 2% SDS, trace amount of bromophenol blue and 10 mg/ml DTT) for 15 minutes with gentle shaking. Then the strips were rinsed in the freshly made equilibration buffer-2 (50 mM Tris-HCl, pH 8.8, containing 6 M urea, 30% glycerol, 2% SDS, trace amount of bromophenol blue and 45 mg/mL Iodoacetamide) for 10 minutes with gentle shaking. Next the IPG strips were rinsed in the SDS-gel running buffer before transferring into 12% SDS-gels. The SDS-gels were run at 15° C. until the dye front ran out of the gels.

Image Scan and Data Analysis:

Gel images were scanned immediately following the SDSPAGE using Typhoon TRIO (GE Healthcare, Waukesha, Wis.). The scanned images were then analyzed by Image Quant software (version 6.0, GE Healthcare, Waukesha, Wis.), followed by quantitation analysis using DeCyder software (version 6.5, GE Healthcare, Waukesha, Wis.). The fold change of the protein expression levels was obtained from in-gel DeCyder analysis.

Protein Identification by Mass Spectrometry

Spot Picking and Trypsin Digestion:

The spots of interest were picked up by Ettan Spot Picker (Amersham BioSciences, Piscataway, N.J.) based on the in-gel analysis and spot picking design by DeCyder software. The gel spots were washed a few times then digested in-gel with modified porcine trypsin protease (Trypsin Gold, Promega, Madison, Wis.). The digested tryptic peptides were desalted by Zip-tip C18 (Millipore, Billerica, Mass.). Peptides were eluted from the Zip-tip with 0.5 µL of matrix solution (α-cyano-4-hydroxycinnamic acid 5 mg/mL in 50% acetonitrile, 0.1% trifluoroacetic acid, 25 mM ammonium bicarbonate) and spotted on the AB SCIEX MALDI plate (Opti-TOF™ 384 Well Insert, AB SCIEX, Framingham, Mass.).

Mass Spectrometry:

MALDI-TOF MS and TOF/TOF tandem MS/MS were performed on an AB SCIEX TOF/TOF™ 5800 System (AB SCIEX, Framingham, Mass.). MALDI-TOF mass spectra were acquired in reflectron positive ion mode, averaging 4000 laser shots per spectrum. TOF/TOF tandem MS fragmentation spectra were acquired for each sample, averaging 4000 laser shots per fragmentation spectrum on each of the 10 most abundant ions present in each sample (excluding trypsin autolytic peptides and other known background ions).

Database Search:

Both of the resulting peptide mass and the associated fragmentation spectra were submitted to GPS Explorer workstation equipped with MASCOT search engine (Matrix Science, Boston, Calif.) to search the Swiss-Prot database. Searches were performed without constraining protein molecular weight or isoelectric point, with variable carbamidomethylation of cysteine and oxidation of methionine residues, and with one missed cleavage also allowed in the search parameters. Candidates with either protein score C.I. % or Ion C.I. % greater than 95 were considered significant.

Spectral Counting and Tandem Mass Tags (TMT) Proteomic Analyses:

Proteomics Materials: Ammonium bicarbonate, dithiothreitol (DTT), and iodoacetamide were from Sigma (St. Louis, Mo.). Sequencing grade modified porcine trypsin was from Promega (Madison, Wis.), Formic acid, HPLC grade acetonitrile, HPLC grade water and Amino reactive TMT reagents (126 to 131) were purchased from ThermoFisher Scientific (Waltham, Mass.). BCA protein assay kit was purchased from Pierce. C18 Magic bead size 5 µm, pore size 300 Å was purchased from Michrom BioResources (Auburn, Calif.). Symmetry 300 C18 5 µm NanoEase trap column was purchased from Waters (Milford, Mass.).

Proteomic Sample Preparation:

Protein digestion and identification by LC-MS/MS was performed as described previously. Briefly, sample concentration was estimated by Pierce BCA protein assay (Thermo Scientific, Waltham, Mass.). Next, in-solution digestion was performed with lyophilized samples that were resuspended, denatured and reduced in 50 mM $NH_4HCO_3$ buffer (pH 8.0) with 10 mM DTT, 0.1% PPS detergent (Agilent Technologies, Santa Clara, Calif.), for 2 h at 56° C. The reaction was cooled to room temperature and the sample was alkylated with 50 mM iodoacetamide for 60 min at room temperature in the dark. The resulting mixtures were diluted 6-fold with 50 mM $NH_4HCO_3$ (pH 8.0), and then trypsin was added at a trypsin-to-protein ratio of 1:50 (w/w). The reaction as incubated for 18 hours at 37° C. The digestion was interrupted and acidified by addition of 5 µL of 10% formic acid solution. For TMT analysis, Amino reactive TMT reagents (126 to 131, 0.8 mg; Thermo Scientific, Waltham, Mass.) were dissolved in 41 µL acetonitrile, and 10 µL of the solution was added to 100 µg of peptides. After incubating for 1 hour at room temperature (22° C.), the reaction was quenched by adding 8 µL of 5% w/v hydroxylamine for 15 minutes. Following labeling, the sample was combined in equal ratios. The peptide-containing samples were then dried using a speed vacuum concentrator. The samples were reconstituted with 10-20 µL of 0.1% (vol/vol) formic acid in water.

Mass Spectrometric Data Acquisition:

Nano-LC-MS/MS was performed using an Eksigent nanoLC 2D system (Dublin, Calif.) interfaced with a LTQ-Velos-Orbitrap mass spectrometer (Thermo Scientific, Waltham, Mass.) which is coupled with a CaptiveSpray source (Michrom BioResources, Auburn, Calif.). The composition of solvent A was 0.1% (v/v) of formic acid in water and solvent B consisted of 0.1% (v/v) of formic acid in HPLC grade acetonitrile. 10 µL of the digested samples were injected using a CTC autosampler (Leap Technologies, Carrboro, N.C.) onto a Symmetry 300 C18 5 µm NanoEase trap column. Samples were loaded onto the trap column at a flow rate of 5 µL/min, for 20 min using 0.1% formic acid in water. The peptides were eluted from the trap column and subsequently separated on an IntegraFrit capillary analytical column (150 mm×75 µm i.d.) packed in-house with Magic C18, using 90 minute linear gradient (3%-40% solvent B) at a flow rate of 600 nL/min. The mass spectrometer was operated in a data dependent MS/MS mode. A single full MS scan, collected in the Orbitrap in profile mode over the mass range of 400-2000 m/z, was accompanied by 10 MS/MS scans, collected in centroid mode in the LTQ, of the 10 most intense peaks. Dynamic exclusion parameters included: repeat count=1, repeat duration=30, exclusion list size=400, exclusion duration=30 s, and dynamic exclusion width=1.5 (high and low by mass). For TMT analysis, HCD fragmentation in the orbitrap was performed.

Peptide and Protein Identification and Quantification:

Acquired data was automatically processed using default parameters, except where noted, by the Computational Proteomics Analysis System V8.2-CPAS. The tandem mass spectra were searched against human protein database (UniProtKB) supplemented with sequences for human and bovine trypsin, common contaminants and reverse decoy sequences. The search was performed with X!Tandem. The mass tolerance for precursor ions was set during the search to 1 AMU with a mass tolerance for fragment ions set to 0.5 Da. However, matches with less than 5 ppm mass accuracy were considered to false positives and discarded. A fixed modification of 6.020129 mass units was added to lysine residues for database searching to account for incorporation of the heavy lysine isotope. All identifications with a PeptideProphet probability greater than 0.9 were submitted to ProteinProphet and the subsequent protein identifications were filtered at a 1% error rate with tryptic fragments (1 missed cleavage) with allowance for fixed modification on C=57.021 and variable modifications on C=−17.027, E=−18.011, K=6.020, M=15.995, and Q=−17.027. TMT data was quantified using both ProteomeDiscoverer and Libra.

Proteins selected for subsequent analysis had PeptideProphet and ProteinProphet confidence P>0.99, a large number of quantified peptides. Data supporting the change in protein abundance for each of these proteins were manually verified by interrogation of the single ion chromatograms.

Protein quantification by spectral counting was determined using NSAF and $SI_N$ as implemented in Crux. To identify proteins with significant fold change between CHR2 and WT media by spectral counting, the EdgeR package was used. Peptide spectral counts were modeled as an overdispersed Poisson/negative binomial distribution in which an empirical Bayes procedure was used to moderate overdispersion across each protein. Proteins whose cumulative counts in both conditions were less than 4 were discarded. Using this approach, confidence in a protein's ChR2 and WT medium difference in abundance is a function of magnitude of difference in normalized counts between conditions and total number of normalized counts. Estimation of absolute abundance of proteins was performed using a weighted spectral count approach as implemented in. Spectral counting rests on the observation that the PSM count for a peptide correlates linearly with its molar concentration in the sample. This approach is essentially a simplification of the APEX method. Estimation of significance of CHR2 and WT medium difference in abundance in TMT experiments was performed using a generalized linear model approach, as implemented in MSStats.

Western Blot Analysis:

Briefly, in FIG. 5, panel A, cells were lysed after 1-hour exposure to 0 nM, 5 nM, 10 nM, or 50 nM recombinant NLGN3 (Origene Technologies, Rockville, Md.), using RIPA buffer and protease inhibitors. In FIG. 5, panel G, cells were exposed to 50 nM NLGN3 for 12 hours, and then allowed to recover in fresh media for 24 hours. After thorough washing, cells were lysed as above. For all experiments, lysates were incubated on ice for 10 minutes and then centrifuged for 10 minutes at 4° C. Protein concentration in the lysate was determined using a Bradford assay. Samples were then normalized to protein concentration, mixed with Laemmli loading buffer (1:4), boiled for 5 minutes, and loaded onto BioRad Mini-Protean TGX precast gels. Protein was transferred to PVDF membranes and blocked with 5% bovine serum albumin (BSA) in TBST for one hour. Primary antibodies were diluted in 1% BSA/TBST and incubated with the membrane overnight. Antibodies against phospho-AKT (Cell Signaling, Danvers, Mass.) and total AKT (Cell Signaling, Danvers, Mass.) were used at a concentration of 1:1000. Anti-Neuroligin-3 (NovusBio, Littleton, Colo.) was used at a concentration of 1:500. Secondary anti-rabbit conjugated to HRP (BioRad, Hercules, Calif.) was then added for one hour (1:1000). Proteins were visualized using Clarity ECL Western Substrate (BioRad, Hercules, Calif.) and quantified using ImageJ.

qPCR Analysis:

500,000 SU-pcGBM2 cells were exposed to either aCSF, 50 nM NLGN3 (Origene Technologies, Rockville), 500 nM BKM120 (SelleckChem, Houston, Tex.), 50 nM EGF (Shenandoah, Warwick, R.I.), or a combination of the above treatments. RNA was extracted using the TRIzol Reagent (Life Technologies, Carlsbad, Calif.) at either 1 hour (FIG. 5C) or 12 hours (FIG. 5D-F) after treatment. For qPCR analysis, cDNA was prepared using iScript cDNA Synthesis Kit (BioRad, Hercules, Calif.). RT-PCR was performed on Eppendorf Mastercyler Realplex2 using Universal SYBR Green Supermix (BioRad, Hercules, Calif.). Differential expression was determined using the delta CT method. Primers used were as follows:

```
                                    (SEQ ID NO: 10)
FOS forward:      5' CCTAACCGCCACGATGATGT 3'

(SEQ ID NO: 11)
FOS reverse:      5' TCTGCGGGTGAGTGGTAGTA 3'

(SEQ ID NO: 12)
NLGN3 forward:    5' GGGAGTCCCCTTTCTGAAGC 3'

(SEQ ID NO: 13)
NLGN3 reverse:    5' CCTTCATGGCCACACTGACT 3'

(SEQ ID NO: 14)
ACTB forward:     5' TGAAGTGTGACGTGGACATC 3'

(SEQ ID NO: 15)
ACTB reverse:     5' GGAGGAGCAATGATCTTGAT 3'
```

RNA Sequencing:

RNA sequencing was performed by Elim Biopharm, (Hayward, Calif.). Total RNA was treated with RiboZero™ (EpiCentre, Madison, Wis.) to remove rRNA. The resulting RNA was subject to cDNA synthesis with standard protocol for the first and second strands of cDNA synthesis. Illumina library was prepared from the ds cDNA according to Illumina's standard NGS library preparation method. The libraries were quantified and Q.C.'ed by Qubit, Bioanalyzer, and qPCR. The libraries were then sequenced on Illumina HiSeq2500 (Madison, Wis.) with 50 by paired-end read run, generating 179.62M reads. For data analysis, TopHat was used for mapping to the reference genome (hg19(UCSC)), and Cufflinks was used for differential expression analysis.

Pharmacologic Inhibition:

SU-pcGBM2 or SU-DIPGXIII were treated with 100 nM BKM120 (SelleckChem, Houston, Tex.) or 100 nM RAD001 (SelleckChem, Houston, Tex.) dissolved in DMSO. All experiments using inhibitor treatments used vehicle DMSO treatment as control.

shRNA Expressing Lentivirus Preparation and Infection:

shRNA expressing lentiviral constructs against human PIK3CA and mTOR from the RNAi consortium human collection were purchased from Sigma. Lentiviral expressing constructs were co-transfected with packaging plasmids (pDelta 8.92+VSV-G) into 293T cells to generate lentiviral particles. Lentiviral particles were then concentrated by the polyethylene glycol precipitation method. The precipitated lentiviruses were resuspended in PBS and aliquoted for −80° C. storage. For lentiviral infection, SU-pcGBM2 cells were incubated with shRNA expressing lentivirus; 48 h post infection, puromycin (0.5 ug/ml) was added to select virally infected cells for further experiments.

Recombinant Proteins Used:

GRP78 (Abcam, Cambridge, Mass.), BDNF (R&D Systems, Minneapolis, Minn.), NLGN3 (Origene, Rockville, Calif.), NRXN1β (R&D Systems, Minneapolis, Minn.).

Statistical Analyses:

Unpaired, two-tailed Student's t-tests were used for analysis of tumor burden among experimental groups and change in HGG proliferation index in vivo, in NLGN3 necessity and sufficiency experiments, as well as analysis of change in Fos and NLGN3 expression by qPCR. Group mean differences were otherwise assessed using one-way analysis of variance (one-way ANOVA) with Tukey post-hoc tests to further examine pairwise differences. A level of P<0.05 was used to designate significant differences.

For human genomic analyses, level 3 gene level transcription estimates (log 2 LOWESS normalized ratio of sample signal to reference signal (cy5/cy3) collapsed by gene) generated on Agilent 244K custom gene expression G4502A_07_2 microarrays were downloaded from The Cancer Genome Atlas (TCGA; www(dot)cancergenome(dot)nih(dot)gov). Survival curves were estimated with the use of the Kaplan-Meier product-limit method, and survival distributions were compared across groups with the use of the log-rank test. Univariate and multivariate Cox proportional-hazards regression analyses was performed, with overall survival as the dependent variable and NLGN3 and NLGN2 expression as the primary predictor. In interpreting hazard ratios, NLGN3 and NLGN2 expression was dichotomized at the median. An independent-samples Kruskal-Wallis test was used to compare NLGN3 expression across various molecular subtypes of glioblastoma. NLGN3 gene mutation data and cross-cancer NLGN3 gene alteration data were downloaded from the International Cancer Genome Consortium (ICGC) data portal (https(colon-slash-slash)dcc(dot)icgc(dot)org, ICGC Data Release 17, Sep. 12, 2014) and the cBioPortal for Cancer Genomics (http(colon-slash-slash)cbioportal(dot)org) respectively. Detailed methods for the generation of simple somatic mutations frequencies and for computed functional impact scores using Functional Analysis Through Hidden Markov Models (FATHMM) are available at: https(colon-slash-slash)docs(dot)icgc(dot)org(slash)methods.

Example 10: Method for Treating a Glioma Tumor with a Small Molecule

A small molecule that inhibits the activity of a neuronal activity-regulated protein, as described herein and shown in Table 1, is formulated into a pharmaceutical composition suitable for administering intravenously to a subject. The pharmaceutical composition containing the small molecule that inhibits the activity of a neuronal activity-regulated protein is then administered intravenously to a subject diagnosed with a glioma tumor, and in some cases administered in combination with other therapies, e.g., other anti-cancer drugs, or an immunotherapy. The dose and administration regimen of the small molecule is adjusted appropriately to treat the glioma tumor in the subject.

After administering a small molecule that inhibits the activity of a neuronal activity-regulated protein to a patient, the therapeutic effect of the small molecule on the patient is monitored using MRI imaging, PET scan, and/or other neurological tests. Reduced rate of growth of the glioma, retarded invasion of the glioma in brain tissue, and/or reduced neurological dysfunction associated with the glioma is observed in the subject, compared to a subject that is not administered with the therapeutic agent, or compared to the same patient before administering the small molecule. The subject method of administering a small molecule that inhibits the activity of a neuronal activity-regulated protein to a patient with glioma results in improved clinical outcomes such as an increase in overall survival rate of treated subjects, an increase in time to progression of the glioma tumor, and/or an increase in progress-free time of the glioma tumor in treated subjects compared to non-treated subjects.

Example 11: Method for Treating a Glioma Tumor with a Polypeptide

A polypeptide that inhibits the activity of a neuronal activity-regulated protein, as described herein and shown in Table 1, is formulated into a pharmaceutical composition suitable for administering intrathecally or intracerebrally to a subject. The pharmaceutical composition containing the polypeptide that inhibits the activity of a neuronal activity-regulated protein is then administered intrathecally or intracerebrally to a subject diagnosed with a glioma tumor, and in some cases administered in combination with other therapies, e.g., other anti-cancer drugs, or an immunotherapy. The dose and administration regimen of the polypeptide is adjusted appropriately to treat the glioma tumor in the subject.

After administering a polypeptide that inhibits the activity of a neuronal activity-regulated protein to a patient, the therapeutic effect of the polypeptide on the patient is monitored using MRI imaging, PET scan, and/or other neurological tests. Reduced rate of growth of the glioma, retarded invasion of the glioma in brain tissue, and/or reduced neurological dysfunction associated with the glioma is observed in the subject, compared to a subject that is not administered with the therapeutic agent, or compared to the same patient before administering the polypeptide. The subject method of administering a polypeptide that inhibits the activity of a neuronal activity-regulated protein to a patient with glioma results in improved clinical outcomes such as an increase in overall survival rate of treated subjects, an increase in time to progression of the glioma tumor, and/or an increase in progress-free time of the glioma tumor in treated subjects compared to non-treated subjects.

Example 12: Method for Treating a Glioma Tumor with an Antibody

An antibody that inhibits the activity of a neuronal activity-regulated protein, as described herein and shown in Table 1, is formulated into a pharmaceutical composition suitable for administering intrathecally or intracerebrally to a subject. The pharmaceutical composition containing the antibody that inhibits the activity of a neuronal activity-regulated protein is then administered intrathecally or intracerebrally to a subject diagnosed with a glioma tumor, and in some cases administered in combination with other therapies, e.g., other anti-cancer drugs, or an immunotherapy. The dose and administration regimen of the antibody is adjusted appropriately to treat the glioma tumor in the subject.

After administering an antibody that inhibits the activity of a neuronal activity-regulated protein to a patient, the therapeutic effect of the antibody on the patient is monitored using MRI imaging, PET scan, and/or other neurological tests. Reduced rate of growth of the glioma, retarded invasion of the glioma in brain tissue, and/or reduced neurological dysfunction associated with the glioma is observed in the subject, compared to a subject that is not administered with the therapeutic agent, or compared to the same patient before administering the antibody. The subject method of administering a antibody that inhibits the activity of a neuronal activity-regulated protein to a patient with glioma results in improved clinical outcomes such as an increase in overall survival rate of treated subjects, an increase in time to progression of the glioma tumor, and/or an increase in progress-free time of the glioma tumor in treated subjects compared to non-treated subjects.

Example 13: NLGN3 is Required for Activity-Regulated Glioma Cell Proliferation Cortical slices were obtained from NLGN3 knock out (KO) mice (NLGN3$^{-/-}$). The cortical slices were acutely stimulated and the effect of the conditioned media on glioma cells was measured. A decrease in the effect of proliferation in the absence of neuroligin-3 was observed.

Figure 36A:
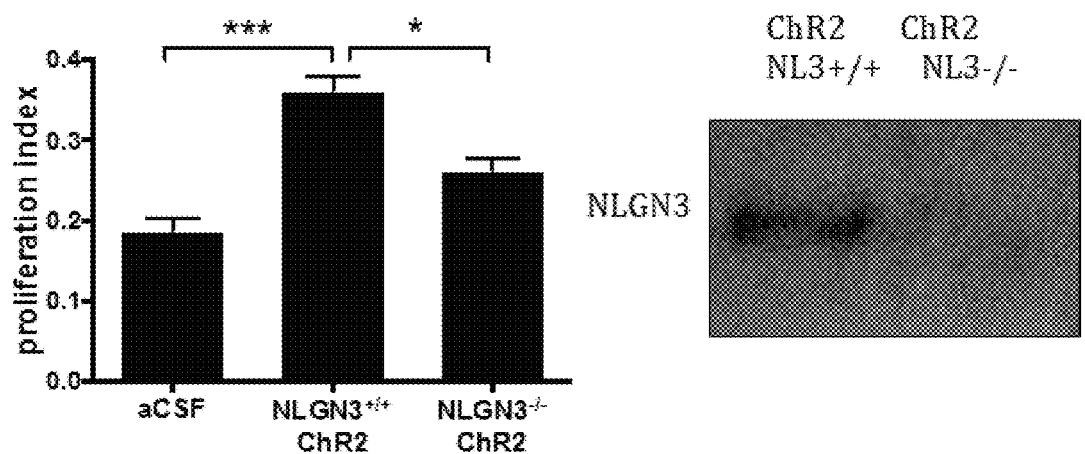
FIG. 36A illustrates that genetic NLGN3 knockout reduces activity-regulated glioma cell proliferation in vitro.
Figure 36B:
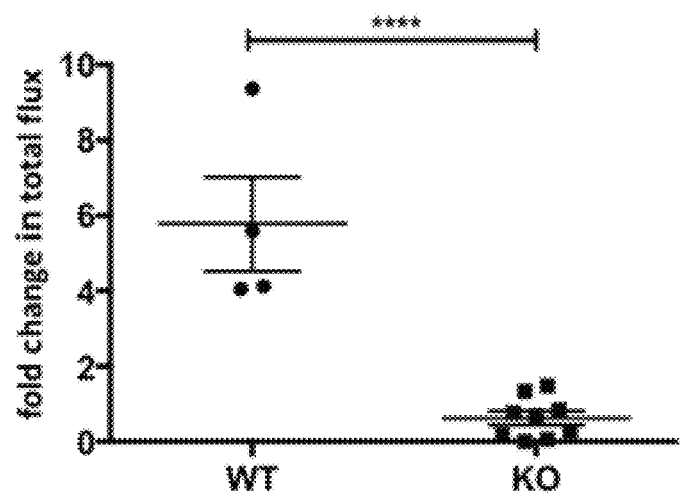
FIG. 36B shows that absence of NLGN3 reduces glioma growth in vivo.

FIG. 36A. Genetic NLGN3 knockout reduces activity-regulated glioma cell proliferation in vitro. Cortical slices from WT Thy1::ChR2 mice and from NLGN3 KO Thy1::ChR2 mice were incubated in culture medium and stimulated optogenetically. The culture media conditioned by the cortical slices during optogenic stimulation was collected. This conditioned media is denoted as active CM. Unconditioned media (artificial cerebrospinal fluid-aCSF) was used in control wells. Data shown as mean±SEM. One-way ANOVA, *P<0.05, ***P<0.001. n.s.=P>0.05.

The NLGN3 knockout mice (NLGN3−/−) were bred with the xenograftable model (NSG). The resulting NLGN3−/−; NSG model was xenografted in the premotor cortex with cortical pHGG cells, side-by-side with identically manipulated NLGN3WT; NSG mice, to evaluate the role of NLGN3 in glioma growth in vivo. Mice were xenografted with a pediatric cortical HGG at P35. Tumor burden was evaluated using IVIS® imaging analysis every 2 weeks over a period of 6 weeks. Mice lacking NLGN3 showed a significant reduction in tumor growth compared to those of their WT littermates.

FIG. 36B.

NLGN3 promotes high-grade glioma growth in vivo. Fold change of tumor burden over 4 weeks as assessed by IVIS imaging of pHGG cells in identically manipulated NLGN3$^{WT}$; NSG (n=4) and NLGN3$^{−/−}$; NSG (n=9) mice. Data shown as mean±SEM. ****P<0.0001 by unpaired two-tailed Student's t-test.

Example 14: Pharmacological Inhibition of Activity-Regulated NLGN3 Secretion

A pilot experiment incubating acute cortical slices with the ADAM10 inhibitor GI254023X (Tocris) during optogenetic stimulation resulted in ~50% reduction in soluble NLGN3 in the CM as detected by 2D-PAGE and mass spectrometry, supporting a role for ADAM10 in NLGN3 secretion.

A series of similar preliminary experiments were performed in which acute cortical slices were incubated with different protease inhibitors during optogenetic stimulation and then the active CM was analyzed by Western blot for secreted NLGN3. In this series of experiments, a significant decrease in NLGN3 levels using the protease inhibitor multi-MMP inhibitor batimastat, the MMP2/9 inhibitor SCBT inhibitor II (Santa Cruz Biotechnology), and the MMP9/13 Inhbitor II (Santa Cruz Biotechnology) was observed. No detectable decrease in secreted NLGN3 with the MMP2-specific inhibitor ARP100 (Tocris), MMP2/3 Inhbitor I (Santa Cruz Biotechnology), or the MMP-13 Inhbitor (Santa Cruz Biotechnology) was observed. Additionally, no direct effect was seen with the MMP-9 Inhibitor I (Santa Cruz Biotechnology) though the inhibitor is widely believed to be in effective. While the effect of ADAM10 inhibition was confirmed, no effect on NLGN3 levels was observed using the ADAM 17 inhibitor TAPI (Selleck-Chem). Together, these results identify a key role for MMP9 and ADAM10 in activity-dependent secretion of NLGN3.

FIG. 37.

Role for MMP9 in NLGN3 secretion: Acute cortical slices from Thy1::ChR2 mice were optogenetically-stimulated in the presence or absence of protease inhibitors as indicated. Conditioned media was analyzed by Western blot for secreted NLGN3 content.

Figure 37:
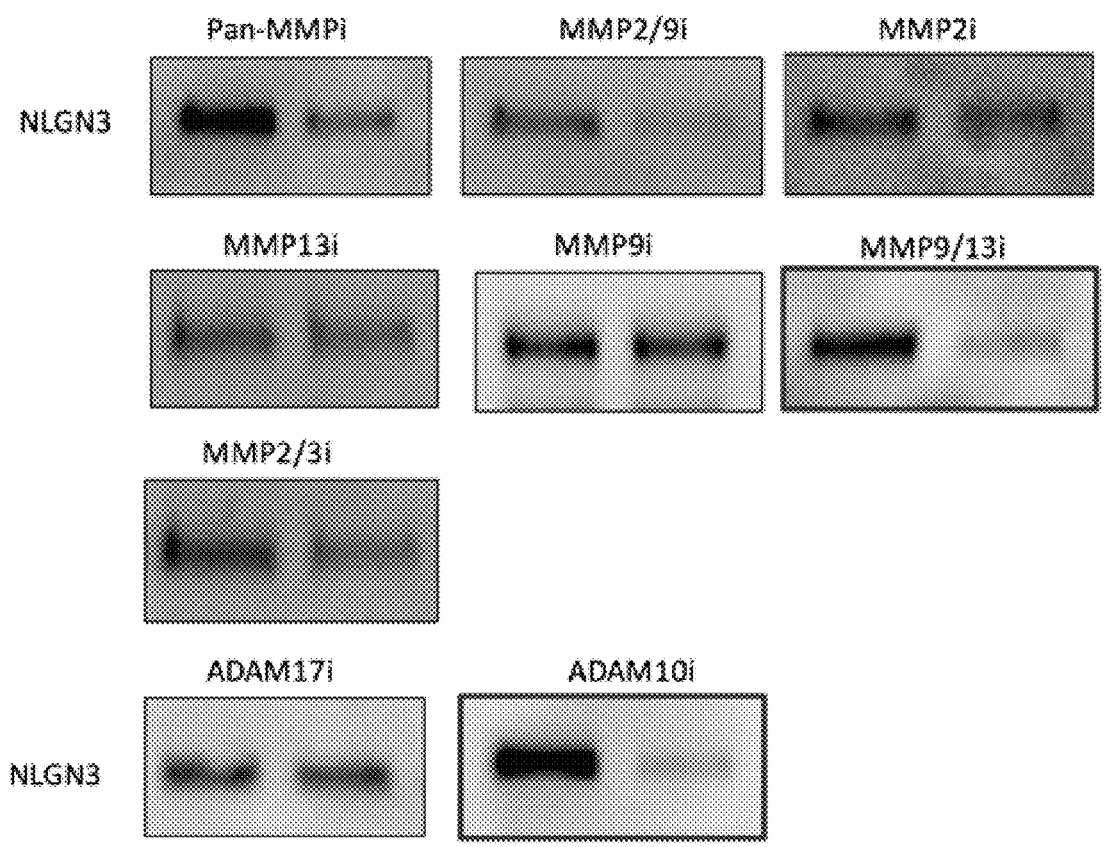
FIG. 37 shows the role of MMP9 in NLGN3 secretion.
Figure 38:
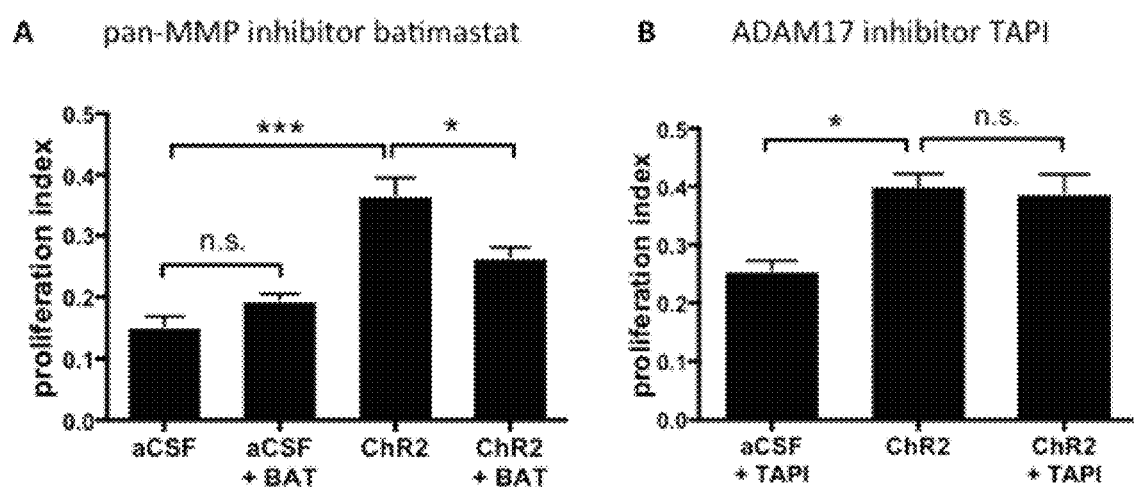
FIG. 38, Panel A illustrates that MMP inhibition in situ reduces activity-regulated glioma cell proliferation in vitro.

Example 15: Protease Inhibitor Mediated Inhibition of Activity-Regulated NLGN3 Secretion Reduces Glioma Cell Growth MMP inhibition abrogates activity-regulated glioma proliferation. Acute cortical slices were optogenetically-stimulated in the presence or absence of a protease inhibitor as in Example 14, and pHGG cells were exposed to the CM. As expected, active CM in the absence of protease inhibitors contained secreted NLGN3 (FIG. 37) and promoted glioma cell proliferation (FIG. 38). Addition of an ADAM17 inhibitor did not decrease NLGN3 levels as detected by Western blot (FIG. 37), and did not alter the mitogenic effect of active CM. In contrast, a multi-MMP inhibitor (batimastat) decreased NLGN3 secretion (FIG. 37) and abrogated the mitogenic effect of active CM (FIG. 38).

FIG. 38.

MMP inhibition in situ reduces activity-regulated glioma cell proliferation in vitro Active CM from Thy1::ChR2 cortical slices were incubated with either the multi-MMP inhibitor batimastat (A) or the ADAM17 inhibitor TAPI (B) during optogenetic stimulation and the active CM collected. Unconditioned media (aCSF) with or without inhibitor was used in control wells. Data shown as mean±SEM. One-way ANOVA, *P<0.05, ***P<0.001. n.s.=P>0.05.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of reducing a neurological dysfunction in a patient with a glioma tumor, the method comprising:
   administering to the patient a therapeutically-effective amount of an ADAM10 inhibitor INCB7839 that reduces secretion of neuroligin-3 in the glioma tumor; and
   measuring a level of secreted neuroligin-3 in cerebrospinal fluid (CSF) from the patient.

2. The method according to claim 1, wherein the neurological dysfunction comprises pain, numbness, seizures, neuromuscular dysfunction, cognitive impairment, or personality changes.

3. The method according to claim 1, wherein INCB7839 is administered to the subject orally, intravenously, locally or intrathecally.

4. The method according to claim 1, wherein INCB7839 is formulated for sustained release.

5. The method according to claim 1, wherein said administering INCB7839 reduces secreted neuroligin-3 by at least 50% as compared to the secreted form of neuroligin-3 in the patient without treatment with the ADAM10 inhibitor INCB7839.

6. The method according to claim 1, wherein said secreted neuroligin-3 is measured using an immunological assay.

7. The method according to claim 6, wherein the immunological assay is a Western-Blot assay.

8. A method of preventing a glioma tumor cell from invading a brain tissue in a patient, the method comprising:
   administering to the patient a therapeutically-effective amount of an ADAM10 inhibitor INCB7839 that reduces secretion of neuroligin-3; and
   measuring a level of secreted neuroligin-3 in cerebrospinal fluid (CSF) from the patient.

9. The method according to claim 8, wherein INCB7839 is administered to the subject orally, intravenously, locally or intrathecally.

10. The method according to claim 8, wherein INCB7839 is formulated for sustained release.

11. A method of reducing a growth rate of a glioma tumor cell in a patient, the method comprising:
    administering to the patient a therapeutically-effective amount of an ADAM10 inhibitor INCB7839 that reduces secretion of neuroligin-3; and
    measuring a level of secreted neuroligin-3 in cerebrospinal fluid (CSF) from the patient.

12. The method according to claim 11, wherein INCB7839 is administered to the subject orally, intravenously, locally or intrathecally.

13. The method according to claim 11, wherein INCB7839 is formulated for sustained release.

14. A method for treating a glioma tumor in a subject, the method comprising:
    administering to the subject a therapeutically-effective amount of an ADAM10 inhibitor INCB7839 that reduces secretion of neuroligin-3.

15. The method according to claim 14, wherein INCB7839 is administered to the subject orally, intravenously, locally or intrathecally.

16. The method according to claim 14, wherein INCB7839 is formulated for sustained release.

* * * * *

SEQUENCE LISTING

<160> NUMBER OF SEQ ID NOS: 27

<210> SEQ ID NO 1
<211> LENGTH: 825
<212> TYPE: PRT
<213> ORGANISM: Mus musculus

<400> SEQUENCE: 1

Met Trp Leu Gln Pro Ser Leu Ser Leu Ser Pro Thr Pro Thr Val Gly
1               5                   10                  15

Arg Ser Leu Cys Leu Thr Leu Gly Phe Leu Ser Leu Val Leu Arg Ala
            20                  25                  30

Ser Thr Gln Ala Pro Ala Pro Thr Val Asn Thr His Phe Gly Lys Leu
        35                  40                  45

Arg Gly Ala Arg Val Pro Leu Pro Ser Glu Ile Leu Gly Pro Val Asp
    50                  55                  60

Gln Tyr Leu Gly Val Pro Tyr Ala Ala Pro Pro Ile Gly Glu Lys Arg
65                  70                  75                  80

Phe Leu Pro Pro Glu Pro Pro Ser Trp Ser Gly Ile Arg Asn Ala
            85                  90                  95

Thr His Phe Pro Pro Val Cys Pro Gln Asn Ile His Thr Ala Val Pro
            100                 105                 110

Glu Val Met Leu Pro Val Trp Phe Thr Ala Asn Leu Asp Ile Val Ala
            115                 120                 125

Thr Tyr Ile Gln Glu Pro Asn Glu Asp Cys Leu Tyr Leu Asn Val Tyr
    130                 135                 140

Val Pro Thr Glu Asp Gly Ser Gly Ala Lys Lys Gln Gly Glu Asp Leu
145                 150                 155                 160

Ala Asp Asn Asp Gly Asp Glu Asp Ile Arg Asp Ser Gly Ala
            165                 170                 175

Lys Pro Val Met Val Tyr Ile His Gly Gly Ser Tyr Met Glu Gly Thr
            180                 185                 190

Gly Asn Met Ile Asp Gly Ser Val Leu Ala Ser Tyr Gly Asn Val Ile
        195                 200                 205

Val Ile Thr Leu Asn Tyr Arg Val Gly Val Leu Gly Phe Leu Ser Thr
    210                 215                 220

Gly Asp Gln Ala Ala Lys Gly Asn Tyr Gly Leu Leu Asp Gln Ile Gln
225                 230                 235                 240

Ala Leu Arg Trp Val Ser Glu Asn Ile Ala Phe Phe Gly Gly Asp Pro
            245                 250                 255

Arg Arg Ile Thr Val Phe Gly Ser Gly Ile Gly Ala Ser Cys Val Ser
            260                 265                 270

Leu Leu Thr Leu Ser His His Ser Glu Gly Leu Phe Gln Arg Ala Ile
    275                 280                 285

Ile Gln Ser Gly Ser Ala Leu Ser Ser Trp Ala Val Asn Tyr Gln Pro
        290                 295                 300

Val Lys Tyr Thr Ser Leu Leu Ala Asp Lys Val Gly Cys Asn Val Leu
305                 310                 315                 320

Asp Thr Val Asp Met Val Asp Cys Leu Arg Gln Lys Ser Ala Lys Glu
            325                 330                 335

Leu Val Glu Gln Asp Ile Gln Pro Ala Arg Tyr His Val Ala Phe Gly
            340                 345                 350

Pro Val Ile Asp Gly Asp Val Ile Pro Asp Asp Pro Glu Ile Leu Met
            355                 360                 365

-continued

```
Glu Gln Gly Glu Phe Leu Asn Tyr Asp Ile Met Leu Gly Val Asn Gln
    370                 375                 380
Gly Glu Gly Leu Lys Phe Val Glu Gly Val Asp Pro Glu Asp Gly
385                 390                 395                 400
Val Ser Gly Thr Asp Phe Asp Tyr Ser Val Ser Asn Phe Val Asp Asn
                405                 410                 415
Leu Tyr Gly Tyr Pro Glu Gly Lys Asp Thr Leu Arg Glu Thr Ile Lys
                420                 425                 430
Phe Met Tyr Thr Asp Trp Ala Asp Arg Asp Asn Pro Glu Thr Arg Arg
                435                 440                 445
Lys Thr Leu Val Ala Leu Phe Thr Asp His Gln Trp Val Glu Pro Ser
450                 455                 460
Val Val Thr Ala Asp Leu His Ala Arg Tyr Gly Ser Pro Thr Tyr Phe
465                 470                 475                 480
Tyr Ala Phe Tyr His His Cys Gln Ser Leu Met Lys Pro Ala Trp Ser
                485                 490                 495
Asp Ala Ala His Gly Asp Glu Val Pro Tyr Val Phe Gly Val Pro Met
                500                 505                 510
Val Gly Pro Thr Asp Leu Phe Pro Cys Asn Phe Ser Lys Asn Asp Val
            515                 520                 525
Met Leu Ser Ala Val Val Met Thr Tyr Trp Thr Asn Phe Ala Lys Thr
530                 535                 540
Gly Asp Pro Asn Lys Pro Val Pro Gln Asp Thr Lys Phe Ile His Thr
545                 550                 555                 560
Lys Ala Asn Arg Phe Glu Glu Val Ala Trp Ser Lys Tyr Asn Pro Arg
                565                 570                 575
Asp Gln Leu Tyr Leu His Ile Gly Leu Lys Pro Arg Val Arg Asp His
                580                 585                 590
Tyr Arg Ala Thr Lys Val Ala Phe Trp Lys His Leu Val Pro His Leu
            595                 600                 605
Tyr Asn Leu His Asp Met Phe His Tyr Thr Ser Thr Thr Thr Lys Val
        610                 615                 620
Pro Pro Pro Asp Thr Thr His Ser Ser His Ile Thr Arg Arg Pro Asn
625                 630                 635                 640
Gly Lys Thr Trp Ser Thr Lys Arg Pro Ala Ile Ser Pro Ala Tyr Ser
                645                 650                 655
Asn Glu Asn Ala Pro Gly Ser Trp Asn Gly Asp Gln Asp Ala Gly Pro
                660                 665                 670
Leu Leu Val Glu Asn Pro Arg Asp Tyr Ser Thr Glu Leu Ser Val Thr
            675                 680                 685
Ile Ala Val Gly Ala Ser Leu Leu Phe Leu Asn Val Leu Ala Phe Ala
690                 695                 700
Ala Leu Tyr Tyr Arg Lys Asp Lys Arg Arg Gln Glu Pro Leu Arg Gln
705                 710                 715                 720
Pro Ser Pro Gln Arg Gly Thr Gly Ala Pro Glu Leu Gly Thr Ala Pro
                725                 730                 735
Glu Glu Glu Leu Ala Ala Leu Gln Leu Gly Pro Thr His His Glu Cys
                740                 745                 750
Glu Ala Gly Pro Pro His Asp Thr Leu Arg Leu Thr Ala Leu Pro Asp
            755                 760                 765
Tyr Thr Leu Thr Leu Arg Arg Ser Pro Asp Asp Ile Pro Leu Met Thr
770                 775                 780
Pro Asn Thr Ile Thr Met Ile Pro Asn Ser Leu Val Gly Leu Gln Thr
```

```
            785                 790                 795                 800
Leu His Pro Tyr Asn Thr Phe Ala Ala Gly Phe Asn Ser Thr Gly Leu
                    805                 810                 815

Pro His Ser His Ser Thr Thr Arg Val
                820                 825

<210> SEQ ID NO 2
<211> LENGTH: 1547
<212> TYPE: PRT
<213> ORGANISM: Homo sapiens

<400> SEQUENCE: 2

Met Gly Thr Ala Leu Leu Gln Arg Gly Gly Cys Phe Leu Leu Cys Leu
1               5                   10                  15

Ser Leu Leu Leu Leu Gly Cys Trp Ala Glu Leu Gly Ser Gly Leu Glu
                20                  25                  30

Phe Pro Gly Ala Glu Gly Gln Trp Thr Arg Phe Pro Lys Trp Asn Ala
            35                  40                  45

Cys Cys Glu Ser Glu Met Ser Phe Gln Leu Lys Thr Arg Ser Ala Arg
        50                  55                  60

Gly Leu Val Leu Tyr Phe Asp Asp Glu Gly Phe Cys Asp Phe Leu Glu
65                  70                  75                  80

Leu Ile Leu Thr Arg Gly Gly Arg Leu Gln Leu Ser Phe Ser Ile Phe
                85                  90                  95

Cys Ala Glu Pro Ala Thr Leu Leu Ala Asp Thr Pro Val Asn Asp Gly
            100                 105                 110

Ala Trp His Ser Val Arg Ile Arg Arg Gln Phe Arg Asn Thr Thr Leu
        115                 120                 125

Phe Ile Asp Gln Val Glu Ala Lys Trp Val Glu Val Lys Ser Lys Arg
    130                 135                 140

Arg Asp Met Thr Val Phe Ser Gly Leu Phe Val Gly Gly Leu Pro Pro
145                 150                 155                 160

Glu Leu Arg Ala Ala Ala Leu Lys Leu Thr Leu Ala Ser Val Arg Glu
                165                 170                 175

Arg Glu Pro Phe Lys Gly Trp Ile Arg Asp Val Arg Val Asn Ser Ser
            180                 185                 190

Gln Val Leu Pro Val Asp Ser Gly Glu Val Lys Leu Asp Asp Glu Pro
        195                 200                 205

Pro Asn Ser Gly Gly Gly Ser Pro Cys Glu Ala Gly Glu Glu Gly Glu
    210                 215                 220

Gly Gly Val Cys Leu Asn Gly Gly Val Cys Ser Val Val Asp Asp Gln
225                 230                 235                 240

Ala Val Cys Asp Cys Ser Arg Thr Gly Phe Arg Gly Lys Asp Cys Ser
                245                 250                 255

Gln Glu Ile Lys Phe Gly Leu Gln Cys Val Leu Pro Val Leu Leu His
            260                 265                 270

Asp Asn Asp Gln Gly Lys Tyr Cys Cys Ile Asn Thr Ala Lys Pro Leu
        275                 280                 285

Thr Glu Lys Asp Asn Asn Val Glu Gly Leu Ala His Leu Met Met Gly
    290                 295                 300

Asp Gln Gly Lys Ser Lys Gly Lys Glu Glu Tyr Ile Ala Thr Phe Lys
305                 310                 315                 320

Gly Ser Glu Tyr Phe Cys Tyr Asp Leu Ser Gln Asn Pro Ile Gln Ser
                325                 330                 335
```

-continued

```
Ser Ser Asp Glu Ile Thr Leu Ser Phe Lys Thr Leu Gln Arg Asn Gly
            340                 345                 350

Leu Met Leu His Thr Gly Lys Ser Ala Asp Tyr Val Asn Leu Ala Leu
        355                 360                 365

Lys Asn Gly Ala Val Ser Leu Val Ile Asn Leu Gly Ser Gly Ala Phe
    370                 375                 380

Glu Ala Leu Val Glu Pro Val Asn Gly Lys Phe Asn Asp Asn Ala Trp
385                 390                 395                 400

His Asp Val Lys Val Thr Arg Asn Leu Arg Gln His Ser Gly Ile Gly
                405                 410                 415

His Ala Met Val Asn Lys Leu His Cys Ser Val Thr Ile Ser Val Asp
            420                 425                 430

Gly Ile Leu Thr Thr Thr Gly Tyr Thr Gln Glu Asp Tyr Thr Met Leu
        435                 440                 445

Gly Ser Asp Asp Phe Phe Tyr Val Gly Gly Ser Pro Ser Thr Ala Asp
    450                 455                 460

Leu Pro Gly Ser Pro Val Ser Asn Asn Phe Met Gly Cys Leu Lys Glu
465                 470                 475                 480

Val Val Tyr Lys Asn Asn Asp Val Arg Leu Glu Leu Ser Arg Leu Ala
                485                 490                 495

Lys Gln Gly Asp Pro Lys Met Lys Ile His Gly Val Val Ala Phe Lys
            500                 505                 510

Cys Glu Asn Val Ala Thr Leu Asp Pro Ile Thr Phe Glu Thr Pro Glu
        515                 520                 525

Ser Phe Ile Ser Leu Pro Lys Trp Asn Ala Lys Lys Thr Gly Ser Ile
    530                 535                 540

Ser Phe Asp Phe Arg Thr Thr Glu Pro Asn Gly Leu Ile Leu Phe Ser
545                 550                 555                 560

His Gly Lys Pro Arg His Gln Lys Asp Ala Lys His Pro Gln Met Ile
                565                 570                 575

Lys Val Asp Phe Phe Ala Ile Glu Met Leu Asp Gly His Leu Tyr Leu
            580                 585                 590

Leu Leu Asp Met Gly Ser Gly Thr Ile Lys Ile Lys Ala Leu Leu Lys
        595                 600                 605

Lys Val Asn Asp Gly Glu Trp Tyr His Val Asp Phe Gln Arg Asp Gly
    610                 615                 620

Arg Ser Gly Thr Ile Ser Val Asn Thr Leu Arg Thr Pro Tyr Thr Ala
625                 630                 635                 640

Pro Gly Glu Ser Glu Ile Leu Asp Leu Asp Asp Glu Leu Tyr Leu Gly
                645                 650                 655

Gly Leu Pro Glu Asn Lys Ala Gly Leu Val Phe Pro Thr Glu Val Trp
            660                 665                 670

Thr Ala Leu Leu Asn Tyr Gly Tyr Val Gly Cys Ile Arg Asp Leu Phe
        675                 680                 685

Ile Asp Gly Gln Ser Lys Asp Ile Arg Gln Met Ala Glu Val Gln Ser
    690                 695                 700

Thr Ala Gly Val Lys Pro Ser Cys Ser Lys Glu Thr Ala Lys Pro Cys
705                 710                 715                 720

Leu Ser Asn Pro Cys Lys Asn Asn Gly Met Cys Arg Asp Gly Trp Asn
                725                 730                 735

Arg Tyr Val Cys Asp Cys Ser Gly Thr Gly Tyr Leu Gly Arg Ser Cys
            740                 745                 750

Glu Arg Glu Ala Thr Val Leu Ser Tyr Asp Gly Ser Met Phe Met Lys
```

-continued

```
              755                 760                 765
Ile Gln Leu Pro Val Val Met His Thr Glu Ala Glu Asp Val Ser Leu
770                 775                 780

Arg Phe Arg Ser Gln Arg Ala Tyr Gly Ile Leu Met Ala Thr Thr Ser
785                 790                 795                 800

Arg Asp Ser Ala Asp Thr Leu Arg Leu Glu Leu Asp Ala Gly Arg Val
                805                 810                 815

Lys Leu Thr Val Asn Leu Asp Cys Ile Arg Ile Asn Cys Asn Ser Ser
                820                 825                 830

Lys Gly Pro Glu Thr Leu Phe Ala Gly Tyr Asn Leu Asn Asp Asn Glu
                835                 840                 845

Trp His Thr Val Arg Val Val Arg Arg Gly Lys Ser Leu Lys Leu Thr
                850                 855                 860

Val Asp Asp Gln Gln Ala Met Thr Gly Gln Met Ala Gly Asp His Thr
865                 870                 875                 880

Arg Leu Glu Phe His Asn Ile Glu Thr Gly Ile Ile Thr Glu Arg Arg
                885                 890                 895

Tyr Leu Ser Ser Val Pro Ser Asn Phe Ile Gly His Leu Gln Ser Leu
                900                 905                 910

Thr Phe Asn Gly Met Ala Tyr Ile Asp Leu Cys Lys Asn Gly Asp Ile
                915                 920                 925

Asp Tyr Cys Glu Leu Asn Ala Arg Phe Gly Phe Arg Asn Ile Ile Ala
                930                 935                 940

Asp Pro Val Thr Phe Lys Thr Lys Ser Ser Tyr Val Ala Leu Ala Thr
945                 950                 955                 960

Leu Gln Ala Tyr Thr Ser Met His Leu Phe Phe Gln Phe Lys Thr Thr
                    965                 970                 975

Ser Leu Asp Gly Leu Ile Leu Tyr Asn Ser Gly Asp Gly Asn Asp Phe
                    980                 985                 990

Ile Val Val Glu Leu Val Lys Gly Tyr Leu His Tyr Val Phe Asp Leu
                    995                 1000                1005

Gly Asn Gly Ala Asn Leu Ile Lys Gly Ser Ser Asn Lys Pro Leu
                    1010                1015                1020

Asn Asp Asn Gln Trp His Asn Val Met Ile Ser Arg Asp Thr Ser
                    1025                1030                1035

Asn Leu His Thr Val Lys Ile Asp Thr Lys Ile Thr Thr Gln Ile
                    1040                1045                1050

Thr Ala Gly Ala Arg Asn Leu Asp Leu Lys Ser Asp Leu Tyr Ile
                    1055                1060                1065

Gly Gly Val Ala Lys Glu Thr Tyr Lys Ser Leu Pro Lys Leu Val
                    1070                1075                1080

His Ala Lys Glu Gly Phe Gln Gly Cys Leu Ala Ser Val Asp Leu
                    1085                1090                1095

Asn Gly Arg Leu Pro Asp Leu Ile Ser Asp Ala Leu Phe Cys Asn
                    1100                1105                1110

Gly Gln Ile Glu Arg Gly Cys Glu Gly Pro Ser Thr Thr Cys Gln
                    1115                1120                1125

Glu Asp Ser Cys Ser Asn Gln Gly Val Cys Leu Gln Gln Trp Asp
                    1130                1135                1140

Gly Phe Ser Cys Asp Cys Ser Met Thr Ser Phe Ser Gly Pro Leu
                    1145                1150                1155

Cys Asn Asp Pro Gly Thr Thr Tyr Ile Phe Ser Lys Gly Gly Gly
                    1160                1165                1170
```

Gln Ile Thr Tyr Lys Trp Pro Pro Asn Asp Arg Pro Ser Thr Arg
1175                1180                1185

Ala Asp Arg Leu Ala Ile Gly Phe Ser Thr Val Gln Lys Glu Ala
1190                1195                1200

Val Leu Val Arg Val Asp Ser Ser Ser Gly Leu Gly Asp Tyr Leu
1205                1210                1215

Glu Leu His Ile His Gln Gly Lys Ile Gly Val Lys Phe Asn Val
1220                1225                1230

Gly Thr Asp Asp Ile Ala Ile Glu Glu Ser Asn Ala Ile Ile Asn
1235                1240                1245

Asp Gly Lys Tyr His Val Val Arg Phe Thr Arg Ser Gly Gly Asn
1250                1255                1260

Ala Thr Leu Gln Val Asp Ser Trp Pro Val Ile Glu Arg Tyr Pro
1265                1270                1275

Ala Gly Asn Asn Asp Asn Glu Arg Leu Ala Ile Ala Arg Gln Arg
1280                1285                1290

Ile Pro Tyr Arg Leu Gly Arg Val Val Asp Glu Trp Leu Leu Asp
1295                1300                1305

Lys Gly Arg Gln Leu Thr Ile Phe Asn Ser Gln Ala Thr Ile Ile
1310                1315                1320

Ile Gly Gly Lys Glu Gln Gly Gln Pro Phe Gln Gly Gln Leu Ser
1325                1330                1335

Gly Leu Tyr Tyr Asn Gly Leu Lys Val Leu Asn Met Ala Ala Glu
1340                1345                1350

Asn Asp Ala Asn Ile Ala Ile Val Gly Asn Val Arg Leu Val Gly
1355                1360                1365

Glu Val Pro Ser Ser Met Thr Thr Glu Ser Thr Ala Thr Ala Met
1370                1375                1380

Gln Ser Glu Met Ser Thr Ser Ile Met Glu Thr Thr Thr Thr Leu
1385                1390                1395

Ala Thr Ser Thr Ala Arg Arg Gly Lys Pro Pro Thr Lys Glu Pro
1400                1405                1410

Ile Ser Gln Thr Thr Asp Asp Ile Leu Val Ala Ser Ala Glu Cys
1415                1420                1425

Pro Ser Asp Asp Glu Asp Ile Asp Pro Cys Glu Pro Ser Ser Gly
1430                1435                1440

Gly Leu Ala Asn Pro Thr Arg Ala Gly Gly Arg Glu Pro Tyr Pro
1445                1450                1455

Gly Ser Ala Glu Val Ile Arg Glu Ser Ser Ser Thr Thr Gly Met
1460                1465                1470

Val Val Gly Ile Val Ala Ala Ala Ala Leu Cys Ile Leu Ile Leu
1475                1480                1485

Leu Tyr Ala Met Tyr Lys Tyr Arg Asn Arg Asp Glu Gly Ser Tyr
1490                1495                1500

His Val Asp Glu Ser Arg Asn Tyr Ile Ser Asn Ser Ala Gln Ser
1505                1510                1515

Asn Gly Ala Val Val Lys Glu Lys Gln Pro Ser Ser Ala Lys Ser
1520                1525                1530

Ser Asn Lys Asn Lys Lys Asn Lys Asp Lys Glu Tyr Tyr Val
1535                1540                1545

<210> SEQ ID NO 3
<211> LENGTH: 442

<212> TYPE: PRT
<213> ORGANISM: Homo sapiens

<400> SEQUENCE: 3

Met Tyr Gln Arg Met Leu Arg Cys Gly Ala Glu Leu Gly Ser Pro Gly
1               5                   10                  15

Gly Gly Gly Gly Gly Gly Gly Gly Ala Gly Gly Arg Leu Ala
            20                  25                  30

Leu Leu Trp Ile Val Pro Leu Thr Leu Ser Gly Leu Leu Gly Val Ala
            35                  40                  45

Trp Gly Ala Ser Ser Leu Gly Ala His His Ile His His Phe His Gly
        50                  55                  60

Ser Ser Lys His His Ser Val Pro Ile Ala Ile Tyr Arg Ser Pro Ala
65                  70                  75                  80

Ser Leu Arg Gly Gly His Ala Gly Thr Thr Tyr Ile Phe Ser Lys Gly
                85                  90                  95

Gly Gly Gln Ile Thr Tyr Lys Trp Pro Pro Asn Asp Arg Pro Ser Thr
            100                 105                 110

Arg Ala Asp Arg Leu Ala Ile Gly Phe Ser Thr Val Gln Lys Glu Ala
        115                 120                 125

Val Leu Val Arg Val Asp Ser Ser Gly Leu Gly Asp Tyr Leu Glu
130                 135                 140

Leu His Ile His Gln Gly Lys Ile Gly Val Lys Phe Asn Val Gly Thr
145                 150                 155                 160

Asp Asp Ile Ala Ile Glu Glu Ser Asn Ala Ile Ile Asn Asp Gly Lys
                165                 170                 175

Tyr His Val Val Arg Phe Thr Arg Ser Gly Gly Asn Ala Thr Leu Gln
            180                 185                 190

Val Asp Ser Trp Pro Val Ile Glu Arg Tyr Pro Ala Gly Arg Gln Leu
        195                 200                 205

Thr Ile Phe Asn Ser Gln Ala Thr Ile Ile Gly Gly Lys Glu Gln
    210                 215                 220

Gly Gln Pro Phe Gln Gly Gln Leu Ser Gly Leu Tyr Tyr Asn Gly Leu
225                 230                 235                 240

Lys Val Leu Asn Met Ala Ala Glu Asn Asp Ala Asn Ile Ala Ile Val
                245                 250                 255

Gly Asn Val Arg Leu Val Gly Glu Val Pro Ser Ser Met Thr Thr Glu
            260                 265                 270

Ser Thr Ala Thr Ala Met Gln Ser Glu Met Ser Thr Ser Ile Met Glu
        275                 280                 285

Thr Thr Thr Thr Leu Ala Thr Ser Thr Ala Arg Arg Gly Lys Pro Pro
    290                 295                 300

Thr Lys Glu Pro Ile Ser Gln Thr Thr Asp Asp Ile Leu Val Ala Ser
305                 310                 315                 320

Ala Glu Cys Pro Ser Asp Asp Glu Asp Ile Asp Pro Cys Glu Pro Ser
                325                 330                 335

Ser Gly Gly Leu Ala Asn Pro Thr Arg Ala Gly Gly Arg Glu Pro Tyr
            340                 345                 350

Pro Gly Ser Ala Glu Val Ile Arg Glu Ser Ser Ser Thr Thr Gly Met
        355                 360                 365

Val Val Gly Ile Val Ala Ala Ala Ala Leu Cys Ile Leu Ile Leu Leu
    370                 375                 380

Tyr Ala Met Tyr Lys Tyr Arg Asn Arg Asp Glu Gly Ser Tyr His Val
385                 390                 395                 400

Asp Glu Ser Arg Asn Tyr Ile Ser Asn Ser Ala Gln Ser Asn Gly Ala
                405                 410                 415

Val Val Lys Glu Lys Gln Pro Ser Ser Ala Lys Ser Ser Asn Lys Asn
            420                 425                 430

Lys Lys Asn Lys Asp Lys Glu Tyr Tyr Val
        435                 440

<210> SEQ ID NO 4
<211> LENGTH: 1712
<212> TYPE: PRT
<213> ORGANISM: Homo sapiens

<400> SEQUENCE: 4

Met Ala Ser Gly Ser Arg Trp Arg Pro Thr Pro Pro Leu Leu Leu Leu
1               5                   10                  15

Leu Leu Leu Leu Ala Leu Ala Ala Arg Ala Asp Gly Leu Glu Phe Gly
                20                  25                  30

Gly Gly Pro Gly Gln Trp Ala Arg Tyr Ala Arg Trp Ala Gly Ala Ala
            35                  40                  45

Ser Ser Gly Glu Leu Ser Phe Ser Leu Arg Thr Asn Ala Thr Arg Ala
50                  55                  60

Leu Leu Leu Tyr Leu Asp Asp Gly Gly Asp Cys Asp Phe Leu Glu Leu
65                  70                  75                  80

Leu Leu Val Asp Gly Arg Leu Arg Leu Arg Phe Thr Leu Ser Cys Ala
                85                  90                  95

Glu Pro Ala Thr Leu Gln Leu Asp Thr Pro Val Ala Asp Asp Arg Trp
            100                 105                 110

His Met Val Leu Leu Thr Arg Asp Ala Arg Thr Ala Leu Ala Val
            115                 120                 125

Asp Gly Glu Ala Arg Ala Ala Glu Val Arg Ser Lys Arg Arg Glu Met
            130                 135                 140

Gln Val Ala Ser Asp Leu Phe Val Gly Gly Ile Pro Pro Asp Val Arg
145                 150                 155                 160

Leu Ser Ala Leu Thr Leu Ser Thr Val Lys Tyr Glu Pro Pro Phe Arg
                165                 170                 175

Gly Leu Leu Ala Asn Leu Lys Leu Gly Glu Arg Pro Pro Ala Leu Leu
            180                 185                 190

Gly Ser Gln Gly Leu Arg Gly Ala Thr Ala Asp Pro Leu Cys Ala Pro
            195                 200                 205

Ala Arg Asn Pro Cys Ala Asn Gly Gly Leu Cys Thr Val Leu Ala Pro
        210                 215                 220

Gly Glu Val Gly Cys Asp Cys Ser His Thr Gly Phe Gly Gly Lys Phe
225                 230                 235                 240

Cys Ser Glu Glu Glu His Pro Met Glu Gly Pro Ala His Leu Thr Leu
                245                 250                 255

Asn Ser Glu Val Gly Ser Leu Leu Phe Ser Glu Gly Gly Ala Gly Arg
            260                 265                 270

Gly Gly Ala Gly Asp Val His Gln Pro Thr Lys Gly Lys Glu Glu Phe
        275                 280                 285

Val Ala Thr Phe Lys Gly Asn Glu Phe Phe Cys Tyr Asp Leu Ser His
            290                 295                 300

Asn Pro Ile Gln Ser Ser Thr Asp Glu Ile Thr Leu Ala Phe Arg Thr
305                 310                 315                 320

Leu Gln Arg Asn Gly Leu Met Leu His Thr Gly Lys Ser Ala Asp Tyr

|     |     |     |     | 325 |     |     |     | 330 |     |     |     | 335 |     |     |
| --- | --- | --- | --- | --- | --- | --- | --- | --- | --- | --- | --- | --- | --- | --- |
| Val | Asn | Leu | Ser | Leu | Lys | Ser | Gly | Ala | Val | Trp | Leu | Val | Ile | Asn | Leu |
|     |     |     | 340 |     |     |     | 345 |     |     |     | 350 |     |     |     |
| Gly | Ser | Gly | Ala | Phe | Glu | Ala | Leu | Val | Glu | Pro | Val | Asn | Gly | Lys | Phe |
|     |     | 355 |     |     |     | 360 |     |     |     | 365 |     |     |     |     |
| Asn | Asp | Asn | Ala | Trp | His | Asp | Val | Arg | Val | Thr | Arg | Asn | Leu | Arg | Gln |
|     | 370 |     |     |     | 375 |     |     |     | 380 |     |     |     |     |     |
| His | Ala | Gly | Ile | Gly | His | Ala | Met | Val | Asn | Lys | Leu | His | Tyr | Leu | Val |
| 385 |     |     |     | 390 |     |     |     | 395 |     |     |     | 400 |     |     |
| Thr | Ile | Ser | Val | Asp | Gly | Ile | Leu | Thr | Thr | Thr | Gly | Tyr | Thr | Gln | Glu |
|     |     |     | 405 |     |     |     | 410 |     |     |     | 415 |     |     |     |
| Asp | Tyr | Thr | Met | Leu | Gly | Ser | Asp | Asp | Phe | Phe | Tyr | Ile | Gly | Gly | Ser |
|     |     | 420 |     |     |     | 425 |     |     |     | 430 |     |     |     |     |
| Pro | Asn | Thr | Ala | Asp | Leu | Pro | Gly | Ser | Pro | Val | Ser | Asn | Asn | Phe | Met |
|     | 435 |     |     |     | 440 |     |     |     | 445 |     |     |     |     |     |
| Gly | Cys | Leu | Lys | Asp | Val | Val | Tyr | Lys | Asn | Asn | Asp | Phe | Lys | Leu | Glu |
| 450 |     |     |     | 455 |     |     |     | 460 |     |     |     |     |     |     |
| Leu | Ser | Arg | Leu | Ala | Lys | Glu | Gly | Asp | Pro | Lys | Met | Lys | Leu | Gln | Gly |
| 465 |     |     |     | 470 |     |     |     | 475 |     |     |     | 480 |     |     |
| Asp | Leu | Ser | Phe | Arg | Cys | Glu | Asp | Val | Ala | Ala | Leu | Asp | Pro | Val | Thr |
|     |     |     | 485 |     |     |     | 490 |     |     |     | 495 |     |     |     |
| Phe | Glu | Ser | Pro | Glu | Ala | Phe | Val | Ala | Leu | Pro | Arg | Trp | Ser | Ala | Lys |
|     |     | 500 |     |     |     | 505 |     |     |     | 510 |     |     |     |     |
| Arg | Thr | Gly | Ser | Ile | Ser | Leu | Asp | Phe | Arg | Thr | Thr | Glu | Pro | Asn | Gly |
|     | 515 |     |     |     | 520 |     |     |     | 525 |     |     |     |     |     |
| Leu | Leu | Leu | Phe | Ser | Gln | Gly | Arg | Arg | Ala | Gly | Gly | Ala | Gly | Ser |
| 530 |     |     |     | 535 |     |     |     | 540 |     |     |     |     |     |
| His | Ser | Ser | Ala | Gln | Arg | Ala | Asp | Tyr | Phe | Ala | Met | Glu | Leu | Leu | Asp |
| 545 |     |     |     | 550 |     |     |     | 555 |     |     |     | 560 |     |     |
| Gly | His | Leu | Tyr | Leu | Leu | Leu | Asp | Met | Gly | Ser | Gly | Gly | Ile | Lys | Leu |
|     |     |     | 565 |     |     |     | 570 |     |     |     | 575 |     |     |     |
| Arg | Ala | Ser | Ser | Arg | Lys | Val | Asn | Asp | Gly | Glu | Trp | Cys | His | Val | Asp |
|     |     | 580 |     |     |     | 585 |     |     |     | 590 |     |     |     |     |
| Phe | Gln | Arg | Asp | Gly | Arg | Lys | Gly | Ser | Ile | Ser | Val | Asn | Ser | Arg | Ser |
|     | 595 |     |     |     | 600 |     |     |     | 605 |     |     |     |     |     |
| Thr | Pro | Phe | Leu | Ala | Thr | Gly | Asp | Ser | Glu | Ile | Leu | Asp | Leu | Glu | Ser |
| 610 |     |     |     | 615 |     |     |     | 620 |     |     |     |     |     |     |
| Glu | Leu | Tyr | Leu | Gly | Gly | Leu | Pro | Glu | Gly | Gly | Arg | Val | Asp | Leu | Pro |
| 625 |     |     |     | 630 |     |     |     | 635 |     |     |     | 640 |     |     |
| Leu | Pro | Pro | Glu | Val | Trp | Thr | Ala | Ala | Leu | Arg | Ala | Gly | Tyr | Val | Gly |
|     |     |     | 645 |     |     |     | 650 |     |     |     | 655 |     |     |     |
| Cys | Val | Arg | Asp | Leu | Phe | Ile | Asp | Gly | Arg | Ser | Arg | Asp | Leu | Arg | Gly |
|     |     | 660 |     |     |     | 665 |     |     |     | 670 |     |     |     |     |
| Leu | Ala | Glu | Ala | Gln | Gly | Ala | Val | Gly | Val | Ala | Pro | Phe | Cys | Ser | Arg |
|     | 675 |     |     |     | 680 |     |     |     | 685 |     |     |     |     |     |
| Glu | Thr | Leu | Lys | Gln | Cys | Ala | Ser | Ala | Pro | Cys | Arg | Asn | Gly | Gly | Val |
| 690 |     |     |     | 695 |     |     |     | 700 |     |     |     |     |     |     |
| Cys | Arg | Glu | Gly | Trp | Asn | Arg | Phe | Ile | Cys | Asp | Cys | Ile | Gly | Thr | Gly |
| 705 |     |     |     | 710 |     |     |     | 715 |     |     |     | 720 |     |     |
| Phe | Leu | Gly | Arg | Val | Cys | Glu | Arg | Glu | Ala | Thr | Val | Leu | Ser | Tyr | Asp |
|     |     |     | 725 |     |     |     | 730 |     |     |     | 735 |     |     |     |
| Gly | Ser | Met | Tyr | Met | Lys | Ile | Met | Leu | Pro | Asn | Ala | Met | His | Thr | Glu |
|     |     | 740 |     |     |     | 745 |     |     |     | 750 |     |     |     |     |

```
Ala Glu Asp Val Ser Leu Arg Phe Met Ser Gln Arg Ala Tyr Gly Leu
        755                 760                 765

Met Met Ala Thr Thr Ser Arg Glu Ser Ala Asp Thr Leu Arg Leu Glu
        770                 775                 780

Leu Asp Gly Gly Gln Met Lys Leu Thr Val Asn Leu Asp Cys Leu Arg
785                 790                 795                 800

Val Gly Cys Ala Pro Ser Lys Gly Pro Glu Thr Leu Phe Ala Gly His
                805                 810                 815

Lys Leu Asn Asp Asn Glu Trp His Thr Val Arg Val Arg Arg Gly
        820                 825                 830

Lys Ser Leu Gln Leu Ser Val Asp Asn Val Thr Val Glu Gly Gln Met
        835                 840                 845

Ala Gly Ala His Met Arg Leu Glu Phe His Asn Ile Glu Thr Gly Ile
850                 855                 860

Met Thr Glu Arg Arg Phe Ile Ser Val Val Pro Ser Asn Phe Ile Gly
865                 870                 875                 880

His Leu Ser Gly Leu Val Phe Asn Gly Gln Pro Tyr Met Asp Gln Cys
                885                 890                 895

Lys Asp Gly Asp Ile Thr Tyr Cys Glu Leu Asn Ala Arg Phe Gly Leu
                900                 905                 910

Arg Ala Ile Val Ala Asp Pro Val Thr Phe Lys Ser Arg Ser Ser Tyr
        915                 920                 925

Leu Ala Leu Ala Thr Leu Gln Ala Tyr Ala Ser Met His Leu Phe Phe
930                 935                 940

Gln Phe Lys Thr Thr Ala Pro Asp Gly Leu Leu Leu Phe Asn Ser Gly
945                 950                 955                 960

Asn Gly Asn Asp Phe Ile Val Ile Glu Leu Val Lys Gly Tyr Ile His
                965                 970                 975

Tyr Val Phe Asp Leu Gly Asn Gly Pro Ser Leu Met Lys Gly Asn Ser
                980                 985                 990

Asp Lys Pro Val Asn Asp Asn Gln Trp His Asn Val Val Val Ser Arg
        995                 1000                1005

Asp Pro Gly Asn Val His Thr Leu Lys Ile Asp Ser Arg Thr Val
    1010                1015                1020

Thr Gln His Ser Asn Gly Ala Arg Asn Leu Asp Leu Lys Gly Glu
    1025                1030                1035

Leu Tyr Ile Gly Gly Leu Ser Lys Asn Met Phe Ser Asn Leu Pro
    1040                1045                1050

Lys Leu Val Ala Ser Arg Asp Gly Phe Gln Gly Cys Leu Ala Ser
    1055                1060                1065

Val Asp Leu Asn Gly Arg Leu Pro Asp Leu Ile Ala Asp Ala Leu
    1070                1075                1080

His Arg Ile Gly Gln Val Glu Arg Gly Cys Asp Gly Pro Ser Thr
    1085                1090                1095

Thr Cys Thr Glu Glu Ser Cys Ala Asn Gln Gly Val Cys Leu Gln
    1100                1105                1110

Gln Trp Asp Gly Phe Thr Cys Asp Cys Thr Met Thr Ser Tyr Gly
    1115                1120                1125

Gly Pro Val Cys Asn Asp Pro Gly Thr Thr Tyr Ile Phe Gly Lys
    1130                1135                1140

Gly Gly Ala Leu Ile Thr Tyr Thr Trp Pro Pro Asn Asp Arg Pro
    1145                1150                1155
```

```
Ser Thr Arg Met Asp Arg Leu Ala Val Gly Phe Ser Thr His Gln
    1160                1165                1170

Arg Ser Ala Val Leu Val Arg Val Asp Ser Ala Ser Gly Leu Gly
    1175                1180                1185

Asp Tyr Leu Gln Leu His Ile Asp Gln Gly Thr Val Gly Val Ile
    1190                1195                1200

Phe Asn Val Gly Thr Asp Asp Ile Thr Ile Asp Glu Pro Asn Ala
    1205                1210                1215

Ile Val Ser Asp Gly Lys Tyr His Val Val Arg Phe Thr Arg Ser
    1220                1225                1230

Gly Gly Asn Ala Thr Leu Gln Val Asp Ser Trp Pro Val Asn Glu
    1235                1240                1245

Arg Tyr Pro Ala Gly Asn Phe Asp Asn Glu Arg Leu Ala Ile Ala
    1250                1255                1260

Arg Gln Arg Ile Pro Tyr Arg Leu Gly Arg Val Val Asp Glu Trp
    1265                1270                1275

Leu Leu Asp Lys Gly Arg Gln Leu Thr Ile Phe Asn Ser Gln Ala
    1280                1285                1290

Ala Ile Lys Ile Gly Arg Asp Gln Gly Arg Pro Phe Gln Gly
    1295                1300                1305

Gln Val Ser Gly Leu Tyr Tyr Asn Gly Leu Lys Val Leu Ala Leu
    1310                1315                1320

Ala Ala Glu Ser Asp Pro Asn Val Arg Thr Glu Gly His Leu Arg
    1325                1330                1335

Leu Val Gly Glu Gly Pro Ser Val Leu Leu Ser Ala Glu Thr Thr
    1340                1345                1350

Ala Thr Thr Leu Leu Ala Asp Met Ala Thr Thr Ile Met Glu Thr
    1355                1360                1365

Thr Thr Thr Met Ala Thr Thr Thr Thr Arg Arg Gly Arg Ser Pro
    1370                1375                1380

Thr Leu Arg Asp Ser Thr Thr Gln Asn Thr Asp Asp Leu Leu Val
    1385                1390                1395

Ala Ser Ala Glu Cys Pro Ser Asp Asp Glu Asp Leu Glu Glu Cys
    1400                1405                1410

Glu Pro Ser Thr Gly Gly Glu Leu Ile Leu Pro Ile Ile Thr Glu
    1415                1420                1425

Asp Ser Leu Asp Pro Pro Pro Val Ala Thr Arg Ser Pro Phe Val
    1430                1435                1440

Pro Pro Pro Pro Thr Phe Tyr Pro Phe Leu Thr Gly Val Gly Ala
    1445                1450                1455

Thr Gln Asp Thr Leu Pro Pro Ala Ala Arg Arg Pro Pro Ser
    1460                1465                1470

Gly Gly Pro Cys Gln Ala Glu Arg Asp Asp Ser Asp Cys Glu Glu
    1475                1480                1485

Pro Ile Glu Ala Ser Gly Phe Ala Ser Gly Glu Val Phe Asp Ser
    1490                1495                1500

Ser Leu Pro Pro Thr Asp Asp Glu Asp Phe Tyr Thr Thr Phe Pro
    1505                1510                1515

Leu Val Thr Asp Arg Thr Thr Leu Leu Ser Pro Arg Lys Pro Ala
    1520                1525                1530

Pro Arg Pro Asn Leu Arg Thr Asp Gly Ala Thr Gly Ala Pro Gly
    1535                1540                1545

Val Leu Phe Ala Pro Ser Ala Pro Ala Pro Asn Leu Pro Ala Gly
```

```
            1550                1555                1560
Lys Met Asn His Arg Asp Pro Leu Gln Pro Leu Leu Glu Asn Pro
    1565                1570                1575

Pro Leu Gly Pro Gly Ala Pro Thr Ser Phe Glu Pro Arg Arg Pro
    1580                1585                1590

Pro Pro Leu Arg Pro Gly Val Thr Ser Ala Pro Gly Phe Pro His
    1595                1600                1605

Leu Pro Thr Ala Asn Pro Thr Gly Pro Gly Glu Arg Gly Pro Pro
    1610                1615                1620

Gly Ala Val Glu Val Ile Arg Glu Ser Ser Thr Thr Gly Met
    1625                1630                1635

Val Val Gly Ile Val Ala Ala Ala Leu Cys Ile Leu Ile Leu
    1640                1645                1650

Leu Tyr Ala Met Tyr Lys Tyr Arg Asn Arg Asp Glu Gly Ser Tyr
    1655                1660                1665

Gln Val Asp Gln Ser Arg Asn Tyr Ile Ser Asn Ser Ala Gln Ser
    1670                1675                1680

Asn Gly Ala Val Val Lys Glu Lys Ala Pro Ala Ala Pro Lys Thr
    1685                1690                1695

Pro Ser Lys Ala Lys Lys Asn Lys Asp Lys Glu Tyr Tyr Val
    1700                1705                1710
```

<210> SEQ ID NO 5
<211> LENGTH: 666
<212> TYPE: PRT
<213> ORGANISM: Homo sapiens

<400> SEQUENCE: 5

```
Met Pro Pro Gly Gly Ser Gly Pro Gly Gly Cys Pro Arg Arg Pro
1               5                   10                  15

Ala Leu Ala Gly Pro Leu Pro Pro Pro Pro Pro Pro Pro Pro Pro
                20                  25                  30

Leu Leu Pro Leu Leu Pro Leu Leu Leu Leu Leu Leu Gly Ala Ala
            35                  40                  45

Glu Gly Ala Arg Val Ser Ser Leu Ser Thr Thr His His Val His
    50                  55                  60

His Phe His Ser Lys His Gly Thr Val Pro Ile Ala Ile Asn Arg Met
65                  70                  75                  80

Pro Phe Leu Thr Arg Gly Gly His Ala Gly Thr Thr Tyr Ile Phe Gly
                85                  90                  95

Lys Gly Gly Ala Leu Ile Thr Tyr Thr Trp Pro Pro Asn Asp Arg Pro
                100                 105                 110

Ser Thr Arg Met Asp Arg Leu Ala Val Gly Phe Ser Thr His Gln Arg
            115                 120                 125

Ser Ala Val Leu Val Arg Val Asp Ser Ala Ser Gly Leu Gly Asp Tyr
    130                 135                 140

Leu Gln Leu His Ile Asp Gln Gly Thr Val Gly Val Ile Phe Asn Val
145                 150                 155                 160

Gly Thr Asp Asp Ile Thr Ile Asp Glu Pro Asn Ala Ile Val Ser Asp
                165                 170                 175

Gly Lys Tyr His Val Val Arg Phe Thr Arg Ser Gly Gly Asn Ala Thr
            180                 185                 190

Leu Gln Val Asp Ser Trp Pro Val Asn Glu Arg Tyr Pro Ala Gly Asn
    195                 200                 205
```

```
Phe Asp Asn Glu Arg Leu Ala Ile Ala Arg Gln Arg Ile Pro Tyr Arg
    210                 215                 220

Leu Gly Arg Val Val Asp Glu Trp Leu Leu Asp Lys Gly Arg Gln Leu
225                 230                 235                 240

Thr Ile Phe Asn Ser Gln Ala Ala Ile Lys Ile Gly Gly Arg Asp Gln
            245                 250                 255

Gly Arg Pro Phe Gln Gly Gln Val Ser Gly Leu Tyr Tyr Asn Gly Leu
            260                 265                 270

Lys Val Leu Ala Leu Ala Ala Glu Ser Asp Pro Asn Val Arg Thr Glu
            275                 280                 285

Gly His Leu Arg Leu Val Gly Glu Gly Pro Ser Val Leu Leu Ser Ala
290                 295                 300

Glu Thr Thr Ala Thr Thr Leu Leu Ala Asp Met Ala Thr Thr Ile Met
305                 310                 315                 320

Glu Thr Thr Thr Thr Met Ala Thr Thr Thr Thr Arg Arg Gly Arg Ser
                325                 330                 335

Pro Thr Leu Arg Asp Ser Thr Thr Gln Asn Thr Asp Asp Leu Leu Val
            340                 345                 350

Ala Ser Ala Glu Cys Pro Ser Asp Asp Glu Asp Leu Glu Glu Cys Glu
            355                 360                 365

Pro Ser Thr Gly Gly Glu Leu Ile Leu Pro Ile Ile Thr Glu Asp Ser
    370                 375                 380

Leu Asp Pro Pro Pro Val Ala Thr Arg Ser Pro Phe Val Pro Pro Pro
385                 390                 395                 400

Pro Thr Phe Tyr Pro Phe Leu Thr Gly Val Gly Ala Thr Gln Asp Thr
            405                 410                 415

Leu Pro Pro Pro Ala Ala Arg Arg Pro Pro Ser Gly Gly Pro Cys Gln
            420                 425                 430

Ala Glu Arg Asp Asp Ser Asp Cys Glu Glu Pro Ile Glu Ala Ser Gly
            435                 440                 445

Phe Ala Ser Gly Glu Val Phe Asp Ser Ser Leu Pro Pro Thr Asp Asp
    450                 455                 460

Glu Asp Phe Tyr Thr Thr Phe Pro Leu Val Thr Asp Arg Thr Thr Leu
465                 470                 475                 480

Leu Ser Pro Arg Lys Pro Ala Pro Arg Pro Asn Leu Arg Thr Asp Gly
            485                 490                 495

Ala Thr Gly Ala Pro Gly Val Leu Phe Ala Pro Ser Ala Pro Ala Pro
            500                 505                 510

Asn Leu Pro Ala Gly Lys Met Asn His Arg Asp Pro Leu Gln Pro Leu
            515                 520                 525

Leu Glu Asn Pro Pro Leu Gly Pro Gly Ala Pro Thr Ser Phe Glu Pro
    530                 535                 540

Arg Arg Pro Pro Pro Leu Arg Pro Gly Val Thr Ser Ala Pro Gly Phe
545                 550                 555                 560

Pro His Leu Pro Thr Ala Asn Pro Thr Gly Pro Gly Glu Arg Gly Pro
            565                 570                 575

Pro Gly Ala Val Glu Val Ile Arg Glu Ser Ser Thr Thr Gly Met
            580                 585                 590

Val Val Gly Ile Val Ala Ala Ala Leu Cys Ile Leu Ile Leu Leu
            595                 600                 605

Tyr Ala Met Tyr Lys Tyr Arg Asn Arg Asp Glu Gly Ser Tyr Gln Val
    610                 615                 620

Asp Gln Ser Arg Asn Tyr Ile Ser Asn Ser Ala Gln Ser Asn Gly Ala
```

```
                625                 630                 635                 640
Val Val Lys Glu Lys Ala Pro Ala Ala Pro Lys Thr Pro Ser Lys Ala
                        645                 650                 655
Lys Lys Asn Lys Asp Lys Glu Tyr Tyr Val
            660                 665

<210> SEQ ID NO 6
<211> LENGTH: 1061
<212> TYPE: PRT
<213> ORGANISM: Homo sapiens

<400> SEQUENCE: 6

Met Leu Gly Ser Asp Asp Phe Phe Tyr Val Gly Gly Ser Pro Ser Thr
1               5                   10                  15

Ala Asp Leu Pro Gly Ser Pro Val Ser Asn Asn Phe Met Gly Cys Leu
            20                  25                  30

Lys Glu Val Val Tyr Lys Asn Asn Asp Ile Arg Leu Glu Leu Ser Arg
        35                  40                  45

Leu Ala Arg Ile Ala Asp Thr Lys Met Lys Ile Tyr Gly Glu Val Val
    50                  55                  60

Phe Lys Cys Glu Asn Val Ala Thr Leu Asp Pro Ile Asn Phe Glu Thr
65                  70                  75                  80

Pro Glu Ala Tyr Ile Ser Leu Pro Lys Trp Asn Thr Lys Arg Met Gly
                85                  90                  95

Ser Ile Ser Phe Asp Phe Arg Thr Thr Glu Pro Asn Gly Leu Ile Leu
            100                 105                 110

Phe Thr His Gly Lys Pro Gln Glu Arg Lys Asp Ala Arg Ser Gln Lys
        115                 120                 125

Asn Thr Lys Val Asp Phe Phe Ala Val Glu Leu Leu Asp Gly Asn Leu
130                 135                 140

Tyr Leu Leu Leu Asp Met Gly Ser Gly Thr Ile Lys Val Lys Ala Thr
145                 150                 155                 160

Gln Lys Lys Ala Asn Asp Gly Glu Trp Tyr His Val Asp Ile Gln Arg
                165                 170                 175

Asp Gly Arg Ser Gly Thr Ile Ser Val Asn Ser Arg Arg Thr Pro Phe
            180                 185                 190

Thr Ala Ser Gly Glu Ser Glu Ile Leu Asp Leu Glu Gly Asp Met Tyr
        195                 200                 205

Leu Gly Gly Leu Pro Glu Asn Arg Ala Gly Leu Ile Leu Pro Thr Glu
    210                 215                 220

Leu Trp Thr Ala Met Leu Asn Tyr Gly Tyr Val Gly Cys Ile Arg Asp
225                 230                 235                 240

Leu Phe Ile Asp Gly Arg Ser Lys Asn Ile Arg Gln Leu Ala Glu Met
                245                 250                 255

Gln Asn Ala Ala Gly Val Lys Ser Ser Cys Ser Arg Met Ser Ala Lys
            260                 265                 270

Gln Cys Asp Ser Tyr Pro Cys Lys Asn Asn Ala Val Cys Lys Asp Gly
        275                 280                 285

Trp Asn Arg Phe Ile Cys Asp Cys Thr Gly Thr Gly Tyr Trp Gly Arg
    290                 295                 300

Thr Cys Glu Arg Glu Ala Ser Ile Leu Ser Tyr Asp Gly Ser Met Tyr
305                 310                 315                 320

Met Lys Ile Ile Met Pro Met Val Met His Thr Glu Ala Glu Asp Val
                325                 330                 335
```

```
Ser Phe Arg Phe Met Ser Gln Arg Ala Tyr Gly Leu Leu Val Ala Thr
            340                 345                 350

Thr Ser Arg Asp Ser Ala Asp Thr Leu Arg Leu Glu Leu Asp Gly Gly
            355                 360                 365

Arg Val Lys Leu Met Val Asn Leu Asp Cys Ile Arg Ile Asn Cys Asn
            370                 375                 380

Ser Ser Lys Gly Pro Glu Thr Leu Tyr Ala Gly Gln Lys Leu Asn Asp
385                 390                 395                 400

Asn Glu Trp His Thr Val Arg Val Arg Arg Gly Lys Ser Leu Lys
                405                 410                 415

Leu Thr Val Asp Asp Val Ala Glu Gly Thr Met Val Gly Asp His
            420                 425                 430

Thr Arg Leu Glu Phe His Asn Ile Glu Thr Gly Ile Met Thr Glu Lys
            435                 440                 445

Arg Tyr Ile Ser Val Val Pro Ser Ser Phe Ile Gly His Leu Gln Ser
            450                 455                 460

Leu Met Phe Asn Gly Leu Leu Tyr Ile Asp Leu Cys Lys Asn Gly Asp
465                 470                 475                 480

Ile Asp Tyr Cys Glu Leu Lys Ala Arg Phe Gly Leu Arg Asn Ile Ile
                485                 490                 495

Ala Asp Pro Val Thr Phe Lys Thr Lys Ser Ser Tyr Leu Ser Leu Ala
            500                 505                 510

Thr Leu Gln Ala Tyr Thr Ser Met His Leu Phe Phe Gln Phe Lys Thr
            515                 520                 525

Thr Ser Pro Asp Gly Phe Ile Leu Phe Asn Ser Gly Asp Gly Asn Asp
            530                 535                 540

Phe Ile Ala Val Glu Leu Val Lys Gly Tyr Ile His Tyr Val Phe Asp
545                 550                 555                 560

Leu Gly Asn Gly Pro Asn Val Ile Lys Gly Asn Ser Asp Arg Pro Leu
                565                 570                 575

Asn Asp Asn Gln Trp His Asn Val Val Ile Thr Arg Asp Asn Ser Asn
            580                 585                 590

Thr His Ser Leu Lys Val Asp Thr Lys Val Val Thr Gln Val Ile Asn
            595                 600                 605

Gly Ala Lys Asn Leu Asp Leu Lys Gly Asp Leu Tyr Met Ala Gly Leu
            610                 615                 620

Ala Gln Gly Met Tyr Ser Asn Leu Pro Lys Leu Val Ala Ser Arg Asp
625                 630                 635                 640

Gly Phe Gln Gly Cys Leu Ala Ser Val Asp Leu Asn Gly Arg Leu Pro
                645                 650                 655

Asp Leu Ile Asn Asp Ala Leu His Arg Ser Gly Gln Ile Glu Arg Gly
            660                 665                 670

Cys Glu Gly Pro Ser Thr Thr Cys Gln Glu Asp Ser Cys Ala Asn Gln
            675                 680                 685

Gly Val Cys Met Gln Gln Trp Glu Gly Phe Thr Cys Asp Cys Ser Met
            690                 695                 700

Thr Ser Tyr Ser Gly Asn Gln Cys Asn Asp Pro Gly Ala Thr Tyr Ile
705                 710                 715                 720

Phe Gly Lys Ser Gly Gly Leu Ile Leu Tyr Thr Trp Pro Ala Asn Asp
                725                 730                 735

Arg Pro Ser Thr Arg Ser Asp Arg Leu Ala Val Gly Phe Ser Thr Thr
            740                 745                 750

Val Lys Asp Gly Ile Leu Val Arg Ile Asp Ser Ala Pro Gly Leu Gly
```

```
                755                 760                 765
Asp Phe Leu Gln Leu His Ile Glu Gln Gly Lys Ile Gly Val Val Phe
770                 775                 780

Asn Ile Gly Thr Val Asp Ile Ser Ile Lys Glu Glu Arg Thr Pro Val
785                 790                 795                 800

Asn Asp Gly Lys Tyr His Val Val Arg Phe Thr Arg Asn Gly Gly Asn
                805                 810                 815

Ala Thr Leu Gln Val Asp Asn Trp Pro Val Asn Glu His Tyr Pro Thr
                820                 825                 830

Gly Arg Gln Leu Thr Ile Phe Asn Thr Gln Ala Gln Ile Ala Ile Gly
                835                 840                 845

Gly Lys Asp Lys Gly Arg Leu Phe Gln Gly Gln Leu Ser Gly Leu Tyr
                850                 855                 860

Tyr Asp Gly Leu Lys Val Leu Asn Met Ala Ala Glu Asn Asn Pro Asn
865                 870                 875                 880

Ile Lys Ile Asn Gly Ser Val Arg Leu Val Gly Glu Val Pro Ser Ile
                885                 890                 895

Leu Gly Thr Thr Gln Thr Thr Ser Met Pro Pro Glu Met Ser Thr Thr
                900                 905                 910

Val Met Glu Thr Thr Thr Thr Met Ala Thr Thr Thr Arg Lys Asn
                915                 920                 925

Arg Ser Thr Ala Ser Ile Gln Pro Thr Ser Asp Asp Leu Val Ser Ser
930                 935                 940

Ala Glu Cys Ser Ser Asp Asp Glu Asp Phe Val Glu Cys Glu Pro Ser
945                 950                 955                 960

Thr Ala Asn Pro Thr Glu Pro Gly Ile Arg Arg Val Pro Gly Ala Ser
                965                 970                 975

Glu Val Ile Arg Glu Ser Ser Ser Thr Thr Gly Met Val Val Gly Ile
                980                 985                 990

Val Ala Ala Ala Ala Leu Cys Ile Leu Ile Leu Leu Tyr Ala Met Tyr
                995                 1000                1005

Lys Tyr Arg Asn Arg Asp Glu Gly Ser Tyr Gln Val Asp Glu Thr
1010                1015                1020

Arg Asn Tyr Ile Ser Asn Ser Ala Gln Ser Asn Gly Thr Leu Met
1025                1030                1035

Lys Glu Lys Gln Gln Ser Ser Lys Ser Gly His Lys Lys Gln Lys
1040                1045                1050

Asn Lys Asp Arg Glu Tyr Tyr Val
1055                1060

<210> SEQ ID NO 7
<211> LENGTH: 637
<212> TYPE: PRT
<213> ORGANISM: Homo sapiens

<400> SEQUENCE: 7

Met His Leu Arg Ile His Ala Arg Arg Ser Pro Pro Arg Arg Pro Ala
1                   5                   10                  15

Trp Thr Leu Gly Ile Trp Phe Leu Phe Trp Gly Cys Ile Val Ser Ser
                20                  25                  30

Val Trp Ser Ser Ser Asn Val Ala Ser Ser Ser Thr Ser Ser Ser
                35                  40                  45

Pro Gly Ser His Ser Gln His Glu His Phe His Gly Ser Lys His
                50                  55                  60
```

His Ser Val Pro Ile Ser Ile Tyr Arg Ser Pro Val Ser Leu Arg Gly
 65                  70                  75                  80

Gly His Ala Gly Ala Thr Tyr Ile Phe Gly Lys Ser Gly Gly Leu Ile
             85                  90                  95

Leu Tyr Thr Trp Pro Ala Asn Asp Arg Pro Ser Thr Arg Ser Asp Arg
            100                 105                 110

Leu Ala Val Gly Phe Ser Thr Thr Val Lys Asp Gly Ile Leu Val Arg
            115                 120                 125

Ile Asp Ser Ala Pro Gly Leu Gly Asp Phe Leu Gln Leu His Ile Glu
            130                 135                 140

Gln Gly Lys Ile Gly Val Val Phe Asn Ile Gly Thr Val Asp Ile Ser
145                 150                 155                 160

Ile Lys Glu Glu Arg Thr Pro Val Asn Asp Gly Lys Tyr His Val Val
                165                 170                 175

Arg Phe Thr Arg Asn Gly Gly Asn Ala Thr Leu Gln Val Asp Asn Trp
            180                 185                 190

Pro Val Asn Glu His Tyr Pro Thr Gly Arg Gln Leu Thr Ile Phe Asn
            195                 200                 205

Thr Gln Ala Gln Ile Ala Ile Gly Gly Lys Asp Lys Gly Arg Leu Phe
210                 215                 220

Gln Gly Gln Leu Ser Gly Leu Tyr Tyr Asp Gly Leu Lys Val Leu Asn
225                 230                 235                 240

Met Ala Ala Glu Asn Asn Pro Asn Ile Lys Ile Asn Gly Ser Val Arg
                245                 250                 255

Leu Val Gly Glu Val Pro Ser Ile Leu Gly Thr Thr Gln Thr Thr Ser
            260                 265                 270

Met Pro Pro Glu Met Ser Thr Thr Val Met Glu Thr Thr Thr Met
            275                 280                 285

Ala Thr Thr Thr Arg Lys Asn Arg Ser Thr Ala Ser Ile Gln Pro
            290                 295                 300

Thr Ser Asp Asp Leu Val Ser Ser Ala Glu Cys Ser Ser Asp Asp Glu
305                 310                 315                 320

Asp Phe Val Glu Cys Glu Pro Ser Thr Gly Gly Glu Leu Val Ile Pro
                325                 330                 335

Leu Leu Val Glu Asp Pro Leu Ala Thr Pro Pro Ile Ala Thr Arg Ala
            340                 345                 350

Pro Ser Ile Thr Leu Pro Pro Thr Phe Arg Pro Leu Leu Thr Ile Ile
            355                 360                 365

Glu Thr Thr Lys Asp Ser Leu Ser Met Thr Ser Glu Ala Gly Leu Pro
            370                 375                 380

Cys Leu Ser Asp Gln Gly Ser Asp Gly Cys Asp Asp Asp Gly Leu Val
385                 390                 395                 400

Ile Ser Gly Tyr Gly Ser Gly Glu Thr Phe Asp Ser Asn Leu Pro Pro
            405                 410                 415

Thr Asp Asp Glu Asp Phe Tyr Thr Thr Phe Ser Leu Val Thr Asp Lys
            420                 425                 430

Ser Leu Ser Thr Ser Ile Phe Glu Gly Gly Tyr Lys Ala His Ala Pro
            435                 440                 445

Lys Trp Glu Ser Lys Asp Phe Arg Pro Asn Lys Val Ser Glu Thr Ser
            450                 455                 460

Arg Thr Thr Thr Ser Leu Ser Pro Glu Leu Ile Arg Phe Thr Ala
465                 470                 475                 480

Ser Ser Ser Ser Gly Met Val Pro Lys Leu Pro Ala Gly Lys Met Asn

```
                        485                 490                 495
Asn Arg Asp Leu Lys Pro Gln Pro Asp Ile Val Leu Pro Leu Pro
                500                 505                 510

Thr Ala Tyr Glu Leu Asp Ser Thr Lys Leu Lys Ser Pro Leu Ile Thr
                515                 520                 525

Ser Pro Met Phe Arg Asn Val Pro Thr Ala Asn Pro Thr Glu Pro Gly
            530                 535                 540

Ile Arg Arg Val Pro Gly Ala Ser Glu Val Ile Arg Glu Ser Ser Ser
545                 550                 555                 560

Thr Thr Gly Met Val Val Gly Ile Val Ala Ala Ala Leu Cys Ile
                565                 570                 575

Leu Ile Leu Leu Tyr Ala Met Tyr Lys Tyr Arg Asn Arg Asp Glu Gly
                580                 585                 590

Ser Tyr Gln Val Asp Glu Thr Arg Asn Tyr Ile Ser Asn Ser Ala Gln
            595                 600                 605

Ser Asn Gly Thr Leu Met Lys Glu Lys Gln Gln Ser Ser Lys Ser Gly
            610                 615                 620

His Lys Lys Gln Lys Asn Lys Asp Arg Glu Tyr Tyr Val
625                 630                 635

<210> SEQ ID NO 8
<211> LENGTH: 2768
<212> TYPE: PRT
<213> ORGANISM: Homo sapiens

<400> SEQUENCE: 8

Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
                20                  25                  30

Pro Cys Glu Leu Gln Arg Glu Thr Ala Phe Leu Lys Gln Ala Asp Tyr
            35                  40                  45

Val Pro Gln Cys Ala Glu Asp Gly Ser Phe Gln Thr Val Gln Cys Gln
        50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
        115                 120                 125

Val Gln Cys Asp Val Gln Gln Val Gln Cys Trp Cys Val Asp Ala Glu
    130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
            180                 185                 190

Gln Cys Lys Phe Val Asn Thr Thr Asp Met Met Ile Phe Asp Leu Val
        195                 200                 205

His Ser Tyr Asn Arg Phe Pro Asp Ala Phe Val Thr Phe Ser Ser Phe
    210                 215                 220
```

```
Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Asp Glu
            245                 250                 255

Ile Tyr Asp Thr Ile Phe Ala Gly Leu Asp Leu Pro Ser Thr Phe Thr
                260                 265                 270

Glu Thr Thr Leu Tyr Arg Ile Leu Gln Arg Arg Phe Leu Ala Val Gln
        275                 280                 285

Ser Val Ile Ser Gly Arg Phe Arg Cys Pro Thr Lys Cys Glu Val Glu
    290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
                340                 345                 350

Gly Glu Pro Pro Ser Cys Ala Glu Gly Gln Ser Cys Ala Ser Glu Arg
            355                 360                 365

Gln Gln Ala Leu Ser Arg Leu Tyr Phe Gly Thr Ser Gly Tyr Phe Ser
    370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415

Val Asp Ser Gly Leu Leu Arg Pro Met Val Glu Gly Gln Ser Gln Gln
            420                 425                 430

Phe Ser Val Ser Glu Asn Leu Leu Lys Glu Ala Ile Arg Ala Ile Phe
    435                 440                 445

Pro Ser Arg Gly Leu Ala Arg Leu Ala Leu Gln Phe Thr Thr Asn Pro
450                 455                 460

Lys Arg Leu Gln Gln Asn Leu Phe Gly Gly Lys Phe Leu Val Asn Val
465                 470                 475                 480

Gly Gln Phe Asn Leu Ser Gly Ala Leu Gly Thr Arg Gly Thr Phe Asn
                485                 490                 495

Phe Ser Gln Phe Phe Gln Gln Leu Gly Leu Ala Ser Phe Leu Asn Gly
            500                 505                 510

Gly Arg Gln Glu Asp Leu Ala Lys Pro Leu Ser Val Gly Leu Asp Ser
        515                 520                 525

Asn Ser Ser Thr Gly Thr Pro Glu Ala Ala Lys Lys Asp Gly Thr Met
530                 535                 540

Asn Lys Pro Thr Val Gly Ser Phe Gly Phe Glu Ile Asn Leu Gln Glu
545                 550                 555                 560

Asn Gln Asn Ala Leu Lys Phe Leu Ala Ser Leu Leu Glu Leu Pro Glu
            565                 570                 575

Phe Leu Leu Phe Leu Gln His Ala Ile Ser Val Pro Glu Asp Val Ala
            580                 585                 590

Arg Asp Leu Gly Asp Val Met Glu Thr Val Leu Ser Ser Gln Thr Cys
        595                 600                 605

Glu Gln Thr Pro Glu Arg Leu Phe Val Pro Ser Cys Thr Thr Glu Gly
        610                 615                 620

Ser Tyr Glu Asp Val Gln Cys Phe Ser Gly Glu Cys Trp Cys Val Asn
625                 630                 635                 640

Ser Trp Gly Lys Glu Leu Pro Gly Ser Arg Val Arg Gly Gly Gln Pro
```

-continued

```
                645                 650                 655
Arg Cys Pro Thr Asp Cys Glu Lys Gln Arg Ala Arg Met Gln Ser Leu
                660                 665                 670
Met Gly Ser Gln Pro Ala Gly Ser Thr Leu Phe Val Pro Ala Cys Thr
                675                 680                 685
Ser Glu Gly His Phe Leu Pro Val Gln Cys Phe Asn Ser Glu Cys Tyr
                690                 695                 700
Cys Val Asp Ala Glu Gly Gln Ala Ile Pro Gly Thr Arg Ser Ala Ile
705                 710                 715                 720
Gly Lys Pro Lys Lys Cys Pro Thr Pro Cys Gln Leu Gln Ser Glu Gln
                725                 730                 735
Ala Phe Leu Arg Thr Val Gln Ala Leu Leu Ser Asn Ser Ser Met Leu
                740                 745                 750
Pro Thr Leu Ser Asp Thr Tyr Ile Pro Gln Cys Ser Thr Asp Gly Gln
                755                 760                 765
Trp Arg Gln Val Gln Cys Asn Gly Pro Pro Glu Gln Val Phe Glu Leu
                770                 775                 780
Tyr Gln Arg Trp Glu Ala Gln Asn Lys Gly Gln Asp Leu Thr Pro Ala
785                 790                 795                 800
Lys Leu Leu Val Lys Ile Met Ser Tyr Arg Glu Ala Ala Ser Gly Asn
                805                 810                 815
Phe Ser Leu Phe Ile Gln Ser Leu Tyr Glu Ala Gly Gln Gln Asp Val
                820                 825                 830
Phe Pro Val Leu Ser Gln Tyr Pro Ser Leu Gln Asp Val Pro Leu Ala
                835                 840                 845
Ala Leu Glu Gly Lys Arg Pro Gln Pro Arg Glu Asn Ile Leu Leu Glu
850                 855                 860
Pro Tyr Leu Phe Trp Gln Ile Leu Asn Gly Gln Leu Ser Gln Tyr Pro
865                 870                 875                 880
Gly Ser Tyr Ser Asp Phe Ser Thr Pro Leu Ala His Phe Asp Leu Arg
                885                 890                 895
Asn Cys Trp Cys Val Asp Glu Ala Gly Gln Glu Leu Glu Gly Met Arg
                900                 905                 910
Ser Glu Pro Ser Lys Leu Pro Thr Cys Pro Gly Ser Cys Glu Glu Ala
                915                 920                 925
Lys Leu Arg Val Leu Gln Phe Ile Arg Glu Thr Glu Glu Ile Val Ser
                930                 935                 940
Ala Ser Asn Ser Ser Arg Phe Pro Leu Gly Glu Ser Phe Leu Val Ala
945                 950                 955                 960
Lys Gly Ile Arg Leu Arg Asn Glu Asp Leu Gly Leu Pro Pro Leu Phe
                965                 970                 975
Pro Pro Arg Glu Ala Phe Ala Glu Gln Phe Leu Arg Gly Ser Asp Tyr
                980                 985                 990
Ala Ile Arg Leu Ala Ala Gln Ser Thr Leu Ser Phe Tyr Gln Arg Arg
                995                 1000                1005
Arg Phe Ser Pro Asp Asp Ser Ala Gly Ala Ser Ala Leu Leu Arg
                1010                1015                1020
Ser Gly Pro Tyr Met Pro Gln Cys Asp Ala Phe Gly Ser Trp Glu
                1025                1030                1035
Pro Val Gln Cys His Ala Gly Thr Gly His Cys Trp Cys Val Asp
                1040                1045                1050
Glu Lys Gly Gly Phe Ile Pro Gly Ser Leu Thr Ala Arg Ser Leu
                1055                1060                1065
```

```
Gln Ile Pro Gln Cys Pro Thr Thr Cys Glu Lys Ser Arg Thr Ser
    1070                1075                1080

Gly Leu Leu Ser Ser Trp Lys Gln Ala Arg Ser Gln Glu Asn Pro
    1085                1090                1095

Ser Pro Lys Asp Leu Phe Val Pro Ala Cys Leu Glu Thr Gly Glu
    1100                1105                1110

Tyr Ala Arg Leu Gln Ala Ser Gly Ala Gly Thr Trp Cys Val Asp
    1115                1120                1125

Pro Ala Ser Gly Glu Glu Leu Arg Pro Gly Ser Ser Ser Ser Ala
    1130                1135                1140

Gln Cys Pro Ser Leu Cys Asn Val Leu Lys Ser Gly Val Leu Ser
    1145                1150                1155

Arg Arg Val Ser Pro Gly Tyr Val Pro Ala Cys Arg Ala Glu Asp
    1160                1165                1170

Gly Gly Phe Ser Pro Val Gln Cys Asp Gln Ala Gln Gly Ser Cys
    1175                1180                1185

Trp Cys Val Met Asp Ser Gly Glu Glu Val Pro Gly Thr Arg Val
    1190                1195                1200

Thr Gly Gly Gln Pro Ala Cys Glu Ser Pro Arg Cys Pro Leu Pro
    1205                1210                1215

Phe Asn Ala Ser Glu Val Val Gly Gly Thr Ile Leu Cys Glu Thr
    1220                1225                1230

Ile Ser Gly Pro Thr Gly Ser Ala Met Gln Gln Cys Gln Leu Leu
    1235                1240                1245

Cys Arg Gln Gly Ser Trp Ser Val Phe Pro Pro Gly Pro Leu Ile
    1250                1255                1260

Cys Ser Leu Glu Ser Gly Arg Trp Glu Ser Gln Leu Pro Gln Pro
    1265                1270                1275

Arg Ala Cys Gln Arg Pro Gln Leu Trp Gln Thr Ile Gln Thr Gln
    1280                1285                1290

Gly His Phe Gln Leu Gln Leu Pro Pro Gly Lys Met Cys Ser Ala
    1295                1300                1305

Asp Tyr Ala Asp Leu Leu Gln Thr Phe Gln Val Phe Ile Leu Asp
    1310                1315                1320

Glu Leu Thr Ala Arg Gly Phe Cys Gln Ile Gln Val Lys Thr Phe
    1325                1330                1335

Gly Thr Leu Val Ser Ile Pro Val Cys Asn Asn Ser Ser Val Gln
    1340                1345                1350

Val Gly Cys Leu Thr Arg Glu Arg Leu Gly Val Asn Val Thr Trp
    1355                1360                1365

Lys Ser Arg Leu Glu Asp Ile Pro Val Ala Ser Leu Pro Asp Leu
    1370                1375                1380

His Asp Ile Glu Arg Ala Leu Val Gly Lys Asp Leu Leu Gly Arg
    1385                1390                1395

Phe Thr Asp Leu Ile Gln Ser Gly Ser Phe Gln Leu His Leu Asp
    1400                1405                1410

Ser Lys Thr Phe Pro Ala Glu Thr Ile Arg Phe Leu Gln Gly Asp
    1415                1420                1425

His Phe Gly Thr Ser Pro Arg Thr Trp Phe Gly Cys Ser Glu Gly
    1430                1435                1440

Phe Tyr Gln Val Leu Thr Ser Glu Ala Ser Gln Asp Gly Leu Gly
    1445                1450                1455
```

-continued

```
Cys Val Lys Cys Pro Glu Gly Ser Tyr Ser Gln Asp Glu Glu Cys
    1460                1465                1470

Ile Pro Cys Pro Val Gly Phe Tyr Gln Glu Gln Ala Gly Ser Leu
    1475                1480                1485

Ala Cys Val Pro Cys Pro Val Gly Arg Thr Thr Ile Ser Ala Gly
    1490                1495                1500

Ala Phe Ser Gln Thr His Cys Val Thr Asp Cys Gln Arg Asn Glu
    1505                1510                1515

Ala Gly Leu Gln Cys Asp Gln Asn Gly Gln Tyr Arg Ala Ser Gln
    1520                1525                1530

Lys Asp Arg Gly Ser Gly Lys Ala Phe Cys Val Asp Gly Glu Gly
    1535                1540                1545

Arg Arg Leu Pro Trp Trp Glu Thr Glu Ala Pro Leu Glu Asp Ser
    1550                1555                1560

Gln Cys Leu Met Met Gln Lys Phe Glu Lys Val Pro Glu Ser Lys
    1565                1570                1575

Val Ile Phe Asp Ala Asn Ala Pro Val Ala Val Arg Ser Lys Val
    1580                1585                1590

Pro Asp Ser Glu Phe Pro Val Met Gln Cys Leu Thr Asp Cys Thr
    1595                1600                1605

Glu Asp Glu Ala Cys Ser Phe Phe Thr Val Ser Thr Thr Glu Pro
    1610                1615                1620

Glu Ile Ser Cys Asp Phe Tyr Ala Trp Thr Ser Asp Asn Val Ala
    1625                1630                1635

Cys Met Thr Ser Asp Gln Lys Arg Asp Ala Leu Gly Asn Ser Lys
    1640                1645                1650

Ala Thr Ser Phe Gly Ser Leu Arg Cys Gln Val Lys Val Arg Ser
    1655                1660                1665

His Gly Gln Asp Ser Pro Ala Val Tyr Leu Lys Lys Gly Gln Gly
    1670                1675                1680

Ser Thr Thr Thr Leu Gln Lys Arg Phe Glu Pro Thr Gly Phe Gln
    1685                1690                1695

Asn Met Leu Ser Gly Leu Tyr Asn Pro Ile Val Phe Ser Ala Ser
    1700                1705                1710

Gly Ala Asn Leu Thr Asp Ala His Leu Phe Cys Leu Leu Ala Cys
    1715                1720                1725

Asp Arg Asp Leu Cys Cys Asp Gly Phe Val Leu Thr Gln Val Gln
    1730                1735                1740

Gly Gly Ala Ile Ile Cys Gly Leu Leu Ser Ser Pro Ser Val Leu
    1745                1750                1755

Leu Cys Asn Val Lys Asp Trp Met Asp Pro Ser Glu Ala Trp Ala
    1760                1765                1770

Asn Ala Thr Cys Pro Gly Val Thr Tyr Asp Gln Glu Ser His Gln
    1775                1780                1785

Val Ile Leu Arg Leu Gly Asp Gln Glu Phe Ile Lys Ser Leu Thr
    1790                1795                1800

Pro Leu Glu Gly Thr Gln Asp Thr Phe Thr Asn Phe Gln Gln Val
    1805                1810                1815

Tyr Leu Trp Lys Asp Ser Asp Met Gly Ser Arg Pro Glu Ser Met
    1820                1825                1830

Gly Cys Arg Lys Asp Thr Val Pro Arg Pro Ala Ser Pro Thr Glu
    1835                1840                1845

Ala Gly Leu Thr Thr Glu Leu Phe Ser Pro Val Asp Leu Asn Gln
```

-continued

```
               1850                1855                1860
Val Ile Val Asn Gly Asn Gln Ser Leu Ser Ser Gln Lys His Trp
   1865                1870                1875
Leu Phe Lys His Leu Phe Ser Ala Gln Gln Ala Asn Leu Trp Cys
   1880                1885                1890
Leu Ser Arg Cys Val Gln Glu His Ser Phe Cys Gln Leu Ala Glu
   1895                1900                1905
Ile Thr Glu Ser Ala Ser Leu Tyr Phe Thr Cys Thr Leu Tyr Pro
   1910                1915                1920
Glu Ala Gln Val Cys Asp Asp Ile Met Glu Ser Asn Ala Gln Gly
   1925                1930                1935
Cys Arg Leu Ile Leu Pro Gln Met Pro Lys Ala Leu Phe Arg Lys
   1940                1945                1950
Lys Val Ile Leu Glu Asp Lys Val Lys Asn Phe Tyr Thr Arg Leu
   1955                1960                1965
Pro Phe Gln Lys Leu Met Gly Ile Ser Ile Arg Asn Lys Val Pro
   1970                1975                1980
Met Ser Glu Lys Ser Ile Ser Asn Gly Phe Phe Glu Cys Glu Arg
   1985                1990                1995
Arg Cys Asp Ala Asp Pro Cys Cys Thr Gly Phe Gly Phe Leu Asn
   2000                2005                2010
Val Ser Gln Leu Lys Gly Gly Glu Val Thr Cys Leu Thr Leu Asn
   2015                2020                2025
Ser Leu Gly Ile Gln Met Cys Ser Glu Glu Asn Gly Gly Ala Trp
   2030                2035                2040
Arg Ile Leu Asp Cys Gly Ser Pro Asp Ile Glu Val His Thr Tyr
   2045                2050                2055
Pro Phe Gly Trp Tyr Gln Lys Pro Ile Ala Gln Asn Asn Ala Pro
   2060                2065                2070
Ser Phe Cys Pro Leu Val Val Leu Pro Ser Leu Thr Glu Lys Val
   2075                2080                2085
Ser Leu Asp Ser Trp Gln Ser Leu Ala Leu Ser Ser Val Val Val
   2090                2095                2100
Asp Pro Ser Ile Arg His Phe Asp Val Ala His Val Ser Thr Ala
   2105                2110                2115
Ala Thr Ser Asn Phe Ser Ala Val Arg Asp Leu Cys Leu Ser Glu
   2120                2125                2130
Cys Ser Gln His Glu Ala Cys Leu Ile Thr Thr Leu Gln Thr Gln
   2135                2140                2145
Pro Gly Ala Val Arg Cys Met Phe Tyr Ala Asp Thr Gln Ser Cys
   2150                2155                2160
Thr His Ser Leu Gln Gly Gln Asn Cys Arg Leu Leu Leu Arg Glu
   2165                2170                2175
Glu Ala Thr His Ile Tyr Arg Lys Pro Gly Ile Ser Leu Leu Ser
   2180                2185                2190
Tyr Glu Ala Ser Val Pro Ser Val Pro Ile Ser Thr His Gly Arg
   2195                2200                2205
Leu Leu Gly Arg Ser Gln Ala Ile Gln Val Gly Thr Ser Trp Lys
   2210                2215                2220
Gln Val Asp Gln Phe Leu Gly Val Pro Tyr Ala Ala Pro Pro Leu
   2225                2230                2235
Ala Glu Arg Arg Phe Gln Ala Pro Glu Pro Leu Asn Trp Thr Gly
   2240                2245                2250
```

-continued

```
Ser Trp Asp Ala Ser Lys Pro Arg Ala Ser Cys Trp Gln Pro Gly
2255                2260                2265

Thr Arg Thr Ser Thr Ser Pro Gly Val Ser Glu Asp Cys Leu Tyr
2270                2275                2280

Leu Asn Val Phe Ile Pro Gln Asn Val Ala Pro Asn Ala Ser Val
2285                2290                2295

Leu Val Phe Phe His Asn Thr Met Asp Arg Glu Ser Glu Gly
2300                2305                2310

Trp Pro Ala Ile Asp Gly Ser Phe Leu Ala Ala Val Gly Asn Leu
2315                2320                2325

Ile Val Val Thr Ala Ser Tyr Arg Val Gly Val Phe Gly Phe Leu
2330                2335                2340

Ser Ser Gly Ser Gly Glu Val Ser Gly Asn Trp Gly Leu Leu Asp
2345                2350                2355

Gln Val Ala Ala Leu Thr Trp Val Gln Thr His Ile Arg Gly Phe
2360                2365                2370

Gly Gly Asp Pro Arg Arg Val Ser Leu Ala Ala Asp Arg Gly Gly
2375                2380                2385

Ala Asp Val Ala Ser Ile His Leu Leu Thr Ala Arg Ala Thr Asn
2390                2395                2400

Ser Gln Leu Phe Arg Arg Ala Val Leu Met Gly Gly Ser Ala Leu
2405                2410                2415

Ser Pro Ala Ala Val Ile Ser His Glu Arg Ala Gln Gln Gln Ala
2420                2425                2430

Ile Ala Leu Ala Lys Glu Val Ser Cys Pro Met Ser Ser Ser Gln
2435                2440                2445

Glu Val Val Ser Cys Leu Arg Gln Lys Pro Ala Asn Val Leu Asn
2450                2455                2460

Asp Ala Gln Thr Lys Leu Leu Ala Val Ser Gly Pro Phe His Tyr
2465                2470                2475

Trp Gly Pro Val Ile Asp Gly His Phe Leu Arg Glu Pro Pro Ala
2480                2485                2490

Arg Ala Leu Lys Arg Ser Leu Trp Val Glu Val Asp Leu Leu Ile
2495                2500                2505

Gly Ser Ser Gln Asp Asp Gly Leu Ile Asn Arg Ala Lys Ala Val
2510                2515                2520

Lys Gln Phe Glu Glu Ser Arg Gly Arg Thr Ser Ser Lys Thr Ala
2525                2530                2535

Phe Tyr Gln Ala Leu Gln Asn Ser Leu Gly Gly Glu Asp Ser Asp
2540                2545                2550

Ala Arg Val Glu Ala Ala Ala Thr Trp Tyr Tyr Ser Leu Glu His
2555                2560                2565

Ser Thr Asp Asp Tyr Ala Ser Phe Ser Arg Ala Leu Glu Asn Ala
2570                2575                2580

Thr Arg Asp Tyr Phe Ile Ile Cys Pro Ile Ile Asp Met Ala Ser
2585                2590                2595

Ala Trp Ala Lys Arg Ala Arg Gly Asn Val Phe Met Tyr His Ala
2600                2605                2610

Pro Glu Asn Tyr Gly His Gly Ser Leu Glu Leu Leu Ala Asp Val
2615                2620                2625

Gln Phe Ala Leu Gly Leu Pro Phe Tyr Pro Ala Tyr Glu Gly Gln
2630                2635                2640
```

```
Phe Ser Leu Glu Glu Lys Ser Leu Ser Leu Lys Ile Met Gln Tyr
    2645                2650                2655

Phe Ser His Phe Ile Arg Ser Gly Asn Pro Asn Tyr Pro Tyr Glu
    2660                2665                2670

Phe Ser Arg Lys Val Pro Thr Phe Ala Thr Pro Trp Pro Asp Phe
    2675                2680                2685

Val Pro Arg Ala Gly Glu Asn Tyr Lys Glu Phe Ser Glu Leu
    2690                2695                2700

Leu Pro Asn Arg Gln Gly Leu Lys Lys Ala Asp Cys Ser Phe Trp
    2705                2710                2715

Ser Lys Tyr Ile Ser Ser Leu Lys Thr Ser Ala Asp Gly Ala Lys
    2720                2725                2730

Gly Gly Gln Ser Ala Glu Ser Glu Glu Glu Glu Leu Thr Ala Gly
    2735                2740                2745

Ser Gly Leu Arg Glu Asp Leu Leu Ser Leu Gln Glu Pro Gly Ser
    2750                2755                2760

Lys Thr Tyr Ser Lys
    2765

<210> SEQ ID NO 9
<211> LENGTH: 838
<212> TYPE: PRT
<213> ORGANISM: Homo sapiens

<400> SEQUENCE: 9

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
        50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240
```

```
Asn Glu Thr Ser His Thr Gln Gly Ser Leu Arg Ile Thr Asn Ile Ser
            245                 250                 255

Ser Asp Asp Ser Gly Lys Gln Ile Ser Cys Val Ala Glu Asn Leu Val
        260                 265                 270

Gly Glu Asp Gln Asp Ser Val Asn Leu Thr Val His Phe Ala Pro Thr
    275                 280                 285

Ile Thr Phe Leu Glu Ser Pro Thr Ser Asp His His Trp Cys Ile Pro
290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Ser Ala Ser Pro
                485                 490                 495

Leu His His Ile Ser Asn Gly Ser Asn Thr Pro Ser Ser Glu Gly
            500                 505                 510

Gly Pro Asp Ala Val Ile Ile Gly Met Thr Lys Ile Pro Val Ile Glu
        515                 520                 525

Asn Pro Gln Tyr Phe Gly Ile Thr Asn Ser Gln Leu Lys Pro Asp Thr
    530                 535                 540

Phe Val Gln His Ile Lys Arg His Asn Ile Val Leu Lys Arg Glu Leu
545                 550                 555                 560

Gly Glu Gly Ala Phe Gly Lys Val Phe Leu Ala Glu Cys Tyr Asn Leu
                565                 570                 575

Cys Pro Glu Gln Asp Lys Ile Leu Val Ala Val Lys Thr Leu Lys Asp
            580                 585                 590

Ala Ser Asp Asn Ala Arg Lys Asp Phe His Arg Glu Ala Glu Leu Leu
        595                 600                 605

Thr Asn Leu Gln His Glu His Ile Val Lys Phe Tyr Gly Val Cys Val
    610                 615                 620

Glu Gly Asp Pro Leu Ile Met Val Phe Glu Tyr Met Lys His Gly Asp
625                 630                 635                 640

Leu Asn Lys Phe Leu Arg Ala His Gly Pro Asp Ala Val Leu Met Ala
                645                 650                 655
```

Glu Gly Asn Pro Pro Thr Glu Leu Thr Gln Ser Gln Met Leu His Ile
            660                 665                 670

Ala Gln Gln Ile Ala Ala Gly Met Val Tyr Leu Ala Ser Gln His Phe
        675                 680                 685

Val His Arg Asp Leu Ala Thr Arg Asn Cys Leu Val Gly Glu Asn Leu
    690                 695                 700

Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                725                 730                 735

Pro Pro Glu Ser Ile Met Tyr Arg Lys Phe Thr Thr Glu Ser Asp Val
            740                 745                 750

Trp Ser Leu Gly Val Val Leu Trp Glu Ile Phe Thr Tyr Gly Lys Gln
        755                 760                 765

Pro Trp Tyr Gln Leu Ser Asn Asn Glu Val Ile Glu Cys Ile Thr Gln
    770                 775                 780

Gly Arg Val Leu Gln Arg Pro Arg Thr Cys Pro Gln Glu Val Tyr Glu
785                 790                 795                 800

Leu Met Leu Gly Cys Trp Gln Arg Glu Pro His Met Arg Lys Asn Ile
                805                 810                 815

Lys Gly Ile His Thr Leu Leu Gln Asn Leu Ala Lys Ala Ser Pro Val
            820                 825                 830

Tyr Leu Asp Ile Leu Gly
        835

<210> SEQ ID NO 10
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 10
cctaaccgcc acgatgatgt                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 11
tctgcgggtg agtggtagta                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 12
gggagtcccc tttctgaagc                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 13
ccttcatggc cacactgact                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 14
tgaagtgtga cgtggacatc                                               20

<210> SEQ ID NO 15
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 15
ggaggagcaa tgatcttgat                                               20

<210> SEQ ID NO 16
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 16

Lys Glu Leu Val Glu Gln Asp Ile Gln Pro Ala Arg Tyr
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 17

Lys Phe Met Tyr Thr Asp Trp Ala Asp Arg Asp
1               5                   10

<210> SEQ ID NO 18
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 18

Lys Gly Asn Tyr Gly Leu Leu Asp Gln Ile Gln Ala Leu Arg Trp
1               5                   10                  15

<210> SEQ ID NO 19
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 19

Lys Lys Gln Gly Glu Asp Leu Ala Asp Asn Asp Gly Asp Glu Asp Glu

<210> SEQ ID NO 20
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 20

Lys Gln Gly Glu Asp Leu Ala Asp Asn Asp Gly Asp Glu Asp Glu Asp
1               5                   10                  15

Ile Arg Asp

<210> SEQ ID NO 21
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 21

Lys Thr Gly Asp Pro Asn Lys Pro Val Pro Gln Asp Thr Lys Phe
1               5                   10                  15

<210> SEQ ID NO 22
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 22

Lys Tyr Thr Ser Leu Leu Ala Asp Lys Val
1               5                   10

<210> SEQ ID NO 23
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 23

Arg Phe Leu Pro Pro Glu Pro Pro Ser Trp Ser Gly Ile Arg Asn
1               5                   10                  15

<210> SEQ ID NO 24
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 24

Arg Val Gly Val Leu Gly Phe Leu Ser Thr Gly Asp Gln Ala Ala Lys
1               5                   10                  15

Gly

<210> SEQ ID NO 25
<211> LENGTH: 29
<212> TYPE: PRT
<213> ORGANISM: Artificial sequence

```
<220> FEATURE:
<223> OTHER INFORMATION: Synthetic polypeptide

<400> SEQUENCE: 25

Arg Val Pro Leu Pro Ser Glu Ile Leu Gly Pro Val Asp Gln Tyr Leu
1               5                   10                  15

Gly Val Pro Tyr Ala Ala Pro Pro Ile Gly Glu Lys Arg
            20                  25

<210> SEQ ID NO 26
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 26

Arg Val Pro Leu Pro Ser Glu Ile Leu Gly Pro Val Asp Gln Tyr Leu
1               5                   10                  15

Gly Val Pro Tyr Ala Ala Pro Pro Ile Gly Glu Lys Arg Phe
            20                  25                  30

<210> SEQ ID NO 27
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 27

Arg Trp Val Ser Glu Asn Ile Ala Phe Phe Gly Gly Asp Pro Arg Arg
1               5                   10                  15
```